(12) United States Patent
Brown et al.

(10) Patent No.: US 7,572,934 B2
(45) Date of Patent: Aug. 11, 2009

(54) SUBSTITUTED BIPHENYL GPR40 MODULATORS

(75) Inventors: Sean P. Brown, San Francisco, CA (US); Paul Dransfield, San Francisco, CA (US); Zice Fu, Foster City, CA (US); Jonathan Houze, San Mateo, CA (US); Xian Yun Jiao, Belmont, CA (US); Todd J. Kohn, San Mateo, CA (US); Vatee Pattaropong, Burlingame, CA (US); Marc Vimolratana, San Mateo, CA (US); Michael J. Schmitt, Oakland, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 12/082,645

(22) Filed: Apr. 10, 2008

(65) Prior Publication Data

US 2009/0111859 A1  Apr. 30, 2009

Related U.S. Application Data

(60) Provisional application No. 60/925,014, filed on Apr. 16, 2007.

(51) Int. Cl.
C07C 63/33 (2006.01)
C07C 335/00 (2006.01)
A01N 43/40 (2006.01)
A01N 37/10 (2006.01)

(52) U.S. Cl. .......................... 562/492; 564/26; 514/277; 514/568

(58) Field of Classification Search ........................ None
See application file for complete search history.

(56) References Cited

U.S. PATENT DOCUMENTS

| | | | |
|---|---|---|---|
| 3,507,881 A | 4/1970 | Sandberg et al. | |
| 4,760,089 A | 7/1988 | Chambers et al. | |
| 6,037,367 A | 3/2000 | Christensen, IV et al. | |
| 6,506,757 B1 | 1/2003 | Tajima et al. | |
| 6,620,832 B2 | 9/2003 | Eastwood | |
| 6,645,939 B1 | 11/2003 | Durette et al. | |
| 6,710,063 B1 | 3/2004 | Chao et al. | |
| 6,723,740 B2 | 4/2004 | Chao et al. | |
| 6,875,780 B2 | 4/2005 | Auerbach et al. | |
| 6,939,875 B2 | 9/2005 | Auerbach et al. | |
| 6,964,983 B2 | 11/2005 | Auerbach et al. | |
| 7,338,960 B2 | 3/2008 | Bell et al. | |
| 7,345,068 B2 | 3/2008 | Endou et al. | |
| 2004/0058965 A1 | 3/2004 | Momose et al. | |
| 2005/0089866 A1 | 4/2005 | Hinuma et al. | |
| 2005/0119256 A1 | 6/2005 | Endo et al. | |
| 2006/0003344 A1 | 1/2006 | Houseknecht et al. | |
| 2006/0004012 A1* | 1/2006 | Akerman et al. | 514/249 |
| 2006/0270724 A1 | 11/2006 | Houze et al. | |
| 2007/0066647 A1 | 3/2007 | Akerman et al. | |
| 2007/0149608 A1* | 6/2007 | Yasuma et al. | 514/424 |
| 2007/0244155 A1 | 10/2007 | Sharma et al. | |
| 2007/0265332 A1 | 11/2007 | Ge et al. | |
| 2008/0090840 A1 | 4/2008 | Beck et al. | |
| 2008/0119511 A1 | 5/2008 | Brown et al. | |

FOREIGN PATENT DOCUMENTS

| | | |
|---|---|---|
| AU | A 27141/77 | 1/1979 |
| AU | A 52306/93 | 6/1994 |
| CA | 2111035 | 6/1994 |
| DE | 199 4 1 567 A1 | 4/2000 |
| EP | 0 250 264 | 12/1987 |
| EP | 0 414 289 | 2/1994 |
| EP | 1 357 115 A1 | 10/2003 |
| EP | 1 380 562 | 1/2004 |
| EP | 1 535 915 A1 | 6/2005 |
| EP | 1 559 422 A1 | 8/2005 |
| EP | 1559422 * | 8/2005 |
| EP | 1 630 152 A1 | 3/2006 |
| JP | 10316641 | 2/1998 |
| JP | 2001242165 | 9/2001 |
| JP | 2002003368 | 1/2002 |
| WO | WO 93/23040 | 11/1993 |
| WO | WO 93/23041 | 11/1993 |
| WO | WO 95/01326 | 1/1995 |
| WO | WO 95/01348 | 1/1995 |
| WO | WO 97/12867 | 4/1997 |
| WO | WO 99/11255 | 3/1999 |
| WO | WO 01/00603 | 1/2001 |

(Continued)

OTHER PUBLICATIONS

Bachmann, W. E. et al., "The Synthesis of an Analog of the Sex Hormones," *J. Am. Chem. Soc.*, 64, 94-97 (1942).

(Continued)

*Primary Examiner*—Karl J Puttlitz
(74) *Attorney, Agent, or Firm*—Bernard Friedrichsen

(57) ABSTRACT

The present invention provides compounds useful, for example, for treating metabolic disorders in a subject. Such compounds have the general formula I:

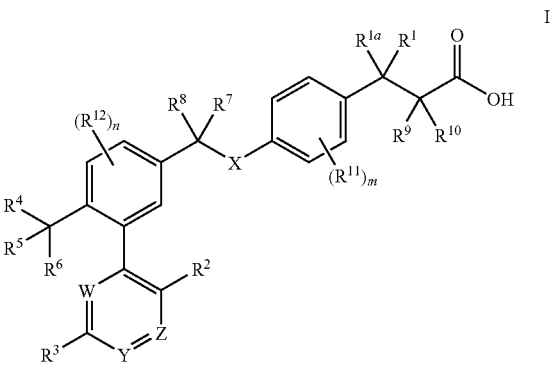

where the definitions of the variables are provided herein. The present invention also provides compositions that include, and methods for using, the compounds in preparing medicaments and for treating metabolic disorders such as, for example, type II diabetes.

70 Claims, No Drawings

FOREIGN PATENT DOCUMENTS

| | | |
|---|---|---|
| WO | WO 01/36351 | 5/2001 |
| WO | WO 01/36365 | 5/2001 |
| WO | WO 02/057783 | 7/2002 |
| WO | WO 02/062774 | 8/2002 |
| WO | WO 00/63196 | 10/2002 |
| WO | WO 02/100403 | 12/2002 |
| WO | WO 03/074050 | 9/2003 |
| WO | WO 03/099793 | 12/2003 |
| WO | WO 04/000315 | 12/2003 |
| WO | WO 2004/092117 | 10/2004 |
| WO | WO 2004/106276 | 12/2004 |
| WO | WO 2005/051890 | 6/2005 |
| WO | WO 2005/058848 | 6/2005 |
| WO | WO 2005/063725 | 7/2005 |
| WO | WO 2005/063729 | 7/2005 |
| WO | WO 2005/087710 | 9/2005 |
| WO | WO 2006/001092 | 1/2006 |
| WO | WO 2006/011615 | 2/2006 |
| WO | WO 2006/083612 | 8/2006 |
| WO | WO 2006/083781 | 8/2006 |
| WO | WO 2007/123225 | 11/2007 |
| WO | WO 2007/131619 | 11/2007 |
| WO | WO 2007/131620 | 11/2007 |
| WO | WO 2007/131622 | 11/2007 |

OTHER PUBLICATIONS

Berthelot et al., "Synthesis and Pharmacological Evaluation of y-Aminobutyric Acid Analogues. New Ligand for $GABA_B$ Sites," *J. Med. Chem.*, 30, 743-746 (1987).

Boyle, Thomas F. et al., "Applications of the Spiroannulation of Tetralins with Alkynes; Towards New Anti-Estrogenic Compounds," *J. Chem. Soc. Perkin Trans. I: Organic and Bioorganic Chem.*, 18, 2707-2711 (1997).

Briscoe et al., "The Orphan G Protein-Coupled Receptor GPR40 is Activated by Medium and Long Chain Fatty Acids," *J. of Biol. Chem.*, 278(13), 11303-11311 (2003).

Briscoe, C. P. et al., "Pharmacological Regulation of Insulin Secretion in MIN6 Cells Through the Fatty Acid Receptor GPR40: Identification of Agonist and Antagonist Small Molecules," *Brit. J. of Pharmacology*, 148, 619-628 (2006).

Burnop, V.C.E. et al., "Fused Carbon Rings. Part XIX. Experiments on the Synthesis of Tetracyclic Compounds of the Sexual Hormonal Type," *J. Chem. Soc.*, 727-735 (1940).

Chatterjee, A., et al., "Studies on Nucleophilic Ring Opening of Some Epoxides in Polar Protic Solvents," *Tetrahedron*, 33, 85-94 (1977).

Ray, Chhanda et al., "Synthesis of some angularly cyclopentanone fused hydrophenanthrene and hydrofluorene derivatives by acid-catalyzed intramolecular C-alkylation of γ, δ-unsaturated α'-diazomethyl ketones," *Synthetic Commun.*, 21(10-11), 1223-1242 (1991).

Collins, David J. et al., "The Structure and Function of Oestrogens. IX*. Synthesis of the trans Isomer of 5,5, 10b-Trimtehyl-4b,5,6,10b,11,12-hexahydrocvhrysene-2,8-diol," *Aust. J. Chem.*, 41, 735-744 (1988).

Deb, Soumitra et al., "A Stereocontrolled Synthesis of (1'RS, 2'SR)-3-oxo-3',4'-dihydrospiro[cyclopentane-1,1'(2'H)-naphthalen]-2-yl Acetic Acid and its Methoxy Derivatives," *J. Chem. Res. Synops.*, 12, 406 (1985).

DeWolf et al., "Inactivation of Dopamine β-Hydroxylase by β-Ethynyltyramine: Kinetic Characterization and Covalent Modification of an Active Site Peptide," *Biochemistry*, 28, 3833-3842 (1989).

Egan, R. W. et al., "Naphthalenes as Inhibitors of Myeloperoxidase: Direct and Indirect Mechanisms of Inhibition," *Agents and Actions*, 29¾ 266-276 (1990).

Frey et al., "Total Synthesis of Pentacyclic Diterpenoid Tropone Hainanolidol," *Aust. J. Chemistry*, 53, 819-830 (2000).

Galemmo et al., "The Development of a Novel Series of (Quinolin-2-ylmethoxy) phenyl-Containing Compounds as High-Affinity Leukotriene Receptor Antagonists. 3. Structural Variation of the Acidic Side Chain to Give Antagonists of Enhanced Potency," *J. Med. Chem.*, 33, 2828-2841 (1990).

Garrido, D. M., et al., "Synthesis and Activity of Small Molecule GPR40 Agonists," *Bioorg. and Med. Chem. Lett.*, 16, 1840-1845 (2006).

Ghosal, Probit Kumar, et al., "Stereospecific Synthesis of 9bβ-Carbomethoxy-7-methoxy-2,3,3aα,4,5,9bβ-Hexahydro-1H-Benz[e]-Inden-2-one; An Intermediate Towards Physiologically Active Compounds," *Tet. Lett.*, 17, 1463-1464 (1977).

Guthrie, R. W. et al., "Synthesis in the Series of Diterpene Alkaloids VI. A Simple Synthesis of Atisine," *Tet. Lett.*, 38, 4645-4654 (1966).

Haigh et al., "Non-thiazolidinedione Antihyperglycaemic Agents. Part 3: The Effects of Stereochemistry on the Potency of α-Methoxy-β-phenylpropanoic Acids," *Bioorg. & Med. Chem.*, 7, 821-830 (1999).

Hares, Owen et al., "Sythetic Studies of Tricyclospirodienones: Model Chemistry for Novel Mimics of Steroid Substrates," *J. Chem. Soc. Perkin Trans. I: Organic and Bioorganic Chem.*, 13, 1481-1492 (1993).

Iizuka et al., "β-Substituted Phenethylamines as High Affinity Mechanism-Based Inhibitors of Dopamine β-Hydroxylase," *J. Med. Chem.*, 31, 704-706 (1988).

Ishikawa et al., "Actions of the Novel Oral Antidiabetic Agent HQL-975 in Insulin-Resistant Non-Insulin -Dependent Diabetes Mellitus Model Animals," *Diabetes Res. and Clin. Pract.*, 41, 101-111 (1998).

Ishikawa et al., "Effects of the Novel Oral Antidiabetic Agent HQL-975 in Glucose and Lipid Metabolism in Diabetic db/db Mice," *Arzneim. Forsch. Drug Res.*, 48(3), 245-250 (1998).

Itoh et al., "Free Fatty Acids Regulate Insulin Secretion from Pancreatic β Cells Through GPR40," *Nature*, 422, 173-176 (2003).

Johns, William F. et al., "Total Synthesis of Estrajervatetraene," *J. Org. Chem.*, 44(6), 958-961 (1979).

Kolasa et al., "Symmetrical Bis (heteroarylmethoxyphenyl) alkylcarboxylic Acids as Inhibitors of Leukotriene Biosynthesis," *J. Med. Chem.*, 43, 3322-3334 (2000).

Kotarsky et al., "A Human Cell Surface Receptor Activated by Free Fatty Acids and Thiazolidinedione Drugs", *Biochemical and Biophysical Research Communications*, 301, 406-410 (2003).

Kuchar et al., "Benzyloxyarylaliphatic Acids: Synthesis and Quantitative Relations Between Structure and Antiinflammatory Activity," *Collection Czechoslovak Chem, Commun.*, 47, 2514-2524 (1982).

Kuchar et al., "The Effects of Lopophilicity on the Inhibition of Denaturation of Serum Albumin and on the Activation of Fibrionolysis Observed with a Serixes of Benzyloxyarylaliphatic Acids," *Collection Czechoslovak Chem, Commun.*, 48, 1077-1088 (1983).

Lin, LInus S. et al., "The Discovery of Acylated β-Amino Acids as Potent and Orally Bioavailable VLA-4 Antagonists," *Bioorganic and Medicinal Chem. Lett.*, 12, 611-614 (2002).

Liu et al., "Synthesis and Biological Activity of L-Tyrosine-based PPARγ Agonists with Reduced Molecular Weight," *Bioorg. & Med. Chem. Lett.*, 11, 3111-3113 (2001).

Nilsson, N. E. et al., "Identification of a Free Fatty Acid Receptor, $FFA_2R$, Expressed on Leukocytes and Activated by Short-Chain Fatty Acids," *Biochemical and Biophysical Research Communication*, 303 1047-1052 (2003).

Oliver et al., "A Selective Peroxisome Proliferator-Activated Receptor δ Agonist Promotes Reverse Cholesterol Transport," *PNAS*, 98(9), 5306-5311 (2001).

Poitout, Vincent, "The Ins and Outs of Fatty Acids on the Pancreatic β Cells," *Trends in Endocrinology and Metabolism*, 14(5), 201-203 (2003).

Sandberg, Rune et al., "N-Aminoalkylsuccinimides as Local Anaesthetics," *Acta Pharmaceutica Suecica*, 17(4) 169-176 (1980).

Sanyal, Utpal et al., "A Novel Synthesis of a Tricyclo $(7.5.0^{1,5}.0^{1,9})$ Tetradecane Ring System Related to Gascardic Acid," *Tet. Lett.*, 25, 2187-2190 (1978).

Sarma, Aluru Sudarsana et al., "Synthetic Studies on Terpenoids. Parts XVIII. Stereocontrolled Synthesis of (+/-)-1,2,3,4,4a,9,10,10aα-Octahydro-1α-methylenephenanthrene-1β, 4aβ-dicarboxylic acid and the 7-Methoxy Analog: A Potential Intermediate for Diterpinoid Synthesis," *J. Chem. Soc. Perkin Trans. I: Organic and Bioorganic Chem.*, 7, 722-727 (1976).

Sawzdargo et al., "A Cluster of Four Novel Human G Protein-Coupled Receptor Genes Occurring in Close Proximity to CD22 Gene on Chromosome 19q13.1", *Biochemical and Biophysical Research Communications*, 239, 543-547 (1997).

Shaw et al., "Enantioselective Synthesis of (+)-(2S, 3S)-3-Ethyltyrosine," *Tetrahedron Letters*, 31(35), 5081-84 (1990).

Shiotani, Shunsaku et al., "Synthesis of 1,3-Bridged 1,2,3,4,5,6-Hexahydro-2,6-methano-3-benzazocine Derivatives," *Chem. Pharm. Bull.*, 28(6), 1928-1931 (1980).

Waid et al., "Constrained Amino Acids. An Approach to the Synthesis of 3-Substituted Prolines," *Tetrahdeon Letters*, 37(24), 4091-4094 (1996).

Kao et al., "One-Pot Synthesis of the Hydroximoyl Chlorides and [3.3.0] Bicyclic Compounds from the Reactions of β-Nitrostyrenese with Stabilized Nucleophiles," Tetrahedron, 54(46), 13997-14014 (1998).

Booth, C. J. et al., "The Synthesis and Transition Temperatures of Novel Low Molar Mass Chosesteric materials Derives from (R)-2-(4-Hydroxyphenoxy)propanoic Acid," Mol. Cryst. Liq. Cryst., vol. 210, pp. 31-57 (1992).

Booth, C. J. et al., "The Influence of the Liquid Crystalline Core Geometry on the Mesogenicity of Novel Chiral 2-(4-Substituted-phenoxy)propanonitriles," Liquid Crystals, vol. 16(6), pp. 925-940, (1994).

McKeown, S.C. et al., "Solid Phase Synthesis and SAR of Small Molecule Agonists for the GPR40 Receptor," Bioorg. & Med. Chem. Lett., 17, pp. 1584-1589 (2007).

Song, F. et al., "Synthesis and Biological Evaluation of 3-Aryl-3-(4-phenoxy)-propionic Acid as a Novel Series of G Protein-Coupled REceptor 40 Agonists," J. Med. Chem. 50 pp. 2807-2817 (2007).

Houze, J. et al., "Beta-substituted Carboxylic Acids as Potent, Bioavailable Agonists of GPR40", 234th ACS National Meeting Boston, MA Aug. 19-23, 2007.

* cited by examiner

SUBSTITUTED BIPHENYL GPR40 MODULATORS

1. CROSS REFERENCES TO RELATED APPLICATIONS

This application claims the benefit of U.S. Provisional Application No. 60/925,014, filed on Apr. 16, 2007, which is hereby incorporated by reference in its entirety and for all purposes as if fully set forth herein.

2. FIELD OF THE INVENTION

The present invention relates to compounds capable of modulating the G-protein-coupled receptor GPR40, compositions comprising the compounds, and methods for their use for controlling insulin levels in vivo and for the treatment of conditions such as type II diabetes, hypertension, ketoacidosis, obesity, glucose intolerance, and hypercholesterolemia and related disorders associated with abnormally high or low plasma lipoprotein, triglyceride or glucose levels.

3. BACKGROUND OF THE INVENTION

The production of insulin is central to the regulation of carbohydrate and lipid metabolism. Insulin imbalances lead to conditions such as type II diabetes mellitus, a serious metabolic disease that afflicts around 5% of the population in Western Societies and over 150 million people worldwide. Insulin is secreted from pancreatic β cells in response to elevated plasma glucose which is augmented by the presence of fatty acids. The recent recognition of the function of the G-protein coupled receptor GPR40 in modulating insulin secretion has provided insight into regulation of carbohydrate and lipid metabolism in vertebrates, and further provided targets for the development of therapeutic agents for disorders such as obesity, diabetes, cardiovascular disease and dyslipidemia.

GPR40 is a member of the gene superfamily of G-protein coupled receptors ("GPCRs"). GPCRs are membrane proteins characterized as having seven putative transmembrane domains that respond to a variety of molecules by activating intra-cellular signaling pathways critical to a diversity of physiological functions. GPR40 was first identified as an orphan receptor (i.e., a receptor without a known ligand) from a human genomic DNA fragment. Sawzdargo et al. (1997) *Biochem. Biophys. Res. Commun.* 239: 543-547. GPR40 is highly expressed in pancreatic β cells and insulin-secreting cell lines. GPR40 activation is linked to modulation of the $G_q$ family of intra-cellular signaling proteins and concomitant induction of elevated calcium levels. It has been recognized that fatty acids serve as ligands for GPR40, and that fatty acids regulate insulin secretion through GPR40. Itoh et al. (2003) *Nature* 422:173-176; Briscoe et al. (2003) *J. Biol. Chem.* 278:11303-11311; Kotarsky et al. (2003) *Biochem. Biophys. Res. Commun.* 301: 406-410.

Various documents have disclosed compounds reportedly having activity with respect to GPR40. For example, WO 2004/041266 and EP 1559422 disclose compounds that purportedly act as GPR40 receptor function regulators. WO 2004/106276 and EP 1630152 are directed to condensed ring compounds that purportedly possess GPR40 receptor function modulating action. More recently, WO 2005/086661 U.S. Patent Application Publication No. 2006/0004012, U.S. Patent Application Publication No. 2006/0270724, and U.S. Patent Application Publication No. 2007/0066647 disclose compounds useful for modulating insulin levels in subjects and useful for treating type II diabetes.

Although a number of compounds have been disclosed that reportedly modulate GPR40 activity, the prevalence of type II diabetes, obesity, hypertension, cardiovascular disease and dyslipidemia underscores the need for new therapies to effectively treat or prevent these conditions.

4. SUMMARY OF THE INVENTION

Provided herein are compounds, pharmaceutical compositions, and methods useful for treating or preventing a condition or disorder such as type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer or edema.

In one aspect, the present invention provides a compound having the formula I or a pharmaceutically acceptable salt, solvate, stereoisomer, or prodrug thereof; or a tautomer or a pharmaceutically acceptable salt, solvate, stereoisomer, or prodrug thereof; or a mixture thereof:

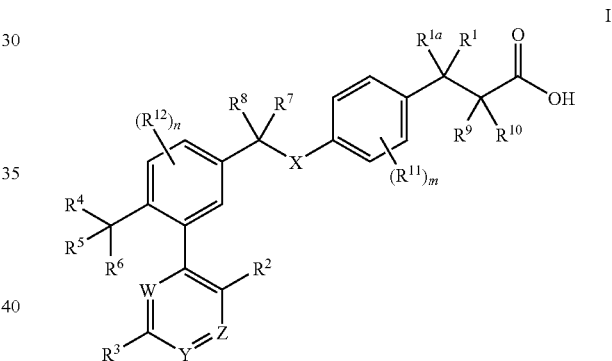

where

X is O or S;

W, Y, and Z are selected from N or C—H; wherein no more than one of W, Y, and Z is N; and further wherein Z is not N if $R^2$ is F;

$R^1$ is selected from H, $(C_1-C_6)$alkyl, $(C_2-C_6)$alkenyl, $(C_2-C_6)$alkynyl, heterocyclyl, or heteroaryl;

$R^{1a}$ is selected from H and $(C_1-C_4)$alkyl;

$R^2$ is selected from F or $(C_3-C_6)$alkoxy;

$R^3$ is $(C_1-C_2)$alkoxy;

$R^4$, $R^5$, and $R^6$ are independently selected from H, $(C_1-C_4)$alkyl, or substituted $(C_1-C_4)$alkyl, and two of $R^4$, $R^5$, and $R^6$ may join together to form a 3-7 membered ring; wherein at least two of $R^4$, $R^5$, and $R^6$ are other than H;

$R^7$ and $R^8$ are independently selected from H and $(C_1-C_4)$alkyl;

$R^9$ and $R^{10}$ are independently selected from H and $(C_1-C_4)$alkyl;

Each $R^{11}$ is independently selected from F, Cl, $(C_1-C_4)$alkyl, or $(C_1-C_4)$alkoxy and m is 0, 1, or 2; and Each $R^{12}$ is independently selected from F, Cl, $(C_1-C_4)$alkyl, or $(C_1-C_4)$alkoxy and n is 0, 1, or 2.

In a second aspect, the invention provides a compound having the formula I or a pharmaceutically acceptable salt, solvate, stereoisomer, or prodrug thereof; or a tautomer or a pharmaceutically acceptable salt, solvate, stereoisomer, or prodrug thereof; or a mixture thereof, wherein X is O, S, or $NR_a$, wherein $R_a$ is selected from H and $(C_1-C_4)$ alkyl;

W, Y, and Z are selected from N or C—H; wherein no more than one of W, Y, and Z is N; and further wherein Z is not N if $R^2$ is F;

$R^1$ is selected from H, $(C_1-C_6)$alkyl, $(C_2-C_6)$alkenyl, $(C_2-C_6)$alkynyl, heterocyclyl, heteroaryl, or aryl;

$R^{1a}$ is selected from H and $(C_1-C_4)$alkyl;

$R^2$ is selected from F or $(C_3-C_6)$alkoxy;

$R^3$ is $(C_1-C_2)$alkoxy;

$R^4$, $R^5$, and $R^6$ are independently selected from H, $(C_1-C_4)$ alkyl, or substituted $(C_1-C_4)$alkyl, and two of $R^4$, $R^5$, and $R^6$ may join together to form a 3-7 membered ring; wherein at least two of $R^4$, $R^5$, and $R^6$ are other than H; and wherein at least one of $R^4$, $R^5$, and $R^6$ may be OH;

$R^7$ and $R^8$ are independently selected from H and $(C_1-C_4)$ alkyl;

$R^9$ and $R^{10}$ are independently selected from H, $(C_1-C_4)$ alkyl, and $(C_2-C_6)$alkenyl;

Each $R^{11}$ is independently selected from F, Cl, $(C_1-C_4)$ alkyl, or $(C_1-C_4)$alkoxy and m is 0, 1, or 2; and Each $R^{12}$ is independently selected from F, Cl, $(C_1-C_4)$ alkyl, or $(C_1-C_4)$alkoxy and n is 0, 1, or 2.

In some embodiments of the second aspect, $R^1$ is an aryl. In some such embodiments, $R^1$ is a phenyl.

In some embodiments of the second aspect, X is $NR_a$. In some such embodiments, $R_a$ is H.

In some embodiments of the second aspect, $R^9$ is selected from $(C_1-C_4)$alkyl, and $(C_2-C_6)$alkenyl. In some such embodiments $R^{10}$ is selected from H. In other such embodiments, $R^{10}$ is a $(C_1-C_4)$alkyl such as a methyl group.

In some embodiments of the compound of formula I, m and n are both 0.

In some embodiments of the compound of formula I, $R^{1a}$ is H or methyl. In some such embodiments, $R^{1a}$ is H.

In some embodiments of the compound of formula I, W, Y, and Z are all C—H.

In some embodiments of the compound of formula I, $R^4$, $R^5$, and $R^6$ are independently selected from H and $(C_1-C_4)$ alkyl groups and at least two of $R^4$, $R^5$, and $R^6$ are $(C_1-C_4)$ alkyl groups. In some such embodiments, each of $R^4$, $R^5$, and $R^6$ are methyl groups. In other embodiments, $R^4$, $R^5$, and $R^6$ are independently selected from H, $(C_1-C_4)$alkyl groups, $(C_1-C_4)$haloalkyl groups, $(C_1-C_4)$perhaloalkyl groups, or $(C_1-C_4)$ alkoxy$(C_1-C_4)$alkyl groups. In some such embodiments, at least one of $R^4$, $R^5$, and $R^6$ is a $CF_3$ group or is a methoxymethyl group.

In some embodiments of the compound of formula I, $R^2$ is F or butoxy. In some such embodiments, $R^2$ is F whereas in other such embodiments, $R^2$ is butoxy.

In some embodiments of the compound of formula I, $R^3$ is methoxy.

In some embodiments of the compound of formula I, X is O.

In some embodiments of the compound of formula I, $R^7$ and $R^8$ are both H.

In some embodiments of the compound of formula I, $R^9$ and $R^{10}$ are both H.

In some embodiments of the compound of formula I, $R^1$ is $(C_1-C_4)$ alkyl). In some such embodiments, $R^1$ is a methyl, ethyl, propyl, or butyl group. In some such embodiments, $R^1$ is a propyl group.

In some embodiments of the compound of formula I, $R^1$ is $(C_2-C_4)$ alkenyl. In some such embodiments, $R^1$ is selected from —CH=$CH_2$, —CH=CH—$CH_3$, —CH=CH—$CH_2$—$CH_3$, or —$CH_2$—CH=$CH_2$. In some such embodiments, $R^1$ is —CH=CH—$CH_3$. In some such embodiments, $R^1$ has the formula

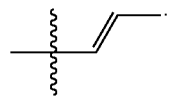

In other such embodiments, $R^1$ has the formula

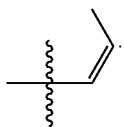

In some embodiments of the compound of formula I, $R^1$ is a $(C_2-C_4)$ alkynyl. For example, in some embodiments, $R^1$ is —C≡C—$CH_3$.

In some embodiments of the compound of formula I, m is 0; n is 0; $R^{1a}$ is H; W is C—H; Y, is C—H; Z is C—H; $R^1$ is a $(C_2-C_4)$alkenyl; $R^2$ is F; $R^3$ is methoxy; $R^4$ is methyl; $R^5$ is methyl; $R^6$ is methyl; $R^7$ is H; $R^8$ is H; $R^9$ is H; $R^{10}$ is H; and X is O.

In some embodiments of the compound of formula I, the compound has the formula IA as shown below where the variables shown in the formula IA have the same definitions as described above with respect to the compound and embodiments of having the formula I:

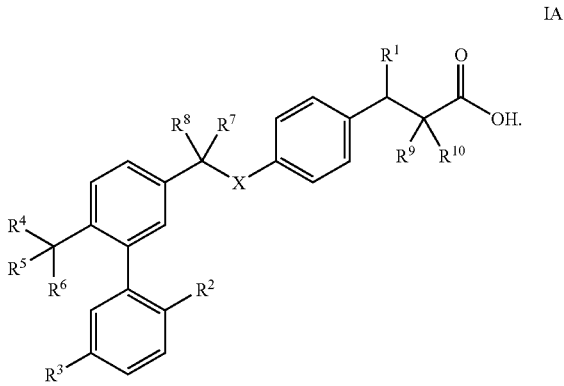

In some embodiments of the compound of formula I, the compound has the formula IB as shown below where the variables shown in formula IB have the same definitions as described above with respect to the compound and embodiments of having the formula I:

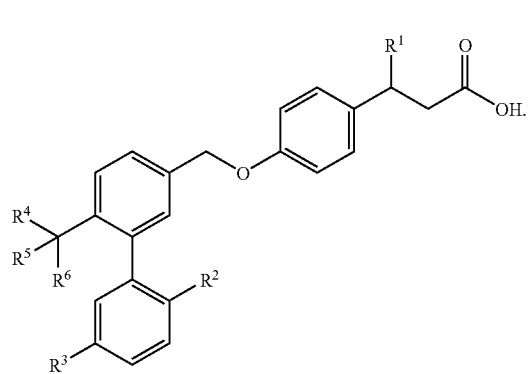

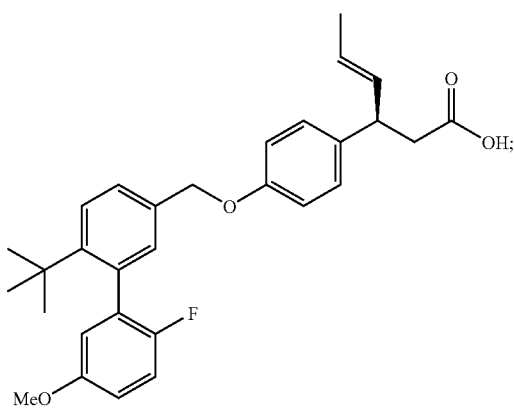

In some embodiments, the compound of formula I is a compound of formula II or a pharmaceutically acceptable salt, solvate, stereoisomer, or prodrug thereof; or a tautomer or a pharmaceutically acceptable salt, solvate, stereoisomer, or prodrug thereof; or a mixture thereof. The compound of formula II has the following structure:

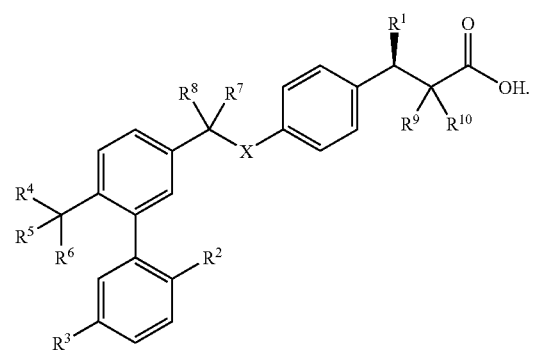

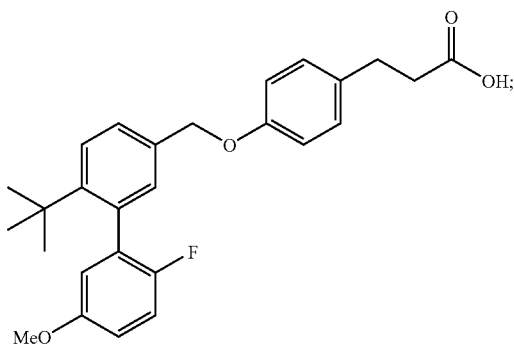

In some embodiments, the compound of formula I is selected from

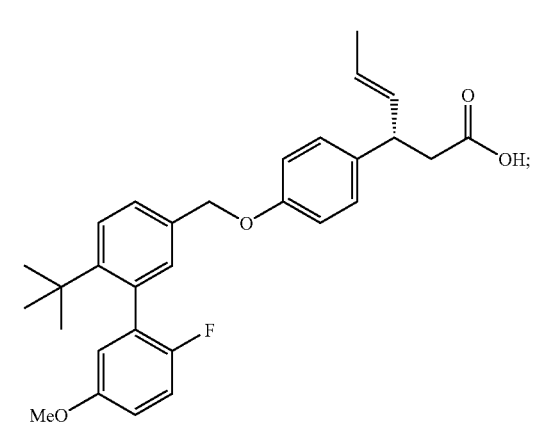

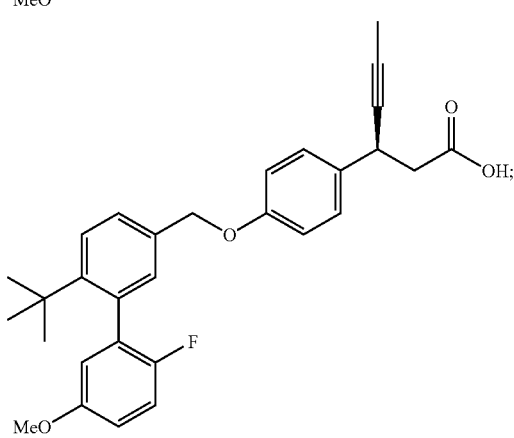

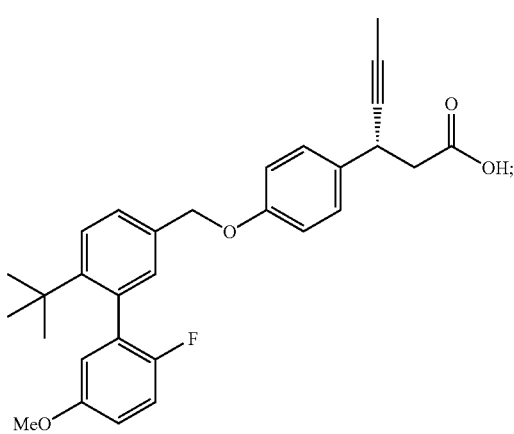

-continued
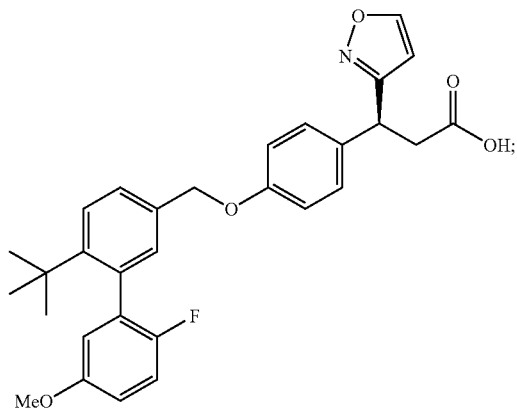
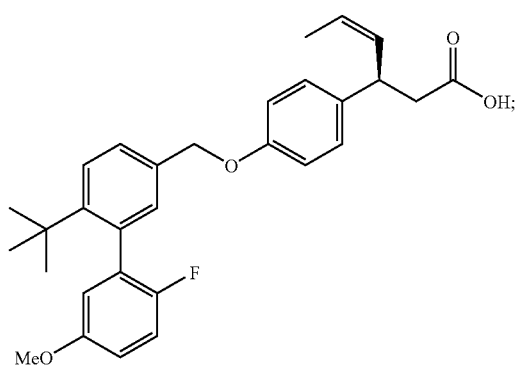
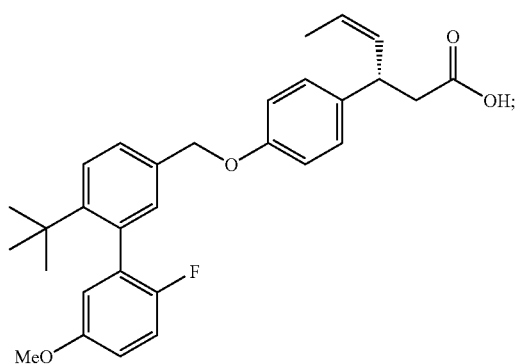
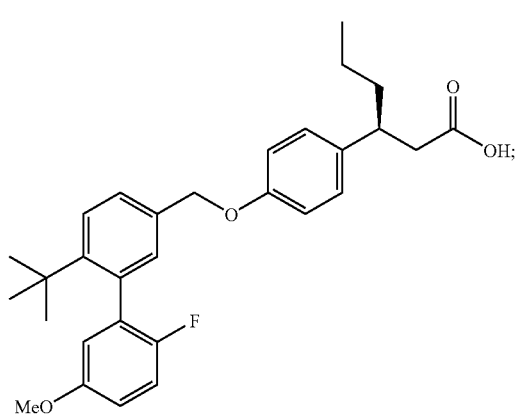
-continued
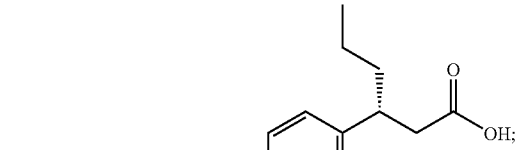
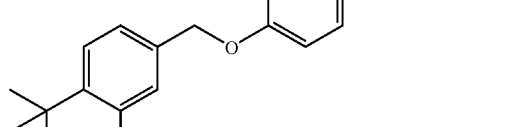
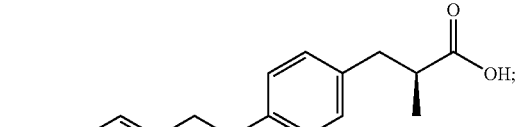
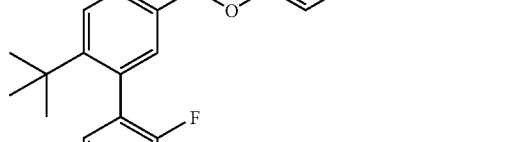
or is a pharmaceutically acceptable salt, solvate, or prodrug thereof.
In some embodiments, the compound of any of the embodiments is a salt. In other embodiments, the compound of any of the embodiments is a prodrug. In some such embodiments, the prodrug is a $C_1$-$C_6$ alkyl ester such as a methyl, ethyl, propyl, butyl, isopropyl, pentyl, or hexyl ester. In some such embodiments, the ester is a methyl or ethyl ester.

In some embodiments, the compound comprises a stereomerically pure S-enantiomer. In other embodiments, the compound comprises a stereomerically pure R-enantiomer. In yet other embodiments, the compound comprises a mixture of S- and R-enantiomers.

In another aspect, the invention provides pharmaceutical compositions comprising a pharmaceutically acceptable carrier, diluent, or excipient, and a compound of any of the embodiments of the invention.

In another aspect, the invention provides methods for treating or preventing a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, and edema. Such methods include administering to a subject in need thereof, a therapeutically effective amount of a compound of any of the embodiments. In some such embodiments, the disease or condition is type II diabetes. In some embodiments, a compound of any of the embodiments is administered in combination with a second therapeutic agent. In some such embodiments, the second therapeutic agent is metformin or is a thiazolidinedione. The second therapeutic agent may be administered before, during, or after administration of the compound of any of the embodiments.

In another aspect, the invention provides methods for treating or preventing a disease or condition responsive to the modulation of GPR40. Such methods include administering to a subject in need thereof, a therapeutically effective amount of a compound of any of the embodiments.

In another aspect, the invention provides methods for treating or preventing a disease or condition mediated, regulated, or influenced by pancreatic β cells. Such methods include administering to a subject in need thereof, a therapeutically effective amount of a compound of any of the embodiments.

In another aspect, the invention provides methods for modulating GPR40 function in a cell. Such methods include contacting a cell with a compound of any of the embodiments.

In another aspect, the invention provides methods for modulating GPR40 function. Such methods include contacting GPR40 with a compound of any of the embodiments.

In another aspect, the invention provides methods for modulating circulating insulin concentration in a subject. Such methods include administering a compound of any of the embodiments to the subject. In some such embodiments, the circulating insulin concentration is increased in the subject after administration whereas in other such embodiments, the circulating insulin concentration is decreased in the subject after administration.

In another aspect, the invention provides the use of a compound of any of the embodiments for treating a disease or condition or for preparing a medicament for treating a disease or condition where the disease or condition is selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, and edema. In some such embodiments, the disease or condition is type II diabetes. The compounds of the invention may also be used to prepare medicaments that include a second therapeutic agent such as metformin or a thiazolidinedione.

In another aspect, the invention provides the use of a compound of any of the embodiments for modulating GPR40 or for use in the preparation of a medicament for modulating GPR40.

In another aspect, the invention provides a therapeutic composition that includes a compound of any of the embodiments and a second therapeutic agent such as those described herein, for example, metformin or a thiazolidinedione, as a combined preparation for simultaneous, separate, or sequential use in the treatment of a disease or condition mediated by GPR40. In some such embodiments, the disease or condition is type II diabetes. In some embodiments, the compound of any of the embodiments and the second therapeutic agent are provided as a single composition, whereas in other embodiments they are provided separately as parts of a kit.

Other objects, features and advantages of the invention will become apparent to those skilled in the art from the following description and claims.

5. DETAILED DESCRIPTION OF THE INVENTION

5.1 Abbreviations and Definitions

The terms "treat", "treating" and "treatment", as used herein, are meant to include alleviating or abrogating a condition or disease and/or its attendant symptoms. The terms "prevent", "preventing" and "prevention", as used herein, refer to a method of delaying or precluding the onset of a condition or disease and/or its attendant symptoms, barring a subject from acquiring a condition or disease, or reducing a subject's risk of acquiring a condition or disease.

The term "therapeutically effective amount" refers to that amount of the compound that will elicit the biological or medical response of a tissue, system, or subject that is being sought. The term "therapeutically effective amount" includes that amount of a compound that, when administered, is sufficient to prevent development of, or alleviate to some extent, one or more of the symptoms of the condition or disorder being treated in a subject. The therapeutically effective amount in a subject will vary depending on the compound, the disease and its severity, and the age, weight, etc., of the subject to be treated.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

The terms "modulate", "modulation" and the like refer to the ability of a compound to increase or decrease the function or activity of GPR40 either directly or indirectly. Inhibitors are compounds that, for example, bind to, partially or totally block stimulation, decrease, prevent, delay activation, inactivate, desensitize, or down regulate signal transduction, such as, for instance, antagonists. Activators are compounds that, for example, bind to, stimulate, increase, activate, facilitate, enhance activation, sensitize or up regulate signal transduction, such as agonists for instance. Modulation may occur in vitro or in vivo.

As used herein, the phrases "GPR40-mediated condition or disorder", "disease or condition mediated by GPR40", and the like refer to a condition or disorder characterized by inappropriate, for example, less than or greater than normal, GPR40 activity. A GPR40-mediated condition or disorder may be completely or partially mediated by inappropriate GPR40 activity. However, a GPR40-mediated condition or disorder is one in which modulation of GPR40 results in some effect on the underlying condition or disease (e.g., a GPR40 modulator results in some improvement in patient well-being in at least some patients). Exemplary GPR40-mediated conditions and disorders include cancer and metabolic disorders, e.g., diabetes, type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, ketoacidosis, hypoglycemia, thrombotic disorders, metabolic syndrome, syndrome X and related disorders, e.g., cardiovascular disease, atherosclerosis, kidney disease, nephropathy, diabetic neuropathy, diabetic retinopathy, sexual dysfunction, dermatopathy, dyspepsia, and edema.

The term "alkyl", by itself or as part of another substituent, means, unless otherwise stated, a straight or branched chain, or cyclic hydrocarbon radical, or combination thereof, which is fully saturated, having the number of carbon atoms designated (e.g., $C_1$-$C_{10}$ means one to ten carbons). Examples of alkyl groups include, but are not limited to, methyl, ethyl, n-propyl, isopropyl, n-butyl, t-butyl, isobutyl, sec-butyl, cyclohexyl, (cyclohexyl)methyl, cyclopropyl, cyclopropylmethyl, and homologs and isomers of, for example, n-pentyl, n-hexyl, n-heptyl, n-octyl, and the like.

The term "alkenyl", by itself or as part of another substituent, means a straight or branched chain, or cyclic hydrocarbon radical, or combination thereof, which may be mono- or polyunsaturated, having the number of carbon atoms designated (i.e., $C_2$-$C_8$ means two to eight carbons) and one or more double bonds. Examples of alkenyl groups include, but are not limited to, vinyl, 2-propenyl, crotyl, 2-isopentenyl, 2-(butadienyl), 2,4-pentadienyl, 3-(1,4-pentadienyl), and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e., $C_2$-$C_8$ means two to eight carbons) and one or more triple bonds. Examples of alkynyl groups include, but are not limited to, ethynyl, 1- and 3-propynyl, 3-butynyl, and higher homologs and isomers thereof.

The term "alkoxy" refers to a group of formula —O-alkyl where alkyl has the definition provided above. An alkoxy group can have a specified number of carbon atoms. For example, a methoxy group (—OCH$_3$) is a $C_1$ alkoxy group. Alkoxy groups typically have from 1 to 10 carbon atoms. Examples of alkoxy group include, but are not limited to, methoxy, ethoxy, propoxy, butoxy, pentoxy, hexoxy, heptoxy, and the like.

The term "cycloalkyl" by itself or in combination with other terms, represents, unless otherwise stated, a cyclic version of "alkyl". Thus, the term "cycloalkyl" is meant to be included in the term "alkyl". Examples of cycloalkyl include cyclopropyl, cyclobutyl, cyclopentyl, cyclohexyl, cycloheptyl, and the like.

The term "heterocyclyl" by itself or in combination with other terms, represents, unless otherwise stated, a ring system in which one or more ring members is a heteratom selected from N, O, or S. The heteroatom can occupy the position at which the heterocycle is attached to the remainder of the molecule. A heterocyclyl group can also be attached to the remainder of the molecule through a carbon atom of the ring. Heterocyclyl groups typically include from 3 to 10 ring members. Heterocyclyl groups can be saturated or may include some unsaturation. Examples of heterocyclyl groups include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, 4,5-dihydroisoxazol-3-yl, and the like.

The terms "halo" or "halogen," by themselves or as part of another substituent, mean, unless otherwise stated, a fluorine, chlorine, bromine, or iodine atom. Additionally, terms such as "haloalkyl", are meant to include alkyl substituted with halogen atoms which can be the same or different, in a number ranging from one to (2m'+1), where m' is the total number of carbon atoms in the alkyl group. For example, the term "halo ($C_1$-$C_4$)alkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms). The term "perhaloalkyl" means, unless otherwise stated, alkyl substituted with (2m'+1) halogen atoms, where m' is the total number of carbon atoms in the alkyl group. For example, the term "perhalo($C_1$-$C_4$)alkyl", is meant to include trifluoromethyl, pentachloroethyl, 1,1,1-trifluoro-2-bromo-2-chloroethyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from one to four heteroatom ring members selected from the group consisting of N, O and S, wherein the nitrogen and sulfur atoms are optionally oxidized, and the nitrogen atom(s) are optionally quaternized. In some embodiments, a heteroaryl group includes 1 or 2 heteroatoms. A heteroaryl group can be attached to the remainder of the molecule through a heteroatom or through a carbon atom of the ring. Non-limiting examples of aryl and heteroaryl groups include phenyl, 1-naphthyl, 2-naphthyl, 4-biphenyl, 1-pyrrolyl, 2-pyrrolyl, 3-pyrrolyl, 1-pyrazolyl, 3-pyrazolyl, 5-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, dibenzofuryl, 2-thienyl, 3-thienyl, 2-pyridyl, 3-pyridyl, 4-pyridyl, 2-pyrimidyl, 4-pyrimidyl, 2-pyrimidinyl, 4-pyrimidinyl, 5-pyrimidinyl, 3-pyridazinyl, 4-pyridazinyl, 5-benzothiazolyl, 2-benzoxazolyl, 5-benzoxazolyl, benzo[c][1,2,5]oxadiazolyl, purinyl, 2-benzimidazolyl, 5-indolyl, 1H-indazolyl, carbazolyl, α-carbolinyl, β-carbolinyl, γ-carbolinyl, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl, and 8-quinolyl.

Preferably, the term "aryl" refers to a phenyl or naphthyl group which is unsubstituted or substituted. Preferably, the term "heteroaryl" refers to a pyrrolyl, pyrazolyl, imidazolyl, pyrazinyl, oxazolyl, oxadiazolyl, isoxazolyl, thiazolyl, furyl, thienyl (thiophenyl), pyridyl, pyrimidyl, benzothiazolyl, purinyl, benzimidazolyl, indolyl, isoquinolyl, triazolyl, tetrazolyl, quinoxalinyl. or quinolyl group which is unsubstituted or substituted.

For brevity, the term "aryl" when used in combination with other terms (e.g., aryloxy, arylalkoxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). As another example, the term "aryl($C_1$-$C_4$)alkoxy" is mean to include radicals in which an aryl group is attached to an alkyl group having 1 to 4 carbon atoms that is bonded to an O which is attached to the rest of the molecule. Examples include substituted and unsubstituted phenylmethoxy, phenylethoxy, phenylpropoxy, pyridylmethoxy, and the like.

Each of the above terms (e.g., "alkyl," "aryl" and "heteroaryl") is meant to include both substituted and unsubstituted forms of the indicated radical, unless otherwise indicated. Preferred substituents for each type of radical are provided below.

Substituents for the alkyl radicals (as well as those groups referred to as alkenyl, alkynyl, cycloalkyl, and heterocyclyl) can be a variety of groups selected from: —OR', =O, =NR', =N—OR', —NR'R", —SR', halogen, —OC(O)R', —C(O)R', —$CO_2$R', —CONR'R", —OC(O)NR'R", —NR"C(O)R', —NR'—C(O)NR"R''', —NR'—$SO_2$NR"R''', —NR"$CO_2$R', —NH—C($NH_2$)=NH, —NR'C($NH_2$)=NH, —NH—C($NH_2$)=NR', —SiR'R"R''', —S(O)R', —$SO_2$R', —$SO_2$NR'R", —NR"$SO_2$R, —CN, —($C_2$-$C_5$) alkynyl, —($C_2$-$C_5$) alkenyl, and —$NO_2$, in a number ranging from zero to three, with those groups having zero, one or two substituents being particularly preferred. R', R" and R''' each independently refer to hydrogen, unsubstituted ($C_1$-$C_8$)alkyl and heteroalkyl, unsubstituted aryl, aryl substituted with one to three halogens, unsubstituted alkyl, alkoxy or thioalkoxy groups, halo($C_1$-$C_4$)alkyl, or aryl-($C_1$-$C_4$)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl.

Typically, an alkyl group will have from zero to three substituents, with those groups having two or fewer substituents being preferred in the present invention. More preferably, an alkyl radical will be unsubstituted or monosubstituted. Most preferably, an alkyl radical will be unsubstituted. From the above discussion of substituents, one of skill in the art will understand that the term "alkyl" is meant to include groups such as trihaloalkyl (e.g., —$CF_3$ and —$CH_2CF_3$).

Preferred substituents for the alkyl radicals are selected from: —OR', =O, —NR'R", —SR', halogen, —OC(O)R', —C(O)R', —$CO_2$R', —CONR'R", —OC(O)NR'R", —NR"C(O)R', —NR"$CO_2$R', —NR'—$SO_2$NR"R''', —S(O)R', —$SO_2$R', —$SO_2$NR'R", —NR"$SO_2$R, —CN, —($C_2$-$C_5$) alkynyl, —($C_2$-$C_5$) alkenyl and —$NO_2$, where R' and R" are as defined above. Further preferred substituents are selected from: —OR', =O, —NR'R", halogen, —OC(O)R', —$CO_2$R', —CONR'R", —OC(O)NR'R", —NR"C(O)R', —NR"$CO_2$R', —NR'—$SO_2$NR"R''', —$SO_2$R', —$SO_2$NR'R", —NR"$SO_2$R, —CN, —($C_2$-$C_5$) alkynyl, —($C_2$-$C_5$) alkenyl, and —$NO_2$.

Similarly, substituents for the aryl and heteroaryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R''', —NH—C($NH_2$)=NH, —NR'C($NH_2$)=NH, —NH—C($NH_2$)=NR', —S(O)R', —S(O)$_2$R', —S(O)$_2$NR'R", —$N_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, ($C_1$-$C_8$)alkyl and heteroalkyl, unsubstituted aryl and heteroaryl, (unsubstituted aryl)-($C_1$-$C_4$)alkyl, (unsubstituted aryl)oxy-($C_1$-$C_4$)alkyl, —($C_2$-$C_5$) alkynyl, and —($C_2$-$C_5$) alkenyl.

Two of the substituents on adjacent atoms of the aryl or heteroaryl ring may optionally be replaced with a substituent of the formula -T-C(O)—($CH_2$)$_q$—U—, wherein T and U are independently —NH—, —O—, —$CH_2$—, or a single bond, and q is an integer of from 0 to 2. Alternatively, two of the substituents on adjacent atoms of the aryl or heteroaryl ring may optionally be replaced with a substituent of the formula -A-($CH_2$)$_r$—B—, wherein A and B are independently —$CH_2$—, —O—, —NH—, —S—, —S(O)—, —S(O)$_2$—, —S(O)$_2$NR'—, or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —($CH_2$)$_s$—X—($CH_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl. Otherwise, R' is as defined above.

As used herein, the term "heteroatom" is meant to include oxygen (O), nitrogen (N), and sulfur (S).

The term "pharmaceutically acceptable salt" is meant to include a salt of the active compound which is prepared with relatively nontoxic acids or bases, depending on the particular substituents found on the compound described herein. When a compound of the invention contains relatively acidic functionalities, a base addition salt can be obtained by contacting the neutral form of such compound with a sufficient amount of the desired base, either neat or in a suitable inert solvent. Examples of pharmaceutically acceptable base addition salts include sodium, potassium, calcium, ammonium, organic amino, or magnesium salt, or a similar salt. When a compound of the invention contains relatively basic functionalities, an acid addition salt can be obtained by contacting the neutral form of such compound with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginine and the like, and salts of organic acids like glucuronic or galacturonic acids and the like (see, for example, Berge et al. (1977) *J. Pharm. Sci.* 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound.

As used herein, "solvate" refers to a compound of the present invention or a salt thereof, that further includes a stoichiometric or non-stoichiometric amount of solvent bound by non-covalent intermolecular forces. Where the solvent is water, the solvate is a hydrate.

Certain compounds of the invention may exist in multiple crystalline or amorphous forms. In general, all physical forms are equivalent for the uses contemplated by the invention and are intended to be within the scope of the invention.

As known by those skilled in the art, certain compounds of the invention may exist in one or more tautomeric forms. Because one chemical structure may only be used to represent one tautomeric form, it will be understood that convenience, referral to a compound of a given structural formula includes tautomers of the structure represented by the structural formula.

Certain compounds of the invention possess asymmetric carbon atoms (optical centers) or double bonds; the racemates, enantiomers, diastereomers, geometric isomers and individual isomers are all intended to be encompassed within the scope of the invention.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al. (1997) *Tetrahedron* 33:2725; Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, research reagents, e.g., GPR40 assay reagents, and diagnostic agents, e.g., in vivo imaging agents. All isotopic variations of the compounds of the invention, whether radioactive or not, are intended to be encompassed within the scope of the invention. For example, if a variable is said to be H, this means that variable may also be deuterium (D) or tritium (T).

5.2 Embodiments of the Invention

In one aspect, a class of compounds that modulates GPR40 is described herein. Depending on the biological environment (e.g., cell type, pathological condition of the subject, etc.), these compounds can modulate, e.g., activate or inhibit, the actions of GPR40. By modulating GPR40, the compounds find use as therapeutic agents capable of regulating insulin levels in a subject. The compounds find use as therapeutic agents for modulating diseases and conditions responsive to modulation of GPR40 and/or mediated by GPR40 and/or mediated by pancreatic β cells. As noted above, examples of such diseases and conditions include diabetes, obesity, hyperglycemia, glucose intolerance, insulin resistance, cancer, hyperinsulinemia, hypercholesterolemia, hypertension, hyperlipoproteinemia, hyperlipidemia, hypertriglylceridemia, dyslipidemia, ketoacidosis, hypoglycemia, metabolic syndrome, syndrome X, cardiovascular disease, atherosclerosis, kidney disease, nephropathy, thrombotic disorders, diabetic neuropathy, diabetic retinopathy, dermatopathy, dyspepsia and edema. Additionally, the compounds are useful for the treatment and/or prevention of complications of these diseases and disorders (e.g., type II diabetes, sexual dysfunction, dyspepsia and so forth).

While the compounds of the invention are believed to exert their effects by interacting with GPR40, the mechanism of action by which the compounds act is not a limiting embodiment of the invention.

Compounds contemplated by the invention include, but are not limited to, the exemplary compounds provided herein.

5.2.1 Compounds

In one aspect, the present invention provides a compound having the formula I or a pharmaceutically acceptable salt, solvate, stereoisomer, or prodrug thereof; or a tautomer or a pharmaceutically acceptable salt, solvate, stereoisomer, or prodrug thereof; or a mixture thereof:

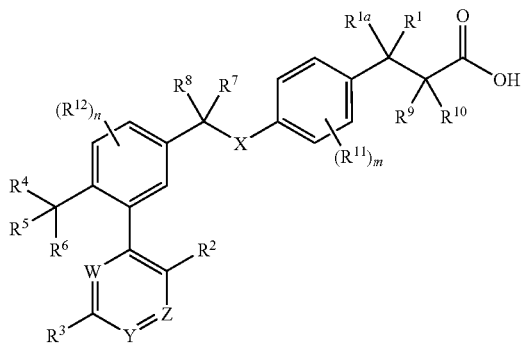

where
X is O or S;

W, Y, and Z are selected from N or C—H; wherein no more than one of W, Y, and Z is N; and further wherein Z is not N if $R^2$ is F;

$R^1$ is selected from H, $(C_1-C_6)$alkyl, $(C_2-C_6)$alkenyl, $(C_2-C_6)$alkynyl, heterocyclyl, or heteroaryl;

$R^{1a}$ is selected from H and $(C_1-C_4)$alkyl;

$R^2$ is selected from F or $(C_3-C_6)$alkoxy;

$R^3$ is $(C_1-C_2)$alkoxy;

$R^4$, $R^5$, and $R^6$ are independently selected from H, $(C_1-C_4)$alkyl, or substituted $(C_1-C_4)$alkyl, and two of $R^4$, $R^5$, and $R^6$ may join together to form a 3-7 membered ring; wherein at least two of $R^4$, $R^5$, and $R^6$ are other than H;

$R^7$ and $R^8$ are independently selected from H and $(C_1-C_4)$alkyl;

$R^9$ and $R^{10}$ are independently selected from H and $(C_1-C_4)$alkyl;

Each $R^{11}$ is independently selected from F, Cl, $(C_1-C_4)$alkyl, or $(C_1-C_4)$alkoxy and m is 0, 1, or 2; and Each $R^{12}$ is independently selected from F, Cl, $(C_1-C_4)$alkyl, or $(C_1-C_4)$alkoxy and n is 0, 1, or 2.

In a second aspect, the invention provides a compound having the formula I or a pharmaceutically acceptable salt, solvate, stereoisomer, or prodrug thereof; or a tautomer or a pharmaceutically acceptable salt, solvate, stereoisomer, or prodrug thereof; or a mixture thereof, wherein X is O, S, or $NR_a$, wherein $R_a$ is selected from H and $(C_1-C_4)$ alkyl;

W, Y, and Z are selected from N or C—H; wherein no more than one of W, Y, and Z is N; and further wherein Z is not N if $R^2$ is F;

$R^1$ is selected from H, $(C_1-C_6)$alkyl, $(C_2-C_6)$alkenyl, $(C_2-C_6)$alkynyl, heterocyclyl, heteroaryl, or aryl;

$R^{1a}$ is selected from H and $(C_1-C_4)$alkyl;

$R^2$ is selected from F or $(C_3-C_6)$alkoxy;

$R^3$ is $(C_1-C_2)$alkoxy;

$R^4$, $R^5$, and $R^6$ are independently selected from H, $(C_1-C_4)$alkyl, or substituted $(C_1-C_4)$alkyl, and two of $R^4$, $R^5$, and $R^6$ may join together to form a 3-7 membered ring; wherein at least two of $R^4$, $R^5$, and $R^6$ are other than H; and wherein at least one of $R^4$, $R^5$, and $R^6$ may be OH;

$R^7$ and $R^8$ are independently selected from H and $(C_1-C_4)$alkyl;

$R^9$ and $R^{10}$ are independently selected from H, $(C_1-C_4)$alkyl, and $(C_2-C_6)$alkenyl;

Each $R^{11}$ is independently selected from F, Cl, $(C_1-C_4)$alkyl, or $(C_1-C_4)$alkoxy and m is 0, 1, or 2; and Each $R^{12}$ is independently selected from F, Cl, $(C_1-C_4)$alkyl, or $(C_1-C_4)$alkoxy and n is 0, 1, or 2.

In some embodiments of the second aspect, $R^1$ is an aryl. In some such embodiments, $R^1$ is a phenyl.

In some embodiments of the second aspect, X is $NR_a$. In some embodiments, $R_a$ is H.

In some embodiments of the second aspect, $R^9$ is selected from $(C_1-C_4)$alkyl, and $(C_2-C_6)$alkenyl. In some such embodiments $R^{10}$ is selected from H. In other such embodiments, $R^{10}$ is a $(C_1-C_4)$alkyl such as a methyl group.

In some embodiments of the compound of formula I, m and n are both 0.

In some embodiments of the compound of formula I, $R^{1a}$ is H or methyl. In some such embodiments, $R^{1a}$ is H.

In some embodiments of the compound of formula I, W, Y, and Z are all C—H.

In some embodiments of the compound of formula I, $R^4$, $R^5$, and $R^6$ are independently selected from H and $(C_1-C_4)$ alkyl groups and at least two of $R^4$, $R^5$, and $R^6$ are $(C_1-C_4)$ alkyl groups. In some such embodiments, all three of $R^4$, $R^5$, and $R^6$ are independently selected from $(C_1-C_4)$alkyl groups. In some such embodiments, each of $R^4$, $R^5$, and $R^6$ is a methyl group. In other embodiments, $R^4$, $R^5$, and $R^6$ are independently selected from H, $(C_1-C_4)$alkyl groups, or a substituted $(C_1-C_4)$ alkyl group selected from $(C_1-C_4)$haloalkyl groups, $(C_1-C_4)$perhaloalkyl groups, or $(C_1-C_4)$alkoxy$(C_1-C_4)$alkyl groups. In some such embodiments, at least one of $R^4$, $R^5$, and $R^6$ is a $CF_3$ group. In other embodiments at least one of $R^4$, $R^5$, and $R^6$ is a methoxymethyl group.

In some embodiments of the compound of formula I, two of $R^4$, $R^5$, and $R^6$, together with the C atom to which they are attached, join to form a 3-7 membered ring, and the other of $R^4$, $R^5$, and $R^6$ is selected from H, $(C_1-C_4)$alkyl, or substituted $(C_1-C_4)$alkyl. In some embodiments the ring is a carbocyclic ring which may be fully saturated cycloalkyl ring. In some such embodiments, the 3-7 membered ring is a 3-6, or a 3-5 membered ring. Examples of such rings include cyclopropyl, cyclobutyl, cyclopentyl, cyclohexyl, and cycloheptyl rings. In some such embodiments, two of $R^4$, $R^5$, and $R^6$ join to form a cyclopropyl ring. In some such embodiments, the other of $R^4$, $R^5$, and $R^6$ is H.

In some embodiments of the compound of formula I, $R^2$ is F or butoxy. In some such embodiments, $R^2$ is F whereas in other such embodiments, $R^2$ is butoxy. In still other embodiments, $R^2$ is propoxy, pentoxy, or hexoxy. In still further embodiments, $R^2$ is selected from F or $(C_3-C_4)$ alkoxy.

In some embodiments of the compound of formula I, $R^3$ is methoxy or ethoxy. In some such embodiments, $R^3$ is methoxy.

In some embodiments of the compound of formula I, X is O. In other embodiments, X is S.

In some embodiments of the compound of formula I, $R^7$ and $R^8$ are both H. In some embodiments one of $R^7$ and $R^8$ is H and the other of $R^7$ and $R^8$ is methyl. Therefore, in some embodiments $R^7$ and $R^8$ are independently selected from H and methyl.

In some embodiments of the compound of formula I, $R^9$ and $R^{10}$ are both H. In other embodiments, $R^9$ and $R^{10}$ are selected from H and methyl. In some such embodiments, one of $R^9$ and $R^{10}$ is H and the other of $R^9$ and $R^{10}$ is methyl.

In some embodiments of the compound of formula I, $R^1$ is selected from $(C_1-C_6)$alkyl, $(C_2-C_6)$alkenyl, $(C_2-C_6)$alkynyl, heterocyclyl, or heteroaryl. In some embodiments, $R^1$ is a $(C_1-C_4)$ alkyl). In some such embodiments, $R^1$ is a methyl, ethyl, propyl, or butyl group. In some such embodiments, $R^1$ is a propyl group.

In some embodiments of the compound of formula I, $R^1$ is a cis ($C_2$-$C_6$) alkenyl group whereas in other embodiments $R^1$ is a trans ($C_2$-$C_6$) alkenyl group. In some embodiments, $R^1$ is a mixture of cis and trans ($C_2$-$C_6$) alkenyl groups. In other embodiments, ($C_2$-$C_4$) alkenyl. In some embodiments $R^1$ is a cis ($C_2$-$C_4$) alkenyl group whereas in other embodiments $R^1$ is a trans ($C_2$-$C_4$) alkenyl group. In some embodiments, $R^1$ is a mixture of cis and trans ($C_2$-$C_4$) alkenyl groups. In some embodiments, $R^1$ is selected from —CH=CH$_2$, —CH=CH—CH$_3$, —CH=CH—CH$_2$—CH$_3$, or —CH$_2$—CH=CH$_2$. In some such embodiments, $R^1$ is —CH=CH—CH$_3$. In some such embodiments, $R^1$ has the formula

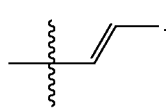

In other such embodiments, $R^1$ has the formula

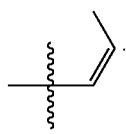

In some embodiments of the compound of formula I, $R^1$ is a ($C_2$-$C_4$) alkynyl. For example, in some embodiments, $R^1$ is —C≡C—CH$_3$.

In some embodiments of the compound of formula I, m is 0; n is 0; $R^{1a}$ is H; W is C—H; Y, is C—H; Z is C—H; $R^1$ is a ($C_2$-$C_4$)alkenyl; $R^2$ is F; $R^3$ is methoxy; $R^4$ is methyl; $R^5$ is methyl; $R^6$ is methyl; $R^7$ is H; $R^8$ is H; $R^9$ is H; $R^{10}$ is H; and X is O.

In some embodiments of the compound of formula I, m is 0; n is 0; W, Y, and Z are each C—H; and $R^{1a}$ is H such that the compound has the formula IA as shown below where the variables shown in the formula IA have the same definitions as described above with respect to the compound having the formula I or any embodiments thereof:

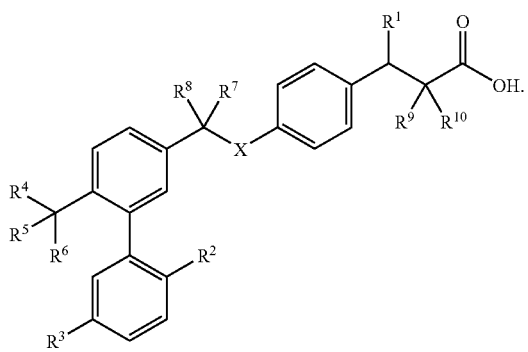

IA

In some embodiments of the compound of formula I, the compound has the formula IB as shown below where the variables shown in formula IB have the same definitions as described above with respect to the compound and embodiments having the formula I:

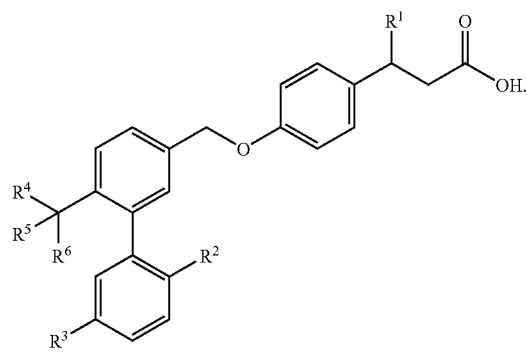

IB

In some embodiments, the compound of formula I is a compound of formula II or a pharmaceutically acceptable salt, solvate, stereoisomer, or prodrug thereof; or a tautomer or a pharmaceutically acceptable salt, solvate, stereoisomer, or prodrug thereof; or a mixture thereof. The compound of formula II has the following structure:

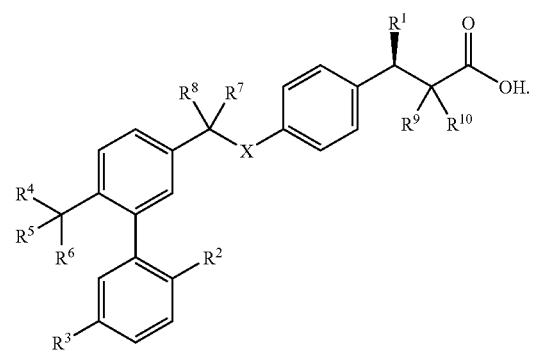

II

In some embodiments, the compound of formula I is selected from

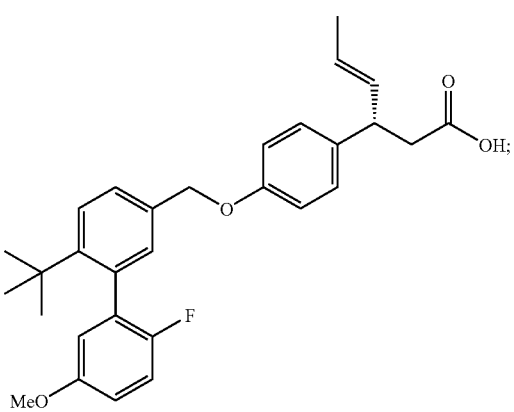

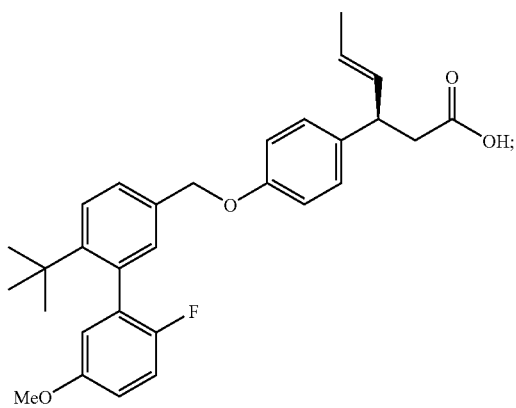
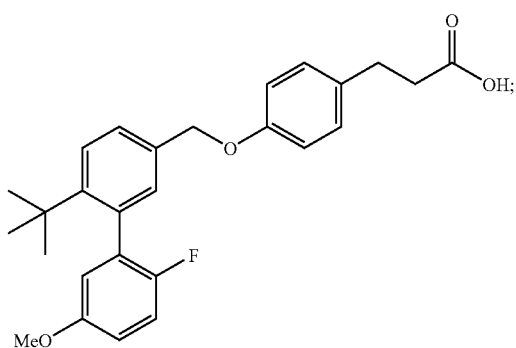
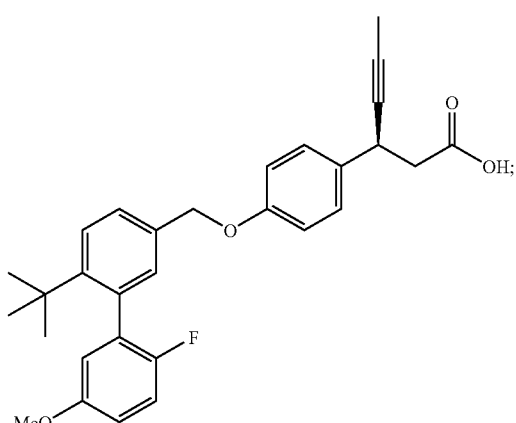
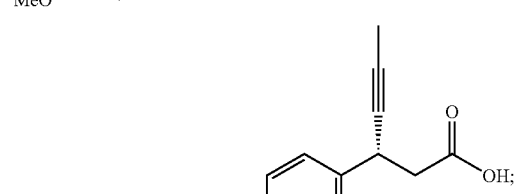
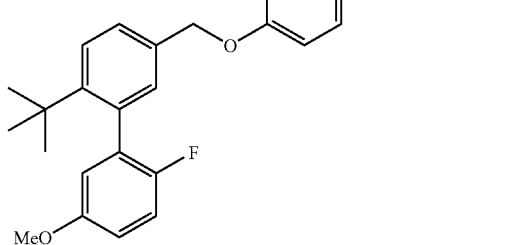
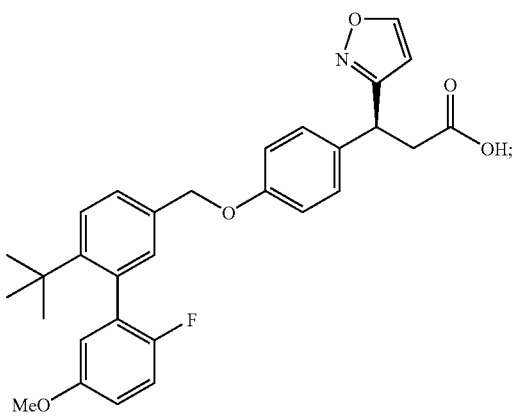
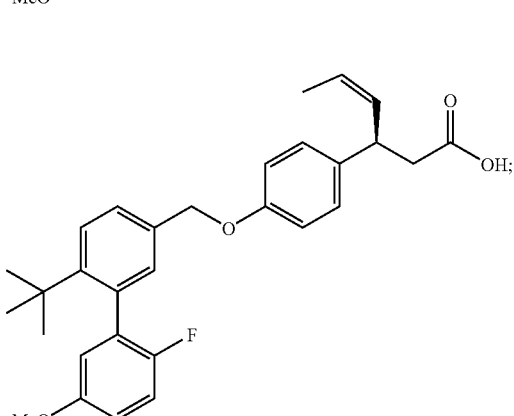
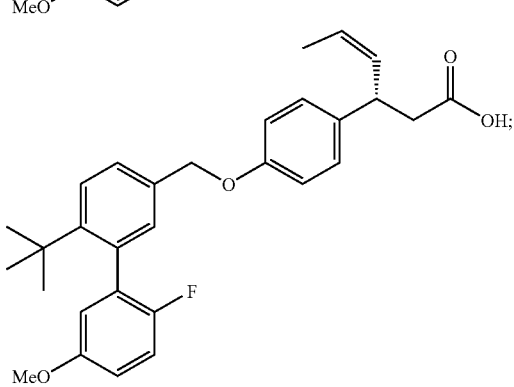
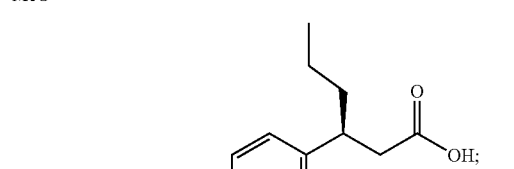
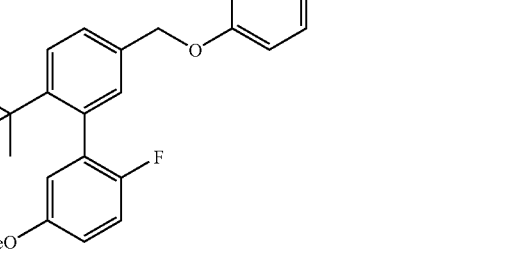

-continued
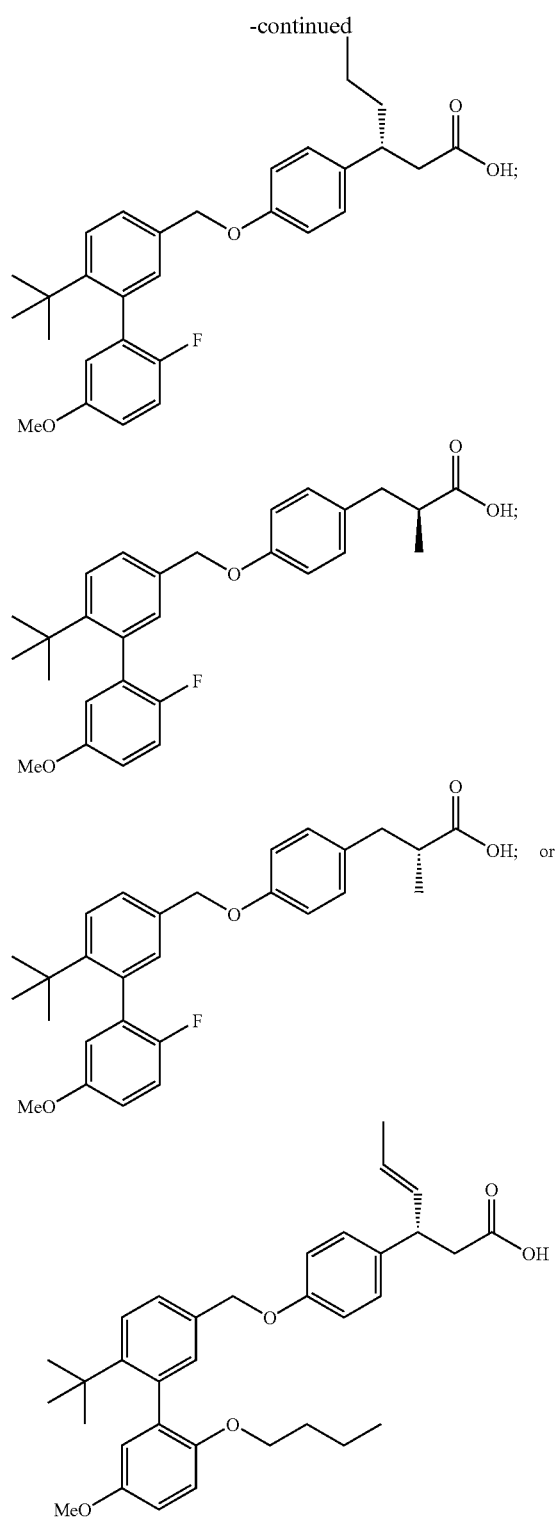
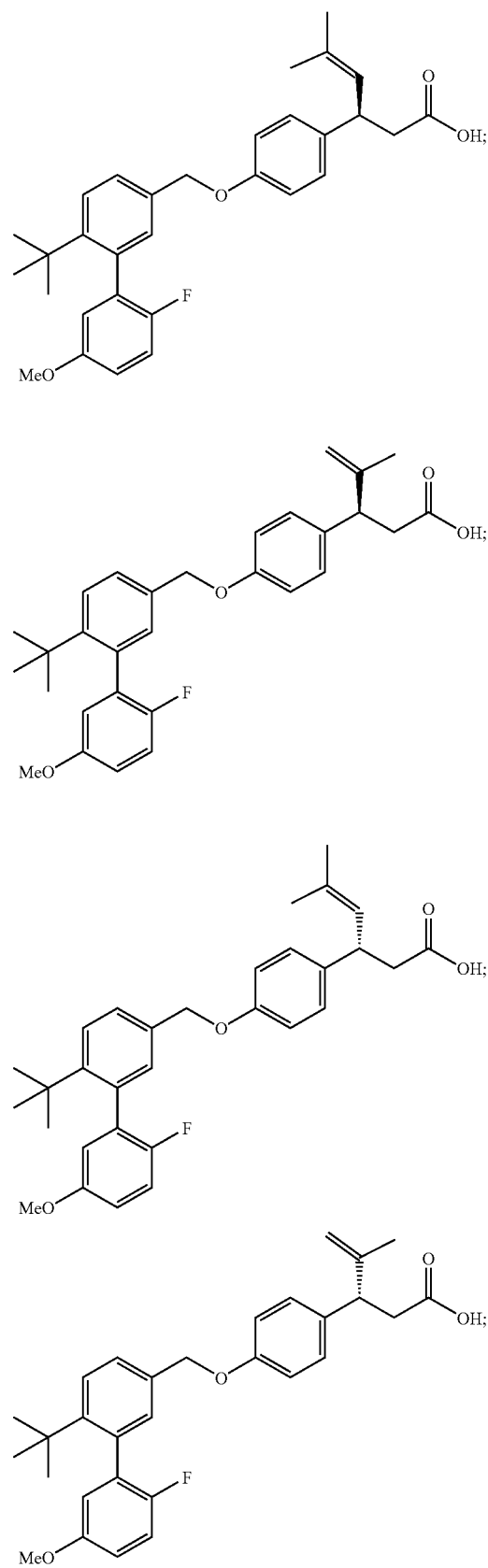
or is a pharmaceutically acceptable salt, solvate, or prodrug thereof. In some such embodiments where the compound has a chiral center, the compound exists as a single enantiomer whereas in other embodiments, the compound is a mixture of enantiomers of the compounds shown above.
In some embodiments, the compound of formula I is selected from -continued
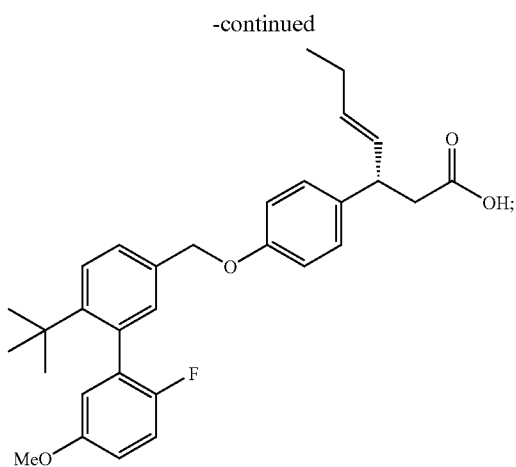
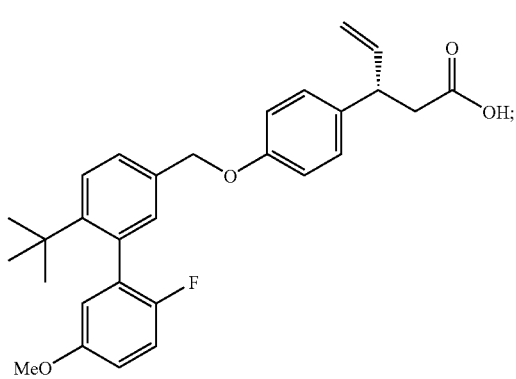
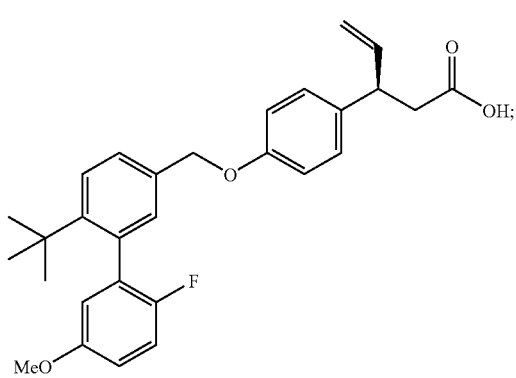
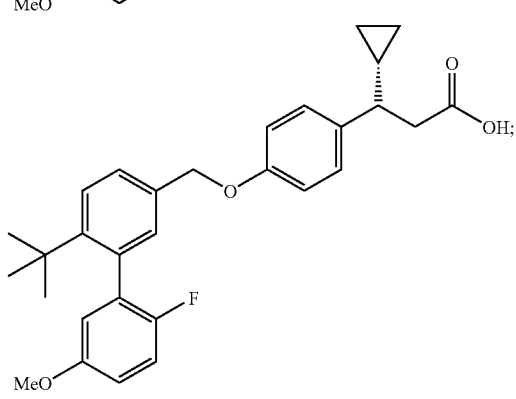
-continued
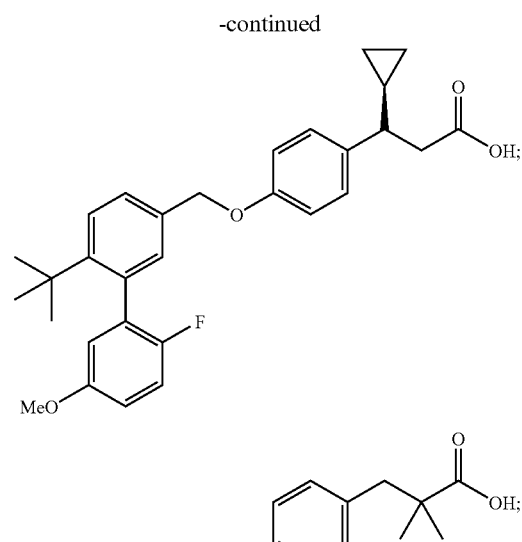
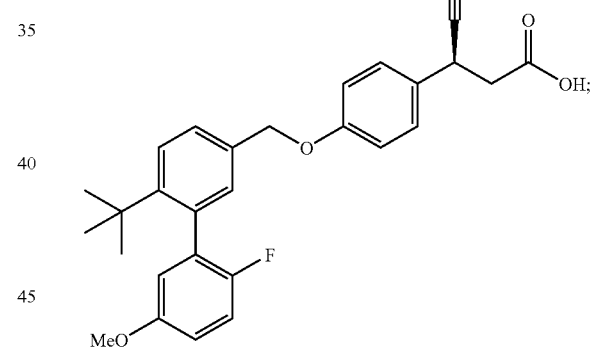
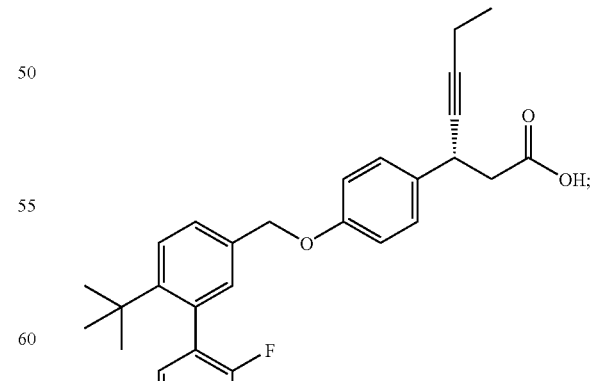

-continued
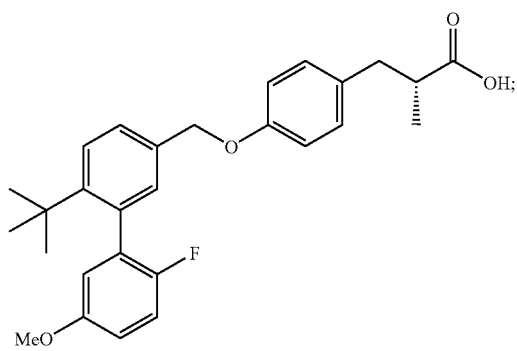
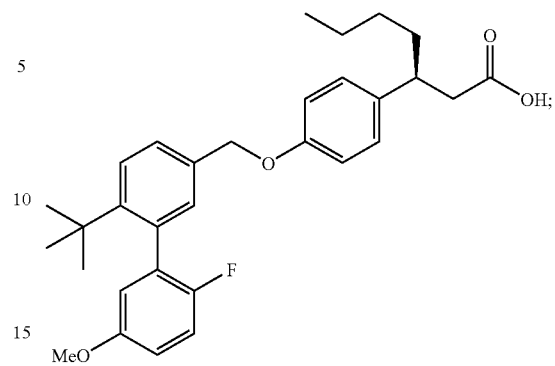
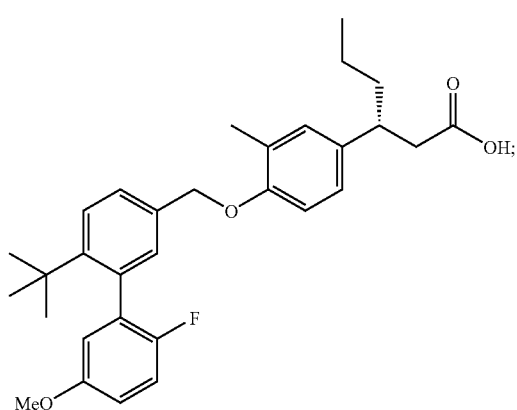
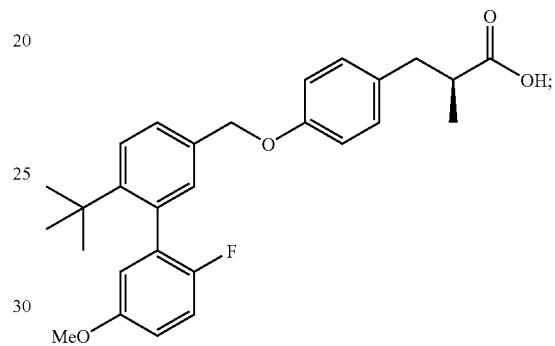
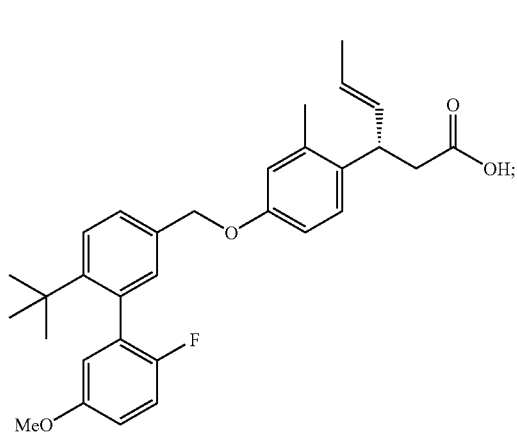
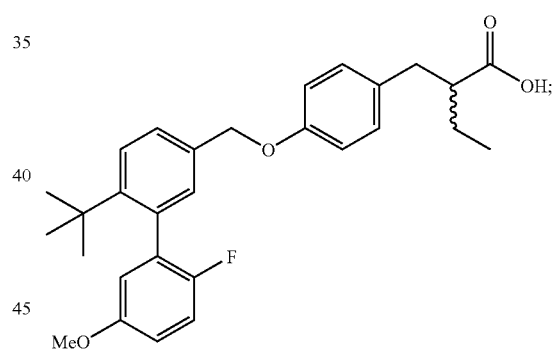
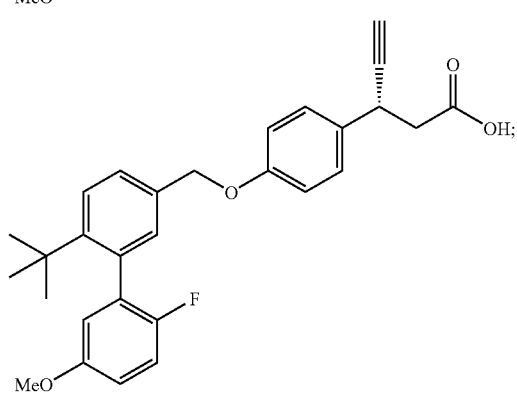
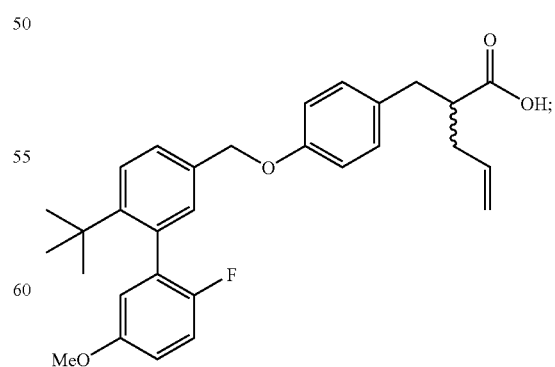

-continued
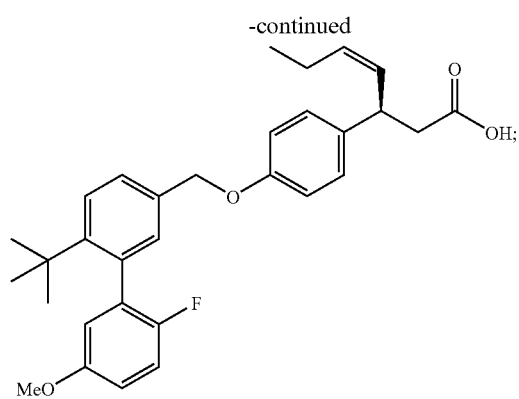
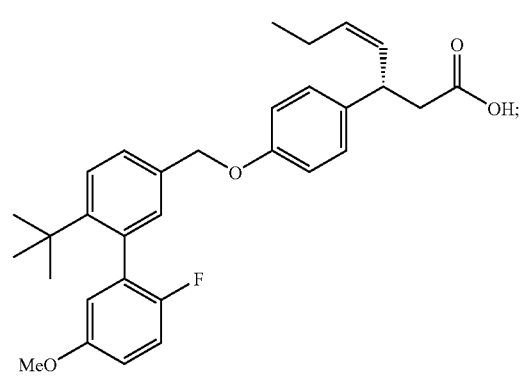
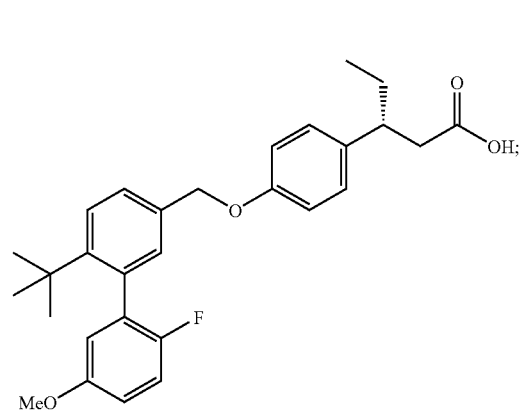
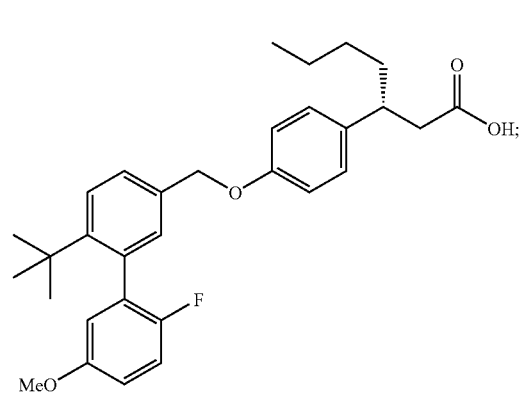
-continued
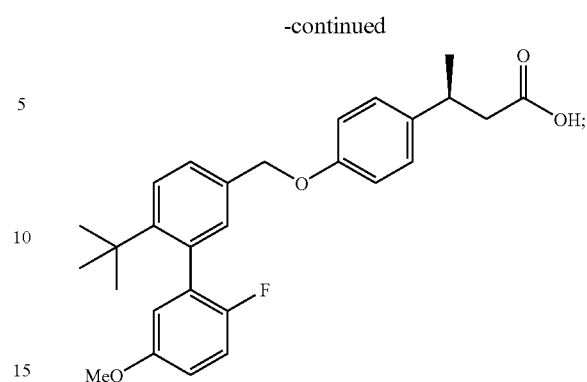
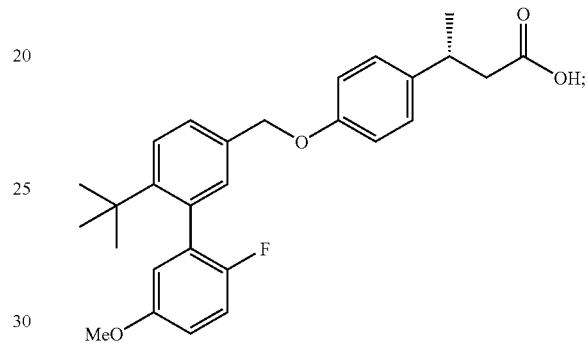
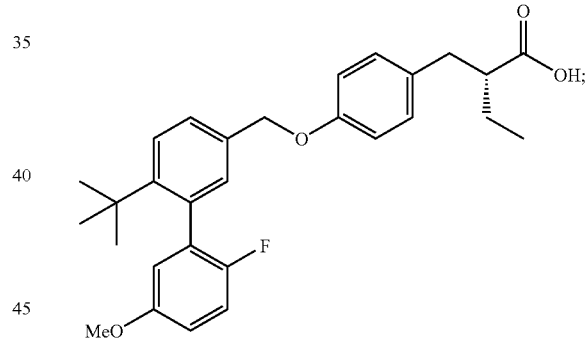
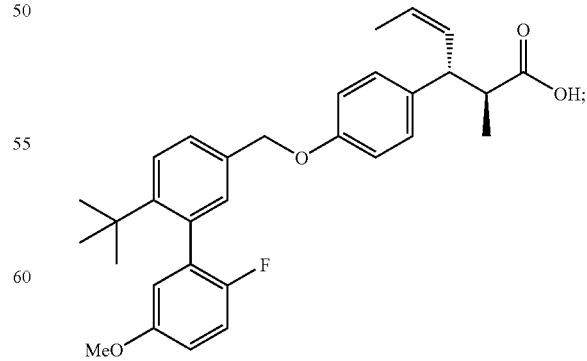

-continued

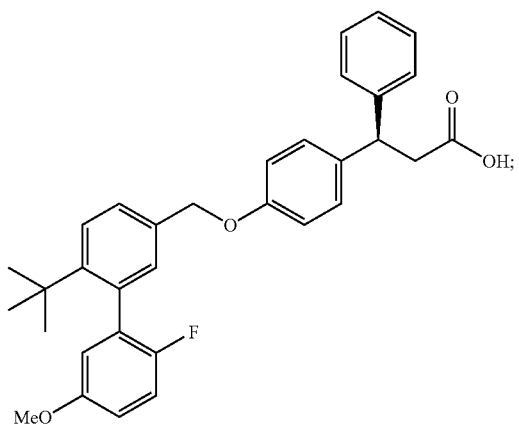

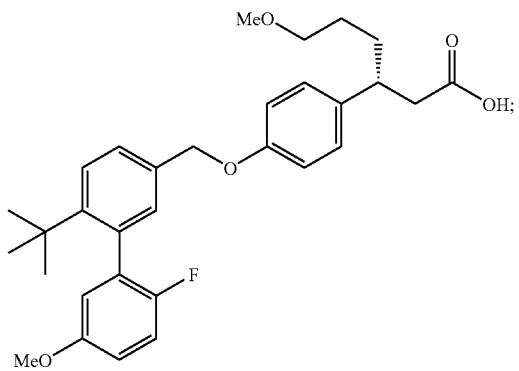

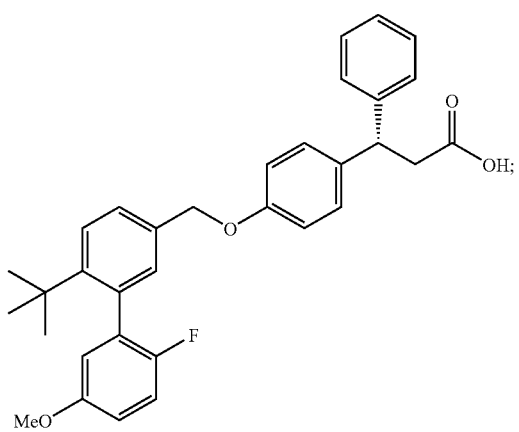

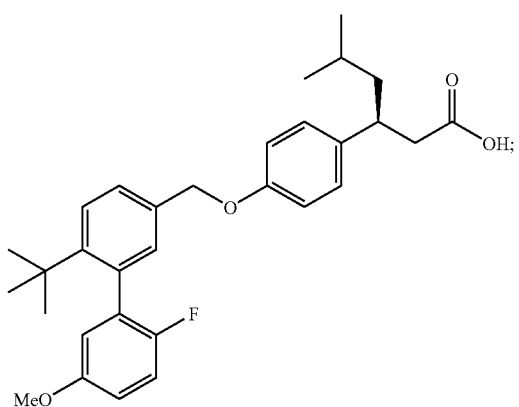

-continued

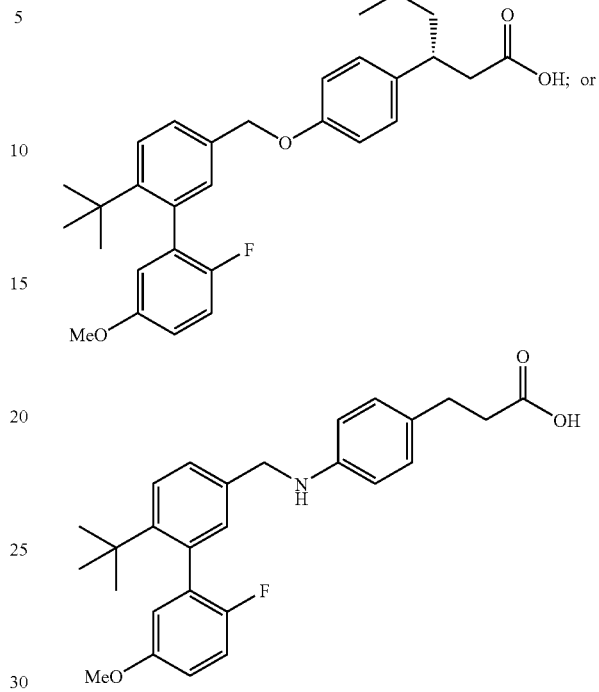

or is a pharmaceutically acceptable salt, solvate, or prodrug thereof. In some such embodiments where the compound has a chiral center, the compound exists as a single enantiomer whereas in other embodiments, the compound is a mixture of enantiomers of the compounds shown above.

In some embodiments, the compound is selected from any of those in Table 1.

In some embodiments, the compound of any of the embodiments is a salt. In other embodiments, the compound of any of the embodiments is a prodrug. In some such embodiments, the prodrug is a $C_1$-$C_6$ alkyl ester such as a methyl, ethyl, propyl, butyl, isopropyl, pentyl, or hexyl ester. In some such embodiments, the ester is a methyl or ethyl ester.

In some embodiments, the compound comprises a stereomerically pure S-enantiomer. In other embodiments, the compound comprises a stereomerically pure R-enantiomer. In yet other embodiments, the compound comprises a mixture of S- and R-enantiomers.

In another aspect, the invention provides pharmaceutical compositions comprising a pharmaceutically acceptable carrier, diluent, or excipient, and a compound of any of the embodiments of the invention.

5.2.2 Preparation of the Compounds

The compounds of the invention can be prepared by a variety of synthetic or semisynthetic techniques. Scheme 1 provides a general synthetic scheme for exemplary compounds of the invention utilizing ester A where the variables in Scheme 1 have any of the values described above with respect to any of the embodiments, V is a OH or a halogen such as, but not limited to a Cl, Br, or I, and Alk is a straight or branched chain alkyl group having from 1-8 carbon atoms. It will be understood that the phenolic OH group of A can be replaced with an SH and reacted with a compound where V is a halogen to produce the analogous S-containing derivative (X=S) to the compounds shown. The synthesis of various groups bipneyls compounds is described in WO 2005/086661 and U.S. Patent Application Publication No. 2006/0004012 which are both hereby incorporated by reference in their entireties and for all purposes as if fully set forth herein. Further relevant synthetic routes for related compounds are also described in these references. Appropriate starting materials can be prepared by techniques known or apparent to those of skill in the art or the starting materials may be commercially available. One of skill in the art will understand that the synthetic routes can be modified to use different starting materials or alternative reagents and that suitable adjustments in conditions (e.g., temperatures, solvents, etc.) can be made to accomplish the desired transformations. One of skill in the art will recognize that protecting groups may be necessary for the preparation of certain compounds and will be aware of those conditions compatible with a selected protecting group. Examples of such protecting groups include, for example, those set forth in Protective Groups in Organic Synthesis, Greene, T. W.; Wuts, P. G. M., John Wiley & Sons, New York, N.Y., (3rd Edition, 1999). Accordingly, the exemplary methods and the examples described herein are illustrative of the present invention and are not to be construed as limiting the scope thereof.

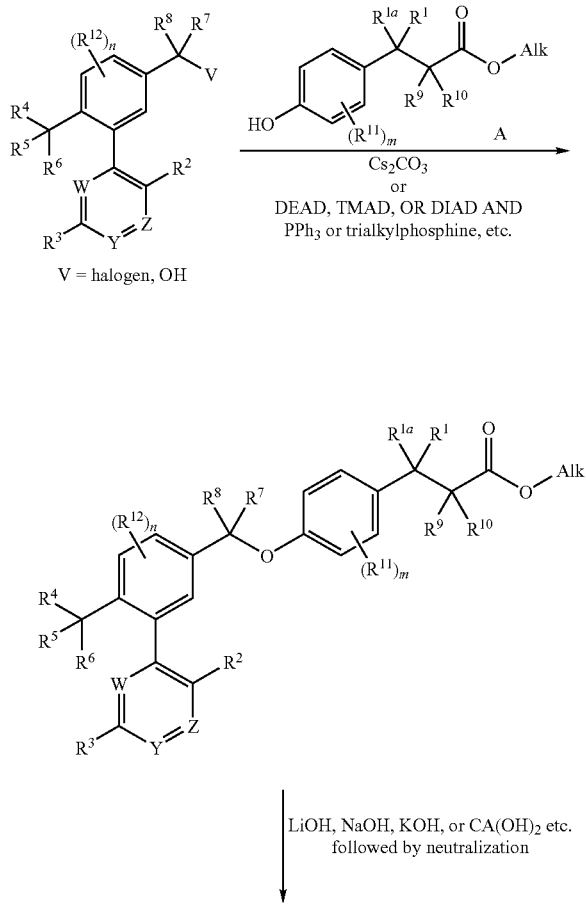

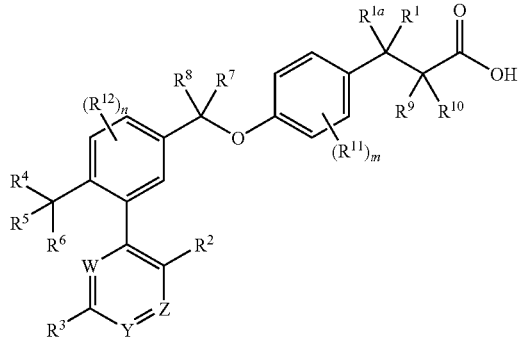

5.2.3 Compositions

In another aspect, the invention provides pharmaceutical compositions suitable for pharmaceutical use comprising one or more compounds of the invention and a pharmaceutically acceptable carrier, excipient, or diluent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the carrier, excipient, or diluent is compatible with the other ingredients of the formulation and is not deleterious to the recipient thereof.

Composition formulation may improve one or more pharmacokinetic properties (e.g., oral bioavailability, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The pharmaceutical compositions and methods of the invention may further comprise other therapeutically active compounds, as noted herein, useful in the treatment of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

5.2.4 Methods of Use

In another aspect, the invention provides methods of treating or preventing a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema, comprising administering to a subject in need thereof a therapeutically effective amount of a compound or composition of the invention.

In one embodiment, the disease or condition is type II diabetes.

In another aspect, the present invention provides a method for treating a disease or condition responsive to the modulation of GPR40 comprising administering to a subject in need thereof a therapeutically effective amount of a compound or composition of the invention.

In some embodiments, the disease or condition is selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

In certain embodiments, the disease or condition is type II diabetes.

In some embodiments, the disease or condition is obesity.

In some embodiments, the disease or condition is hypertension.

In some embodiments of administering the compounds or compositions of the invention, the compound or composition is administered orally.

In other embodiments, the compound or composition is administered parenterally.

In other embodiments, the compound or composition is administered in combination with a second therapeutic agent.

In other embodiments, the second therapeutic agent is an insulin sensitizing agent, such as metformin or a thiazolidinedione, for example.

In another aspect, the invention provides methods of treating or preventing a disease or disorder responsive to modulation of GPR40 comprising administering to a subject having such a disease or disorder, a therapeutically effective amount of one or more of the subject compounds or compositions.

In yet another aspect, the invention provides methods of treating or preventing a GPR40-mediated condition, disease or disorder comprising administering to a subject having such a condition, disease or disorder, a therapeutically effective amount of one or more of the subject compounds or compositions.

In yet another aspect, the invention provides methods of modulating GPR40 comprising contacting a cell with one or more of the subject compounds or compositions.

For example, in some embodiments, a cell that constitutively expresses GPR40 is contacted with one or more of the subject compounds or compositions.

In certain embodiments, a cell to be contacted can be made to express or overexpress GPR40, for example, by expressing GPR40 from heterologous nucleic acid introduced into the cell or, as another example, by upregulating the expression of GPR40 from nucleic acid endogenous to the cell.

Depending on the disease to be treated and the subject's condition, the compounds of the invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration. The invention also contemplates administration of the compounds of the invention in a depot formulation, in which the active ingredient is released over a defined time period.

In the treatment or prevention type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema or other conditions or disorders associated with GPR40, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range, the dosage may be 0.005 to 0.05, 0.05 to 0.5 or 0.5 to 5.0 mg/kg per day. For oral administration, the compositions are preferably provided in the form of tablets containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention can be combined or used in combination with other agents useful in the treatment, prevention, suppression or amelioration of the diseases or conditions for which compounds of the invention are useful, including type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema. Such other agents, or drugs, may be administered, by a route and in an amount commonly used therefore, simultaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients or therapeutic agents, in addition to a compound of the invention.

The compounds of the invention may be used in combination with a second therapeutic agent such as those described herein. Thus, in some embodiments, therapeutic compositions are provided that include a compound of the invention and a second therapeutic agent as a combined preparation for simultaneous, separate or sequential use in the treatment of a subject with a disease or condition mediated by GPR40. In some embodiments, therapeutic compositions are provided that include a compound of the invention and a second therapeutic agent as a combined preparation for simultaneous, separate or sequential use in the prophylactic treatment of a subject at risk for a disease or condition mediated by GPR40. In some such embodiments, the components are provided as a single composition. In other embodiments, the compound and the second therapeutic agent are provided separately as parts of a kit.

Examples of other therapeutic agents that may be combined with a compound of the invention, either administered separately or in the same pharmaceutical compositions, include, but are not limited to: (a) cholesterol lowering agents such as HMG-CoA reductase inhibitors (e.g., lovastatin, simvastatin, pravastatin, fluvastatin, atorvastatin and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acyl-CoA-cholesterol acyltransferase (ACAT) inhibitors such as melinamide), HMG-CoA synthase inhibitors, squalene epoxidase inhibitors and squalene synthetase inhibitors; (b) antithrombotic agents, such as thrombolytic agents (e.g., streptokinase, alteplase, anistreplase and reteplase), heparin, hirudin and warfarin derivatives, β-blockers (e.g., atenolol), β-adrenergic agonists (e.g., isoproterenol), ACE inhibitors and vasodilators (e.g., sodium nitroprusside, nicardipine hydrochloride, nitroglycerin and enaloprilat); and (c) antidiabetic agents such as insulin and insulin mimetics, sulfonylureas (e.g., glyburide, meglinatide), biguanides, e.g., metformin (GLUCOPHAGE®), α-glucosidase inhibitors (acarbose), insulin sensitizers, e.g., thiazolidinone compounds, rosiglitazone (AVANDIA®), troglitazone (REZULIN®), ciglitazone, pioglitazone (ACTOS®) and englitazone, DPP-IV inhibitors, e.g., vildagliptin (Galvus®), sitagliptin (Januvia™), and GLP-I analogs, e.g., exenatide (Byetta®). In some embodiments, a compound of the invention may be administered along with a DPP-IV inhibitor or a GLP-I analog.

The weight ratio of the compound of the invention to the second active ingredient may be varied and will depend upon the effective dose of each ingredient. Generally, an effective dose of each will be used. Combinations of a compound of the invention and other active ingredients will generally also be within the aforementioned range, but in each case, an effective dose of each active ingredient should be used.

In another aspect, the present invention provides a method for modulating circulating insulin concentration in a subject, comprising administering a compound or composition of the invention.

In some embodiments, the insulin concentration is increased.

In other embodiments, the insulin concentration is decreased.

The following examples are offered by way of illustration and are not intended to limit the scope of the invention. Those of skill in the art will readily recognize a variety of noncritical parameters that could be modified to yield essentially similar results.

6. EXAMPLES

Unless otherwise stated, all compounds were obtained from commercial sources or were prepared using the methods and experimental procedures described herein. Various procedures are also set forth in published U.S. Patent Application No. 2006/0004012 which is hereby incorporated by reference in its entirety and for all purposes as if set forth herein. The following abbreviations are used to refer to various reagents, solvents, experimental procedures, or analytical techniques that are described in the examples:

| | |
|---|---|
| AcOH | Acetic acid |
| DCM | Dichloromethane |
| DMF | N,N-Dimethyl Formamide |
| DMAP | Dimethylaminopyridine |
| DMSO | Dimethylsulfoxide |
| ESI | Electrospray Ionization |
| EtOAc | Ethyl acetate |
| EtOH | Ethanol |
| HPLC | High Performance Liquid Chromatography |
| HSA | Human Serum Albumin |
| MeOH | Methanol |
| MS | Mass Spectrometry |
| NMR | Nuclear Magnetic Resonance |
| PPTS | Pyridinium p-Toluenesulfonate |
| TEA | Triethylamine |
| THF | Tetrahydrofuran |
| SPA | Scintilliation Proximity Assay |

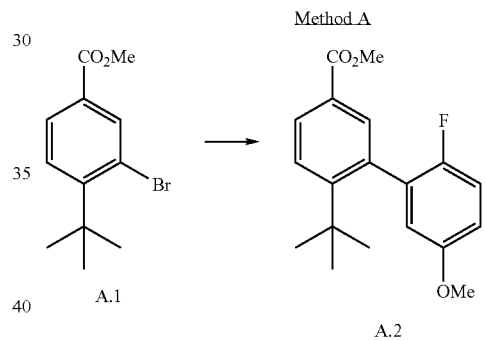

Method A

Methyl 6-(1,1-dimethylethyl)-2'-fluoro-5'-(methyloxy)-1,1'-biphenyl-3-carboxylate (A.2). To a stirred solution of methyl 3-bromo-4-tert-butylbenzoate A.1 (3-bromo-4-tert-butylbenzoic acid is commercially available from Specs, Specs, Kluyverweg 6, 2629 HT Delft, Holland, Internet: http://www.specs.net) (*Australian Journal of Chemistry* 1990, 43, 807-814) (1.00 g, 3.7 mmol) in toluene (4.00 mL, 4.0 mmol) and DMF (1.00 mL, 13.0 mmol) at 23° C. was added 2-fluoro-5-methoxyphenylboronic acid (2.50 g, 15 mmol) and potassium carbonate (1.50 g, 11 mmol), followed by tetrakis(triphenylphosphine)palladium (0.43 g, 0.37 mmol). The mixture was heated at 100° C. for 21 hours and then cooled to room temperature. Water (30 mL) was added to the mixture, and the mixture was extracted with EtOAc (3×50 mL). The combined organic layers were dried over $MgSO_4$ and concentrated in vacuo. The residue was then purified by flash chromatography ($SiO_2$ gel 60, eluted with 0%-10% EtOAc in hexanes) to give a clear oil (2.3 g, 99% yield). MS ESI (pos.) m/e: 339.1 $(M+Na)^+$, 334.1 $(M+H_2O)^+$, 317.2 $(M+H)^+$.

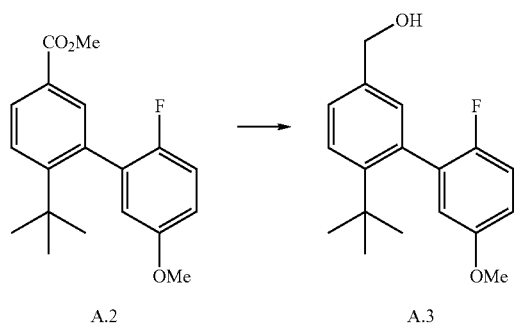

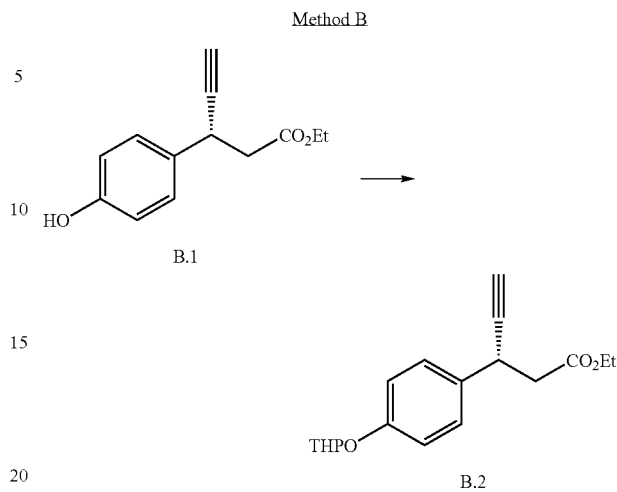

(6-(1,1-Dimethylethyl)-2'-fluoro-5'-(methyloxy)-1,1'-biphenyl-3-yl)methanol (A.3). To a stirred solution of A.2 (0.080 g, 0.3 mmol) in THF (10 mL, 3 mmol) at 0° C. was added lithium aluminum hydride (11.0M solution in THF (0.5 mL, 0.5 mmol)). Stirring continued for 15 minutes. 1N NaOH (5 mL) was added to quench the reaction, and the resulting solution was extracted with EtOAc (3×10 mL), dried over MgSO$_4$, filtered and concentrated in vacuo. The residue was then purified by flash chromatography (SiO$_2$ gel 60, eluted with 0-30% EtOAc in hexanes) to give a clear oil (0.07 g, 96% yield). $^1$H NMR (400 MHz, CDCl$_3$) δ ppm 7.57 (1H, d, J=8.2 Hz), 7.44-7.31 (1H, m), 7.04 (1H, d, J=4.0 Hz), 7.00 (1H, t, J=8.0 Hz), 6.86 (1H, m), 6.78 (1H, dd, J=5.9, 3.1 Hz), 4.68 (1 H, d, J=5.9 Hz), 3.79 (3H, s), 1.63 (1H, t J=5.9 Hz), 1.23 (9H, s).

Ethyl (3S)-3-(4-(tetrahydro-2H-pyran-2-yloxy)phenyl)-4-pentynoate (B.2). Compound B.1 was prepared by a method based on that reported in *Biochemistry* 1989, 28, 3833-3842. To stirred solution of phenol B.1 (1.0 g, 4.6 mmol, 1 eq., MW 218.25) in DCM at 23° C. was added 3,4-dihydro-2H-pyran (839 μL, 9.2 mmol, 2 eq., MW 84.12) followed by PPTS (catalytic, MW 251.31). The resulting mixture was stirred for 16 hours and concentrated in vacuo. The residue was then purified by flash chromatography (SiO$_2$ gel 60, eluted with 0 to 20% EtOAc in hexanes). Fractions containing the desired product were combined and concentrated to a colorless oil (1.3 g, 94%). MS ESI (pos.) m/e: 325.1 (M+Na)$^+$, 320.2 (M+H$_2$O)$^+$.

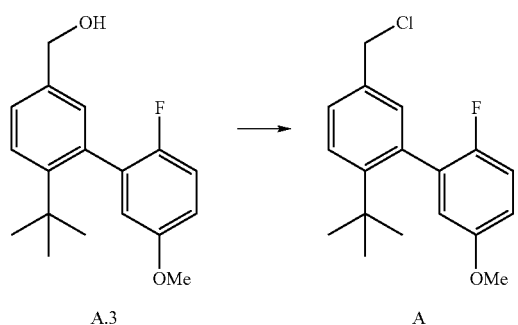

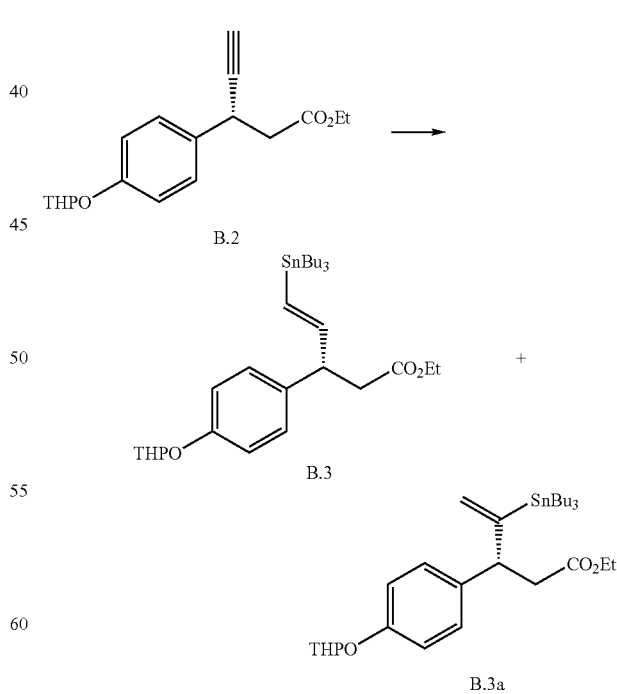

5-(Chloromethyl)-2-(1,1-dimethylethyl)-2'-fluoro-5'-(methyloxy)-1,1'-biphenyl (A). To a stirred solution of A.3 (0.07 g, 0.2 mmol) in DCM (10 mL, 155 mmol) at 23° C. was added thionyl chloride (0.04 mL, 0.5 mmol). Stirring continued for 16 hours. The reaction mixture was concentrated in vacuo. The residue was then purified by flash chromatography (SiO$_2$ gel 60, eluted with 0%-10% EtOAc in hexanes) to give a colorless oil (0.050 g, 67% yield). $^1$H NMR (400 MHz, CDCl$_3$) δ ppm 7.56 (1H, d, J=8.2 Hz), 7.37 (1H, dd, J=8.4, 2.2 Hz), 7.05 (1H, d, J=1.6 Hz), 7.01 (1H, t, J=9.2 Hz), 6.87 (1H, m), 6.79 (1H, dd, J=5.9, 3.1 Hz), 4.57 (2H, s), 3.80 (3H, s), 1.23 (9H, s).

Ethyl (3S)-3-(4-(tetrahydro-2H-pyran-2-yloxy)phenyl)-5-(tributylstannanyl)-4-pentenoate (B.3). To a stirred solution of B.2 (80.0 mg, 0.26 mmol, MW 302.37) in THF at 23° C.

was added PdCl$_2$(PPh$_3$)$_2$ (18.6 mg, 0.026 mmol, MW 701.89) followed by Bu$_3$SnH (84.0 μL, 0.32 mmol, MW 291.05). After the addition, the solution turned black. After a further 2 minutes, the mixture was concentrated in vacuo. The residue was then purified by flash chromatography (SiO$_2$ gel 60, eluted with 0 to 20% EtOAc in hexanes). Fractions containing the desired product B.3 were combined and concentrated to provide a colorless oil (96.0 mg). $^1$H NMR spectroscopy showed the product to be a 3:1 ratio of B.3:B.3a respectively.

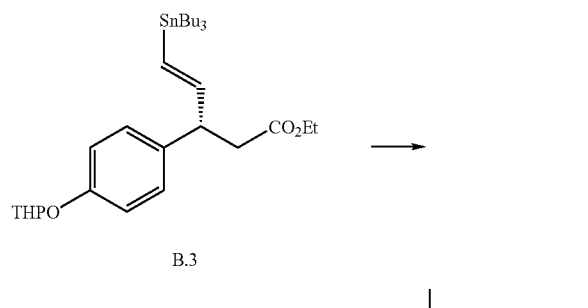

Ethyl (3S,4E)-5-iodo-3-(4-(tetrahydro-2H-pyran-2-yloxy)phenyl)-4-pentenoate (B.4). To a stirred solution of B.3/B.3a (96.0 mg, 0.16 mmol, 1 eq., MW 593.42) in THF (5 mL) at −78° C. was added iodine (45.0 mg, 0.18 mmol, 1.1 eq., MW 253.81) in THF (2 mL) dropwise. After the addition was complete, a saturated solution of NaS$_2$O$_3$ and NaHCO$_3$ were added at the same time to quench the reaction. EtOAc was added to the mixture, and the resulting mixture was washed with NaHCO$_3$ (aq) (2×50 mL) and brine (1×50 mL). The organic layer was dried over MgSO$_4$ and filtered. The organic layer was concentrated in vacuo. The residue was then purified by flash chromatography (SiO$_2$ gel 60, eluted with 0 to 20% EtOAc in hexanes). Fractions containing the desired product were combined and concentrated to a colorless oil B.4 (66 mg, 58% over 2 steps). MS ESI (pos.) m/e: 453.0 (M+Na)$^+$, 448.1 (M+H$_2$O)$^+$.

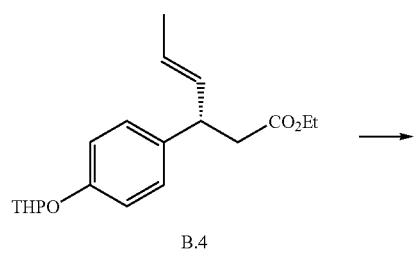

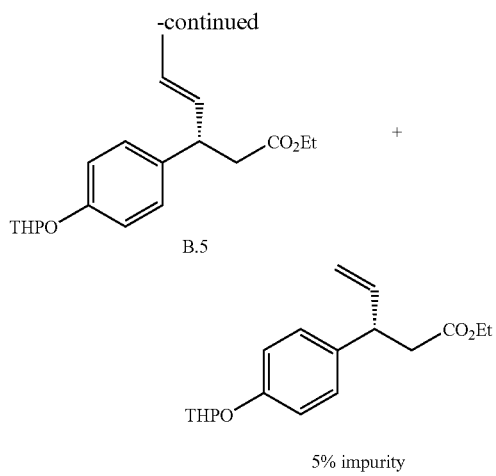

Ethyl (3S,4E)-3-(4-(tetrahydro-2H-pyran-2-yloxy)phenyl)-4-hexenoate (B.5). To a stirred solution of B.4 (350.0 mg, 0.81 mmol, 1 eq., MW 430.29) in THF (20 mL) at 23° C. was added Pd(PPh$_3$)$_4$ (94 mg, 0.081 mmol, 0.1 eq., MW 1155.58) followed by dropwise addition of Me$_2$Zn (976 μL, 0.97 mmol, 1.2 eq., 1.0 M). The yellow color disappeared on addition of the Me$_2$Zn. After 30 minutes, the color returned signaling the end of the reaction. Water (10 mL) was added to quench the reaction. The mixture was extracted with EtOAc (2×50 mL), dried with MgSO$_4$, and filtered. The organic layer was concentrated in vacuo. The residue was then purified by flash chromatography (SiO$_2$ gel 60, eluted with 0 to 20% EtOAc in hexanes). Fractions containing the desired product were combined and concentrated to a colorless oil (180 mg, 69%). MS ESI (pos.) m/e: 341.2 (M+Na)$^+$, 336.2 (M+H$_2$O)$^+$. The desired product was contaminated (~5%) with a further olefinic product (believed to contain a terminal double bond).

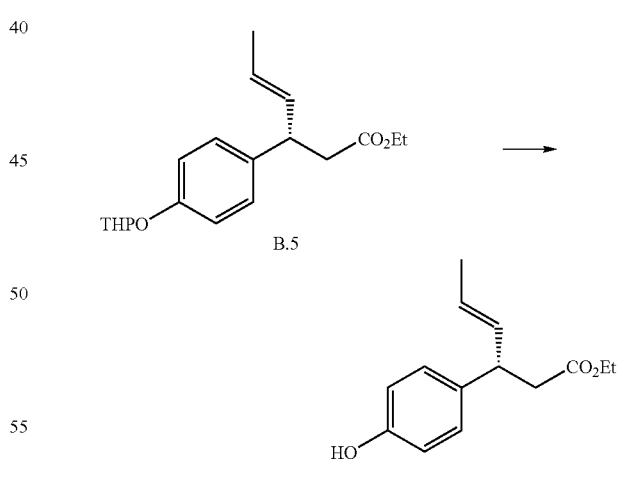

Ethyl (3S,4E)-3-(4-hydroxyphenyl)-4-hexenoate (B). To a stirred solution of B.5 (180.0 mg, 0.57 mmol, MW 318.42) in EtOH (5 mL) at 23° C. was added PPTS (catalytic). Stirring was continued for 16 hours. The reaction was concentrated in vacuo. The residue was then purified by flash chromatography (SiO$_2$ gel 60, eluted with 0 to 20% EtOAc in hexanes). Fractions containing the desired product were combined and concentrated to a colorless oil. The desired product was contaminated (~5%) with a further olefinic product (believed to contain a terminal double bond). This impurity was removed by further purification on silica gel containing 10% AgNO$_3$ eluting with 0 to 20% EtOAc in hexanes. The combined fractions were concentrated under reduced pressure to afford phenol B (120 mg, 91%) as a colorless oil.

CAS# 25015-63-8) in 1,4-dioxane (5.0 mL) was stirred overnight at 95° C. The mixture was cooled to room temperature, quenched with saturated aqueous ammonium chloride, and extracted with ether. The combined organic layers were dried over MgSO$_4$ and concentrated. The crude product was purified by silica gel flash chromatography (0-10% EtOAc/hexane) to afford compound C.3 (0.60 g, 41% yield) as a colorless oil. $^1$H NMR (400 MHz, CDCl$_3$) δ 7.16 (d, J=3.1 Hz, 1H), 6.91 (dd, J=3.1, 9.0 Hz, 1H), 6.79 (d, J=9.0 Hz, 1H), 3.91 (t, J=6.3 Hz, 2H), 3.78 (s, 3H), 1.75 (m, 2H), 1.54 (m, 2H), 1.34 (s, 12H), 0.96 (t, J=7.4, 3H).

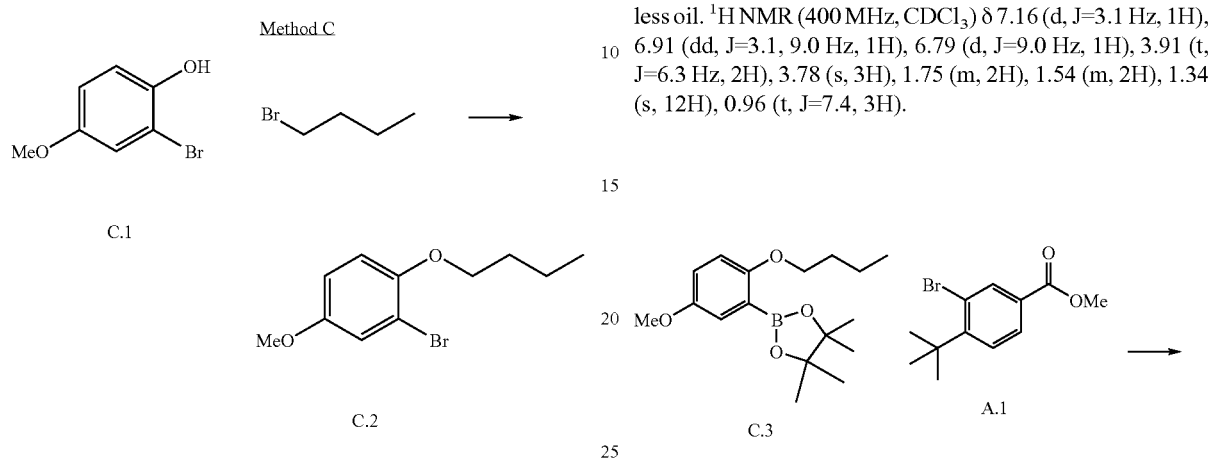

2-Bromo-1-butoxy-4-methoxybenzene (C.2). A mixture of 2-bromo-4-methoxyphenol (1.50 g, 7.39 mmol) (Bionet, CAS# 17332-11-5), 1-bromobutane (0.95 mL, 8.87 mmol) (Acros, CAS# 109-65-9), and cesium carbonate (3.13 g, 9.60 mmol) in DMF (40 mL) was stirred overnight at room temperature. The mixture was diluted with EtOAc, washed with water and brine, dried over Na$_2$SO$_4$, and concentrated. The crude product was purified by silica gel flash chromatography (0-20% EtOAc/hexane) to afford compound C.2 (1.49 g, 78% yield) as a colorless oil. $^1$H NMR (400 MHz, CDCl$_3$) δ 7.15 (d, J=2.7 Hz, 1H), 6.84 (d, J=9.0 Hz, 1H), 6.80 (dd, J=3.1, 9.0 Hz, 1H), 3.97 (t, J=6.5 Hz, 2H), 3.76 (s, 3H), 1.79 (m, 2H), 1.53 (m, 2H), 0.98 (t, J=7.2 Hz, 3H).

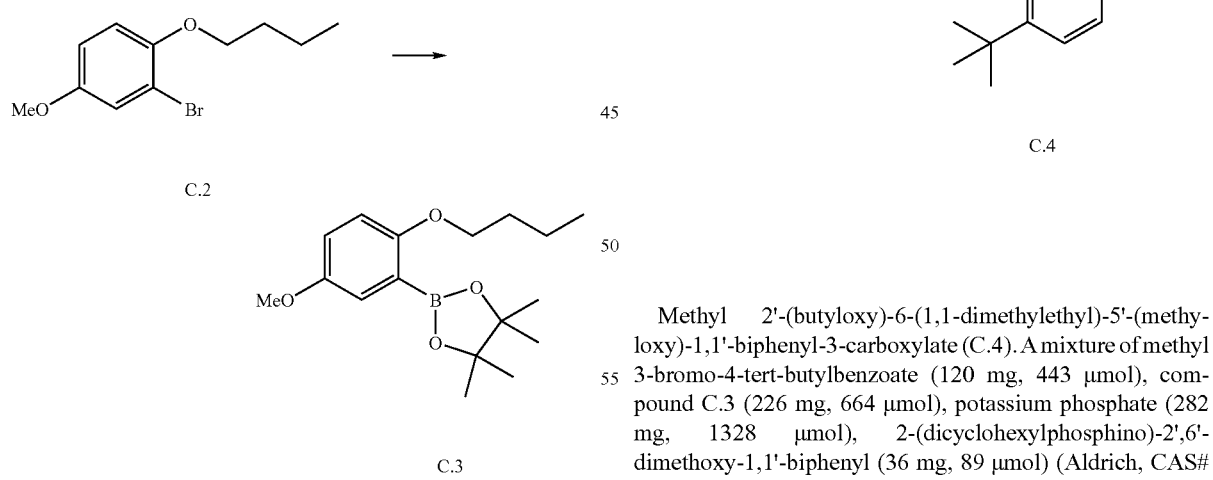

2-(2-(Butyloxy)-5-(methyloxy)phenyl)-4,4,5,5-tetramethyl-1,3,2-dioxaborolane (C.3). A mixture of 2-bromo-1-butoxy-4-methoxybenzene (1.2 g, 4.7 mmol), TEA (2.6 mL, 19 mmol), (oxydi-2,1-phenylene)bis(diphenylphosphine) (0.51 g, 0.95 mmol) (Aldrich, CAS# 166330-10-5), palladium(II) acetate (0.11 g, 0.47 mmol), and 4,4,5,5-tetramethyl-1,3,2-dioxaborolane (2.1 mL, 14 mmol) (Aldrich, Methyl 2'-(butyloxy)-6-(1,1-dimethylethyl)-5'-(methyloxy)-1,1'-biphenyl-3-carboxylate (C.4). A mixture of methyl 3-bromo-4-tert-butylbenzoate (120 mg, 443 μmol), compound C.3 (226 mg, 664 μmol), potassium phosphate (282 mg, 1328 μmol), 2-(dicyclohexylphosphino)-2',6'-dimethoxy-1,1'-biphenyl (36 mg, 89 μmol) (Aldrich, CAS# 657408-07-6), and tris(dibenzylideneacetone)dipalladium (0) (20 mg, 22 μmol) in toluene (1.0 mL) was stirred overnight at 110° C. The mixture was cooled to room temperature, filtered through a pad of celite with EtOAc rinsings, and concentrated. The crude product was purified by silica gel flash chromatography (0-10% EtOAc/hexane) to afford compound C.4 (63 mg, 39% yield) as a colorless oil. MS ESI (pos.) m/e: 388 (M+H$_2$O), 393 (M+Na).

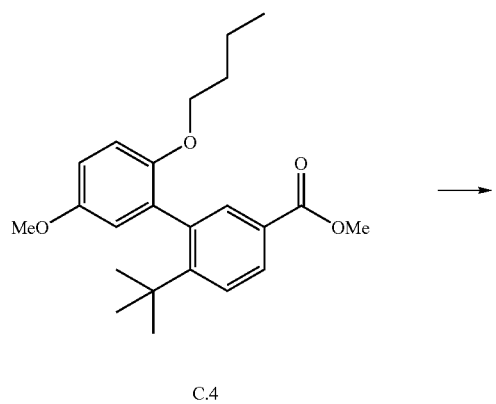

C.4

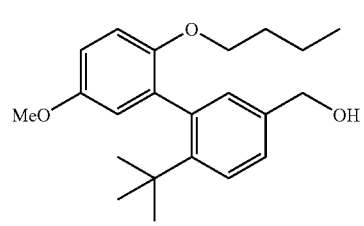

C.5

(2'-(Butyloxy)-6-(1,1-dimethylethyl)-5'-(methyloxy)-1,1'-biphenyl-3-yl)methanol (C.5). To a solution of C.4 (63 mg, 170 μmol) in THF (2.0 mL) was added lithium aluminum hydride (1.0 M solution in THF, 102 μL, 102 μmol) dropwise at room temperature. The solution was stirred for 30 minutes at room temperature, quenched with 10% aqueous Rochelle's salt, and extracted with EtOAc. The combined organic layers were dried over MgSO₄ and concentrated. The crude product was purified by silica gel flash chromatography (0-30% EtOAc/hexane) to afford compound C.5 (34 mg, 59% yield) as a colorless oil. ¹H NMR (400 MHz, CDCl₃) δ 7.52 (d, J=8.2 Hz, 1H), 7.29 (dd, J=2.0, 8.2 Hz, 1H), 6.95 (d, J=2.0 Hz, 1H), 6.82 (m, 2H), 6.74 (dd, J=0.8, 2.7 Hz, 1H), 4.64 (bd, J=3.5 Hz, 2H), 3.83 (dt, J=2.4, 6.7 Hz, 2H), 3.76 (s, 3H), 1.59 (bs, 1H), 1.53 (m, 2H), 1.22 (m, 11H), 0.80 (t, J=7.2 Hz, 3H).

C.5

-continued

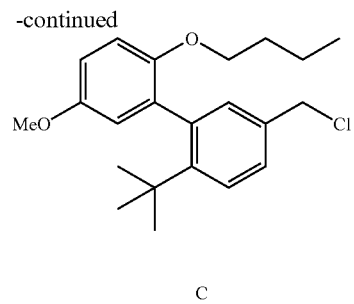

C 2-(Butyloxy)-5'-(chloromethyl)-2'-(1,1-dimethylethyl)-5-(methyloxy)-1,1'-biphenyl (C). To a solution of compound C.5 (34 mg, 100 μmol) and TEA (14 μL, 100 μmol) in DCM (1.0 mL) was added thionyl chloride (15 μL, 200 μmol) in one portion at room temperature. The solution was stirred overnight at room temperature and concentrated. The crude mixture was suspended in hexane, filtered, and concentrated to afford compound C (36 mg, 100% yield) as a yellow oil. ¹H NMR (400 MHz, CDCl₃) δ 7.50 (d, J=8.3 Hz, 1H), 7.30 (dd, J=2.2, 8.3 Hz, 1H), 6.98 (d, J=2.2 Hz, 1H), 6.82 (m, 2H), 6.74 (dd, J=0.8, 2.7 Hz, 1H), 4.55 (s, 2H), 3.82 (m, 2H), 3.77 (s, 3H), 1.51 (m, 2H), 1.20 (m, 1H), 0.79 (t, J=7.2 Hz, 3H).

Example 1

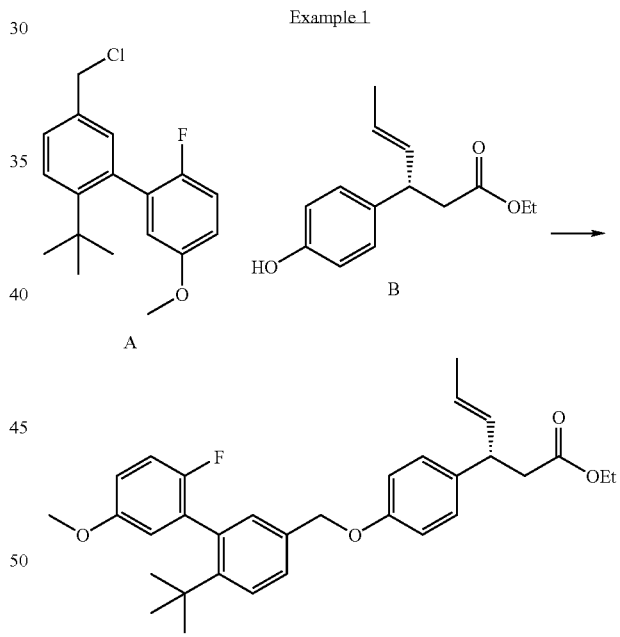

1.1

Ethyl (3S,4E)-3-(4-(((6-(1,1-dimethylethyl)-2'-fluoro-5'-(methyloxy)-1,1'-biphenyl-3-yl)methyl)oxy)phenyl)-4-hexenoate (1.1). To a stirred solution of (3S,4E)-ethyl 3-(4-hydroxyphenyl)hex-4-enoate B (0.025 g, 0.11 mmol) in DMF (2.00 mL, 26 mmol) at 23° C. was added A (0.039 g, 0.13 mmol), followed by cesium carbonate (0.042 g, 0.13 mmol). Stirring continued for 20 hours. Water (5 mL) was added, and the resulting solution was extracted with EtOAc (3×10 mL), dried over MgSO₄, and concentrated in vacuo. The residue was then purified by flash chromatography (SiO₂ gel 60, eluted with 0-20% ethyl acetate in hexane) to give a clear oil (0.030 g, 56% yield). MS ESI (pos.) m/e: 527.2 (M+Na)$^+$, 522.2 (M+H$_2$O)$^+$.

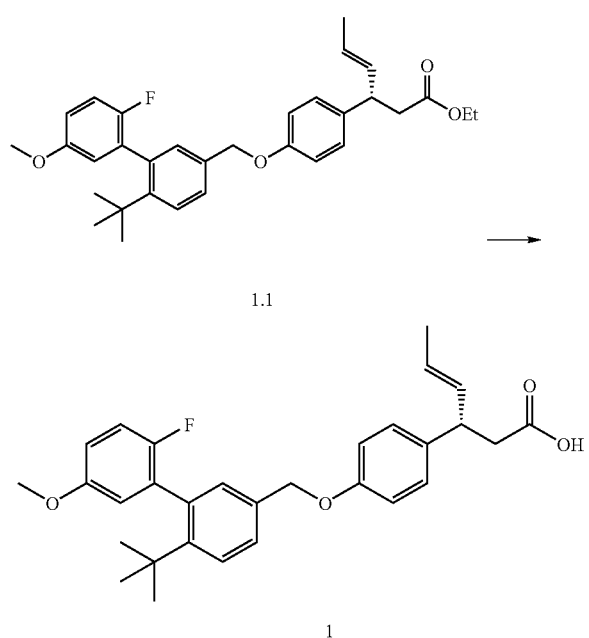

1.1

1

(3S,4E)-3-(4-(((6-(1,1-Dimethylethyl)-2'-fluoro-5'-(methyloxy)-1,1'-biphenyl-3-yl)methyl)oxy)phenyl)-4-hexenoic acid (1). To a stirred solution of 1.1 (0.050 g, 0.099 mmol) in THF (2.00 mL, 24 mmol) and EtOH (2.00 mL, 34 mmol) at 23° C. was added 1N lithium hydroxide (1.00 mL, 1.0 mmol). Stirring was continued for 22 hours. The reaction was concentrated in vacuo. 1N HCl was added to reach pH 1, and the resulting mixture was extracted with EtOAc (3×10 mL), dried over MgSO$_4$ and concentrated in vacuo. The residue was then purified by flash chromatography (SiO$_2$ gel 60, eluted with 0%-20% EtOAc in hexanes) to give a clear oil (0.0443 g, 94% yield). $^1$H NMR (400 MHz, CDCl$_3$) δ ppm 7.58 (1H, d, J=8.6 Hz), 7.40 (1H, dd, J=8.2, 2.0 Hz), 7.13 (2H, d, J=8.6 Hz), 7.08 (1H, d, J=1.5 Hz), 7.00 (1H, t, J=8.8 Hz), 6.92 (2H, d, J=8.6 Hz), 6.86 (1H, m), 6.79 (1H, m), 5.57 (1H, m), 5.50 (1H, m), 4.99 (2H, s), 3.79 (3H, s), 3.76 (1H, dd, J=14.5, 7.6 Hz), 2.71 (2H, dd, J=7.6, 2.5 Hz), 1.66 (3H, d, J=5.9 Hz), 1.23 (9H, m). MS ESI (neg.) m/e: 951.4.1 (2M−H)$^+$, 475.1 (M−H)$^+$.

Example 2

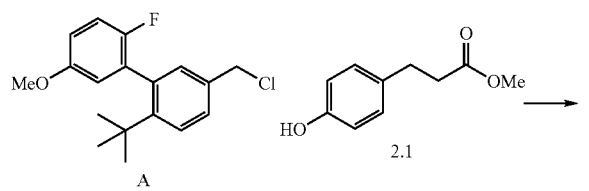

A                                    2.1

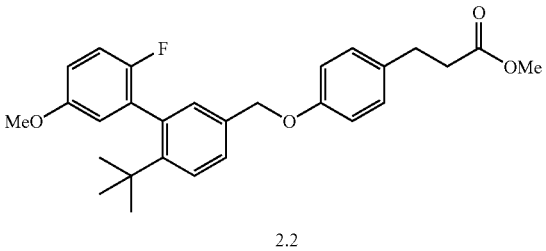

2.2

Methyl 3-(4-(((6-(1,1-dimethylethyl)-2'-fluoro-5'-(methyloxy)-1,1'-biphenyl-3-yl)methyl)oxy)phenyl)propanoate (2.2). To a stirred solution of commercially available methyl 3-(4-hydroxyphenyl)propanoate 2.1 (0.025 g, 0.14 mmol) (commercially available from Aldrich, CAS No. 5597-50-2) in DMF (2.00 mL, 0.14 mmol) at 23° C. was added A (0.043 g, 0.14 mmol) followed by cesium carbonate (0.045 g, 0.14 mmol). Stirring continued for 19 hours. Brine (5 mL) was added to the mixture, and the resulting mixture was extracted with EtOAc (3×10 mL), dried over MgSO$_4$, and concentrated in vacuo. The residue was then purified by flash chromatography (SiO$_2$ gel 60, eluted with 0-20% EtOAc in hexanes) to give compound 2.2 as a clear oil (0.0421 g, 67% yield). MS ESI (pos.) m/e: 473.2 (M+Na)$^+$, 468.2 (M+H$_2$O)$^+$.

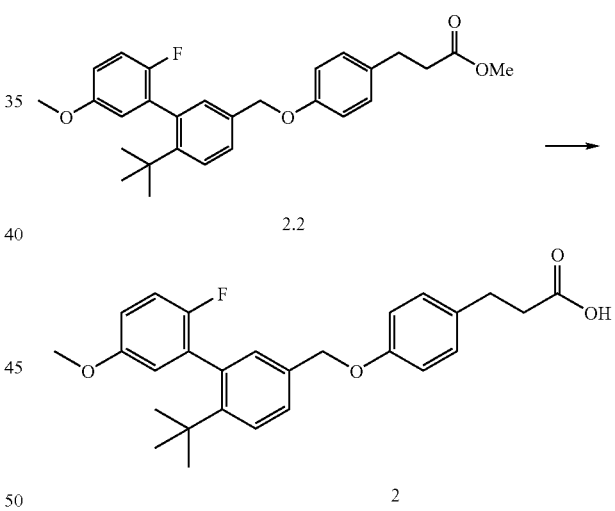

2.2

2

3-(4-(((6-(1,1-Dimethylethyl)-2'-fluoro-5'-(methyloxy)-1,1'-biphenyl-3-yl)methyl)oxy)phenyl)propanoic acid (2). To a stirred solution of 2.2 (0.0421 g, 0.0934 mmol) in THF (2.00 mL) and EtOH (2.00 mL) at 23° C. was added 1N lithium hydroxide (2.00 mL, 2.00 mmol). Stirring continued for 16 hours. The reaction mixture was concentrated in vacuo. 1N HCl was added to reach pH 1, and the resulting mixture was extracted with EtOAc (3×10 mL), dried over MgSO$_4$ and concentrated in vacuo. The residue was then purified by flash chromatography (SiO$_2$ gel 60, eluted with 0%-20% EtOAc in hexanes) to give a clear oil (0.034 g, 82% yield). $^1$H NMR (400 MHz, CDCl$_3$) δ ppm 7.59 (1H, d, J=8.2 Hz), 7.41 (1H, dd, J=8.6, 2.2 Hz), 7.22 (1H, dd, J=9.0, 7.4 Hz), 7.11 (1H, d, J=2.2 Hz), 7.00 (1H, t, J=8.6 Hz), 6.88-6.79 (5H, m), 5.01

(2H, s), 3.79 (3H, s), 2.94 (2H, t, J=7.8 Hz), 2.68 (2H, t, J=7.8 Hz), 1.24 (9H, s). MS ESI (neg.) m/e: 871.3 (2M−H)⁺, 435.1 (M−H)⁺.

Example 3

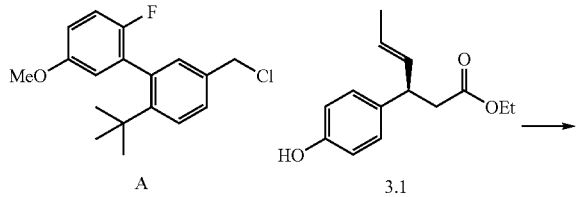

Ethyl (3R,4E)-3-(4-(((6-(1,1-dimethylethyl)-2'-fluoro-5'-(methyloxy)-1,1'-biphenyl-3-yl)methyl)oxy)phenyl)-4-hexenoate (3.2). To a stirred solution of (R,E)-ethyl 3-(4-hydroxyphenyl)hex-4-enoate 3.1 (prepared by a method analogous to Method B) (0.015 g, 0.064 mmol) and benzyl chloride A (0.0234 g, 0.076 mmol) in DMF (2.00 mL, 0.20 mmol) at 23° C. was added cesium carbonate (0.025 g, 0.076 mmol). Stirring continued for 16 hours. Water (5.0 mL) was added, and the mixture was extracted with EtOAc (3×10 mL). The combined organic layers were dried over MgSO₄ and concentrated in vacuo. The residue was then purified by flash chromatography (SiO₂ gel 60, eluted with 0%-20% EtOAc in hexanes) to give a clear oil (0.0313 g, 98% yield). MS ESI (pos.) m/e: 527.2 (M+Na)⁺, 522.2 (M+H₂O)⁺.

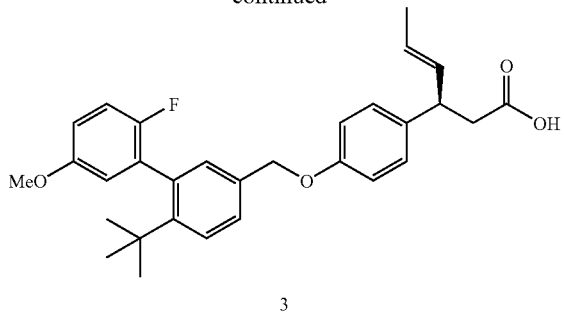

(3R,4E)-3-(4-(((6-(1,1-Dimethylethyl)-2'-fluoro-5'-(methyloxy)-1,1'-biphenyl-3-yl)methyl)oxy)phenyl)-4-hexenoic acid (3). To a stirred solution of 3.2 (0.0313 g, 0.062 mmol) in THF (2.00 mL) and EtOH (2.00 mL) at 23° C. was added 1N lithium hydroxide (2.00 mL, 2.00 mmol). Stirring continued for 20 hours. The reaction mixture was concentrated in vacuo, 1N HCl was added to reach pH 1, and the resulting mixture was extracted with EtOAc (3×10 mL), dried over MgSO₄ and concentrated in vacuo. The residue was then purified by flash chromatography (SiO₂ gel 60, eluted with 0%-20% EtOAc in hexanes) to give a clear oil (0.0241 g, 82% yield). ¹H NMR (400 MHz, CDCl₃) δ ppm 7.58 (1H, d, J=8.2 Hz), 7.40 (1H, dd, J=8.4, 2.2 Hz), 7.13 (2H, d, J=8.6 Hz), 7.08 (1H, d, J=1.5 Hz), 7.00 (1H, t, J=8.6 Hz), 6.92 (2H, d, J=8.6 Hz), 6.86 (1H, m), 6.79 (1H, m), 5.57 (1H, m), 5.50 (1H, m), 4.99 (2H, s), 3.79 (3H, s), 3.76 (1H, dd, J=14.5, 7.8 Hz), 2.71 (2H, dd, J=7.8, 2.3 Hz), 1.66 (3H, d, J=6.3 Hz), 1.23 (9H, m). MS ESI (neg.) m/e: 951.4 (2M−H)⁺, 475.1 (M−H)⁺.

Example 4

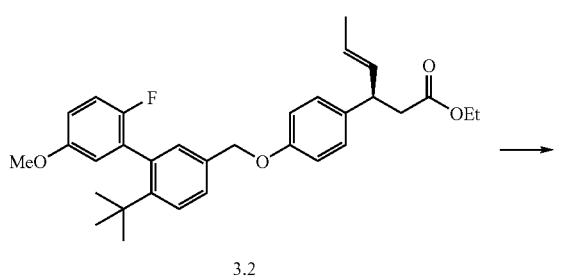

Methyl (3S)-3-(4-(((6-(1,1-dimethylethyl)-2'-fluoro-5'-(methyloxy)-1,1'-biphenyl-3-yl)methyl)oxy)phenyl)-4-hexynoate (4.2). Compound 4.1 was prepared as described in U.S. Patent Application Publication No. 2006/0004012 which is hereby incorporated by reference. To a stirred solution of compound 4.1 (0.05 g, 0.2 mmol) in DMF (2.00 mL, 0.14 mmol) at 23° C. was added A (0.08 g, 0.3 mmol) followed by cesium carbonate (0.09 g, 0.3 mmol). Stirring continued for 22 hours. Water (5.0 mL) was added to the mixture, and the resulting mixture was extracted EtOAc (3×10 mL). The combined organic layers were dried over MgSO₄ and concentrated in vacuo. The residue was then purified by flash chromatography (SiO₂ gel 60, eluted with 0%-20% EtOAc in hexanes) to give compound 4.2 as a clear oil (0.052 g, 46% yield). MS ESI (pos.) m/e: 511.1 (M+Na)⁺, 489.2 (M+H)⁺.

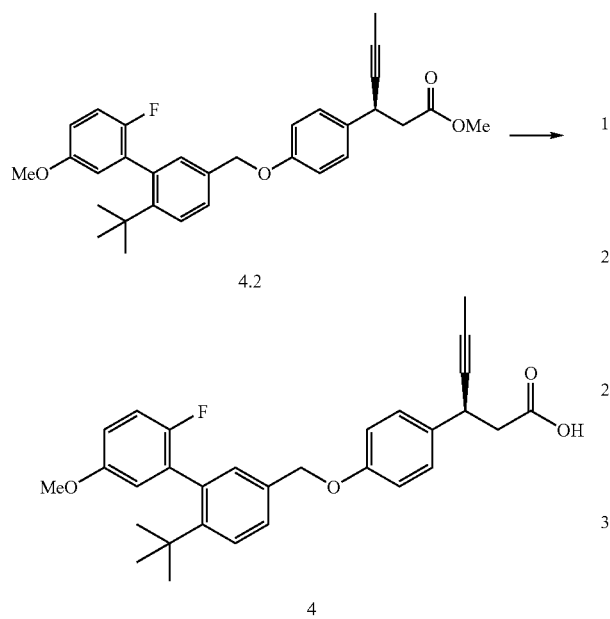

(3S)-3-(4-(((6-(1,1-Dimethylethyl)-2'-fluoro-5'-(methyloxy)-1,1'-biphenyl-3-yl)methyl)oxy)phenyl)-4-hexynoic acid (4). To a stirred solution of 4.2 (0.052 g, 0.11 mmol) in THF (2.00 mL) and EtOH (2.00 mL) at 23° C. was added 1N lithium hydroxide (2.00 mL, 2.00 mmol). Stirring continued for 16 hours. The reaction mixture was concentrated in vacuo, 1N HCl was added to reach pH 1, and the resulting mixture was extracted with EtOAc (3×10 mL), dried over MgSO₄ and concentrated in vacuo. The residue was purified by flash chromatography (SiO₂ gel 60, eluted with 0%-20% EtOAc in hexanes) to give compound 4 as a clear oil (0.0466 g, 92% yield). ¹H NMR (400 MHz, CDCl₃) δ ppm 7.58 (1H, d, J=8.2 Hz), 7.41 (1H, dd, J=8.2, 2.0 Hz), 7.30 (2H, d, J=8.6 Hz), 7.08 (1H, d, J=2.0 Hz), 7.00 (1H, t, J=8.8 Hz), 6.93 (2H, d, J=8.6 Hz), 6.86 (1H, m), 6.80 (1H, dd, J=5.9, 3.3 Hz), 5.00 (2H, s), 4.06 (1H, m), 3.80 (3H, s), 2.81 (1H, dd, J=15.6, 8.4 Hz), 2.72 (1H, dd, J=15.6, 6.6 Hz), 1.84 (3H, d, J=2.3 Hz), 1.24 (9H, s). MS ESI (neg.) m/e: 947.3 (2M−H)⁺, 473.2 (M−H)⁺.

Example 5

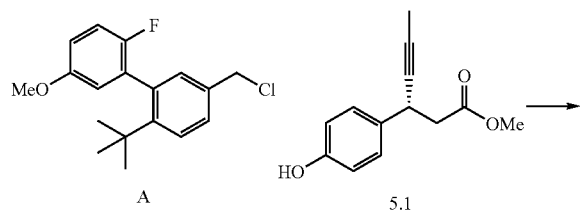

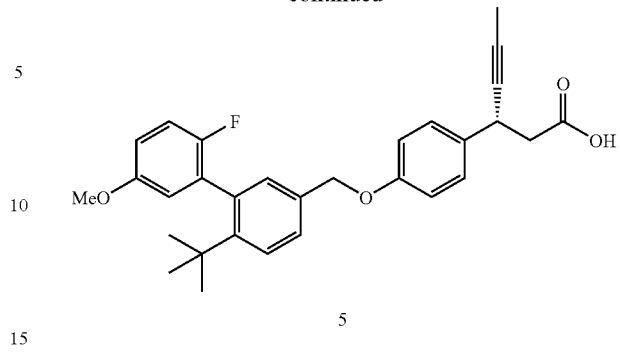

(3R)-3-(4-(((6-(1,1-Dimethylethyl)-2'-fluoro-5'-(methyloxy)-1,1'-biphenyl-3-yl)methyl)oxy)phenyl)-4-hexynoic acid (5). Compound 5.1 was obtained by methods analogous to those used to obtain compound 4.1. Benzyl chloride A (0.077 g, 0.25 mmol) and compound 5.1 (0.050 g, 0.23 mmol) were converted to the title compound 5 (0.0392 g, 72% yield) according to the methods reported in Example 4. ¹H NMR (400 MHz, CDCl₃) δ ppm 7.58 (1H, d, J=8.2 Hz), 7.41 (1H, dd, J=8.4, 2.0 Hz), 7.30 (2H, d, J=8.6 Hz), 7.08 (1H, d, J=2.0 Hz), 7.00 (1H, t, J=8.8 Hz), 6.93 (2H, d, J=8.6 Hz), 6.86 (1H, m), 6.80 (1H, dd, J=5.9, 3.3 Hz), 5.00 (2H, s), 4.06 (1H, m), 3.80 (3H, s), 2.81 (1H, dd, J=15.6, 8.4 Hz), 2.72 (1H, dd, J=15.6, 6.6 Hz), 1.84 (3H, d, J=2.3 Hz), 1.24 (9H, s). MS ESI (neg.) m/e: 947.3 (2M−H)⁺, 473.2 (M−H)⁺.

Example 6

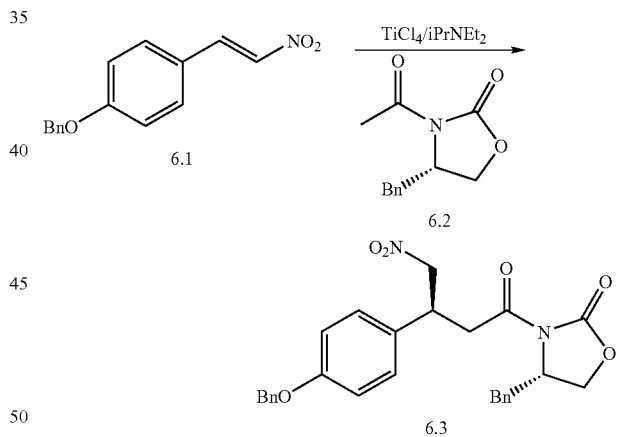

(S)-4-Benzyl-3-((S)-3-(4-(benzyloxy)phenyl)-4-nitrobutanoyl)oxazolidin-2-one (6.3). TiCl₄ (43 mL, 1.0 M solution in DCM) was added slowly to a mixture of 6.2 (8.55 g, 39 mmol, commercially available from Aldrich) in DCM (200 mL) at −78° C., followed by slow addition of iPrNEt₂ (8.14 mL, 46.8 mmol). The mixture was stirred at −78° C. for 45 minutes and then a mixture of 6.1 (9.95 g, 39 mmol, commercially available from Aldrich) in DCM (40 mL) was added over 15 minutes. TiCl₄ (39 mL, 1.0 M solution in DCM) was then added to the reaction. During all the additions, the internal temperature was kept below −72° C. The mixture was stirred at −78° C. for another 4 hours before it was slowly warmed to −10° C. and then quenched by adding NH₄Cl (saturated 100 mL). The organic layer was separated, washed with brine, dried, and concentrated. The crude product was placed in hot MeOH (700 mL). The mixture was stirred vigorously at 75° C. for 3 hours. The mixture was then cooled to room temperature and allowed to stand for 3 hours. The solid product was collected by filtration and washed with MeOH. The product 6.3 (8.5 g) had a d.e. >99%. MS ESI (pos.) m/e: 475 (M+H). $^1$H NMR (CDCl$_3$) δ 7.40(m, 8H), 7.28 (m, 4H), 6.97(d, 2H), 5.05 (s, 2H), 4.63 (m, 3H), 4.17 (m, 3H), 3.53 (dd, 1H), 3.34 (dd, 1H), 3.28 (dd, 1H), 2.75 (dd, 1H).

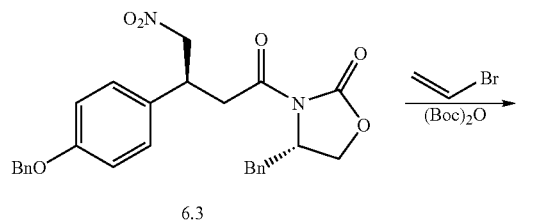

6.3

6.4

(S)-4-Benzyl-3-((S)-3-(4-(benzyloxy)phenyl)-3-(isoxazol-3-yl)propanoyl)oxazolidin-2-one (6.4). (Boc)$_2$O (6.9 g, 31.65 mmol) was added at room temperature to a solution of 6.3 (10 g, 21.1 mmol), vinyl bromide (230 mL, 1.0 M solution in THF), DMAP (256 mg, 2.1 mmol), and TEA (3.5 mL, 25.3 mmol). The mixture was stirred at room temperature for 2.5 days. During the reaction, more (Boc)$_2$O (2×2 g) was added. After HPLC indicated that all 6.3 was consumed, the reaction mixture was placed in EtOAc (500 mL), and saturated NaHCO$_3$ (400 mL) was added. The organic layer was separated, washed with brine, dried, and concentrated under vacuum. The crude product was placed in hot MeOH (70 mL). The mixture was stirred vigorously at 75° C. for 5 hours. The mixture was then cooled to room temperature and allowed to stand for 3 hours. The solid product was collected by filtration and washed with MeOH to give 6.4 (9.5 g). MS ESI (pos.) m/e: 483 (M+H). $^1$H NMR (CDCl$_3$) δ 8.30(d, 1H), 7.30 (m, 12H), 6.95 (d, 2H), 6.15 (d, 1H), 5.05 (s, 2H), 4.76 (dd, 1H), 4.64 (m, 1H), 4.15 (d, 2H), 4.05 (dd, 1H), 3.56 (dd, 1H), 3.23 (dd, 1H), 2.78 (dd, 1H).

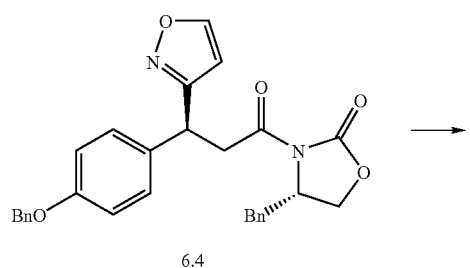

6.4

-continued

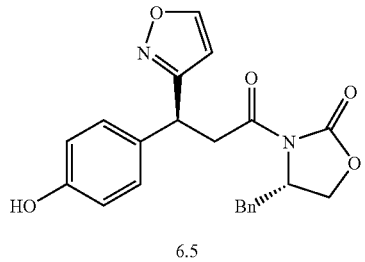

6.5

(S)-4-Benzyl-3-((S)-3-(4-hydroxyphenyl)-3-(isoxazol-3-yl)propanoyl)oxazolidin-2-one (6.5). Boron trichloride methyl sulfide complex (51 mL, 2.0 M solution in DCM) was added to 6.4 (8.2 g, 17 mmol) in DCM (100 mL) at 0° C. After addition, the ice bath was removed, and the mixture was stirred at room temperature for 7 hours. The mixture was cooled in an ice bath and quenched by adding saturated sodium bicarbonate until the mixture was neutralized. More DCM (400 mL) was added, and the organic layer was separated, washed with brine, dried, and concentrated under vacuum. The crude product (6.5 g) was dissolved in 50 mL of hot MeOH. After cooling, the crystallized product was collected by filtration and washed once with MeOH to give 6.5 (4.2 g). The filtrate was concentrated, and the solid that formed was collected and washed to give an additional 1.2 g of compound 6.5. MS ESI (pos.) m/e: 393 (M+H). $^1$H NMR (CDCl$_3$) δ 8.29(d, 1H), 7.30 (m, 3H), 7.20 (d, 2H), 7.15 (d, 2H), 6.95 (d, 2H), 6.14 (d, 1H), 4.71 (dd, 1H), 4.63 (m, 1H), 4.16 (d, 2H), 4.00 (dd, 1H), 3.54 (dd, 1H), 3.21 (dd, 1H), 2.76 (dd, 1H).

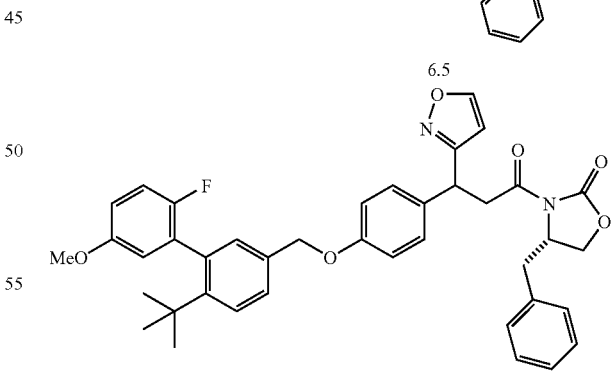

(4S)-3-((3S)-3-(4-(((6-(1,1-Dimethylethyl)-2'-fluoro-5'-(methyloxy)-1,1'-biphenyl-3-yl)methyl)oxy)phenyl)-3-(3-isoxazolyl)propanoyl)-4-(phenylmethyl)-1,3-oxazolidin-2-one (6.6). To a stirred solution of compound 6.5 (0.025 g, 0.064 mmol) in DMF (2.00 mL, 0.14 mmol) at 23° C. was added A (0.023 g, 0.076 mmol) followed by cesium carbonate (0.025 g, 0.076 mmol). Stirring was continued for 18 hours. Water (5.0 mL) was added to the mixture, and the mixture was extracted with EtOAc (3×10 mL). The combined organic layers were dried over MgSO$_4$ and concentrated in vacuo. The residue was then purified by flash chromatography (SiO$_2$ gel 60, eluted with 0%-20% EtOAc in hexanes) to give compound 6.6 as a clear oil (0.0282 g, 67% yield). $^1$H NMR (500 MHz, CDCl$_3$) δ ppm 8.28 (1H, d, 1.2 Hz), 7.57 (1H, d, J=7.9 Hz), 7.38 (2H, dd, J=7.9, 2.8 Hz), 7.34-7.31 (2H, m), 7.28-7.26 (1H, m), 7.23-7.19 (4H, m), 7.07 (1H, d, J=1.8 Hz), 6.99 (1H, t, J=8.6 Hz), 6.93 (1 H, d, J=9.0 Hz), 6.86 (H, dt, J=8.5, 3.6 Hz), 6.79 (H, dd, J=5.4, 3.3 Hz), 6.13 (I H, d, J=1.2 Hz), 4.98 (1H, s), 4.74 (1H, t, J=7.4 Hz), 4.61 (1H, m), 4.15-4.10 (2H, m), 4.01 (1H, ddd, J=17.8, 8.6, 2.0 Hz), 3.78 (3H, s), 3.54 (1H, ddd, J=17.8, 6.7, 1.8 Hz), 3.20 (1H, dd, J=13.4, 3.0 Hz), 2.76 (1H, dd, J=13.4, 9.3 Hz), 1.22 (9H, s).

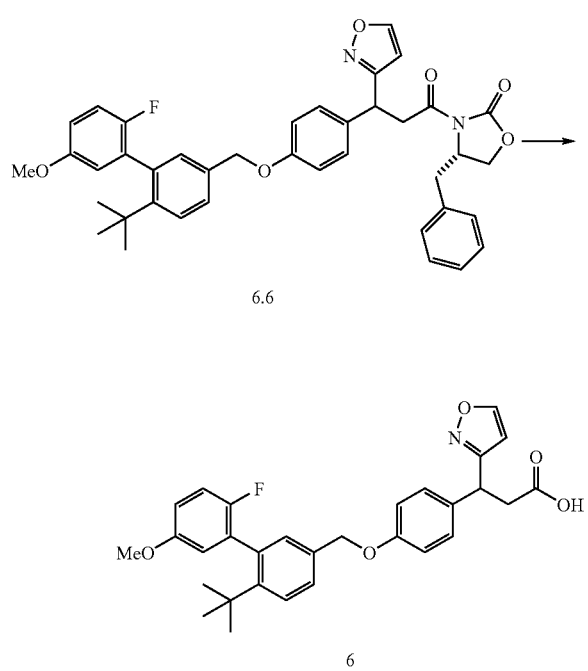

(3S)-3-(4-(((6-(1,1-Dimethylethyl)-2'-fluoro-5'-(methyloxy)-1,1'-biphenyl-3-yl)methyl)oxy)phenyl)-3-(3-isoxazolyl)propanoic acid (6). To a stirred solution of 6.6 (0.0282 g, 0.043 mmol) in THF (3.00 mL, 37 mmol) and water (1.00 mL, 56 mmol) at 0° C. was added 35% hydrogen peroxide (0.025 mL, 0.26 mmol) followed by lithium hydroxide (0.0020 g, 0.085 mmol). Stirring continued for 1 hour and 40 minutes. A saturated solution of Na$_2$SO$_3$ was added, and stirring was continued at 0° C. for 30 minutes. The mixture was extracted with EtOAc (3×10 mL). The combined organic layers were dried over MgSO$_4$ and concentrated in vacuo. The residue was then purified by flash chromatography (SiO$_2$ gel 60, eluted with 0%-30% EtOAc/hexane) to give compound 6 as a clear oil (0.0103 g, 48% yield). $^1$H NMR (400 MHz, CDCl$_3$) δ ppm 8.28 (1H, d, J=1.6 Hz), 7.58 (1H, d, J=8.6 Hz), 7.40 (1H, dd, J=8.2, 2.0 Hz), 7.17 (2H, d, J=8.8 Hz), 6.86 (1H, dt, J=8.0, 3.9 Hz), 6.78 (1H, dd, J=5.9, 3.1 Hz), 6.07 (1H, d, J=1.6 Hz), 4.99 (2H, s), 4.54 (1H, dd, J=7.9, 7.4 Hz), 3.79 (3H, s), 3.35 (1H, dd, J=16.6, 7.9 Hz), 2.98 (1H, dd, J=16.4, 7.4 Hz), 1.23 (9H, s). MS ESI (neg.) m/e: 502.1 (M–H)$^+$.

Example 7

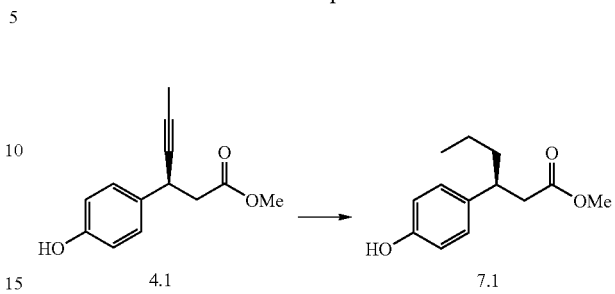

Methyl (3S)-3-(4-hydroxyphenyl)hexanoate (7.1). To a stirred solution of compound 4.1 (0.0500 g, 0.23 mmol) in EtOH (2.00 mL, 34 mmol) and EtOAc (2.00 mL, 23 mmol) at 23° C. was added palladium on carbon (0.024 g, 0.23 mmol). The reaction mixture was placed under an atmosphere of hydrogen and stirring was continued for 5 hours. The mixture was filtered through a pad of silica gel and concentrated in vacuo. The residue was purified by flash chromatography (SiO$_2$ gel 60, eluted with 0%-20% EtOAc in hexanes) to give compound 7.1 as a clear oil (0.051 g, 100% yield). MS ESI (pos.) m/e: 245.1 (M+Na)$^+$, 240.1 (M+H$_2$O)$^+$, 223.1 (M+H)$^+$.

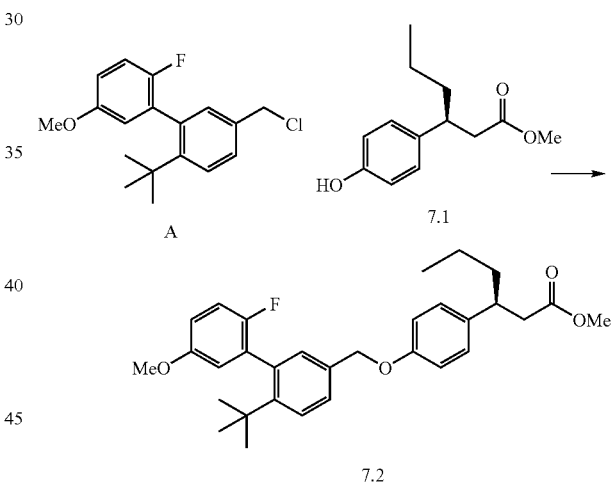

Methyl (3S)-3-(4-(((6-(1,1-dimethylethyl)-2'-fluoro-5'-(methyloxy)-1,1'-biphenyl-3-yl)methyl)oxy)phenyl)hexanoate (7.2). Compound 7.1 (0.051 g, 0.2 mmol) was alkylated by reaction with compound A (0.08 g, 0.3 mmol) according to the method given in Example 1 to give compound 7.2 as a clear oil (0.05 g, 44% yield). MS ESI (pos.) m/e: 515.2 (M+Na)$^+$, 510.2 (M+H$_2$O)$^+$.

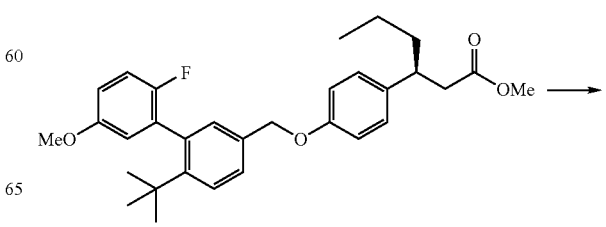

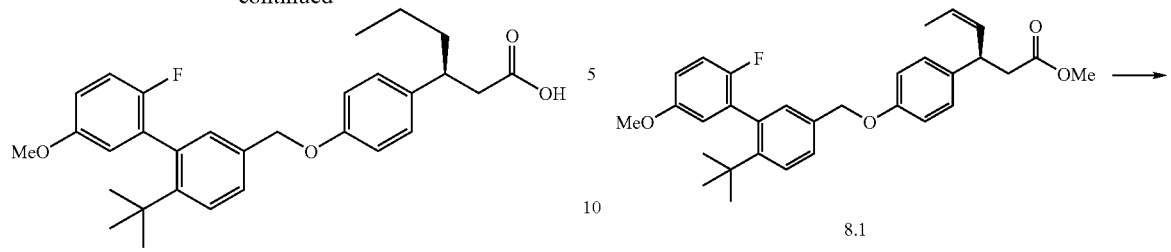

(3S)-3-(4-(((6-(1,1-Dimethylethyl)-2'-fluoro-5'-(methyloxy)-1,1'-biphenyl-3-yl)methyl)oxy)phenyl)hexanoic acid (7). Compound 7.2 (0.05 g, 0.1 mmol) was hydrolyzed according to the method reported for Example 1 to give compound 7 as a clear oil (0.0323 g, 66% yield). $^1$H NMR (400 MHz, CDCl$_3$) δ ppm 7.58 (1H, d, J=8.2 Hz), 7.41 (1H, dd, J=8.4, 1.8 Hz), 7.13-7.08 (3H, m), 7.00 (1H, t, J=8.8 Hz), 6.91 (2H, J=8.6 Hz), 6.85 (1H, dt, J=8.9, 3.5 Hz), 6.80 (1H, ddd, J=5.9, 3.1, 1.2 Hz), 4.99 (2H, s), 3.79 (3H, s), 3.05 (1H, m), 2.60 (2H, dd, J=11.5, 7.6 Hz), 1.67-1.51 (2H, m), 1.24 (9H, s), 1.21-1.13 (2H, m), 0.85 (3H, t, J=7.2 Hz). MS ESI (neg.) m/e: 955.5 (2M−H)$^+$, 477.2 (M−H)$^+$.

Example 8

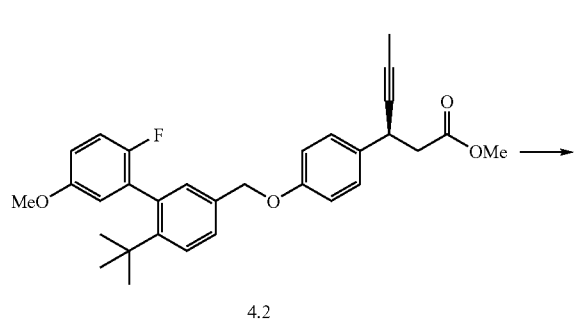

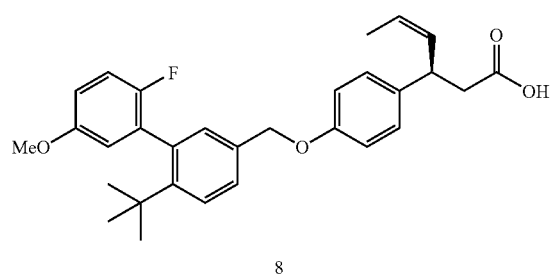

Methyl (3R,4Z)-3-(4-(((6-(1,1-dimethylethyl)-2'-fluoro-5'-(methyloxy)-1,1'-biphenyl-3-yl)methyl)oxy)phenyl)-4-hexenoate (8.1). To a stirred solution of 4.2 (0.055 g, 0.11 mmol) in EtOAc (4.00 mL, 41 mmol) at 23° C. was added quinoline (0.500 mL, 4.2 mmol) followed by Lindlar's Catalyst (0.012 g, 0.11 mmol). The reaction mixture was placed under an atmosphere of hydrogen and stirring was continued for 40 hours. The mixture was filtered through a pad of silica gel. The filtrate was washed with 1N HCl (3×10 mL), and the organic layer was dried over MgSO$_4$ and concentrated in vacuo. The residue was then purified by flash chromatography (SiO$_2$ gel 60, eluted with 0%-20% EtOAc in hexanes) to give compound 8.1 as a clear oil (0.0529 g, 96% yield). MS ESI (pos.) m/e: 513.3 (M+Na)$^+$, 508.3 (M+H$_2$O)$^+$.

(3R,4Z)-3-(4-(((6-(1,1-Dimethylethyl)-2'-fluoro-5'-(methyloxy)-1,1'-biphenyl-3-yl)methyl)oxy)phenyl)-4-hexenoic acid (8). To a stirred solution of 8.1 (0.0529 g, 0.11 mmol) in THF (2.00 mL, 24 mmol) and EtOH (2.00 mL, 34 mmol) at 23° C. was added 1N sodium hydroxide (2.00 mL, 2.0 mmol). Stirring continued for 17 hours. The reaction mixture was concentrated in vacuo, 1N HCl was added to reach pH 1, and the resulting mixture was extracted with EtOAc (3×10 mL) dried over MgSO$_4$ and concentrated in vacuo. The residue was then purified by flash chromatography (SiO$_2$ gel 60, eluted with 0%-20% EtOAc in hexanes) to give compound 8 as a clear oil (0.0382 g, 74% yield). $^1$H NMR (400 MHz, CDCl$_3$) δ ppm 7.58 (1H, d, J=8.2 Hz), 7.40 (1H, dd, J=8.2, 2.0 Hz), 7.16 (2H, d, J=9.0 Hz), 7.08 (1H, d, J=2.0 Hz), 7.00 (1H, t, J=8.8 Hz), 6.92 (2H, d, J=9.0 Hz), 6.87 (1H, dt, J=8.9, 3.9 Hz), 6.80 (1H, m), 5.58-5.49 (2H, m), 4.99 (2H, s), 4.14 (1H, m), 3.79 (3H, s), 2.75 (1H, dd, J=15.1, 6.8 Hz), 2.64 (1H, dd, J=15.1, 8.6 Hz), 1.66 (3H, d, J=5.1 Hz), 1.23 (9H, s). m/e: 951.4 (2M−H)$^+$, 475.1 (M−H)$^+$.

Example 9

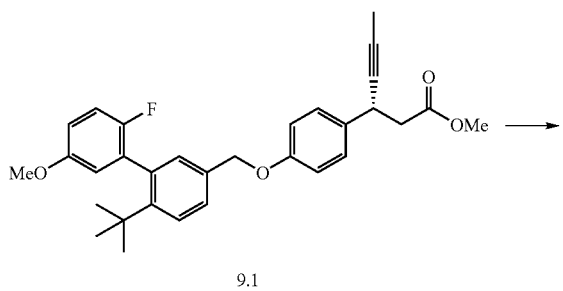

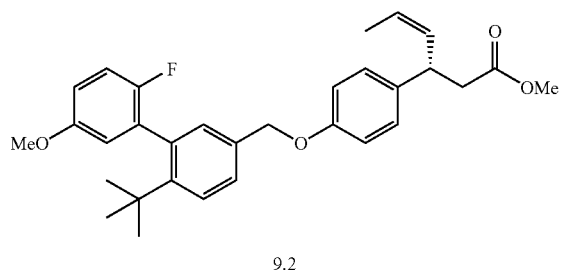

9.2

Methyl (3S,4Z)-3-(4-(((6-(1,1-dimethylethyl)-2'-fluoro-5'-(methyloxy)-1,1'-biphenyl-3-yl)methyl)oxy)phenyl)-4-hexenoate (9.2). Compound 9.1 (0.070 g, 0.14 mmol) was reduced according to the procedure given in Example 8 to give compound 9.2 as a clear oil (0.0349 g, 50% yield). MS ESI (pos.) m/e: 513.3 (M+Na)+, 491.2 (M+H)+.

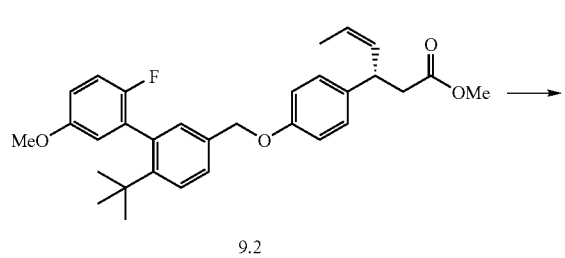

9.2

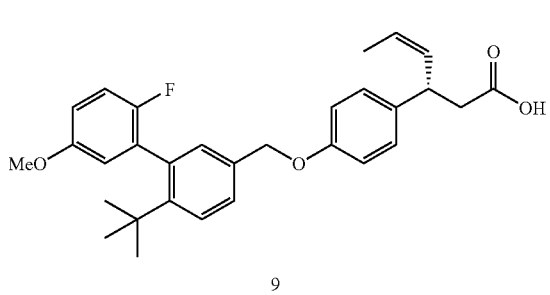

9

(3S,4Z)-3-(4-(((6-(1,1-Dimethylethyl)-2'-fluoro-5'-(methyloxy)-1,1'-biphenyl-3-yl)methyl)oxy)phenyl)-4-hexenoic acid (9). Compound 9.2 (0.0349 g, 0.071 mmol) was hydrolyzed according to the method given in Example 1 to give compound 9 as a clear oil (0.0274 g, 81% yield). $^1$H NMR (400 MHz, CDCl$_3$) δ ppm 7.58 (1H, d, J=8.2 Hz), 7.40 (1H, dd, J=8.4, 2.2 Hz), 7.16 (2H, d, J=8.6 Hz), 7.08 (1H, d, J=2.0 Hz), 7.00 (1H, t, J=8.6 Hz), 6.92 (2H, d, J=8.6 Hz), 6.87 (1H, dt, J=9.0, 4.0 Hz), 6.79 (1H, m), 5.58-5.51 (2H, m), 4.99 (2H, s), 4.14 (1H, m), 3.79 (3H, s), 2.75 (1H, dd, J=15.5, 6.9 Hz), 2.64 (1H, dd, J=15.5, 8.1 Hz), 1.66 (3H, d, J=5.2 Hz), 1.23 (9H, s). m/e: 951.4 (2M–H)+, 475.1 (M–H)+.

Example 10

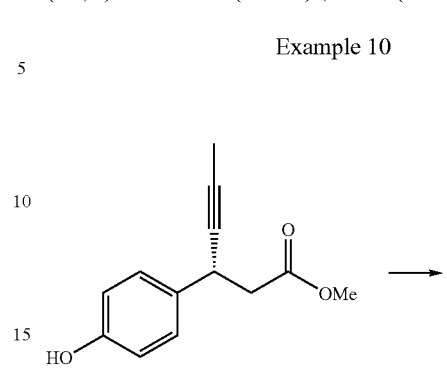

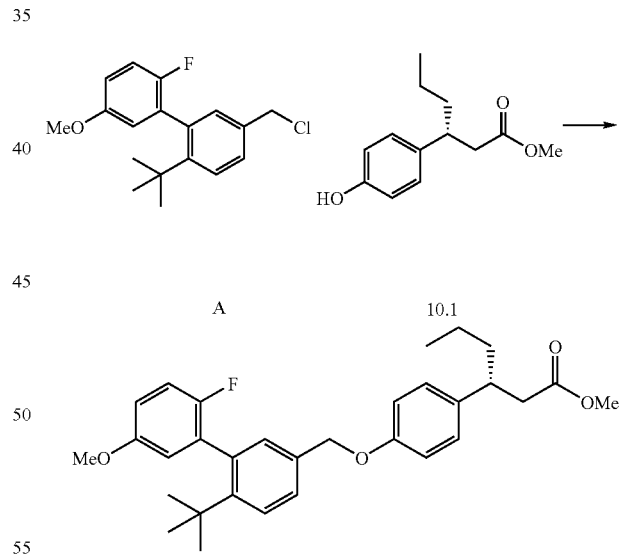

Methyl (3R)-3-(4-hydroxyphenyl)hexanoate (10.1). Compound 5.1 (0.0500 g, 0.23 mmol) was reduced according to the method of Example 7 to obtain compound 10.1 as a clear oil (0.050 g, 98% yield). MS ESI (pos.) m/e: 245.1 (M+Na)+, 240.1 (M+H$_2$O)+, 223.1 (M+H)+.

Methyl (3R)-3-(4-(((6-(1,1-dimethylethyl)-2'-fluoro-5'-(methyloxy)-1,1'-biphenyl-3-yl)methyl)oxy)phenyl)hexanoate (10.2). Compound 10.1 (0.050 g, 0.22 mmol) was alkylated by reaction with benzyl chloride A (0.076 g, 0.25 mmol) according to the method of Example 1 to obtain compound 10.2 as a clear oil (0.018 g, 16% yield). MS ESI (pos.) m/e: 515.2 (M+Na)+, 510.2 (M+H$_2$O)+.

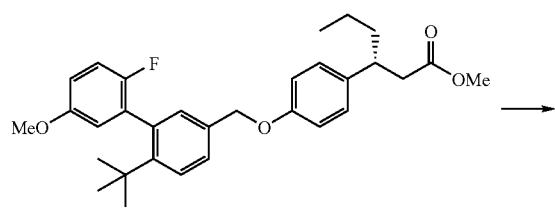

10.2

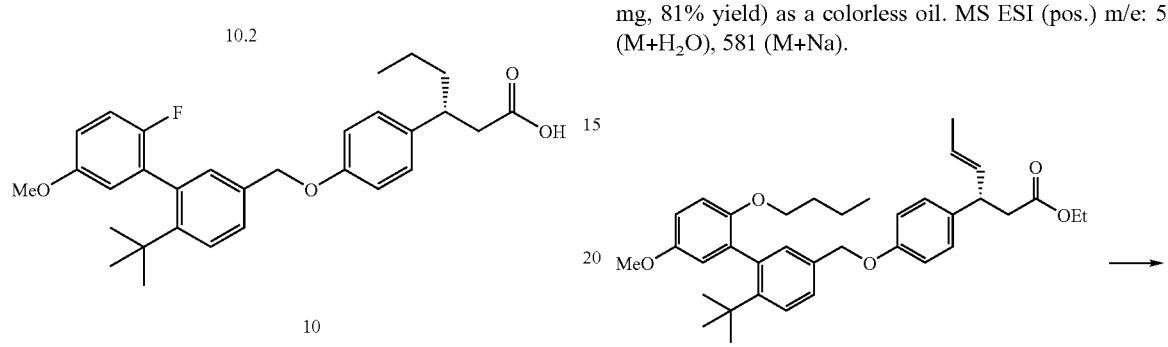

10

(3R)-3-(4-(((6-(1,1-Dimethylethyl)-2'-fluoro-5'-(methyloxy)-1,1'-biphenyl-3-yl)methyl)oxy)phenyl)hexanoic Acid (10). Compound 10.2 (0.018 g, 0.037 mmol) was hydrolyzed according to the method of Example 1 to obtain compound 10 as a clear oil (0.016 g, 91% yield). $^1$H NMR (400 MHz, CDCl$_3$) δ ppm 7.59 (1H, d, J=8.2 Hz), 7.42 (1H, dd, J=8.2, 2.0 Hz), 7.13-7.07 (3H, m), 7.00 (1H, t, J=8.8 Hz), 6.91 (2H, J=8.5 Hz), 6.85 (1H, dt, J=8.8, 3.4 Hz), 6.80 (1H, m), 4.99 (2H, s), 3.79 (3H, s), 3.05 (1H, m), 2.60 (2H, dd, J=11.0, 7.4 Hz), 1.67-1.51 (2H, m), 1.24 (9H, s), 1.21-1.13 (2H, m), 0.86 (3H, t, J=7.2 Hz). MS ESI (neg.) m/e: 955.5 (2M−H)$^+$, 477.2 (M−H)$^+$.

Example 11

Ethyl (3S,4E)-3-(4-(((2'-(butyloxy)-6-(1,1-dimethylethyl)-5'-(methyloxy)-1,1'-biphenyl-3-yl)methyl)oxy)phenyl)-4-hexenoate (11.1). A mixture of compound B (11 mg, 47 μmol), compound C (17 mg, 47 μmol), and cesium carbonate (23 mg, 70 μmol) in DMF (1.0 mL) was stirred for 16 hours at 23° C. The mixture was diluted with EtOAc, washed with water and brine, dried over MgSO$_4$, and concentrated. The crude product was purified by silica gel flash chromatography (0-10% EtOAc/hexane) to afford compound 11.1 (21 mg, 81% yield) as a colorless oil. MS ESI (pos.) m/e: 576 (M+H$_2$O), 581 (M+Na).

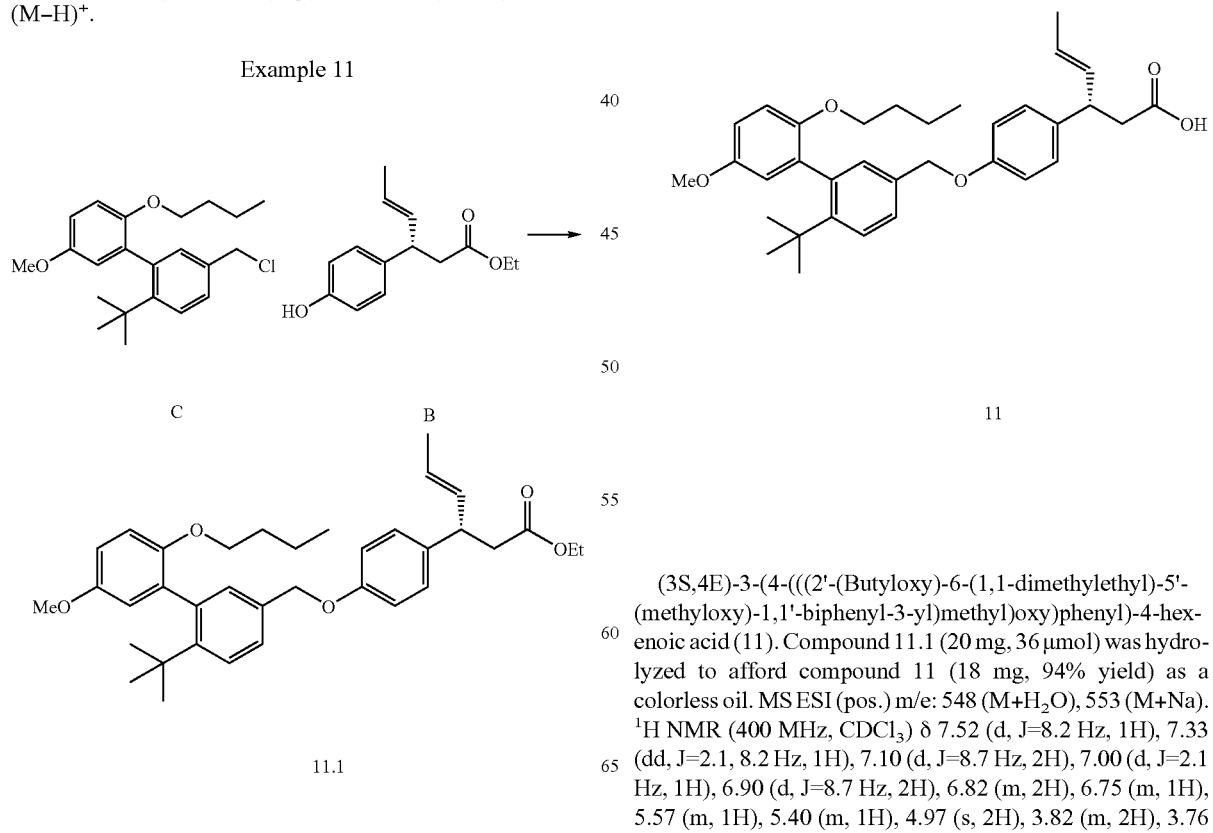

(3S,4E)-3-(4-(((2'-(Butyloxy)-6-(1,1-dimethylethyl)-5'-(methyloxy)-1,1'-biphenyl-3-yl)methyl)oxy)phenyl)-4-hexenoic acid (11). Compound 11.1 (20 mg, 36 μmol) was hydrolyzed to afford compound 11 (18 mg, 94% yield) as a colorless oil. MS ESI (pos.) m/e: 548 (M+H$_2$O), 553 (M+Na). $^1$H NMR (400 MHz, CDCl$_3$) δ 7.52 (d, J=8.2 Hz, 1H), 7.33 (dd, J=2.1, 8.2 Hz, 1H), 7.10 (d, J=8.7 Hz, 2H), 7.00 (d, J=2.1 Hz, 1H), 6.90 (d, J=8.7 Hz, 2H), 6.82 (m, 2H), 6.75 (m, 1H), 5.57 (m, 1H), 5.40 (m, 1H), 4.97 (s, 2H), 3.82 (m, 2H), 3.76

(s, 3H), 3.74 (m, 1H), 2.69 (m, 2H), 1.65 (m, 3H), 1.51 (m, 2H), 1.21 (m, 11H), 0.79 (t, J=7.4 Hz, 3H).

Example 12

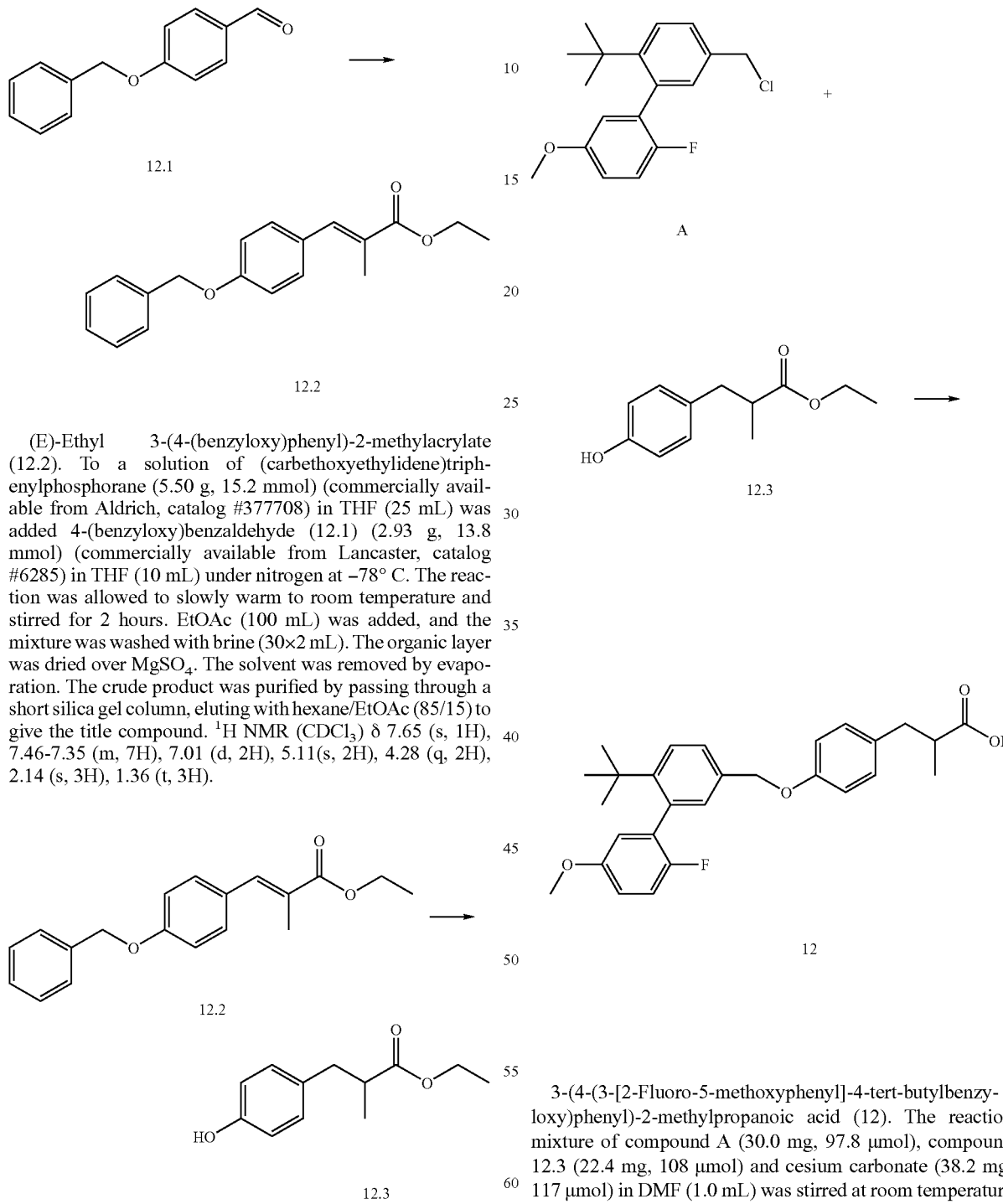

(E)-Ethyl 3-(4-(benzyloxy)phenyl)-2-methylacrylate (12.2). To a solution of (carbethoxyethylidene)triphenylphosphorane (5.50 g, 15.2 mmol) (commercially available from Aldrich, catalog #377708) in THF (25 mL) was added 4-(benzyloxy)benzaldehyde (12.1) (2.93 g, 13.8 mmol) (commercially available from Lancaster, catalog #6285) in THF (10 mL) under nitrogen at −78° C. The reaction was allowed to slowly warm to room temperature and stirred for 2 hours. EtOAc (100 mL) was added, and the mixture was washed with brine (30×2 mL). The organic layer was dried over MgSO$_4$. The solvent was removed by evaporation. The crude product was purified by passing through a short silica gel column, eluting with hexane/EtOAc (85/15) to give the title compound. $^1$H NMR (CDCl$_3$) δ 7.65 (s, 1H), 7.46-7.35 (m, 7H), 7.01 (d, 2H), 5.11(s, 2H), 4.28 (q, 2H), 2.14 (s, 3H), 1.36 (t, 3H).

Ethyl 3-(4-hydroxyphenyl)-2-methylpropanoate (12.3). The reaction mixture compound 12.2 (2.80 g, 9.45 mmol) and Pd/C (0.40 g, wt 10% on activated carbon) in EtOH (35 mL) was purged with hydrogen three times and stirred under hydrogen at ambient temperature overnight. The catalyst was removed by filtration. The filtrate was evaporated to give the crude compound 12.3 which was used in the next step without further purification. MS ESI (pos.) m/e: 209 (M+H). $^1$H NMR (CDCl$_3$) δ 7.02(d, 2H), 6.75(d, 2H), 4.11(q, 2H), 2.93(dd, 1H), 2.68(m, 2H), 1.21(t, 3H), 1.16(d, 3H).

3-(4-(3-[2-Fluoro-5-methoxyphenyl]-4-tert-butylbenzyloxy)phenyl)-2-methylpropanoic acid (12). The reaction mixture of compound A (30.0 mg, 97.8 μmol), compound 12.3 (22.4 mg, 108 μmol) and cesium carbonate (38.2 mg, 117 μmol) in DMF (1.0 mL) was stirred at room temperature overnight. The resulting reaction mixture was treated with lithium hydroxide (23.4 mg, 978 μmol) in water (0.5 mL), and stirred at room temperature for 5 hours. The reaction mixture was purified by reverse phase preparative HPLC to give the title compound. MS ESI (neg.) m/e: 449 (M−H). $^1$H NMR (CD$_3$CN) δ 7.61(d, 1H), 7.41(d, 1H), 7.11(d, 2H), 7.06(m, 2H), 6.93(m, 1H), 6.89(d, 2H), 6.81(d, 1H), 5.02(s, 2H), 3.77 (s, 3H), 2.86(dd, 1H), 2.63(m, 2H), 1.21(s, 9H), 1.09(d, 3H).

Example 13

(1H, t, J=9.0 Hz), 6.93 (1H, dt, J=9.0, 3.5 Hz), 6.82 (1H, dd, J=5.1, 3.1 Hz), 3.93 (3H, s), 3.83 (3H, s).

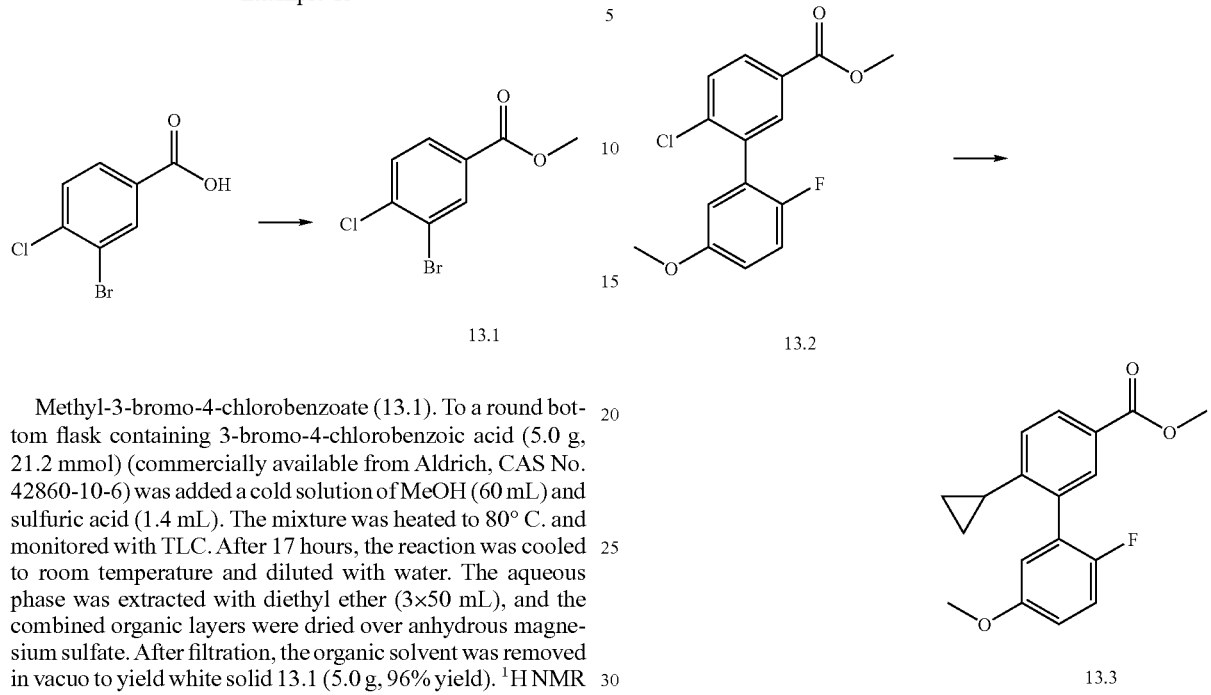

Methyl-3-bromo-4-chlorobenzoate (13.1). To a round bottom flask containing 3-bromo-4-chlorobenzoic acid (5.0 g, 21.2 mmol) (commercially available from Aldrich, CAS No. 42860-10-6) was added a cold solution of MeOH (60 mL) and sulfuric acid (1.4 mL). The mixture was heated to 80° C. and monitored with TLC. After 17 hours, the reaction was cooled to room temperature and diluted with water. The aqueous phase was extracted with diethyl ether (3×50 mL), and the combined organic layers were dried over anhydrous magnesium sulfate. After filtration, the organic solvent was removed in vacuo to yield white solid 13.1 (5.0 g, 96% yield). $^1$H NMR (400 MHz, CDCl$_3$) δ ppm 8.28 (1H, d, J=2.0 Hz), 7.93 (1H, m), 7.52 (1H, d, J=8.2 Hz), 3.93 (3H, s).

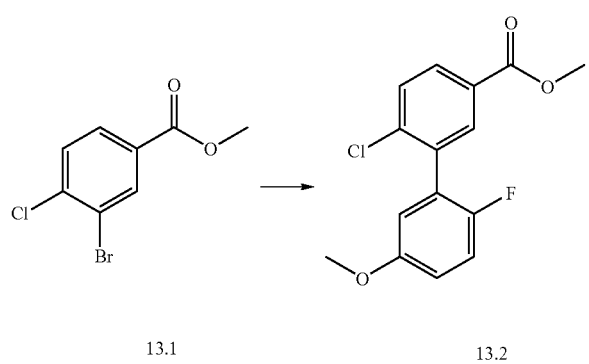

Methyl-3-chloro-2'-fluoro-5'-(methyloxy)-1,1'-biphenyl-5-carboxylate (13.2). To a round bottom flask containing 13.1 (1.75 g, 7.01 mmol), 2-fluoro-5-methoxyphenylboronic acid (2.0 g, 11.8 mmol), tetrakis(triphenylphosphine)palladium (0) (0.81 g, 0.70 mmol), and potassium carbonate (2.91 g, 21.0 mmol) was added a premixed 3:1 solution of toluene (18 mL) and DMF (6 mL, 7.01 mmol). The mixture was heated at 100° C. and monitored with TLC. After 17 hours, the reaction was cooled to room temperature then partitioned between EtOAc and water. The aqueous layer was further extracted with EtOAc (2×20 mL). The organic layers were combined, washed with brine, and dried over anhydrous magnesium sulfate. The magnesium sulfate was removed by filtering, and the organic phase was concentrated under reduced pressure. The residue was purified by flash chromatography (SiO$_2$ gel 60, eluted with 0 to 20% EtOAc in hexanes) to yield a colorless oil 13.2 (1.01 g, 49% yield.) $^1$H NMR (400 MHz, CDCl$_3$) δ ppm 8.04 (1H, m), 8.02 (1H, m) 7.57 (1H, d, J=8.2 Hz), 7.09

Methyl-6-cyclopropyl-2'-fluoro-5'-(methyloxy)-1,1'-biphenyl-3-carboxylate (13.3). To a round bottom flask containing 13.2 (0.46 g, 1.56 mmol), cyclopropylboronic acid (0.40 g, 4.67 mmol), 2-dicyclohexylphosphino-2',6'-dimethoxybiphenyl (0.26 g, 0.638 mmol), palladium acetate (0.07 g, 0.31 mmol), and potassium phosphate tribasic (1.00 g, 4.71 mmol), was added a premixed solution of 1,4-dioxane (1.0 mL) and water (0.3 mL). The mixture was stirred at room temperature for 5 minutes and then heated to 88° C. and monitored with TLC. After 4 hours, the reaction was cooled to room temperature and diluted with EtOAc. The mixture was then filtered through a pad of silica gel (eluting with EtOAc) and concentrated under reduced pressure. The crude residue was purified by flash chromatography (SiO$_2$ gel 60, eluted with 0 to 25% EtOAc in hexanes) to yield a colorless oil 13.3 (0.4 g, 85% yield.) $^1$H NMR (400 MHz, CDCl$_3$) δ ppm 7.99 (2H, m), 7.07 (1H, t, J=8.8 Hz), 6.96 (1H, d, J=8.2 Hz), 6.91 (2H, m), 3.89 (3H, s), 3.81 (3H, s), 1.84 (1H, dt, J=8.6, 4.3 Hz), 0.93 (2H, m), 0.75 (2H, m).

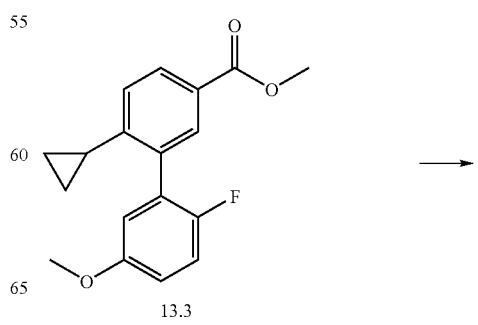

-continued

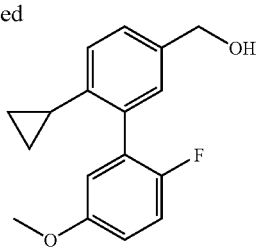

13.4

(6-Cyclopropyl-2'-fluoro-5'-(methyloxy)-1,1'-biphenyl-3-yl)methanol (13.4). To a dry round bottom flask containing 13.3 (0.4 g, 1.328 mmol) under an argon atmosphere was added dry THF (6 mL). The resulting mixture was cooled to 0° C. After 15 minutes, lithium aluminum hydride (1.0 M solution in THF) (2.0 mL, 2.00 mmol) was carefully added at 0° C. Upon complete addition, the reaction was allowed to warm to room temperature. After 2 hours, the reaction was cooled in an ice bath, and then carefully quenched with water and diluted with EtOAc. The organic phase was washed with 2M HCl and then with brine. After drying over anhydrous magnesium sulfate, the organic solvent was removed under reduced pressure, and the residue was purified by flash chromatography (SiO₂ gel 60, eluted with 0 to 40% EtOAc in hexanes) to yield a colorless oil 13.4 (0.24 g, 66% yield.).

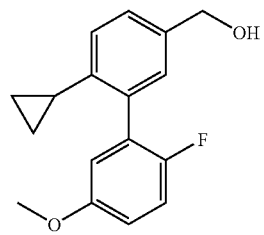

13.4

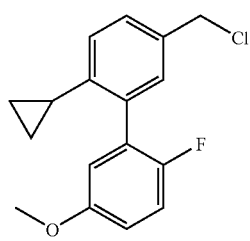

13.5

3-(Chloromethyl)-6-cyclopropyl-2'-fluoro-5'-(methyloxy)-1,1'-biphenyl (13.5). To a dry, round bottom flask containing 13.4 (0.24 g, 0.88 mmol) under an argon atmosphere was added dry DCM (5 mL). The resulting homogeneous solution was cooled to 0° C. After 15 minutes, thionyl chloride (0.20 mL, 2.74 mmol) was added dropwise at 0° C. Upon complete addition of thionyl chloride, the mixture was allowed to warm to room temperature and for 16 hours. After 19 hours, the solvent was removed under reduced pressure. The crude material was purified by flash chromatography (SiO₂ gel 60, eluted with 0 to 15% EtOAc in hexanes) to yield a colorless oil 13.5 (0.13 g, 49% yield.) ¹H NMR (400 MHz, CDCl₃) δ ppm 7.36 (2H, dd, J=8.2, 2.0 Hz), 7.13 (1H, m), 6.98 (1H, d, J=8.2 Hz), 6.93 (2H, m), 4.62 (2H, s), 3.84 (3H, s), 1.87 (1H, m), 0.91 (2H, m), 0.7 (2H, m).

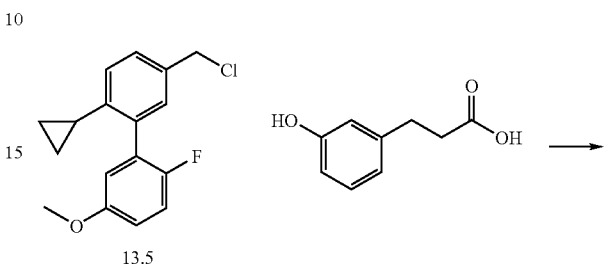

13.5

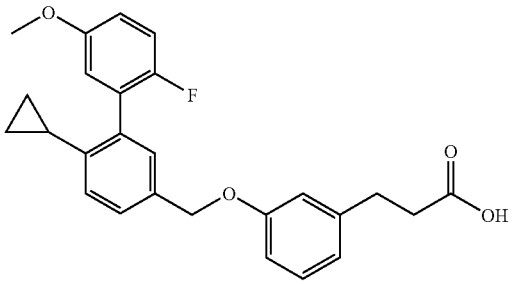

13

3-(3-(((6-Cyclopropyl-2'-fluoro-5'-(methyloxy)-1,1'-biphenyl-3-yl)methyl)oxy)phenyl)propanoic acid (13). To a solution of 3-(3-hydroxyphenyl)-propionic acid (0.031 g, 0.186 mmol) (commercially available from Alfa, CAS No. 621-54-5) in THF (1 mL) was added tetrabutylphosphonium hydroxide (40 wt % solution in water) (0.27 g, 0.39 mmol). The mixture was then cooled in an ice bath to 0° C. After 10 minutes, 13.5 (0.055 g, 0.191 mmol) was added at 0° C. Upon complete addition, the reaction was allowed to warm to room temperature. After 44 hours, the solvent was removed under vacuum. The residue was diluted with water and acidified with 2M HCl to pH 2. The mixture was extracted with EtOAc. The layers were separated and the solvent was removed under vacuum to yield an oil that was purified by flash chromatography (SiO₂ gel 60, eluted with 0 to 65% EtOAc in hexanes) to yield a colorless film 13 (0.023 g, 28% yield.) ¹H NMR (400 MHz, CDCl₃) δ ppm 7.39 (1H, dd, J=8.0, 1.8 Hz), 7.31 (1H, d, J=2.0 Hz), 7.23 (1H, t, J=8.0 Hz), 7.10 (1H, m), 6.99

(1H, d, J=7.8 Hz), 6.90 (5H, m), 5.04 (2H, s), 3.82 (3H, s), 2.95 (2H, t, J=7.8 Hz), 2.72 (2H, m), 1.85 (1H, m), 0.87 (2H, m), 0.68 (2H, m).

Example 14

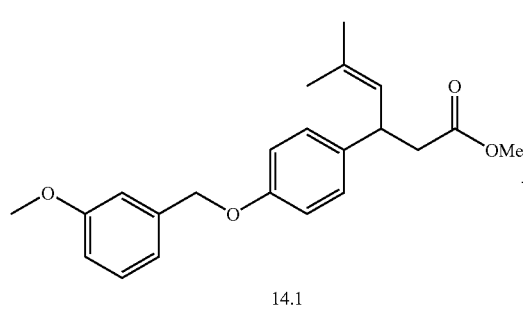

14.1

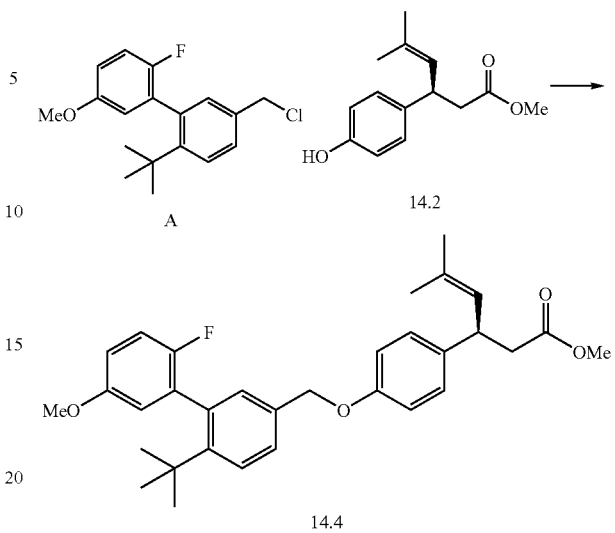

Methyl (3R)-3-(4-(((6-(1,1-dimethylethyl)-2'-fluoro-5'-(methyloxy)-1,1'-biphenyl-3-yl)methyl)oxy)phenyl)-5-methyl-4-hexenoate (14.4). To a stirred solution of methyl (3R)-3-(4-hydroxyphenyl)-5-methylhex-4-enoate 14.2 (0.025 g, 0.10 mmol) in DMF (1.0 mL, 0.10 mmol) at 0° C. was added A (0.034 g, 0.11 mmol), followed by cesium carbonate (0.036 g, 0.11 mmol). The reaction mixture was stirred at 23° C. for 23 hours. Water was added to the reaction, and the resulting mixture was extracted with EtOAc. The organic layer was dried over MgSO₄, and concentrated. The crude product was purified by silica gel flash chromatography (0-20% EtOAc/hexane) to afford compound 14.4 (0.048 g, 92% yield). MS ESI (pos.) m/e: 536.3 (M+H₂O).

Methyl (3R)-3-(4-hydroxyphenyl)-5-methyl-4-hexenoate (14.2) and methyl (3S)-3-(4-hydroxyphenyl)-5-methyl-4-hexenoate (14.3). Compound 14.1 is prepared as described in U.S. Patent Application Publication No. 2006/0004012 which is hereby incorporated by reference in its entirety and for all purposes as if specifically set forth herein. Debenzylation of compound 14.1 is accomplished by treatment with the strong acid resin Amberlyst-15 and 4 equivalents of MeOH in toluene at 80° C. using the method described in *J. Org. Chem.* 2006, 71, 2892-95. The racemic mixture thus obtained is separated using chiral HPLC by methods known to those skilled in the art to provide 14.2 and 14.3. It is believed that 14.2 and 14.3 have the stereochemistry shown, but this could be incorrect. Therefore, the stereochemistry of the products and intermediates shown in Examples 14, 16, 45, and 46 could be the opposite of that shown. However, both 14.2 and 14.3 were used to generate these Example compounds so both enantiomers were synthesized.

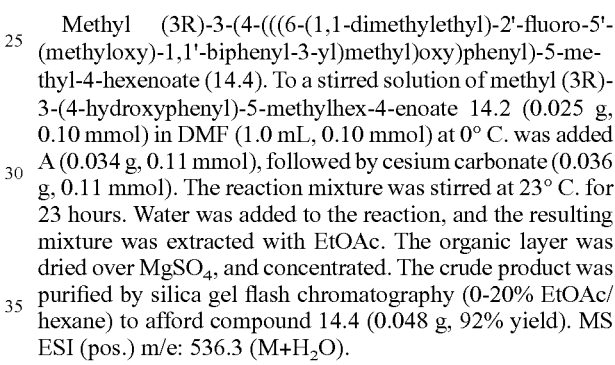

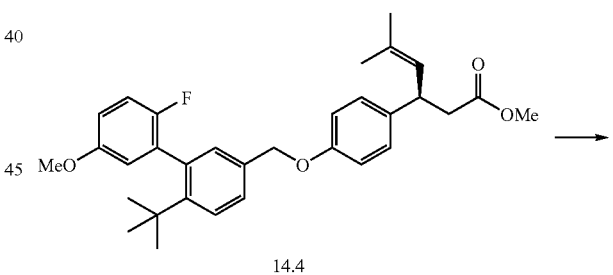

(3R)-3-(4-(((6-(1,1-Dimethylethyl)-2'-fluoro-5'-(methyloxy)-1,1'-biphenyl-3-yl)methyl)oxy)phenyl)-5-methyl-4-hexenoic acid (14). To a stirred solution of 14.4 (0.048 g, 0.10 mmol) in THF (2.00 mL, 0.10 mmol) and EtOH (2.00 mL, 0.10 mmol) at 23° C. was added a 1 M solution of sodium hydroxide (1 mL, 1 mmol). Stirring was continued for 15 hours. The resulting reaction was concentrated in vacuo. 1N HCl was added to bring the pH to 1, and the resulting mixture was extracted with EtOAc, dried over MgSO₄, and concentrated. The crude product was purified by silica gel flash chromatography (0-20% EtOAc/hexane) to afford compound 14 (30 mg, 64% yield) as a colorless oil. MS ESI (neg.) m/e: 489.2 (M−H)⁺.

Example 15

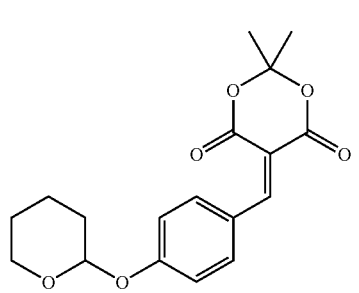

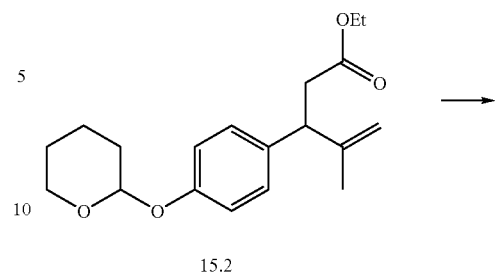

15.2

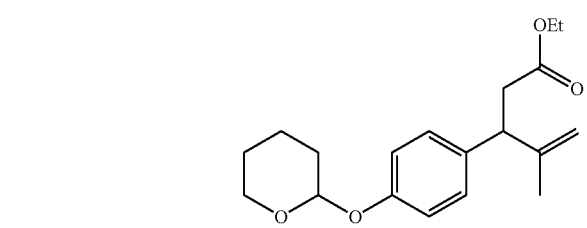

15.2

Ethyl 4-methyl-3-(4-(tetrahydro-2H-pyran-2-yloxy)phenyl)-4-pentenoate (15.2). To a stirred solution of 15.1 (5.00 g, 15.0 mmol) (prepared in an analogous manner to the procedure of Example 52 set forth in U.S. Patent Application Publication No. 2006/0004012 which is hereby incorporated by reference) in THF (50 mL) under nitrogen was added isopropenyl magnesium bromide in diethyl ether (75.0 mL, 38 mmol) over a period of 20 minutes. After the addition was complete, the reaction mixture was stirred for 45 minutes, quenched with a saturated aqueous solution of NH₄Cl (50 mL) and extracted with EtOAc (3×50 mL). The combined extracts were washed with water, dried over MgSO₄, filtered, and concentrated to a yellow solid. A solution of this yellow solid in pyridine:EtOH (5:1, v:v, 55 mL) was heated at 100° C. for 24 hours. The reaction mixture was cooled to room temperature and then concentrated in vacuo. The residue was then purified by flash chromatography (SiO₂ gel 60, eluted with 0%-20% EtOAc in hexanes). Fractions containing the desired product were combined and concentrated to provide 15.2 (0.30 g, 4.1%) as a colorless oil.

Ethyl 3-(4-hydroxyphenyl)-4-methyl-4-pentenoate (15.3). To a stirred solution of 15.2 (0.30 g, 0.90 mmol) in EtOH (100 mL) at room temperature was added PPTS (0.20 g, 0.90 mmol). The resulting solution was stirred for 16 hours and then concentrated in vacuo. The residue was then purified by flash chromatography (SiO₂ gel 60, eluted with 0%-20% EtOAc in hexanes) to give 15.3 (0.220 g, 100%) as a clear oil. MS ESI (pos.) m/e: 257.1 (M+Na)⁺, 252.1 (M+H₂O)⁺, 235.1 (M+H)⁺.

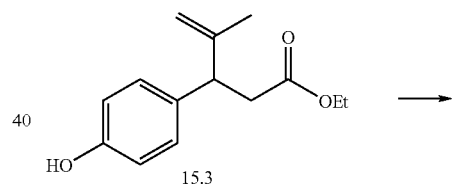

15.3

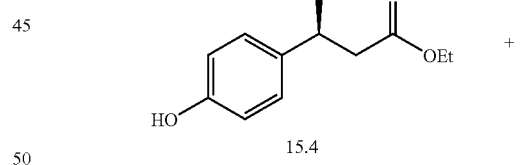

15.4

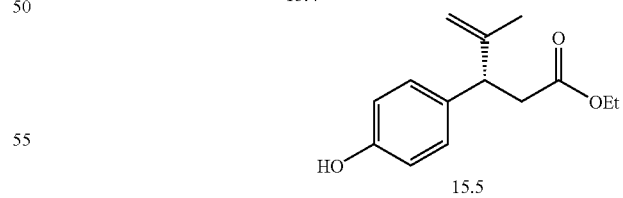

15.5

Ethyl (3R)-3-(4-hydroxyphenyl)-4-methyl-4-pentenoate (15.4) and ethyl (3S)-3-(4-hydroxyphenyl)-4-methyl-4-pentenoate (15.3). The racemic mixture was separated using chiral HPLC by methods known to those skilled in the art to provide compounds 15.4 and 15.5. It is believed that 15.4 and 15.5 have the stereochemistry shown, but this could be incorrect. Therefore, the stereochemistry of the products and intermediates shown in Examples 15 and 17 could be the opposite

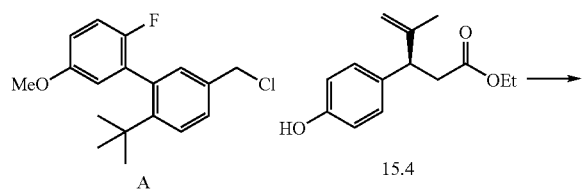

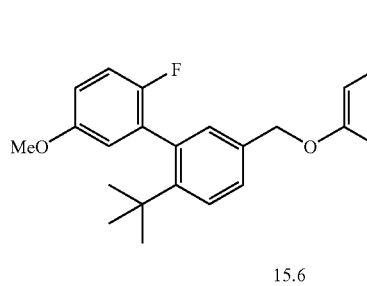

Ethyl (3R)-3-(4-(((6-(1,1-dimethylethyl)-2'-fluoro-5'-(methyloxy)-1,1'-biphenyl-3-yl)methyl)oxy)phenyl)-4-methyl-4-pentenoate (15.6). To a stirred solution of ethyl (3R)-3-(4-hydroxyphenyl)-4-methyl-4-pentenoate (15.4) (0.025 g, 0.11 mmol) in DMF (2.00 mL, 0.11 mmol) at 23° C. was added A (0.036 g, 0.12 mmol) followed by cesium carbonate (0.042 g, 0.13 mmol). Stirring was continued for 23 hours. Water was added to the reaction, and the resulting mixture was extracted with EtOAc. The organic layer was dried over MgSO$_4$, and concentrated. The crude product was purified by silica gel flash chromatography (0-20% EtOAc/hexane) to afford compound 15.6 (0.044 g, 82% yield). MS ESI (pos.) m/e: 522.2 (M+H$_2$O).

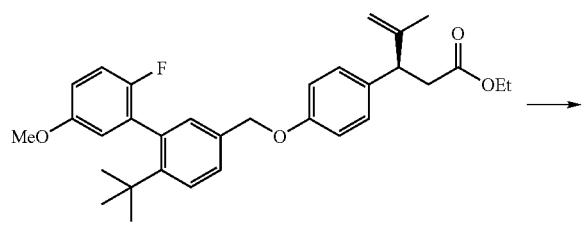

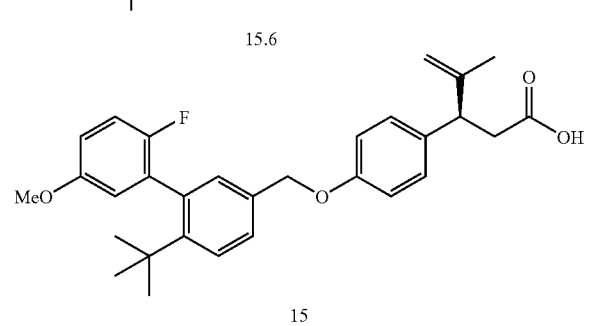

(3R)-3-(4-(((6-(1,1-Dimethylethyl)-2'-fluoro-5'-(methyloxy)-1,1'-biphenyl-3-yl)methyl)oxy)phenyl)-4-methyl-4-pentenoic acid (15). To a stirred solution of 15.6 (0.044 g, 0.087 mmol) in EtOH (2.00 mL, 0.087 mmol) and THF (2.00 mL, 0.087 mmol) at 23° C. was added a solution of 1M sodium hydroxide (1.00 mL, 1.0 mmol). Stirring was continued for 18 hours. The resulting reaction was concentrated in vacuo. 1N HCl was added to pH 1, the resulting mixture was extracted EtOAc, dried over MgSO$_4$, and concentrated. The crude product was purified by silica gel flash chromatography (0-20% EtOAc/hexane) to afford compound 15 (31 mg, 74% yield) as a colorless oil. MS ESI (neg.) m/e: 951.4 (2M–H)$^+$, 475.1 (M–H)$^+$.

Example 16

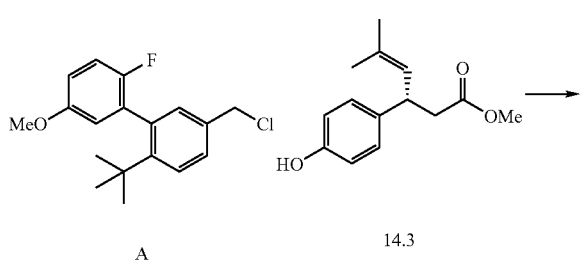

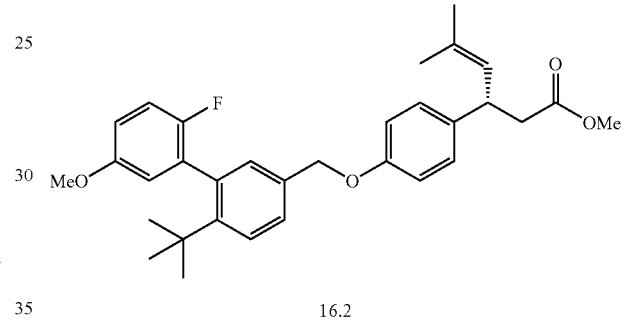

Methyl (3S)-3-(4-(((6-(1,1-dimethylethyl)-2'-fluoro-5'-(methyloxy)-1,1'-biphenyl-3-yl)methyl)oxy)phenyl)-5-methyl-4-hexenoate (16.2). To a stirred solution of (S)-ethyl 3-(4-hydroxyphenyl)-5-methylhex-4-enoate 14.3 (0.025 g, 0.10 mmol) in DMF (1.0 mL, 0.10 mmol) at 0° C. was added A (0.034 g, 0.11 mmol), followed by cesium carbonate (0.036 g, 0.11 mmol). See Example 14—it is possible that 14.3 is the R enantiomer and that 14.2 is the S enantiomer although it is believed that 14.3 is the enantiomer shown. Stirring was continued at 23° C. for 16 hours. Water was added to the reaction, and the resulting mixture was extracted with EtOAc. The organic layer was dried over MgSO$_4$, and concentrated. The crude product was purified by silica gel flash chromatography (0-20% EtOAc/hexane) to afford compound 16.2 (0.047 g, 90% yield). MS ESI (pos.) m/e: 536.3 (M+H$_2$O).

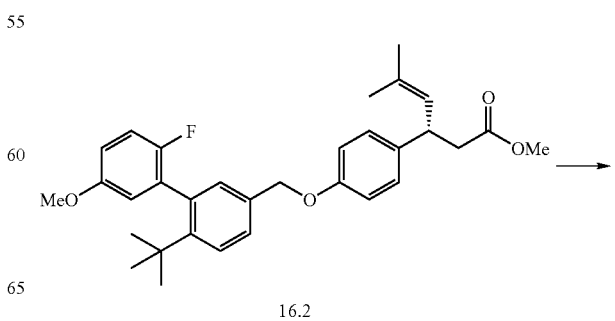

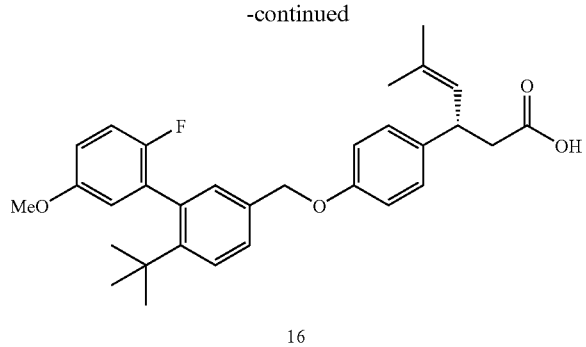

16

(3S)-3-(4-(((6-(1,1-Dimethylethyl)-2'-fluoro-5'-(methyloxy)-1,1'-biphenyl-3-yl)methyl)oxy)phenyl)-5-methyl-4-hexenoic acid (16). To a stirred solution of 16.2 (0.047 g, 0.09 mmol) in THF (2.00 mL, 0.10 mmol) and EtOH (2.00 mL, 0.10 mmol) at 23° C. was added a 1 M solution of sodium hydroxide (1 mL, 1 mmol). Stirring was continued for 15 hours. The resulting reaction was concentrated in vacuo. 1 N HCl was added to bring the pH to 1, and the resulting mixture was extracted with EtOAc, dried over MgSO$_4$, and concentrated. The crude product was purified by silica gel flash chromatography (0-20% EtOAc/hexane) to afford compound 14 (38 mg, 82% yield) as a colorless oil. MS ESI (neg.) m/e: 489.2 (M–H)$^+$.

Example 17

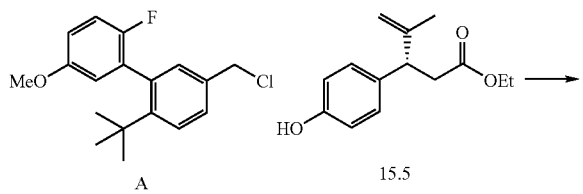

A          15.5

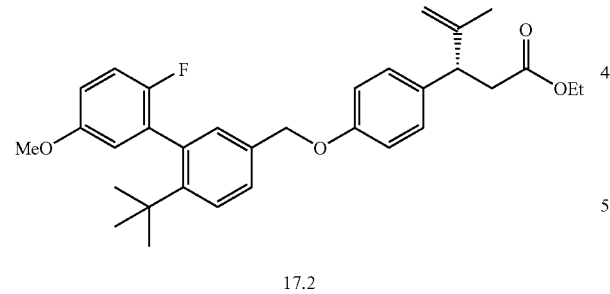

17.2

Ethyl (3S)-3-(4-(((6-(1,1-dimethylethyl)-2'-fluoro-5'-(methyloxy)-1,1'-biphenyl-3-yl)methyl)oxy)phenyl)-4-methyl-4-pentenoate (17.2). To a stirred solution of 15.5 (0.025 g, 0.11 mmol) in DMF (2.00 mL, 0.11 mmol) at 23° C. was added A (0.036 g, 0.12 mmol) followed by cesium carbonate (0.042 g, 0.13 mmol). See Example 15—it is possible that 15.5 is the enantiomer of the compound shown and that 15.4 is the enantiomer shown although it is believed that 15.5 is the enantiomer shown. Stirring was continued for 24 hours. Water was added to the reaction, and the resulting mixture was extracted with EtOAc. The organic layer was dried over MgSO$_4$, and concentrated. The crude product was purified by silica gel flash chromatography (0-20% EtOAc/hexane) to afford compound 17.2 (0.048 g, 89% yield). MS ESI (pos.) m/e: 522.2 (M+H$_2$O).

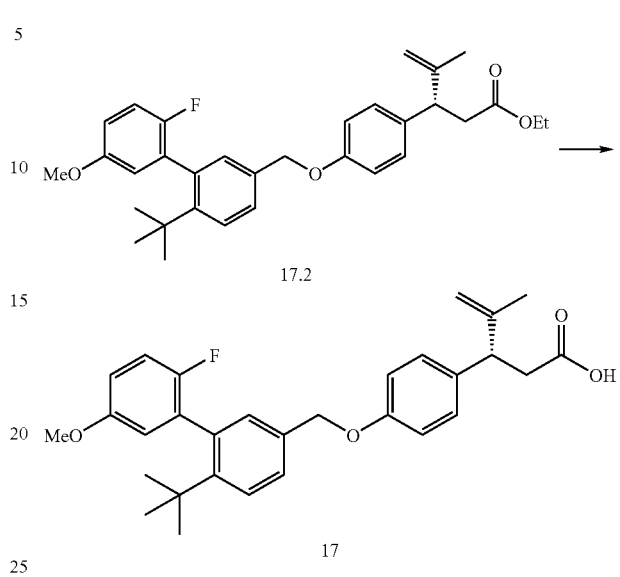

(3S)-3-(4-(((6-(1,1-Dimethylethyl)-2'-fluoro-5'-(methyloxy)-1,1'-biphenyl-3-yl)methyl)oxy)phenyl)-4-methyl-4-pentenoic acid (17). To a stirred solution of 17.2 (0.048 g, 0.095 mmol) in EtOH (2.00 mL, 0.087 mmol) and THF (2.00 mL, 0.087 mmol) at 23° C. was added a solution of 1 M sodium hydroxide (1.00 mL, 1.0 mmol). Stirring was continued for 18 hours. The resulting reaction was concentrated in vacuo. 1 N HCl was added to bring the pH to 1, and the resulting mixture was extracted with EtOAc, dried over MgSO$_4$, and concentrated. The crude product was purified by silica gel flash chromatography (0-20% EtOAc/hexane) to afford compound 17 (36 mg, 79% yield) as a colorless oil. MS ESI (neg.) m/e: 475.1 (M–H)$^+$.

Example 18

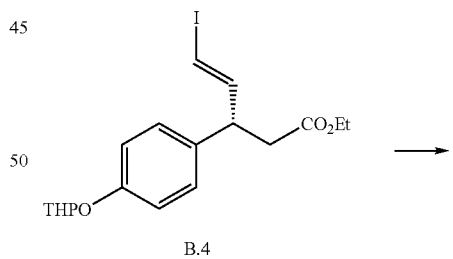

B.4

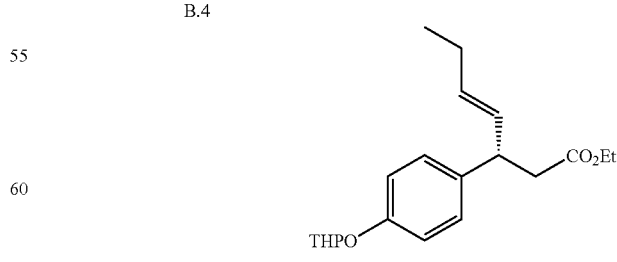

18.1

Ethyl (3S,4E)-3-(4-(tetrahydro-2H-pyran-2-yloxy)phenyl)-4-heptenoate (18.1). To a stirred solution of B.4 (340.2 mg, 0.79 mmol, 1 eq., MW 430.29) in THF (20 mL) at 23° C. was added Pd(PPh₃)₄ (91 mg, 0.079 mmol, 0.1 eq., MW 1155.58) followed by dropwise addition of Et₂Zn (950 µL, 0.95 mmol, 1.2 eq., 1.0 M). The yellow color disappeared on addition of the Et₂Zn. After 30 minutes, the color returned signaling the end of the reaction. Water (10 mL) was added to quench the reaction. The mixture was extracted with EtOAc (2×50 mL), dried with MgSO₄, and filtered. The organic layer was concentrated in vacuo. The residue was then purified by flash chromatography (SiO₂ gel 60, eluted with 0 to 20% EtOAc in hexanes). Fractions containing the desired product were combined and concentrated to provide 18.1 (180 mg, 69%) as a colorless oil.

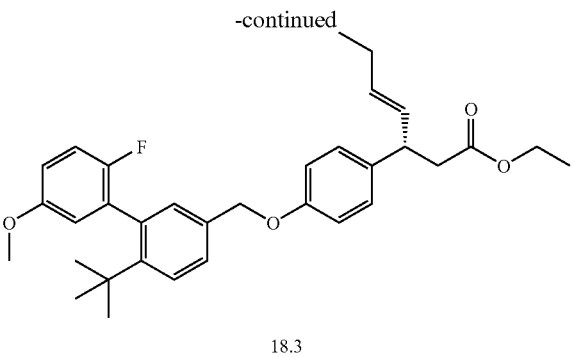

Ethyl (3S,4E)-3-(4-(((6-(1,1-dimethylethyl)-2'-fluoro-5'-(methyloxy)-1,1'-biphenyl-3-yl)methyl)oxy)phenyl)-4-heptenoate (18.3). To a flask containing 18.2 (0.020 g, 0.081 mmol) and cesium carbonate (0.034 g, 0.11 mmol) in DMF (1 mL) was added A (0.030 g, 0.097 mmol), and the resulting mixture was stirred overnight. The reaction was diluted with water and extracted with EtOAc. The organic layers were combined and washed with brine, dried over Na₂SO₄, filtered, concentrated, and then purified by silica gel chromatography (0 to 20% EtOAc/Hexanes) to provide 18.3.

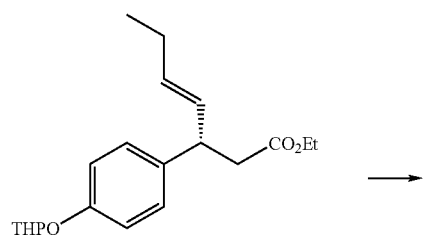

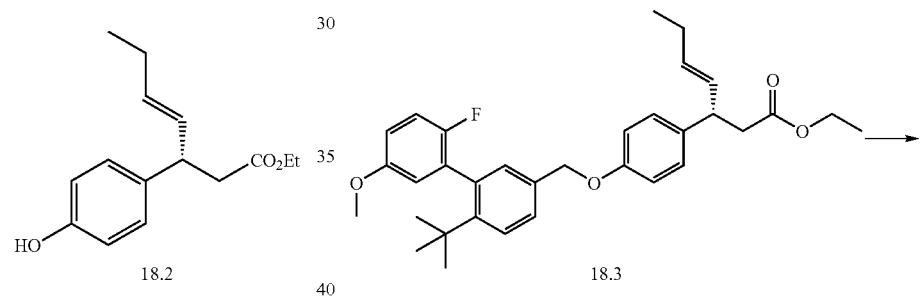

Ethyl (3S,4E)-3-(4-hydroxyphenyl)-4-heptenoate (18.2). To a stirred solution of 18.1 (180 mg, 0.57 mmol) in EtOH (5 mL) at 23 C was added PPTS (catalytic). Stirring was continued for 16 hours. The reaction was concentrated in vacuo. The residue was then purified by flash chromatography (SiO₂ gel 60, eluted with 0 to 20% EtOAc in hexanes). Fractions containing the desired product were combined and concentrated to give a colorless oil. The residue was purified by flash chromatography (SiO₂ gel 60, eluted with 0 to 20% EtOAc in hexanes). The combined fractions were concentrated under reduced pressure to afford phenol 18.2 (120 mg, 89%) as a colorless oil.

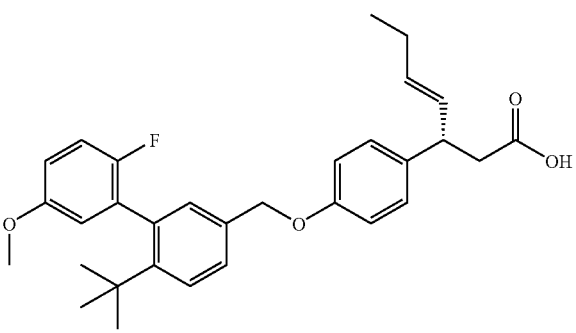

(3S,4E)-3-(4-(((6-(1,1-Dimethylethyl)-2'-fluoro-5'-(methyloxy)-1,1'-biphenyl-3-yl)methyl)oxy)phenyl)-4-heptenoic acid (18). To a solution of 18.3 (0.040 g, 0.077 mmol) in THF/MeOH (2/1) (1.5 mL) was added LiOH (0.50 mL, 0.50 mmol). The resulting mixture was stirred overnight at 23° C., quenched with excess 1 N HCl, and extracted with EtOAc. The combined organic layers were dried over Na₂SO₄ and concentrated. The residue was purified by silica gel chro-

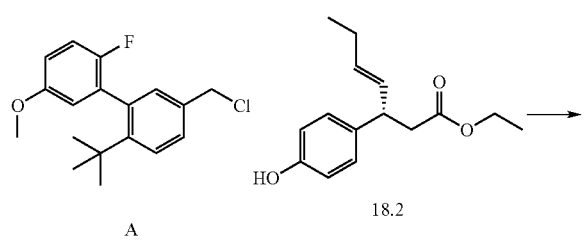

matography (0 to 40% EtOAc/hexanes) to afford 18 (0.0130 g, 34% yield). MS ESI (neg.) m/e: 489.2 (M–H)+.

Example 19

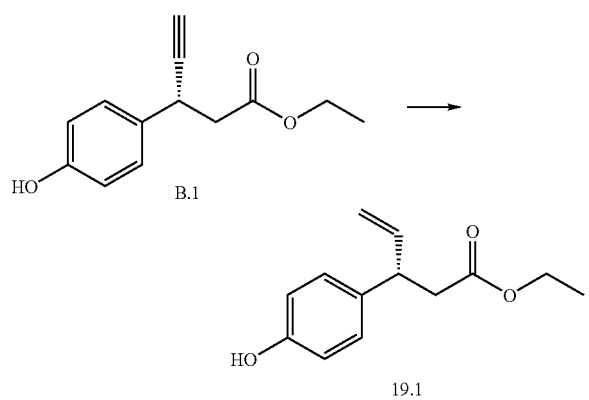

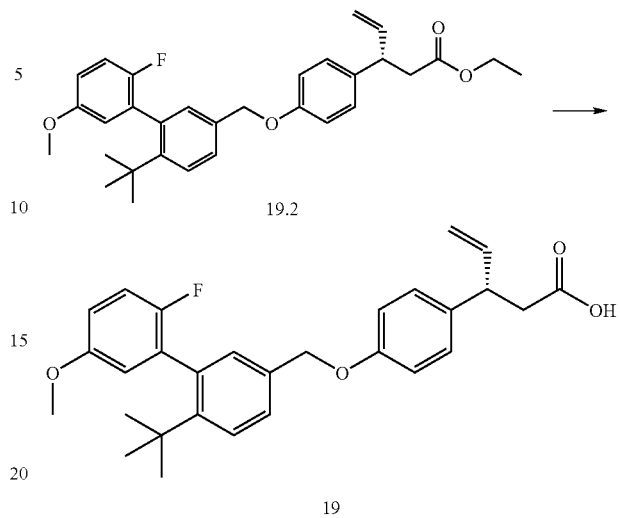

Ethyl (3S)-3-(4-hydroxyphenyl)-4-pentenoate (6.1). Compound B.1 was prepared by a method based on the procedure reported in *Biochemistry* 1989, 28, 3833-3842. B.1 (5.0 g, 23 mmol) was dissolved in 100 mL of EtOAc, and 2 mL of quinoline (129.16 MW, 1.093 g/mL, 16.93 mmol) was added. Nitrogen was bubbled through the solution for 5 minutes. Lindlar's catalyst (500 mg) was added, and a hydrogen balloon was attached. After 8 hours, the mixture was filtered through a plug of silica with EtOAc. The organic layer was washed with 2 N HCl(aq) (2×50 mL), saturated NaHCO$_3$(aq) (1×50 mL), brine (1×50 mL) and dried with MgSO$_4$. The organic layer was filtered and concentrated under reduced pressure to provide 19.1 (5.0 g, 99% yield).

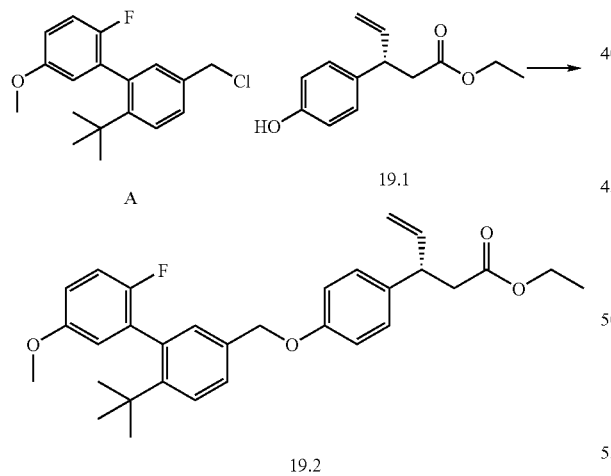

Ethyl (3S)-3-(4-(((6-(1,1-dimethylethyl)-2'-fluoro-5'-(methyloxy)-1,1'-biphenyl-3-yl)methyl)oxy)phenyl)-4-pentenoate (19.2). To a flask containing 19.1 (0.020 g, 0.091 mmol) and cesium carbonate (0.039 g, 0.12 mmol) in DMF (1 mL) was added A (0.033 g, 0.11 mmol), and the resulting mixture was stirred overnight. The reaction was diluted with water and extracted with EtOAc. The combined organic layers were washed with brine, dried over Na$_2$SO$_4$, filtered, concentrated, and then purified by silica gel chromatography (0 to 20% EtOAc/Hexanes) to provide 19.2.

(3S)-3-(4-(((6-(1,1-Dimethylethyl)-2'-fluoro-5'-(methyloxy)-1,1'-biphenyl-3-yl)methyl)oxy)phenyl)-4-pentenoic acid (19). To a solution of 1 (0.040 g, 0.082 mmol) in THF/MeOH (2/1) (1.5 mL) was added a 1 M solution of LiOH (0.50 mL, 0.50 mmol). The resulting mixture was stirred overnight at 23° C., quenched with excess 1 N HCl, and extracted with EtOAc. The combined organic layers were dried over Na$_2$SO$_4$ and concentrated. The crude residue was purified by silica gel chromatography (0 to 40% EtOAc/hexanes) to afford 19 (0.022 g, 59% yield). MS ESI (neg.) m/e: 461.2 (M–H)+.

Example 20

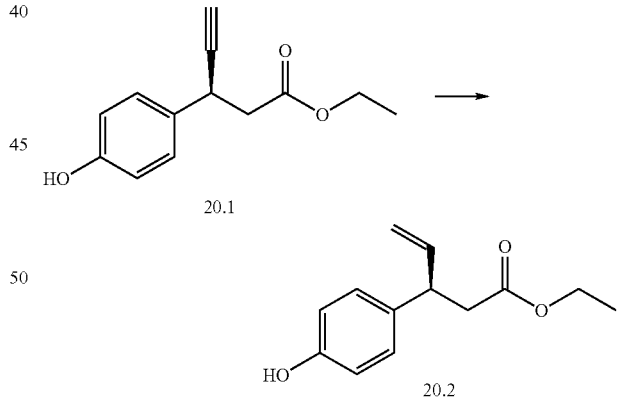

Ethyl (3R)-3-(4-hydroxyphenyl)-4-pentenoate (20.1). Compound 20.1 was prepared by a method based on that reported in *Biochemistry* 1989, 28, 3833-3842. Compound 20.1 (5.0 g, 23 mmol) was dissolved in EtOAc (100 mL) and quinoline (2 mL, 129.16 MW, 1.093 g/mL, 16.93 mmol) was added. Nitrogen was bubbled through the solution for 5 minutes. Lindlar's catalyst (500 mg) was added, and a hydrogen balloon was attached. After 8 hours, the mixture was filtered through a plug of silica with EtOAc. The organic layer was washed with 2 N HCl(aq) (2×50 mL), saturated NaHCO$_3$(aq) (1×50 mL), brine (1×50 mL) and dried with MgSO4. The organic layer was filtered and concentrated under reduced pressure to provide 20.2 (5.0 g, 99% yield).

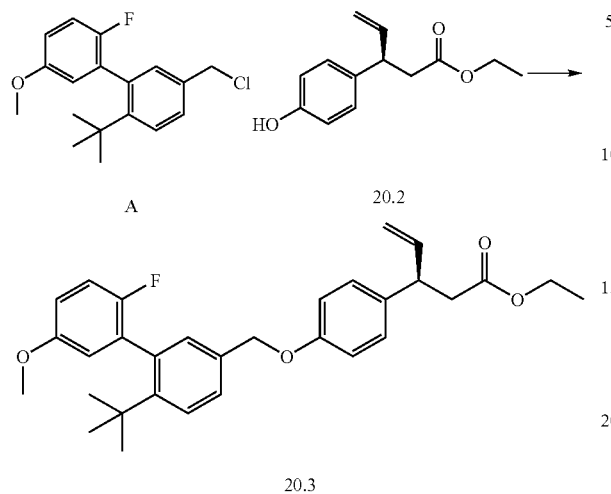

Ethyl (3R)-3-(4-(((6-(1,1-dimethylethyl)-2'-fluoro-5'-(methyloxy)-1,1'-biphenyl-3-yl)methyl)oxy)phenyl)-4-pentenoate (20.3). To a flask containing 20.2 (0.020 g, 0.091 mmol) and cesium carbonate (0.039 g, 0.12 mmol) in DMF (1 mL) was added A (0.033 g, 0.11 mmol), and the resulting mixture was stirred overnight. The reaction was diluted with water and extracted with EtOAc. The combined organic layers were washed with brine, dried over Na$_2$SO$_4$, filtered, concentrated, and then purified by silica gel chromatography (0 to 20% EtOAc/Hexanes) to provide 20.3.

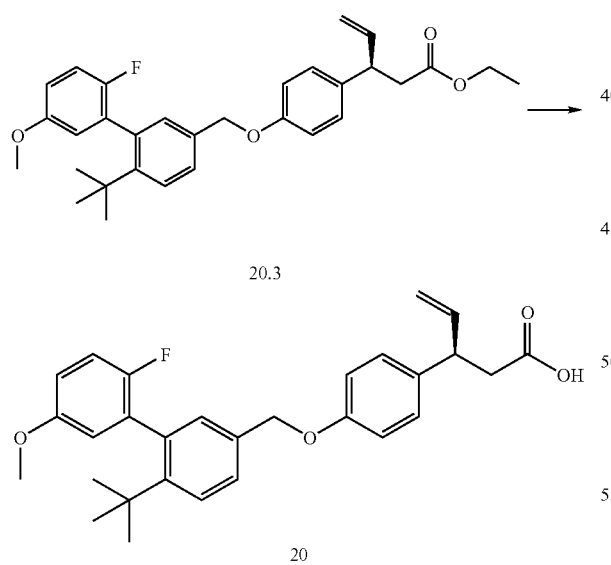

(3R)-3-(4-(((6-(1,1-Dimethylethyl)-2'-fluoro-5'-(methyloxy)-1,1'-biphenyl-3-yl)methyl)oxy)phenyl)-4-pentenoic acid (20). To a solution of 20.3 (0.040 g, 0.082 mmol) in THF/MeOH (2/1) (1.5 mL) was added a 1 M solution of LiOH (0.50 mL, 0.50 mmol). The resulting mixture was stirred overnight at 23° C., quenched with excess 1 N HCl, and extracted with EtOAc. The combined organic layers were dried over Na$_2$SO$_4$ and concentrated. The crude residue was purified by silica gel chromatography (0 to 40% EtOAc/hexanes) to afford a 20 (0.022 g, 58% yield). MS ESI (neg.) m/e: 461.2 (M−H)$^+$.

Example 21

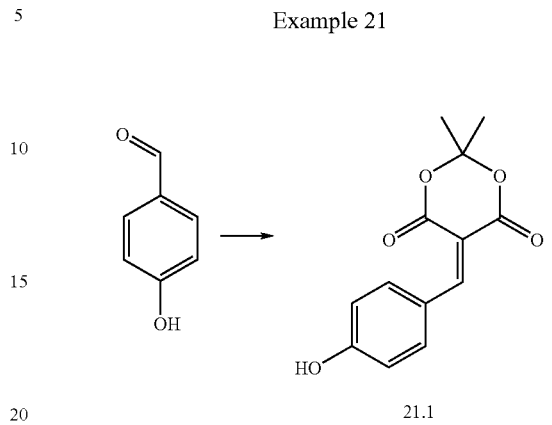

5-(4-Hydroxy-benzylidene)-2,2-dimethyl-[1,3]dioxane-4,6-dione (21.1). Condensation with Meldrum's acid was carried out according to the method of Bigi et. al. *Tet. Lett.* 2001, 42, 5203-5205. A 2 L pear-shaped flask was charged with 4-hydroxybenzaldehyde (50 g, 409 mmol) (commercially available from Aldrich) and water (400 mL). The flask was placed in a water bath at 75° C. and Meldrum's acid (62 g, 430 mmol) (commercially available from Aldrich) was added as a slurry in water (400 mL). The reaction mixture was agitated for 2 hours and then cooled in an ice bath for 2 hours. The product was collected by filtration and rinsed with cold water. After drying thoroughly, 95 g (94%) of adduct 21.1 was obtained as a fine yellow powder. $^1$H NMR (500 MHz) (DMSO-d$_6$) δ 9.75 (br s, 1H); 8.27 (s, 1H); 8.24 (d, 2H, J=10 Hz); 6.98 (d, 2H, J=10 Hz), 1.76 (s, 6H). MS ESI (pos.) m/e: 519.0 (2M+Na).

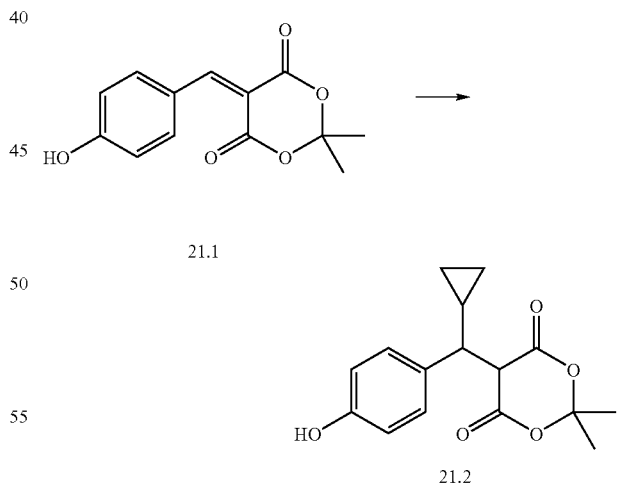

5-(Cyclopropyl(4-hydroxyphenyl)methyl)-2,2-dimethyl-1,3-dioxane-4,6-dione (21.2). To a solution of 21.1 (8.00 g, 32 mmol) in THF (100 mL) was added a 2.0 M solution of cyclopropylmagnesium chloride in THF (97 mL, 193 mmol (commercially available from Aldrich)) dropwise at 0° C. over 1 hour. Upon completion of the addition, the mixture was quenched with 1 N HCl and extracted with EtOAc. The combined organic layers were washed with brine, dried over MgSO₄, filtered, and concentrated. The crude product was chromatographed on silica gel (20-30% EtOAc/hexane) to afford 21.2.

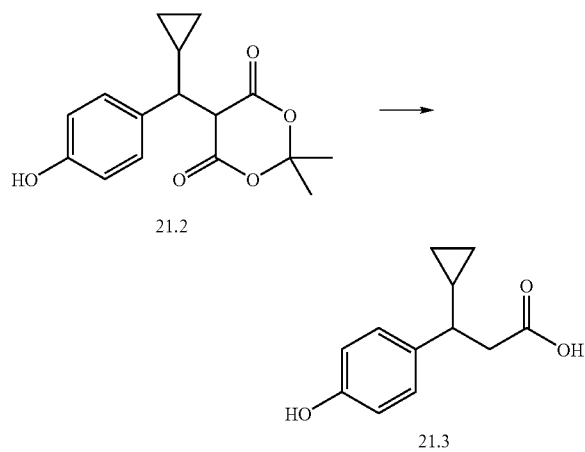

3-Cyclopropyl-3-(4-hydroxyphenyl)propanoic acid (21.3). A solution of 21.2 in 10:1 DMF/water (48 mL) was stirred overnight at 90° C. The mixture was cooled to room temperature, diluted with EtOAc, washed with 1 N HCl and brine, dried (MgSO₄), and concentrated to afford 21.3. The crude product was used without further purification.

Methyl 3-cyclopropyl-3-(4-hydroxyphenyl)propanoate (21.4). To a solution of 21.3 (2.4 g, 12 mmol) in MeOH (25 mL) was added five drops of sulfuric acid. The mixture was stirred overnight at reflux, cooled to room temperature, diluted with EtOAc, washed with water and brine, dried over MgSO₄, filtered, and concentrated. The crude product was chromatographed on silica gel (0-25% EtOAc/hexane) to afford 21.4 (2.2 g, 84%) as a colorless oil.

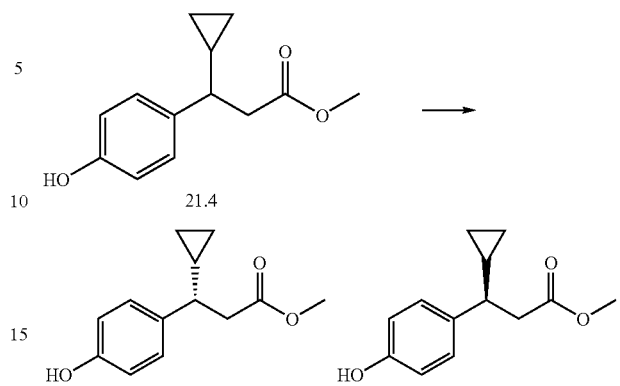

Methyl (3S)-3-cyclopropyl-3-(4-hydroxyphenyl)propanoate (21.5) and methyl (3R)-3-cyclopropyl-3-(4-hydroxyphenyl)propanoate (21.6). Racemate 21.4 (2.16 g, 9.81 mmol) was resolved by chiral HPLC (Chiralcel OD column, 3% i-PrOH/hexane, 220 nm) to afford 21.5 and 21.6. It is believed that 21.5 and 21.6 have the stereochemistry shown, but this could be incorrect. Therefore, the stereochemistry of the products and intermediates shown in Examples 21 and 22 could be the opposite of that shown. However, both 21.5 and 21.5 were used to generate these Example compounds so both enantiomers were synthesized.

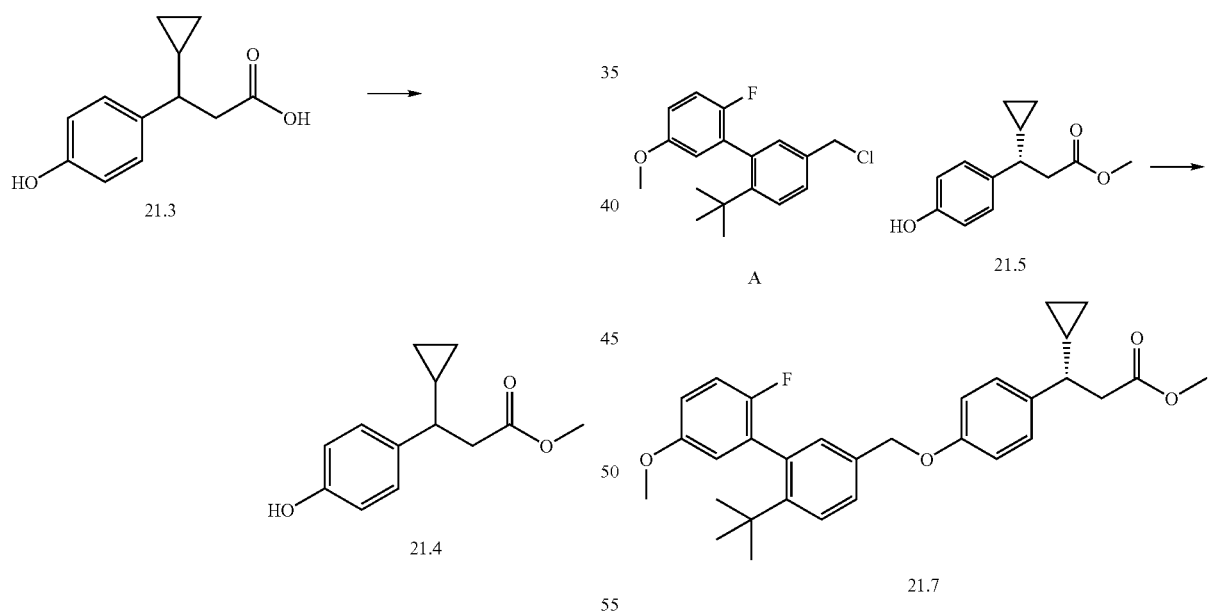

Methyl (3S)-3-cyclopropyl-3-(4-(((6-(1,1-dimethylethyl)-2'-fluoro-5'-(methyloxy)-1,1'-biphenyl-3-yl)methyl)oxy)phenyl)propanoate (21.7). To a flask containing 21.5 (0.020 g, 0.091 mmol) and cesium carbonate (0.039 g, 0.12 mmol) in DMF (1 mL) was added A (0.033 g, 0.11 mmol), and the resulting mixture was stirred overnight. The reaction was diluted with water and extracted with EtOAc. The combined organic layers were washed with brine, dried over Na₂SO₄, filtered, concentrated, and then purified by silica gel chromatography (0 to 20% EtOAc/Hexanes) to provide 21.7.

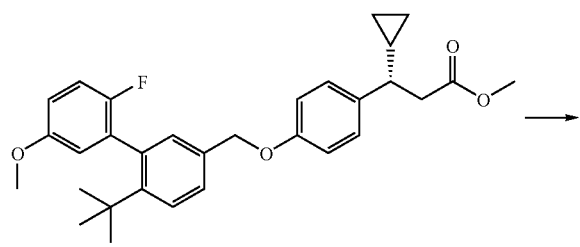

21.7

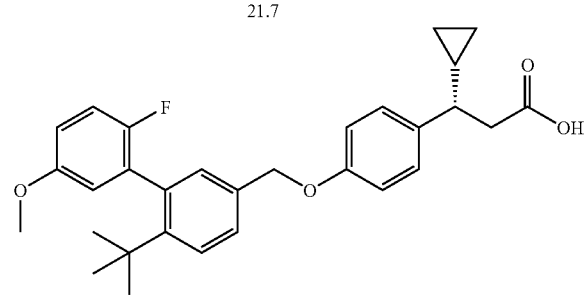

21

(3S)-3-Cyclopropyl-3-(4-(((6-(1,1-dimethylethyl)-2'-fluoro-5'-(methyloxy)-1,1'-biphenyl-3-yl)methyl)oxy)phenyl)propanoic acid (21.7). To a solution of 21.7 (0.040 g, 0.082 mmol) in THF/MeOH (2/1) (1.5 mL) was added LiOH (0.50 mL, 0.50 mmol). The resulting mixture was stirred overnight at 23° C., quenched with excess 1 N HCl, and extracted with EtOAc. The combined organic layers were dried over Na$_2$SO$_4$ and concentrated. The crude residue was purified by silica gel chromatography (0 to 40% EtOAc/hexanes) to afford a 21 (0.019 g, 48% yield). MS ESI (neg.) m/e: 475.3 (M–H)$^+$.

Example 22

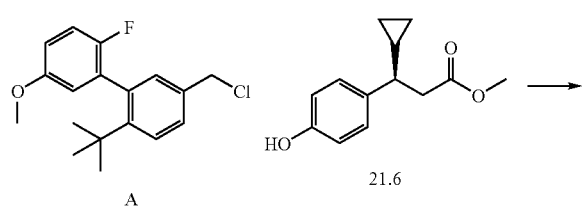

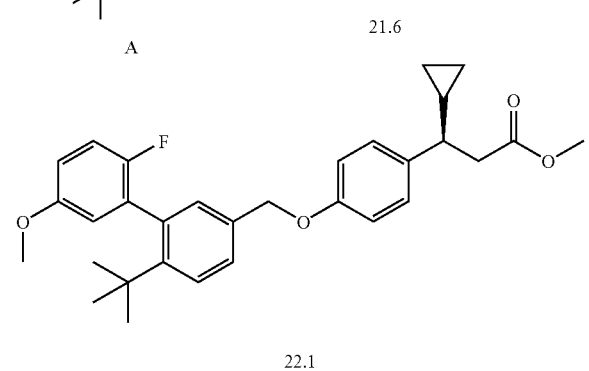

22.1

Methyl (3R)-3-cyclopropyl-3-(4-(((6-(1,1-dimethylethyl)-2'-fluoro-5'-(methyloxy)-1,1'-biphenyl-3-yl)methyl)oxy)phenyl)propanoate (22.1). To a flask containing 21.6 (0.020 g, 0.091 mmol) and cesium carbonate (0.039 g, 0.2 mmol) in DMF (1 mL) was added A (0.033 g, 0.11 mmol), and the resulting mixture was stirred overnight. See Example 21—it is possible that 21.6 is the enantiomer of the compound shown and that 21.5 is the enantiomer shown although it is believed that 21.6 is the enantiomer shown. The reaction was diluted with water and extracted with EtOAc. The combined organic layers were washed with brine, dried over Na$_2$SO$_4$, filtered, concentrated, and then purified by silica gel chromatography (0 to 20% EtOAc/Hexanes) to provide 22.1.

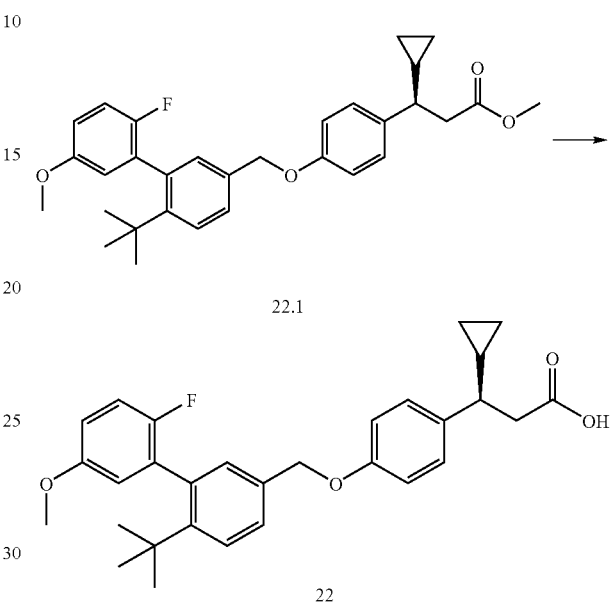

22.1

22

(3S)-3-Cyclopropyl-3-(4-(((6-(1,1-dimethylethyl)-2'-fluoro-5'-(methyloxy)-1,1'-biphenyl-3-yl)methyl)oxy)phenyl)propanoic acid (22). To a solution of 22.1 (0.040 g, 0.082 mmol) in THF/MeOH (2/1) (1.5 mL) was added a 1 M solution of LiOH (0.50 mL, 0.500 mmol). The resulting mixture was stirred overnight at 23° C., quenched with excess 1 N HCl, and extracted with EtOAc. The combined organic layers were dried over Na$_2$SO$_4$, filtered, and concentrated. The residue was purified by silica gel chromatography (0 to 40% EtOAc/hexanes) to afford a 22 (0.019 g, 50% yield). MS ESI (neg.) m/e: 475.3 (M–H)$^+$.

Example 23

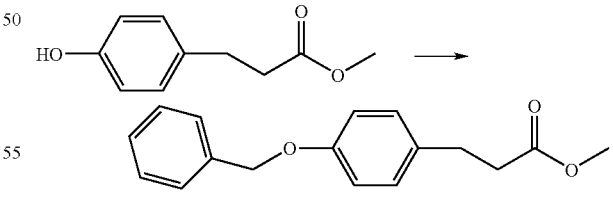

23.1

Methyl 3-(4-((phenylmethyl)oxy)phenyl)propanoate (23.1). A reaction mixture of methyl 3-(4-hydroxyphenyl)propanoate (commercially available, from Aldrich) (4.0 g, 22 mmol), 1-(bromomethyl)benzene (3.8 g, 22 mmol (commercially available from Aldrich)) and cesium carbonate (14.30 g, 44 mmol) in DMSO (20.0 mL) was stirred at room temperature for 2.5 hours. The reaction mixture was poured into water (50.0 mL) and extracted with EtOAc (100.0 mL), and the organic layer was washed with water (3×30 mL) and brine (30 mL), and dried with MgSO$_4$. The crude product was recrystallized with hexane/EtOAc (98/2) to the title compound 23.1. $^1$H NMR (500 MHz, CDCl$_3$) δ ppm 2.65 (t, J=7.83 Hz, 2H) 2.94 (t, J=7.83 Hz, 2H) 3.71 (s, 3H) 5.08 (s, 2H) 6.95 (d, J=8.56 Hz, 2H) 7.16 (d, J=8.56 Hz, 2H) 7.34-7.50 (m, 5H).

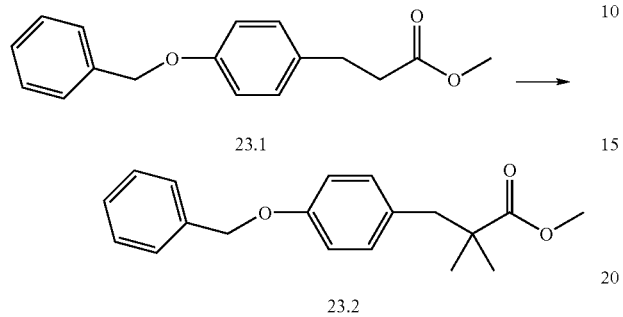

Methyl 2,2-dimethyl-3-(4-((phenylmethyl)oxy)phenyl)propanoate (23.2). To a solution of lithium diisopropylamide, (9.0 mL, 2M in heptane/THF/ethylbenzene) in THF (30.0 mL) and 1,3-dimethyl-3,4,5,6-tetrahydro-2(1H)-pyrimidinone (4.0 mL) was added methyl 3-(4-(benzyloxy)phenyl)propanoate 23.1 (4.00 g, 15 mmol) in THF (15.0 mL) at −78° C. The resulting mixture was stirred at −78° C. for 0.5 hours, and then iodomethane (1.11 mL, 17.80 mmol) was added to the mixture. The reaction mixture was stirred at −78° C. for 0.6 hours. The reaction mixture was maintained at −78° C. and lithium diisopropylamide (8.0 mL, 2 M in heptane/THF/ethylbenzene) was added slowly at −78° C. The resulting mixture was stirred at −78° C. for 10 minutes. n-Butyllithium (7.2 mL, 2.5 M in hexane) was then added. The reaction mixture was then stirred for 20 minutes at −78° C. Iodomethane (2.22 mL, excess) was added, and the reaction was stirred at ambient temperature for 16 hours. The solvent was removed under vacuum, and the salt was filtered by Celite. The crude product was purified by silica gel column (eluent with hexane/EtOAc, 90/10) to give the product 23.2. $^1$H NMR (500 MHz, CDCl$_3$) δ ppm 1.21(s, 6H) 2.83 (s, 2H) 3.69 (s, 3H) 5.07 (s, 2H) 6.89-6.99 (m, 2H) 7.00-7.16 (m, 2H) 7.34-7.48 (m, 5H). MS ESI (pos.) m/e: 543.1 (M+Na)$^+$.

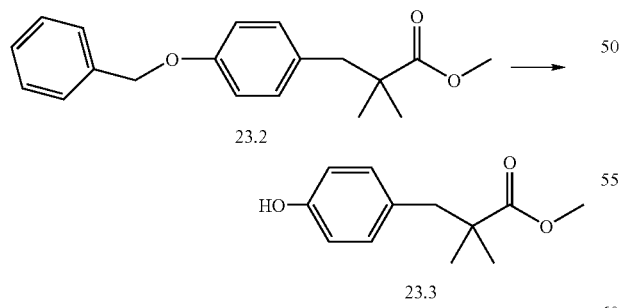

Methyl 3-(4-hydroxyphenyl)-2,2-dimethylpropanoate (23.3) A reaction mixture of methyl 3-(4-(benzyloxy)phenyl)-2,2-dimethylpropanoate 23.2 (0.60 g, 2 mmol) and palladium, 10 wt. % on activated carbon (0.04 mL, 0.4 mmol) in MeOH (10.0 mL) was purged three times with hydrogen and then the reaction mixture was stirred under hydrogen at room temperature for 16 hours. The reaction was concentrated in vacuo and the crude product was used in the next step without further purification. MS ESI (pos.) m/e: 242.1 (M+MeOH)$^+$.

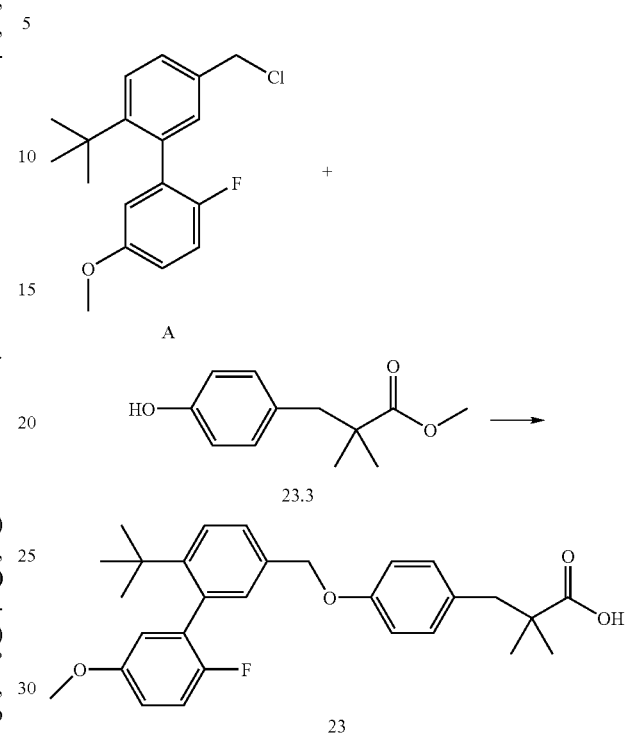

3-(4-(((6-(1,1-Dimethylethyl)-2'-fluoro-5'-(methyloxy)-1,1'-biphenyl-3-yl)methyl)oxy)phenyl)-2,2-dimethylpropanoic acid (23). A reaction mixture of methyl 3-(4-hydroxyphenyl)-2,2-dimethylpropanoate (24.0 mg, 115 μmol), A (35.4 mg, 115 μmol) and cesium carbonate (75.1 mg, 230 μmol) in DMSO (1.0 mL) was stirred at room temperature for 16 hours. Lithium hydroxide (0.3 mL, 3.33 M in water) and DMSO (1.0 mL) were added, and the resulting mixture was stirred at room temperature for 16 hours. The reaction mixture was purified by preparative HPLC (reverse phase) to give the title compound 23. $^1$H NMR (400 MHz, CD$_3$CN) δ ppm 1.14 (s, 6H) 1.23 (s, 9H) 2.79 (s, 2H) 3.79 (s, 3H) 5.04 (s, 2H) 6.84 (dd, J=5.87, 3.13 Hz, 1H) 6.90 (d, J=8.61 Hz, 2H) 6.96 (d, J=3.91 Hz, 1H) 7.07-7.12 (m, 4H) 7.44 (dd, J=8.22, 1.96 Hz, 1H) 7.64 (d, J=8.22 Hz, 1H). MS ESI (neg.) m/e: 463.1 (M−H)$^+$.

Example 24

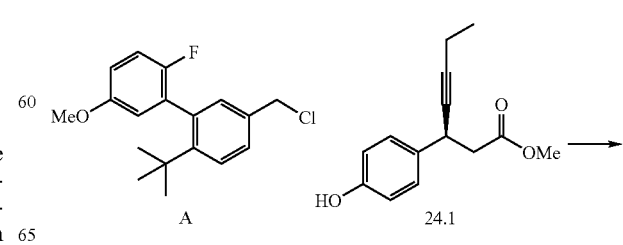

-continued

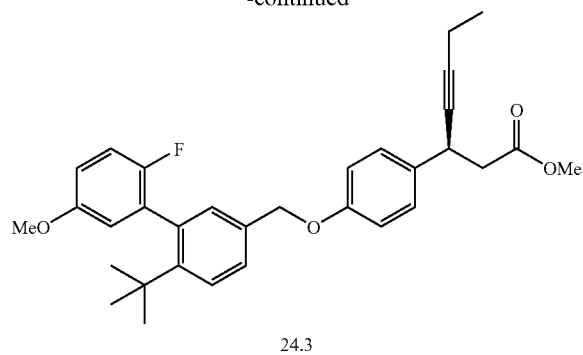

24.3

Methyl (3S)-3-(4-(((6-(1,1-dimethylethyl)-2'-fluoro-5'-(methyloxy)-1,1'-biphenyl-3-yl)methyl)oxy)phenyl)-4-heptynoate (24.3). 24.1 was prepared by a method based on that reported in U.S. Patent Application Publication No. 2006/0004012 which is hereby incorporated by reference. To a stirred solution of (S)-methyl 3-(4-hydroxyphenyl)hept-4-ynoate 24.1 (0.124 g, 0.53 mmol) in DMF (5.3 mL, 0.53 mmol) at 23° C. was added A (0.18 g, 0.59 mmol) followed by cesium carbonate (0.21 g, 0.64 mmol). The resulting mixture was stirred for 17 hours. Water was added to the reaction, and the resulting mixture was extracted with EtOAc. The organic layer was dried over MgSO$_4$, filtered, and concentrated. The product was purified by silica gel flash chromatography (0-20% EtOAc/hexane) to afford compound 24.3 (0.25 g, 93% yield). MS ESI (pos.) m/e: 520.3 (M+H$_2$O).

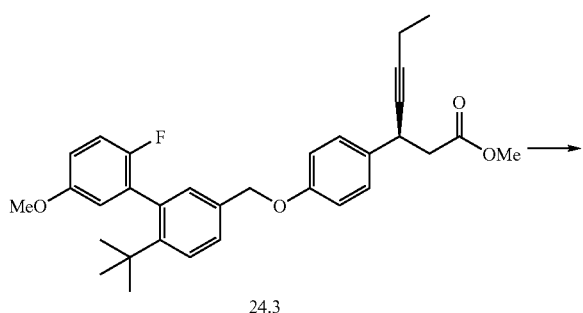

24.3

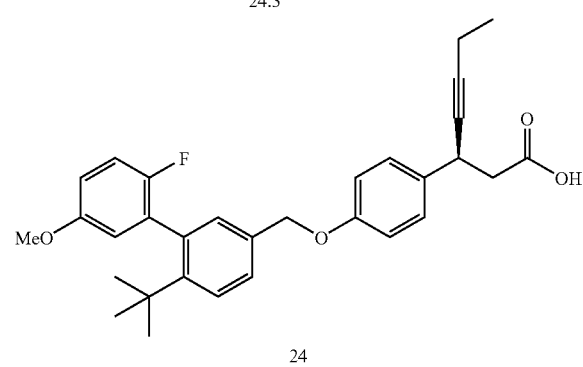

24

(3S)-3-(4-(((6-(1,1-Dimethylethyl)-2'-fluoro-5'-(methyloxy)-1,1'-biphenyl-3-yl)methyl)oxy)phenyl)-4-heptynoic acid (24). To a stirred solution of 24.3 (0.050 g, 0.10 mmol) in THF (2 mL, 0.2 mmol) and EtOH (2 mL, 0.2 mmol) at 23° C. was added a solution of 1 M sodium hydroxide (1.00 mL, 1.0 mmol). The resulting mixture was stirred for 18 hours. The resulting mixture was then concentrated in vacuo. 1 N HCl was added to bring the pH to 1, and the resulting mixture was extracted with EtOAc, dried over MgSO$_4$, filtered, and concentrated. The product was purified by silica gel flash chromatography (0-20% EtOAc/hexane) to afford compound 24 (28 mg, 57% yield) as a colorless oil. MS ESI (neg.) m/e: 487.1 (M–H)$^+$.

Example 25

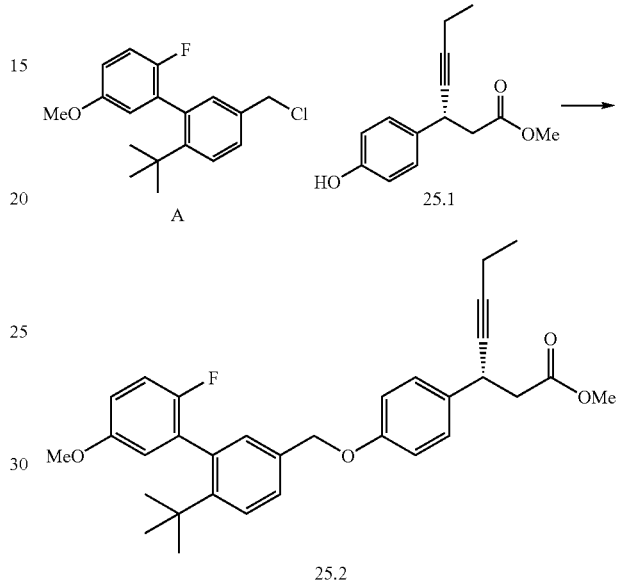

Methyl (3R)-3-(4-(((6-(1,1-dimethylethyl)-2'-fluoro-5'-(methyloxy)-1,1'-biphenyl-3-yl)methyl)oxy)phenyl)-4-heptynoate (25.2). 25.1 was prepared by a method based on that reported in U.S. Patent Application Publication No. 2006/0004012 which is hereby incorporated by reference. To a stirred solution of (S)-methyl 3-(4-hydroxyphenyl)hept-4-ynoate 25.1 (0.114 g, 0.49 mmol) in DMF (4.9 mL, 0.49 mmol) at 23° C. was added A (0.17 g, 0.54 mmol) followed by cesium carbonate (0.19 g, 0.59 mmol). The resulting mixture was stirred for 17 hours. Water was added to the reaction, and the resulting mixture was extracted with EtOAc. The organic layer was dried over MgSO$_4$, filtered, and concentrated. The crude product was purified by silica gel flash chromatography (0-20% EtOAc/hexane) to afford compound 25.2 (0.23 g, 93% yield).

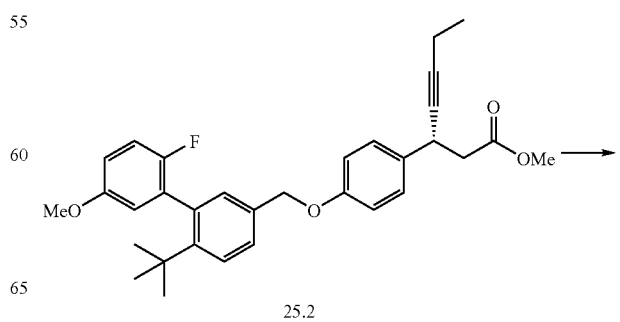

25.2

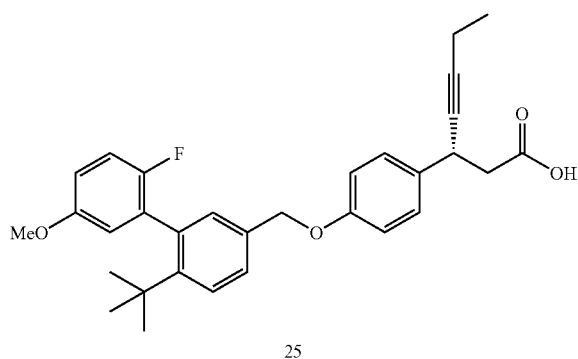

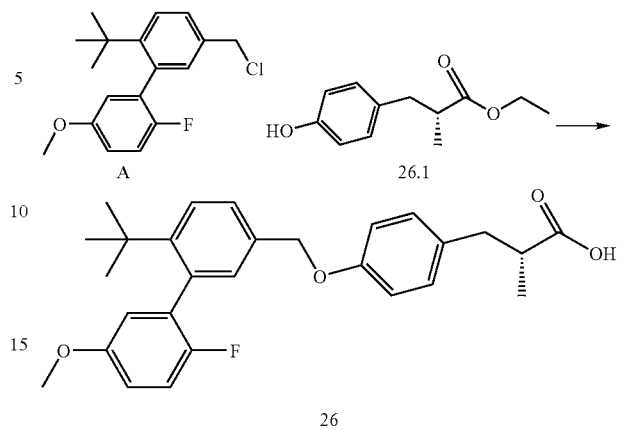

(3R)-3-(4-(((6-(1,1-Dimethylethyl)-2'-fluoro-5'-(methyloxy)-1,1'-biphenyl-3-yl)methyl)oxy)phenyl)-4-heptynoic acid (25). To a stirred solution of 25.2 (0.050 g, 0.10 mmol) in THF (2 mL, 0.2 mmol) and EtOH (2 mL, 0.2 mmol) at 23° C. was added a solution of 1 M sodium hydroxide (1.00 mL, 1.0 mmol). The resulting mixture was stirred for 19 hours. The reaction mixture was then concentrated in vacuo. 1 N HCl was added to bring the pH to 1, and the resulting mixture was extracted with EtOAc, dried over MgSO$_4$, filtered and concentrated. The crude product was purified by silica gel flash chromatography (0-20% EtOAc/hexane) to afford compound 25 (28 mg, 56% yield) as a colorless oil. MS ESI (neg.) m/e: 487.1 (M−H)$^+$.

(2R)-3-(4-(((6-(1,1-Dimethylethyl)-2'-fluoro-5'-(methyloxy)-1,1'-biphenyl-3-yl)methyl)oxy)phenyl)-2-methylpropanoic acid (26). A reaction mixture of (R)-ethyl 3-(4-hydroxyphenyl)-2-methylpropanoate (40.0 mg, 192 µmol), 5-(chloromethyl)-2-(1,1-dimethylethyl)-2'-fluoro-5'-(methyloxy)-1,1'-biphenyl A (58.9 mg, 192 µmol) and cesium carbonate (125.1 mg, 384 µmol) in DMSO (1.0 mL) was stirred at room temperature for 16 hours. Lithium hydroxide (0.3 mL, 3.33 M in water) and DMSO (1.0 mL) were added, and the resulting mixture was stirred at room temperature for 16 hours. The reaction mixture was purified by preparative HPLC (reverse phase) to give the title compound 26. $^1$H NMR (400 MHz, CD$_3$CN) δ ppm 1.11 (d, J=6.65 Hz, 3H) 1.23 (s, 9H) 2.62-2.71 (m, 2H) 2.89 (s, 1H) 3.79 (s, 3H) 5.04 (s, 2H) 6.84-6.98 (m, 4H) 7.07-7.15 (m, 4H) 7.44 (dd, J=8.22, 1.96 Hz, 1H) 7.64 (d, J=8.22 Hz, 1H). MS ESI (neg.) m/e: 449.2 (M−H)$^+$.

Example 26

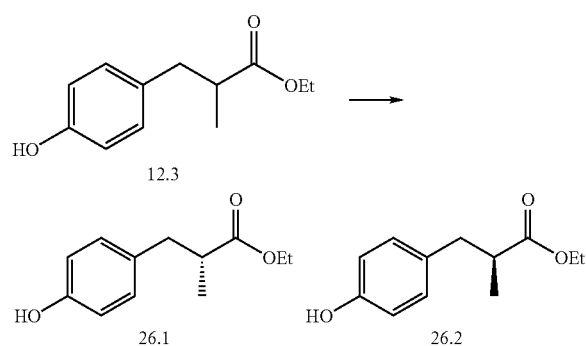

(R)-Ethyl 3-(4-hydroxyphenyl)-2-methylpropanoate (26.1) and (S)-Ethyl 3-(4-hydroxyphenyl)-2-methylpropanoate (26.2). Racemic 12.3 (0.40 g) was separated by ChiralPak OJ-H column, eluted with 10% isopropanol in hexane to give two enantiomer pure compounds, (R)-ethyl 3-(4-hydroxyphenyl)-2-methylpropanoate (26.1) and (S)-ethyl 3-(4-hydroxyphenyl)-2-methylpropanoate (26.2). MS ESI (pos.) m/e: 209.1 (M+H)$^+$. It is believed that 26.1 and 26.2 have the stereochemistry shown, but this could be incorrect. Therefore, the stereochemistry of the products and intermediates shown in Examples 26 and 31 could be the opposite of that shown. However, both 26.1 and 26.2 were used to generate these Example compounds so both enantiomers were synthesized.

Example 27

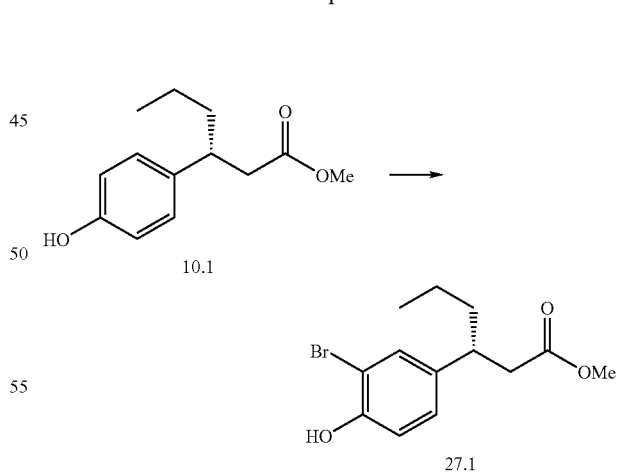

Methyl (3R)-3-(3-bromo-4-hydroxyphenyl)hexanoate (27.1). To 10.1 (50 mg, 0.23 mmol) was added Br$_2$ (36 mg, 11.6 µl, 0.23 mmol) in AcOH (1 mL) at room temperature. After 1 hour, the red color disappeared to give a pale orange solution. The solution was concentrated and purified by silica gel chromatography (0 to 50% EtOAc/hexanes) to afford a 27.1 (0.0629 g, 90.8% yield).

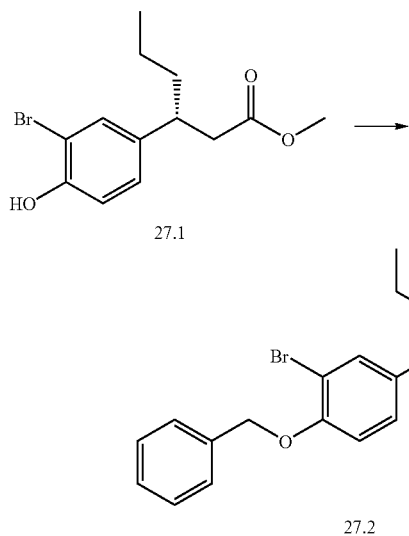

27.1

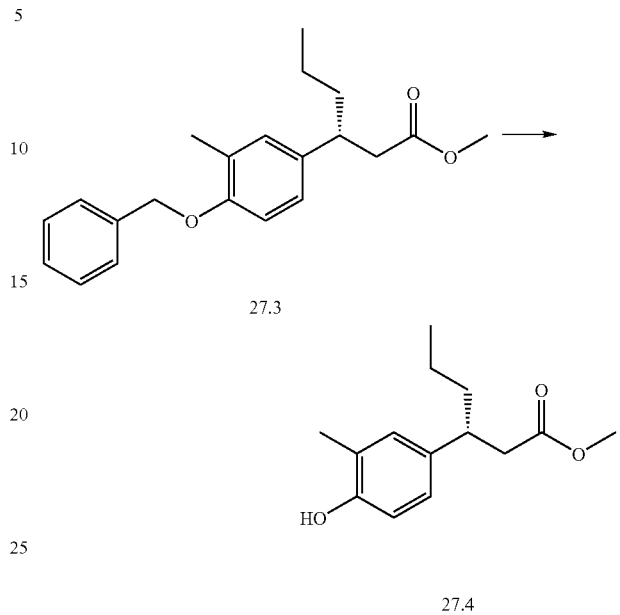

27.3

27.4

Methyl (3R)-3-(3-bromo-4-((phenylmethyl)oxy)phenyl) hexanoate (27.2). To a flask containing 27.1 (0.900 g, 2.99 mmol) and cesium carbonate (1.27 g, 3.88 mmol) in 8 mL of DMF was added benzyl bromide (0.43 mL, 3.59 mmol), and the resulting mixture was stirred overnight. The reaction was diluted with water and extracted with EtOAc. The combined organic layers were washed with brine, dried over Na$_2$SO$_4$, filtered, concentrated, and then purified by silica gel chromatography (0 to 20% EtOAc/Hexanes) to provide 27.2 (1.00 g, 86% yield).

filtered and concentrated. The product was purified by silica gel chromatography (0 to 20% EtOAc/Hexanes) yielding 27.3 (0.46 g, 61% yield).

Methyl (3R)-3-(4-hydroxy-3-methylphenyl)hexanoate (27.4). To a flask containing 27.3 (0.4140 g, 1.268 mmol) under an atmosphere of nitrogen was added 10% Pd/C (0.20 g, 1.88 mmol). The flask was sealed with a rubber septum. To this system was added EtOAc (10 mL) and then vacuum was applied followed by addition of H$_2$ gas (this was repeated three times). A balloon was placed on the flask and the reaction was stirred under H$_2$ overnight. The reaction was filtered, concentrated, and purified by silica gel chromatography (0 to 20% EtOAc/hexanes) to afford a 27.4 (0.102 g, 34% yield).

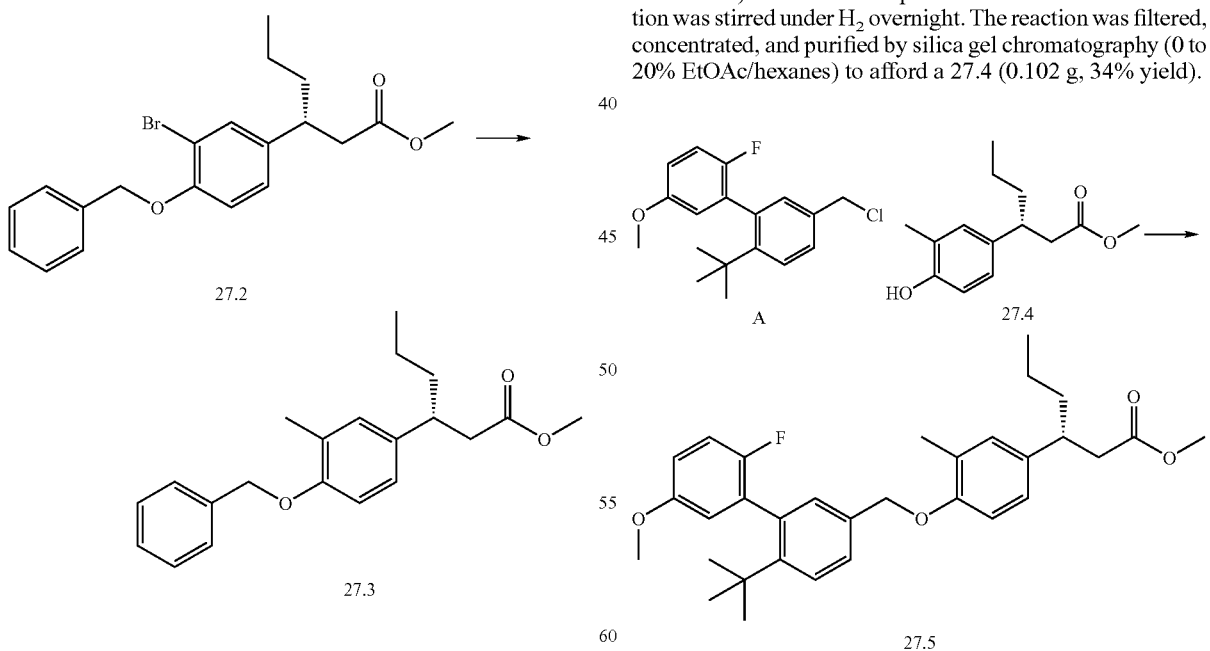

27.2

27.3

Methyl (3R)-3-(3-methyl-4-((phenylmethyl)oxy)phenyl) hexanoate (27.3). To a flask charged with 27.2 (0.8986 g, 2.30 mmol), tetrakis(triphenylphosphine)palladium (0) (0.265 g, 0.230 mmol), and potassium carbonate (0.635 g, 4.59 mmol) in DMF (10 mL) was added trimethylboroxine (0.959 mL, 6.89 mmol). The resulting mixture was then heated at 100° C. overnight. The reaction was allowed to cool and was then

A                27.4

27.5

Methyl (3R)-3-(4-(((6-(1,1-dimethylethyl)-2'-fluoro-5'-(methyloxy)-1,1'-biphenyl-3-yl)methyl)oxy)-3-methylphenyl)hexanoate (27.5). To flask containing 27.4 (0.020 g, 0.085 mmol) and cesium carbonate (0.036 g, 0.110 mmol) in DMF (1 mL) was added A (0.031 g, 0.102 mmol). The resulting mixture was stirred overnight. The reaction was diluted with water and extracted with EtOAc. The combined organic layers were washed with brine, dried over Na$_2$SO$_4$, filtered, concentrated, and then purified by silica gel chromatography (0 to 20% EtOAc/Hexanes) to provide 27.5 (0.039 g, 90% yield).

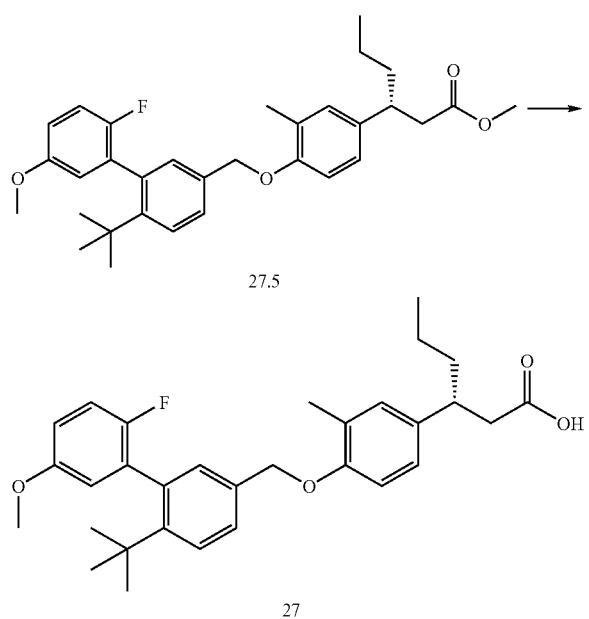

(3R)-3-(4-(((6-(1,1-Dimethylethyl)-2'-fluoro-5'-(methyloxy)-1,1'-biphenyl-3-yl)methyl)oxy)-3-methylphenyl)hexanoic acid (27). To a solution of 27.5 (0.039 g, 0.076 mmol) in THF/MeOH (2/1) (1.5 mL) was added LiOH (0.50 mL, 0.50 mmol). The resulting mixture was stirred overnight at 23° C., quenched with excess 1 N HCl, and extracted with EtOAc. The combined organic layers were dried over Na$_2$SO$_4$ and concentrated. The crude residue was purified by silica gel chromatography (0 to 40% EtOAc/hexanes) to afford a 27 (0.024 g, 64% yield). MS ESI (neg.) m/e: 491.2 (M–H)$^+$.

Example 28

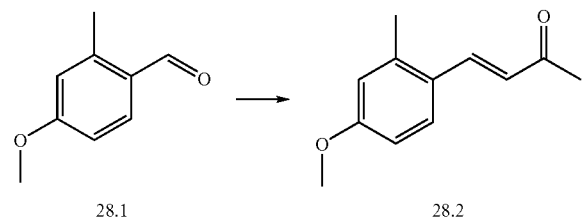

(E)-4-(4-Methoxy-2-methylphenyl)but-3-en-2-one (28.2). To a stirred solution of 28.1 (commercially available from Aldrich, CAS No. 52289-54-0, 5.00 g, 33.0 mmol) in acetone (100 mL) at 23° C. was added a solution of 1 N sodium hydroxide (40.00 mL, 40.0 mmol). The resulting mixture was stirred for for 17 hours. The resulting reaction mixture was concentrated in vacuo, and the resulting mixture was extracted EtOAc, dried over MgSO$_4$, filtered, and concentrated. The crude product was purified by silica gel flash chromatography (0-30% EtOAc/hexane) to afford compound 28.2 as a yellow solid.

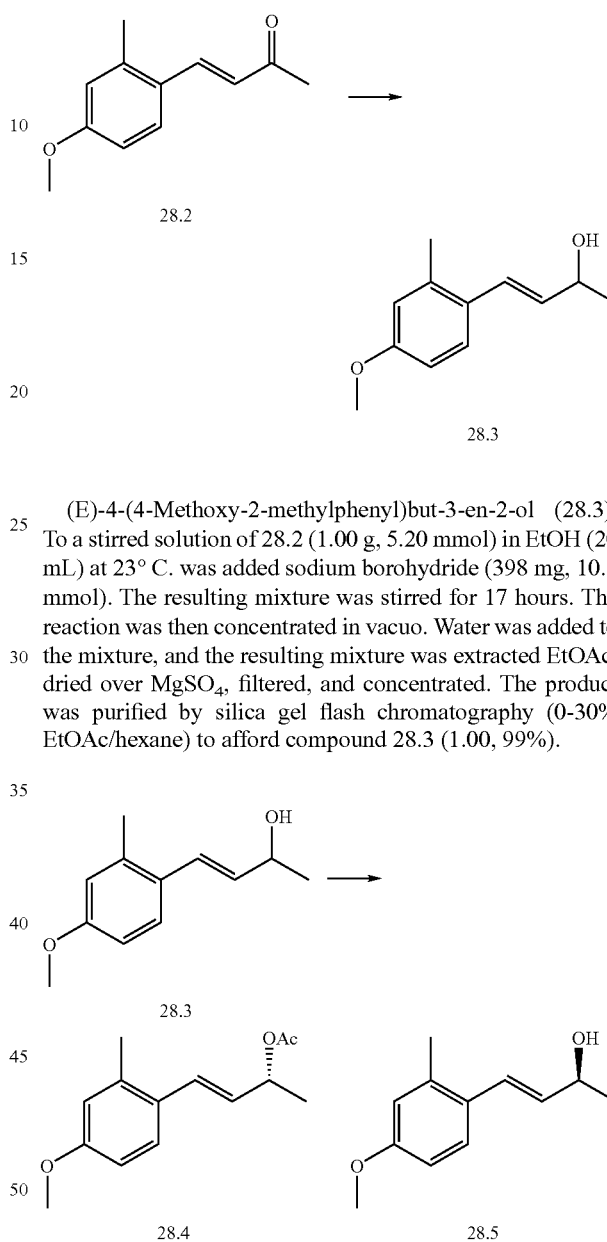

(E)-4-(4-Methoxy-2-methylphenyl)but-3-en-2-ol (28.3). To a stirred solution of 28.2 (1.00 g, 5.20 mmol) in EtOH (20 mL) at 23° C. was added sodium borohydride (398 mg, 10.5 mmol). The resulting mixture was stirred for 17 hours. The reaction was then concentrated in vacuo. Water was added to the mixture, and the resulting mixture was extracted EtOAc, dried over MgSO$_4$, filtered, and concentrated. The product was purified by silica gel flash chromatography (0-30% EtOAc/hexane) to afford compound 28.3 (1.00, 99%).

(S,E)-4-(4-Methoxy-2-methylphenyl)but-3-en-2-ol (28.5). To a stirred solution of 28.3 (1.00 g, 5.20 mmol) in 2-methoxy-2-methylpropane (5.00 mL, 42.0 mmol) and vinyl acetate (1.00 mL, 10.8 mmol) at 23° C. was added Amano Lipase PS, Burkholderia cepacia (0.100 g). The resulting mixture was stirred for 4 days. The solution was then filtered and concentrated in vacuo. The resulting product was purified by silica gel flash chromatography (0-30% EtOAc/hexane) to afford a clear oil 28.4 and a solid 28.5. The % ee determination of 28.5 was conducted on a Daicel Chemical industries OJ-H column (5% 2-propanol/hexane) to yield 28.5 with a 93.9% ee. Further recrystallization provided 28.5 with 99% ee. MS ESI (pos.) m/e: 175.1 (M_H$_2$O)$^+$.

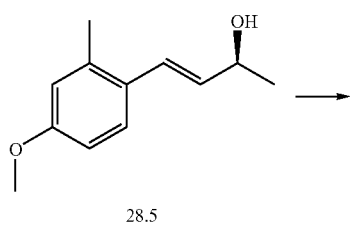

28.5

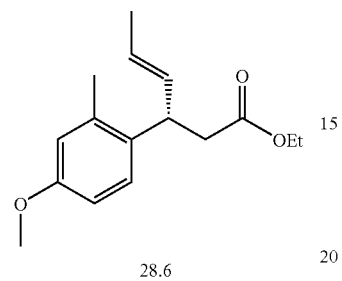

28.6

(S,E)-ethyl 3-(4-methoxy-2-methyl phenyl)hex-4-enoate (28.6). To a stirred solution of (S,E)-4-(4-methoxy-2-methylphenyl)but-3-en-2-ol 28.5 (2.00 g, 10 mmol) (99% ee) in triethyl orthoacetate (20 mL, 109 mmol) at 23° C. was added propanoic acid (0.01 mL, 0.1 mmol). The reaction mixture was heated to 155° C., and stirred for 24 hours. The reaction was cooled to room temperature and concentrated in vacuo. The resulting product was purified by silica gel flash chromatography (0-10% EtOAc/hexane) to afford compound (S,E)-ethyl 3-(4-methoxy-2-methylphenyl)hex-4-enoate 28.6 (1.22 g, 45% yield) as a clear oil. MS ESI (pos.) m/e: 280.1 (M+H$_2$O), 263.1 (M+H).

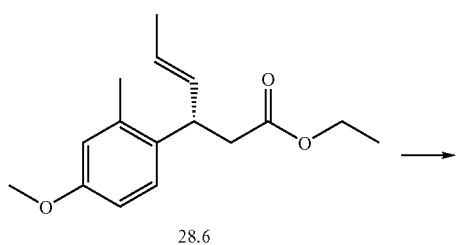

28.6

28.7

(S,E)-Ethyl 3-(4-hydroxy-2-methylphenyl)hex-4-enoate (28.7). To a stirred solution of (S,E)-ethyl 3-(4-methoxy-2-methylphenyl)hex-4-enoate 28.6 (0.500 g, 2 mmol) in DCM (19 mL, 2 mmol) at 0° C. was added boron tribromide (9 mL, 9 mmol). The resulting mixture was stirred for 1 hour. The reaction was quenched by the addition of pH 7 buffer. The resulting mixture was extracted with DCM. The organic layer was dried over MgSO$_4$, filtered and concentrated in vacuo. The resulting product was purified by silica gel flash chromatography (0-10% EtOAc/hexane) to afford (S,E)-ethyl 3-(4-hydroxy-2-methylphenyl)hex-4-enoate (28.7) (0.12 g, 25% yield) as a colorless oil. MS ESI (pos.) m/e: 266.2 (M+H$_2$O), 249.1 (M+H).

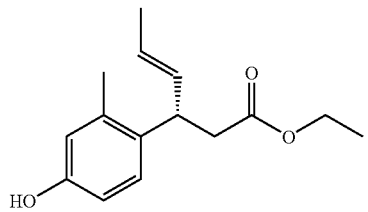

A           28.7

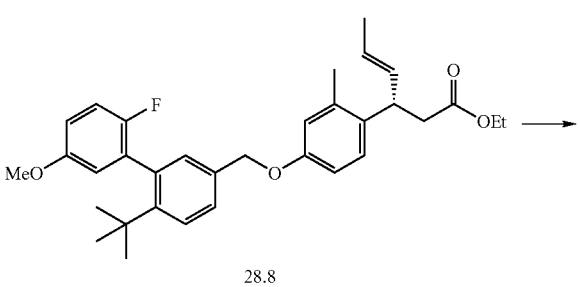

28.8

Ethyl (3S,4E)-3-(4-(((6-(1,1-dimethylethyl)-2'-fluoro-5'-(methyloxy)-1,1'-biphenyl-3-yl)methyl)oxy)-2-methylphenyl)-4-hexenoate (28.8). To a stirred solution of (S)-methyl 3-(4-hydroxyphenyl)hept-4-ynoate 28.7 (0.037 g, 0.1 mmol) in DMF (1.0 mL, 0.1 mmol) at 23° C. was added A (0.05 g, 0.2 mmol) followed by cesium carbonate (0.06 g, 0.2 mmol). The resulting mixture was stirred for 19 hours. Water was added to the reaction, and the resulting mixture was extracted with EtOAc. The organic layer was dried over MgSO$_4$, filtered, and concentrated. The resulting product was purified by silica gel flash chromatography (0-20% EtOAc/hexane) to afford compound 28.8 (0.07 g, 91% yield). MS ESI (pos.) m/e: 536.2 (M+H$_2$O)$^+$.

28.8

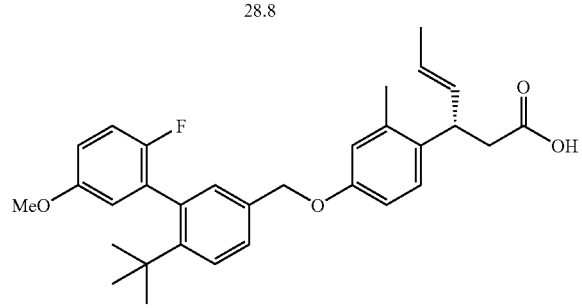

28

(3S,4E)-3-(4-(((6-(1,1-Dimethylethyl)-2'-fluoro-5'-(methyloxy)-1,1'-biphenyl-3-yl)methyl)oxy)-2-methylphenyl)-

4-hexenoic acid (28). To a stirred solution of 28.8 (0.070 g, 0.13 mmol) in THF (2 mL, 0.2 mmol) and EtOH (2 mL, 0.2 mmol) at 23° C. was added a solution of 1 M sodium hydroxide (1.00 mL, 1.0 mmol). The resulting mixture was stirred for 18 hours. The reaction was then concentrated in vacuo. 1 N HCl was added to bring the pH to 1, and the resulting mixture was extracted with EtOAc, dried over MgSO₄, filtered, and concentrated. The resulting product was purified by silica gel flash chromatography (0-20% EtOAc/hexane) to afford compound 28 (44 mg, 67% yield) as a colorless oil. MS ESI (neg.) m/e: 979.5 (2M−H)⁺, 489.2 (M−H)⁺.

Example 29

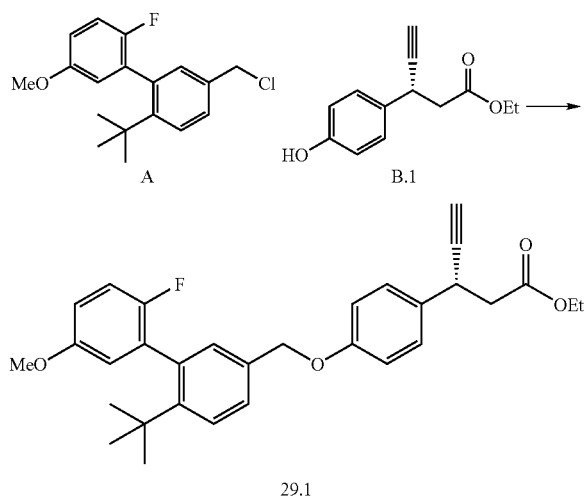

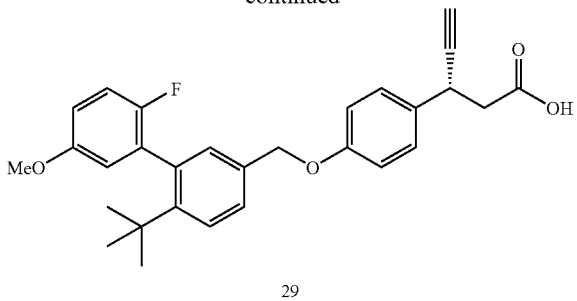

29

(3S)-3-(4-(((6-(1,1-Dimethylethyl)-2'-fluoro-5'-(methyloxy)-1,1'-biphenyl-3-yl)methyl)oxy)phenyl)-4-pentynoic acid (29). To a stirred solution of 29.1 (0.047 g, 0.096 mmol) in THF (2 mL, 0.2 mmol) and EtOH (2 mL, 0.2 mmol) at 23° C. was added a solution of 1 M sodium hydroxide (1.00 mL, 1.0 mmol). The resulting mixture was stirred for 19 hours, and then concentrated in vacuo. 1 N HCl was added to bring the pH to 1, and the resulting mixture was extracted EtOAc, dried over MgSO₄, filtered, and concentrated. The crude product was purified by silica gel flash chromatography (0-20% EtOAc/hexane) to afford compound 29 (24 mg, 54% yield) as a colorless oil. MS ESI (neg.) m/e: 919.3 (2M−H)⁺, 459.1 (M−H)⁺.

Ethyl (3S)-3-(4-(((6-(1,1-dimethylethyl)-2'-fluoro-5'-(methyloxy)-1,1'-biphenyl-3-yl)methyl)oxy)phenyl)-4-pentynoate (21.1). To a stirred solution of (S)-ethyl 3-(4-hydroxyphenyl)pent-4-ynoate B.1 (0.025 g, 0.11 mmol) in DMF (2.00 mL, 0.11 mmol) at 23° C. was added A (0.039 g, 0.13 mmol) followed by cesium carbonate (0.045 g, 0.14 mmol). The resulting mixture was stirred for 17 hours. Water was added to the reaction, and the resulting mixture was extracted with EtOAc. The organic layer was dried over MgSO₄, filtered, and concentrated. The crude product was purified by silica gel flash chromatography (0-20% EtOAc/hexane) to afford compound 29.1 (0.047 g, 84% yield). MS ESI (pos.) m/e: 506.2 (M+H₂O).

Example 30

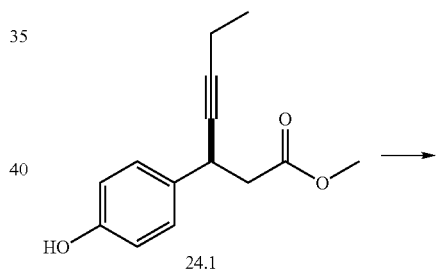

24.1

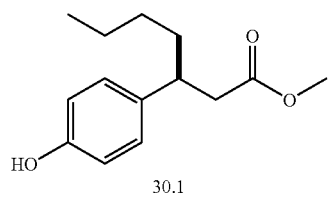

30.1

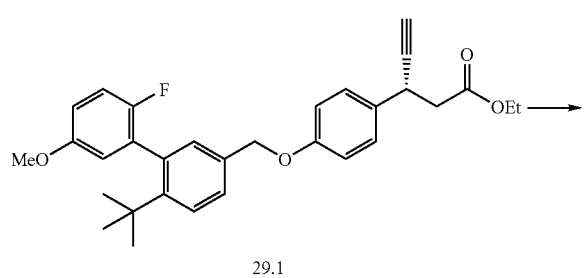

29.1

(S)-Methyl 3-(4-hydroxyphenyl)heptanoate (30.1). To a stirred solution of 24.1 (0.071 g, 0.3 mmol) in EtOAc (3 mL) at 23° C. was added palladium on carbon (0.03 g, 0.3 mmol). The reaction was placed under an atmosphere of hydrogen and then stirred at room temperature. After 5 hours, the reaction mixture was filtered through a pad of silica and then concentrated. After concentration, the residue was purified on silica gel (0%-20% EtOAc/hexane) to give 30.1 (0.06 g, 83%). MS ESI (pos.) m/e: 237.1 (M+H)⁺.

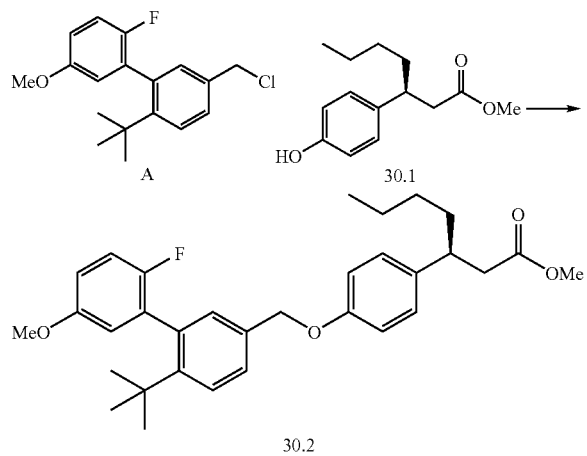

Methyl (3S)-3-(4-(((6-(1,1-dimethylethyl)-2'-fluoro-5'-(methyloxy)-1,1'-biphenyl-3-yl)methyl)oxy)phenyl)heptanoate (30.1). To a stirred solution of (S)-methyl 3-(4-hydroxyphenyl)heptanoate 30.1 (0.025 g, 0.11 mmol) in DMF (2.00 mL, 0.11 mmol) at 23° C. was added A (0.036 g, 0.12 mmol) followed by cesium carbonate (0.041 g, 0.13 mmol). The resulting mixture was stirred for 17 hours. Water was added to the reaction, and the resulting mixture was extracted with EtOAc. The organic layer was dried over MgSO$_4$, filtered, and concentrated. The resulting product was purified by silica gel flash chromatography (0-20% EtOAc/hexane) to afford compound 30.2 (0.054 g, 100% yield). MS ESI (pos.) m/e: 524.2 (M+H$_2$O).

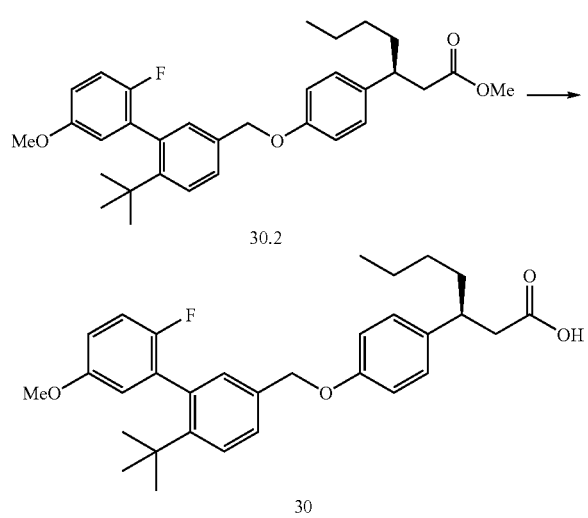

(3S)-3-(4-(((6-(1,1-Dimethylethyl)-2'-fluoro-5'-(methyloxy)-1,1'-biphenyl-3-yl)methyl)oxy)phenyl)heptanoic acid (30). To a stirred solution of 30.1 (0.054 g, 0.11 mmol) in THF (2 mL, 0.2 mmol) and EtOH (2 mL, 0.2 mmol) at 23° C. was added a solution of 1 M sodium hydroxide (1.00 mL, 1.0 mmol). The resulting mixture was stirred for 19 hours. The reaction was then concentrated in vacuo, and 1 N HCl was added to bring the pH to 1. The resulting mixture was extracted with EtOAc, dried over MgSO$_4$, filtered, and concentrated. The resulting product was purified by silica gel flash chromatography (0-20% EtOAc/hexane) to afford compound 30 (40 mg, 76% yield) as a colorless oil. MS ESI (neg.) m/e: 983.5 (2M–H)$^+$, 491.2 (M–H)$^+$.

Example 31

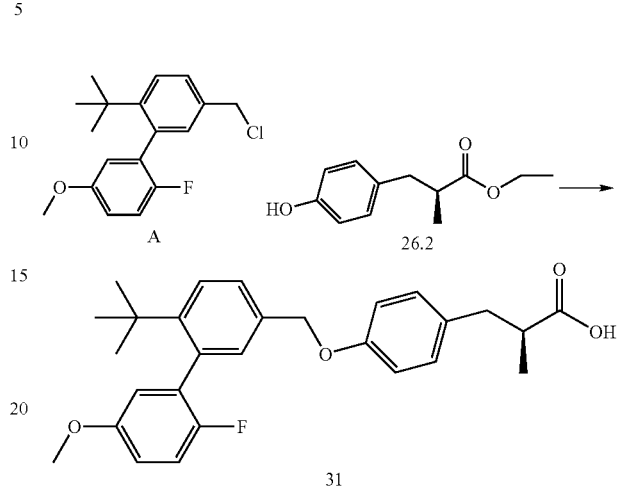

(2S)-3-(4-(((6-(1,1-Dimethylethyl)-2'-fluoro-5'-(methyloxy)-1,1'-biphenyl-3-yl)methyl)oxy)phenyl)-2-methylpropanoic acid (31) A reaction mixture of (S)-ethyl 3-(4-hydroxyphenyl)-2-methylpropanoate 26.2 (45.0 mg, 216 µmol), 5-(chloromethyl)-2-(1,1-dimethylethyl)-2'-fluoro-5'-(methyloxy)-1,1'-biphenyl A (66.3 mg, 216 mmol) and cesium carbonate (141.0 mg, 432 µmol) in DMSO (1.0 mL) was stirred at room temperature for 16 hours. See Example 26—it is possible that 26.2 is the enantiomer of the compound shown and that 26.1 is the enantiomer shown although it is believed that 26.2 is the enantiomer shown. Lithium hydroxide (563.7 mg, 1729 mmol) and DMSO (1.0 mL) were added and the resulting mixture was stirred at room temperature for 16 hours. The reaction mixture was purified by preparative HPLC (reverse phase) to give the title compound 31. $^1$H NMR (500 MHz, CD$_3$CN) δ ppm 1.01 (d, J=6.85 Hz, 3H) 1.13 (s, 9H) 2.51-2.61 (m, 2H) 2.77-2.83 (m, 1H) 3.70 (s, 3H) 4.94 (s, 2H) 6.74 (dd, J=6.11, 3.18 Hz, 1H) 6.80-6.88 (m, 3H) 6.97-7.05 (m, 4H) 7.34 (dd, J=8.31, 1.96 Hz, 1H) 7.54 (d, J=8.31 Hz, 1H). MS ESI (neg.) m/e: 449.2 (M–H)$^+$.

Example 32

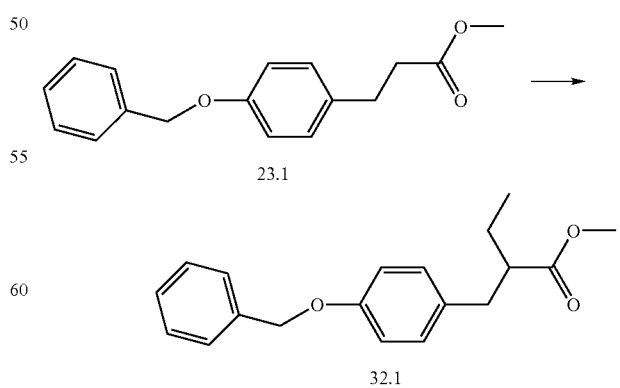

Methyl 2-((4-((phenylmethyl)oxy)phenyl)methyl)butanoate (32.1). To a solution of lithium diisopropylamide (6.5 mL, 2.0 M in heptane/THF/ethylbenzene) in THF (25.0 mL) and 1,3-dimethyl-3,4,5,6-tetrahydro-2(1H)-pyrimidinone (5.0 mL) was added methyl 3-(4-(benzyloxy)phenyl)prowas removed. The crude product was used in the next step without further purification. MS ESI (pos.) m/e: 209.1 (M+H)⁺.

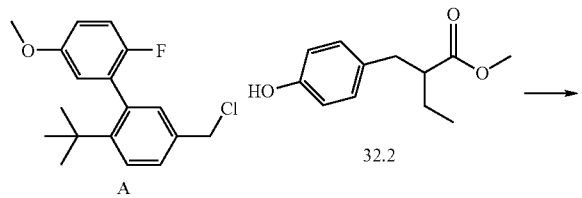

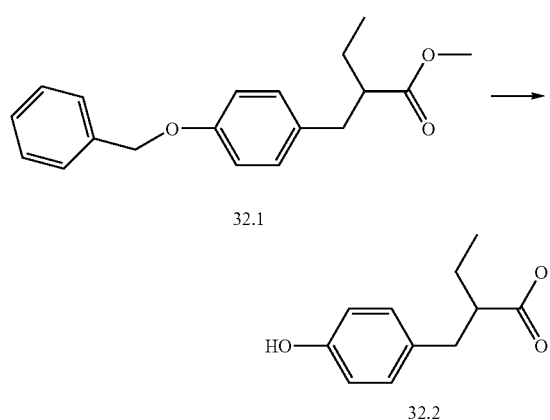

panoate 23.1 (3.00 g, 11 mmol) in THF (10 mL) and 1,3-dimethyl-3,4,5,6-tetrahydro-2(1H)-pyrimidinone (2.5 mL) at −78° C. The resulting mixture was stirred at −78° C. for 30 minutes and then iodoethane (1.0 mL, 13 mmol) in THF (5.0 mL) was added. The reaction mixture was stirred at the same temperature for 20 minutes. The reaction was then stirred at room temperature for 16 hours. The reaction was quenched with water (30.0 mL), and the mixture was concentrated in vacuo. The residue was dissolved in EtOAc (100 mL), washed with brine (2×25 mL), and dried with Na₂SO₄. The residue was purified by silica gel column (eluent with hexane/EtOAc; 85/15) to give the title compound 32.1. MS ESI (pos.) m/e: 299.0 (M+H)⁺.

Methyl 2-(4-hydroxybenzyl)butanoate (32.2) A reaction mixture of methyl 2-(4-(benzyloxy)benzyl)butanoate 32.1 (1.20 g, 4 mmol) and palladium, 10 wt. % on activated carbon (0.80 g, 0.8 mmol) in MeOH (20 mL) was purged with hydrogen three times and then stirred at room temperature under hydrogen overnight. The catalyst was filtered and the solvent 2-((4-(((6-(1,1-Dimethylethyl)-2'-fluoro-5'-(methyloxy)-1,1'-biphenyl-3-yl)methyl)oxy)phenyl)methyl)butanoic acid (32) A reaction mixture of methyl 2-(4-hydroxybenzyl)butanoate 32.2 (45.0 mg, 216 μmol), 5-(chloromethyl)-2-(1,1-dimethylethyl)-2'-fluoro-5'-(methyloxy)-1,1'-biphenyl A (66.3 mg, 216 μmol) and cesium carbonate (141 mg, 432 μmol) in DMSO (1.0 mL) was stirred at room temperature for 16 hours. Lithium hydroxide (0.5 mL, 3.33 mmol/mL in water) and DMSO (2.0 mL) were added, and the resulting mixture was stirred at room temperature for 16 hours. The reaction mixture was purified by preparative HPLC (reverse phase) to give the title compound 32 as a racemic mixture. ¹H NMR (400 MHz, CD₃CN) δ ppm. 0.84 (t, J=7.43 Hz, 3H) 1.13 (s, 9H) 1.42-1.54 (m, 2H) 2.43 (m, 1H) 2.63 (m, 1H) 2.70 (m, 1H) 3.69 (s, 3H) 4.94 (s, 2H) 6.73-6.88 (m, 4H) 6.97-7.05 (m, 4H) 7.34 (dd, J=8.41, 2.15 Hz, 1H) 7.54 (d, J=8.22 Hz, 1H). MS ESI (neg.) m/e: 463.3 (M−H)⁺.

Example 33

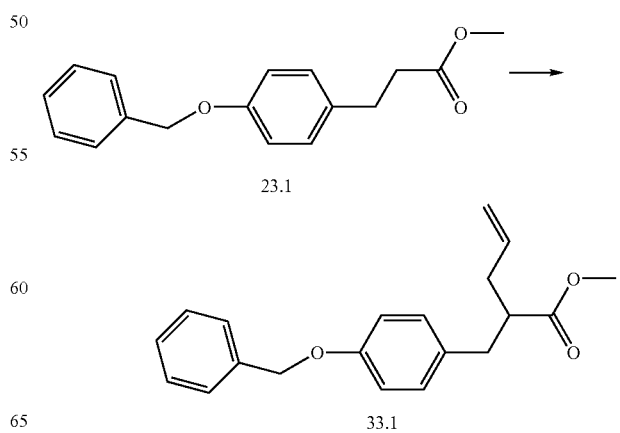

Methyl 2-((4-((phenylmethyl)oxy)phenyl)methyl)-4-pentenoate (33.1) To a solution of lithium diisopropylamide (6.5 mL, 13.0 mmol, 2.0M in heptane/THF/ethylbenzene) in THF (25.0 mL) and 1,3-dimethyl-3,4,5,6-tetrahydro-2(1H)-pyrimidinone (5.0 mL) was slowly added methyl 3-(4-(benzyloxy)phenyl)propanoate 23.1 (3.00 g, 11 mmol) in THF (10 mL) and 1,3-dimethyl-3,4,5,6-tetrahydro-2(1H)-pyrimidinone (2.5 mL) at −78° C. The resulting mixture was stirred at −78° C. for 30 minutes and then allyl iodide (1.08 mL, 13.0 mmol) in THF (5.0 mL) was added. The reaction mixture was stirred at the same temperature for 20 minutes. The reaction was then stirred at room temperature for 16 hours. The reaction was quenched with water (30.0 mL). The solvent was concentrated in vacuo, and the residue was dissolved in EtOAc (100 mL) and washed with brine (2×25 mL) and then dried with $Na_2SO_4$. The product thus obtained was purified on a silica gel column, to give the title compound 33.1. $^1$H NMR (500 MHz, $CDCl_3$) δ ppm 2.29-2.34 (m, 1H) 2.39-2.44 (m, 1H) 2.63-2.79 (m, 2H) 2.91-2.96 (m, 1H) 3.64 (s, 3H) 5.06-5.18 (m, 4H) 5.67-5.85 (m, 1H) 6.88-7.03 (m, 2H) 7.03-7.18 (m, 2H) 7.34-7.49 (m, 5H).

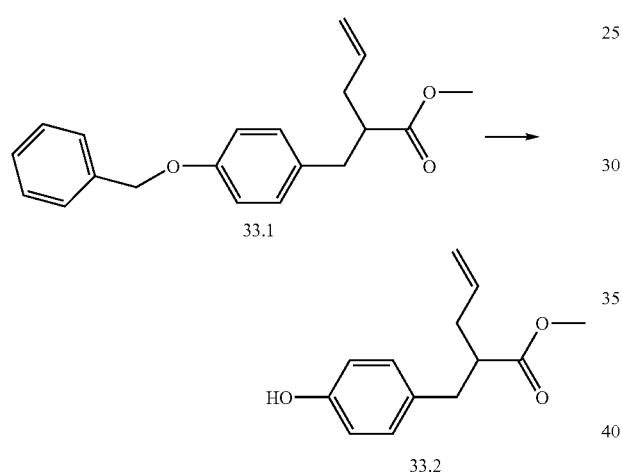

Methyl 2-((4-hydroxyphenyl)methyl)-4-pentenoate (33.2). Compound 33.2 was prepared as described in Example 41. MS ESI (pos.) m/e: 221.1 (M+H)$^+$.

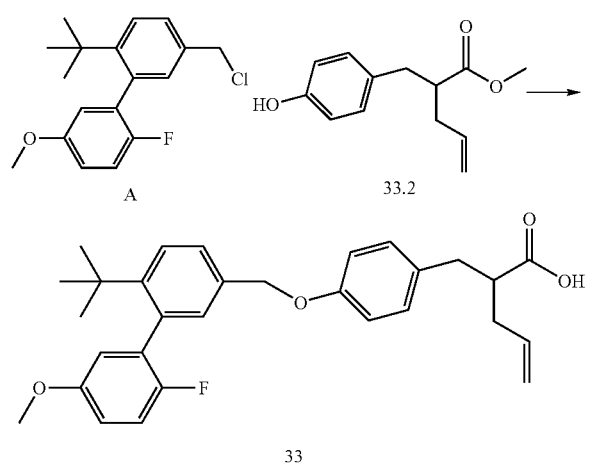

2-((4-(((6-(1,1-Dimethylethyl)-2'-fluoro-5'-(methyloxy)-1,1'-biphenyl-3-yl)methyl)oxy)phenyl)methyl)-4-pentenoic acid (33) Compound 33 was prepared as described in Example 41. $^1$H NMR (500 MHz, $CD_3CN$) δ ppm 1.18(s, 9H) 2.19-2.32 (m, 2H) 2.62-2.71 (m, 2H) 2.76-2.80 (m, 1H) 3.75 (s, 3H) 4.99 (s, 2H) 5.02 (m, 2H) 5.77 (m, 1H) 6.80 (dd, J=5.87, 3.18 Hz, 1H) 6.85-6.93 (m, 3H) 7.03-7.11 (m, 4H) 7.39 (dd, J=8.31, 1.96 Hz, 1H) 7.59 (d, J=8.56 Hz, 1H). MS ESI (neg.) m/e: 475.1 (M−H)$^+$.

Example 34

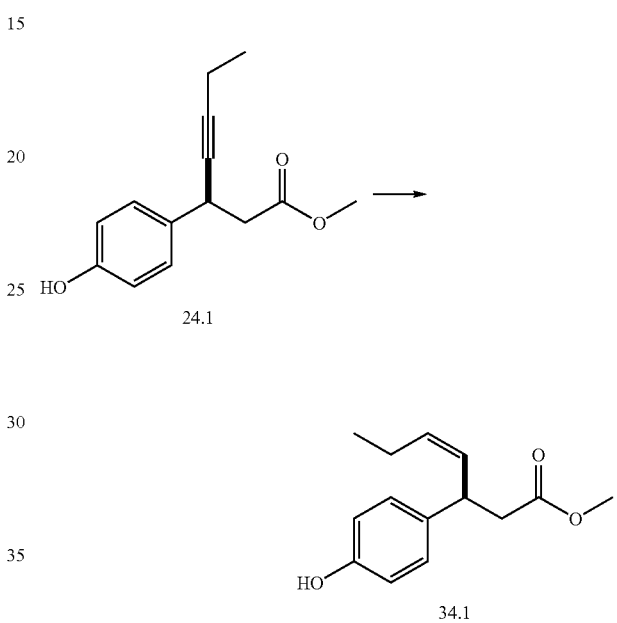

(R,Z)-Methyl 3-(4-hydroxyphenyl)hept-4-enoate (34.1). (S)-methyl 3-(4-hydroxyphenyl)hept-4-ynoate 24.1 was prepared by a method based on that reported in U.S. Patent Application Publication No. 2006/0004012 which is hereby incorporated by reference. To a stirred solution of 24.1 (0.077 g, 0.3 mmol) in EtOAc (3 mL) at 23° C. was added quinoline (0.08 mL, 0.7 mmol), followed by Lindlar Catalyst (0.004 g, 0.03 mmol). The reaction was placed under an atmosphere of hydrogen and then stirred at room temperature. After 15 hours, water was added to the mixture, and the mixture was extracted with EtOAc. After concentration, the residue was purified on silica gel (0%-20% EtOAc/hexane) to give (R,Z)-methyl 3-(4-hydroxyphenyl)hept-4-enoate 34.1 (0.073 g, 94%). MS ESI (pos.) m/e: 235.1 (M+H)$^+$.

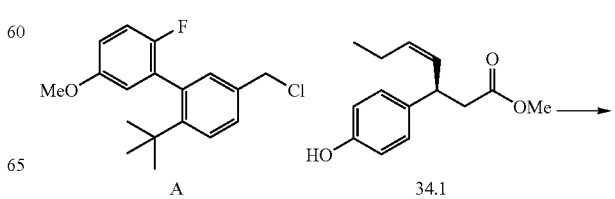

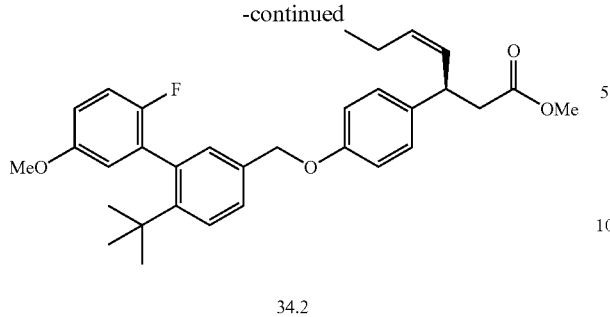

34.2

Methyl (3R,4Z)-3-(4-(((6-(1,1-dimethylethyl)-2'-fluoro-5'-(methyloxy)-1,1'-biphenyl-3-yl)methyl)oxy)phenyl)-4-heptenoate (34.2). To a stirred solution of (R,Z)-methyl 3-(4-hydroxyphenyl)hept-4-enoate 34.1 (0.025 g, 0.11 mmol) in DMF (2.00 mL, 0.11 mmol) at 23° C. was added A (0.036 g, 0.12 mmol) followed by cesium carbonate (0.042 g, 0.13 mmol). The reaction mixture was then stirred for 17 hours. Water was added to the reaction, and the resulting mixture was extracted with EtOAc. The organic layer was dried over MgSO$_4$, filtered, and concentrated. The product thus obtained was purified by silica gel flash chromatography (0-20% EtOAc/hexane) to afford compound 34.2 (0.050 g, 93% yield). MS ESI (pos.) m/e: 522.2 (M+H$_2$O).

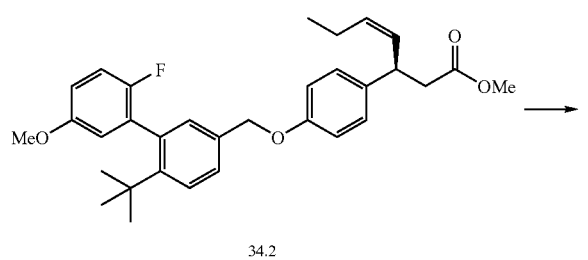

34.2

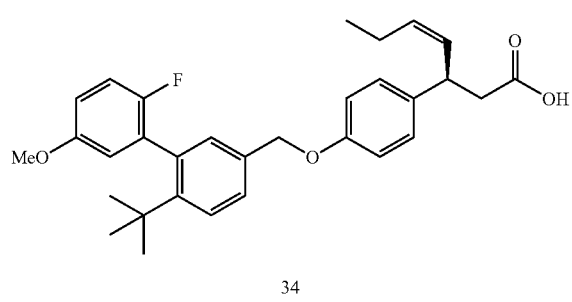

34

(3R,4Z)-3-(4-(((6-(1,1-Dimethylethyl)-2'-fluoro-5'-(methyloxy)-1,1'-biphenyl-3-yl)methyl)oxy)phenyl)-4-heptenoic acid (34). To a stirred solution of 34.2 (0.050 g, 0.10 mmol) in THF (2 mL, 0.2 mmol) and EtOH (2 mL, 0.2 mmol) at 23° C. was added a solution of 1 M sodium hydroxide (1.00 mL, 1.0 mmol). The resulting reaction mixture was stirred for 21 hours, and concentrated in vacuo. 1 N HCl was added to bring the pH to 1, and the resulting mixture was extracted EtOAc, dried over MgSO$_4$, filtered, and concentrated. The resulting product was purified by silica gel flash chromatography (0-20% EtOAc/hexane) to afford compound 34 (35 mg, 71% yield) as a colorless oil. MS ESI (neg.) m/e: 979.5 (2M−H)$^+$, 489.2 (M−H)$^+$.

Example 35

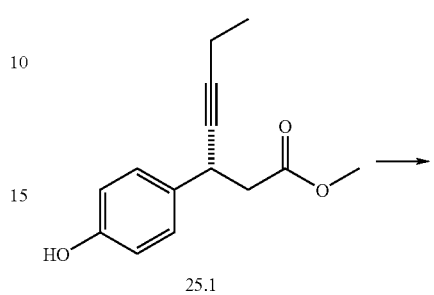

25.1

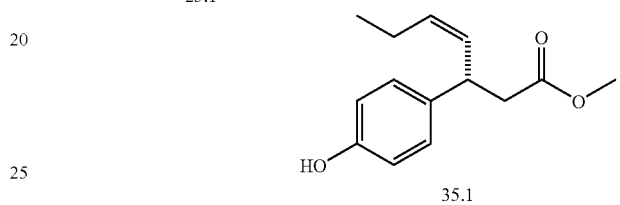

35.1

(S,Z)-methyl 3-(4-hydroxyphenyl)hept-4-enoate (35.1). Compound 25.1 was prepared by a method based on that reported in U.S. Patent Application Publication No. 2006/0004012 which is hereby incorporated by reference) To a stirred solution of 25.1 (0.063 g, 0.3 mmol) in EtOAc (3 mL) at 23° C. was added quinoline (0.06 mL, 0.5 mmol), followed by Lindlar Catalyst (0.003 g, 0.03 mmol). The reaction was placed under an atmosphere of hydrogen and then stirred at room temperature. After 15 hours, water was added to the mixture and then the mixture was extracted with EtOAc. After concentration, the residue was purified on silica gel (0%-20% EtOAc/hexane) to give (S,Z)-methyl 3-(4-hydroxyphenyl) hept-4-enoate 35.1 (0.063 g, 99%). MS ESI (pos.) m/e: 235.1 (M+H)$^+$.

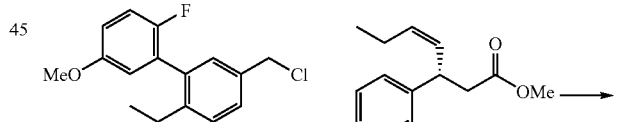

A     35.1

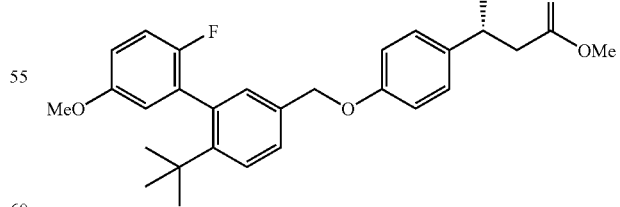

35.2

Methyl (3S,4Z)-3-(4-(((6-(1,1-dimethylethyl)-2'-fluoro-5'-(methyloxy)-1,1'-biphenyl-3-yl)methyl)oxy)phenyl)-4-heptenoate (35.2). To a stirred solution of (S,Z)-methyl 3-(4-hydroxyphenyl)hept-4-enoate 35.1 (0.025 g, 0.11 mmol) in DMF (2.00 mL, 0.11 mmol) at 23° C. was added A (0.036 g, 0.12 mmol) followed by cesium carbonate (0.042 g, 0.13 mmol). The resulting reaction mixture was stirred for 17 hours. Water was added to the reaction, and the resulting mixture was extracted with EtOAc. The organic layer was dried over $MgSO_4$, filtered, and concentrated. The residue was purified by silica gel flash chromatography (0-20% EtOAc/hexane) to afford compound 35.2 (0.047 g, 87% yield). MS ESI (pos.) m/e: 522.2 (M+$H_2O$).

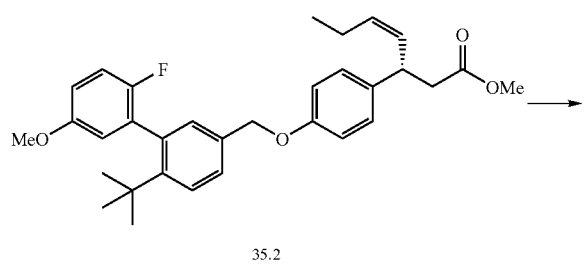

35.2

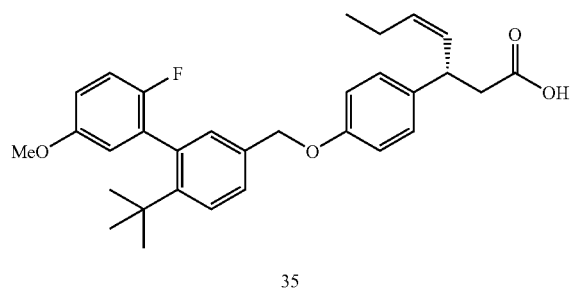

35

(3S,4Z)-3-(4-(((6-(1,1-Dimethylethyl)-2'-fluoro-5'-(methyloxy)-1,1'-biphenyl-3-yl)methyl)oxy)phenyl)-4-heptenoic acid (35). To a stirred solution of 35.2 (0.047 g, 0.09 mmol) in THF (2 mL, 0.2 mmol) and EtOH (2 mL, 0.2 mmol) at 23° C. was added a solution of 1 M sodium hydroxide (1.00 mL, 1.0 mmol). The resulting reaction mixture was stirred for 22 hours, and then was concentrated in vacuo. 1 N HCl was added to bring the pH to 1, and the resulting mixture was extracted EtOAc, dried over $MgSO_4$, filtered and concentrated. The product thus obtained was purified by silica gel flash chromatography (0-20% EtOAc/hexane) to afford compound 35 (19 mg, 42% yield) as a colorless oil. MS ESI (neg.) m/e: 979.5 (2M−H)$^+$, 489.2 (M−H)$^+$.

Example 36

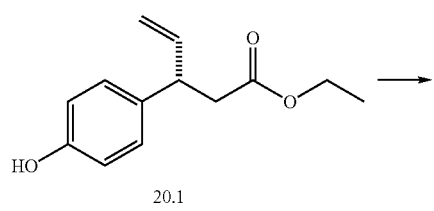

20.1

-continued

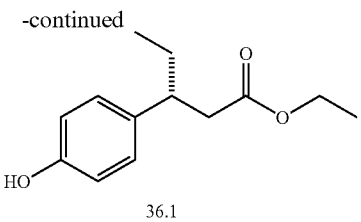

36.1

Ethyl (3R)-3-(4-hydroxyphenyl)-4-pentenoate (36.1). A 50 mL flask containing a solution of 20.1 (0.15 g, 0.68 mmol) in EtOAc (10 mL) was purged with $N_2$, and to it was added palladium, 10 wt. % (dry), on carbon powder, wet (0.145 g, 0.136 mmol). The vial was then purged with $H_2$ and the contents stirred overnight under a $H_2$ balloon. The black mixture was filtered through a pad of celite and concentrated to afford a pink oil. The product thus obtained was purified by silica gel chromatography (0 to 10% EtOAc/hexanes) yielding 36.1 (0.148 g, 97.8% yield).

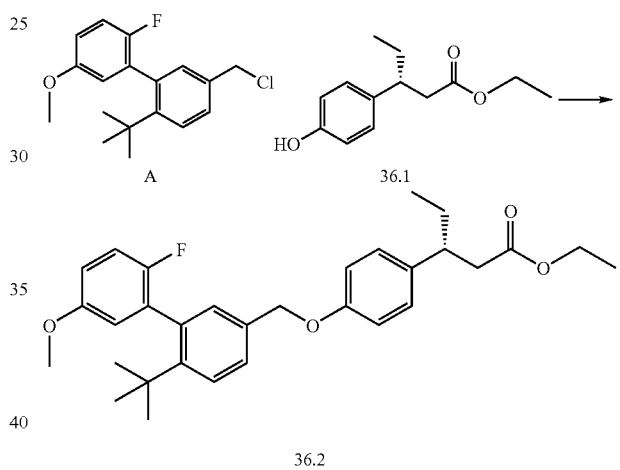

36.2

Ethyl (3R)-3-(4-(((6-(1,1-dimethylethyl)-2'-fluoro-5'-(methyloxy)-1,1'-biphenyl-3-yl)methyl)oxy)phenyl)pentanoate (36.2). To a flask containing 36.1 (0.0300 g, 0.135 mmol) and cesium carbonate (0.057 g, 0.18 mmol) in DMF (1 mL) was added A (0.050 g, 0.16 mmol), and the resulting mixture was stirred overnight. The reaction was diluted with water and extracted with EtOAc. The combined organic layers were washed with brine, dried over $Na_2SO_4$, filtered, concentrated, and then purified by silica gel chromatography (0 to 20% EtOAc/Hexanes) to provide 36.2 (0.056 g, 84% yield).

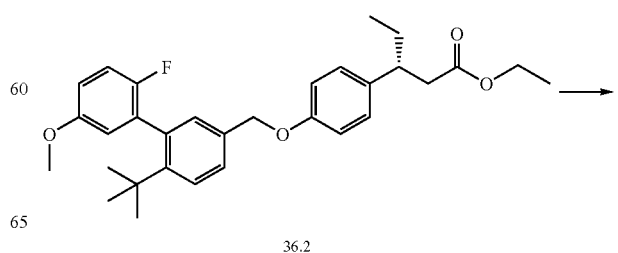

36.2

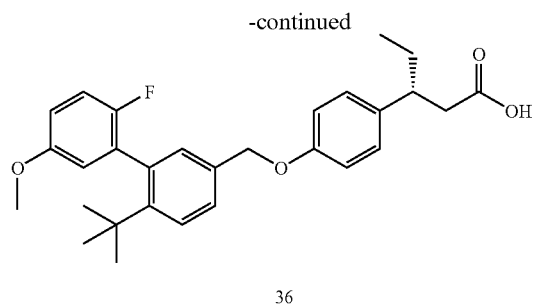

36

(3R)-3-(4-(((6-(1,1-Dimethylethyl)-2'-fluoro-5'-(methyloxy)-1,1'-biphenyl-3-yl)methyl)oxy)phenyl)pentanoic acid (36). To a solution of 36.2 (0.056 g, 0.114 mmol) in THF/MeOH (2/1) (1.5 mL) was added a solution of 1 M lithium hydroxide (0.50 mL, 0.50 mmol). The resulting mixture was stirred overnight at 23° C., and then quenched with excess 1N HCl and extracted with EtOAc. The combined organic layers were dried over $Na_2SO_4$ and concentrated. The residue was purified by silica gel chromatography (0 to 40% EtOAc/hexanes) to afford a 36 (0.046 g, 87% yield). MS ESI (neg.) m/e: 463.3 $(M-H)^+$.

Example 37

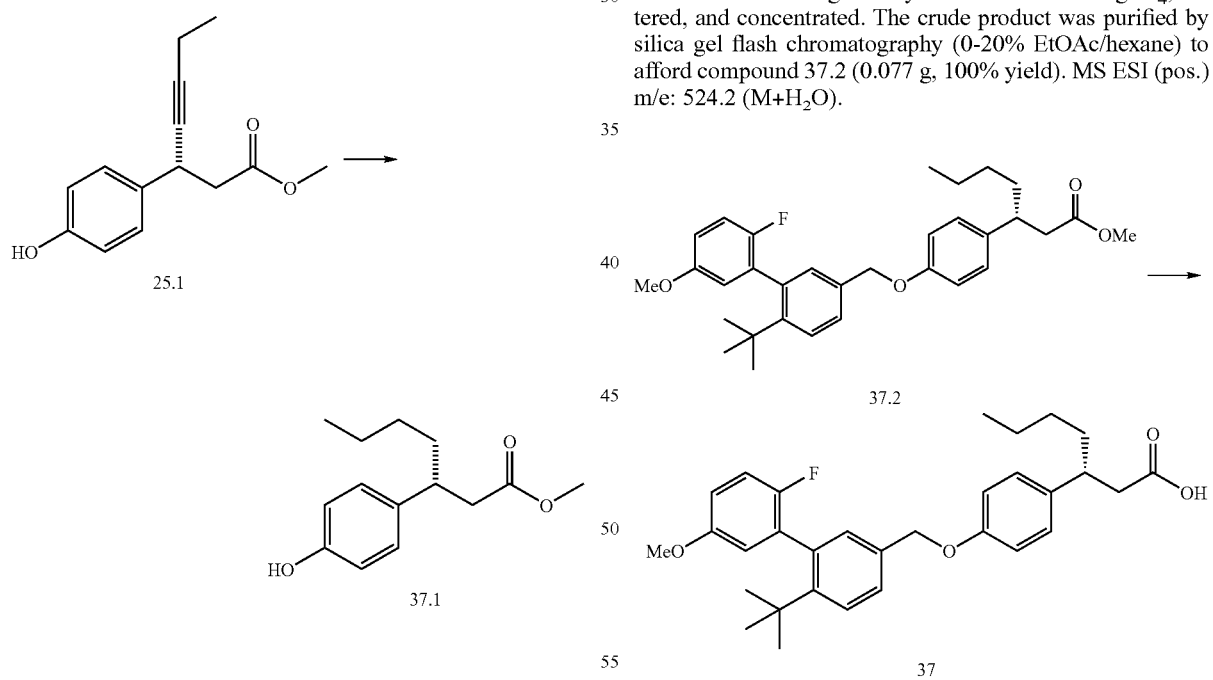

(R)-Methyl 3-(4-hydroxyphenyl)heptanoate (37.1). To a stirred solution of 25.1 (0.067 g, 0.3 mmol) in EtOAc (3 mL) at 23° C. was added palladium on carbon (0.03 g, 0.3 mmol). The reaction was placed under an atmosphere of hydrogen and then stirred at room temperature. After 5 hours, the reaction mixture was filtered through a pad of silica gel and then concentrated. After concentration, the residue was purified on silica gel (0%-20% EtOAc/hexane) to give 37.1 (0.065 g, 95%). MS ESI (pos.) m/e: 237.1 $(M+H)^+$.

Methyl (3R)-3-(4-(((6-(1,1-dimethylethyl)-2'-fluoro-5'-(methyloxy)-1,1'-biphenyl-3-yl)methyl)oxy)phenyl)heptanoate (37.2). To stirred solution of (R)-methyl 3-(4-hydroxyphenyl)heptanoate 37.1 (0.036 g, 0.15 mmol) in DMF (2.00 mL, 0.11 mmol) at 23° C. was added A (0.051 g, 0.17 mmol) followed by cesium carbonate (0.060 g, 0.18 mmol). The resulting reaction mixture was stirred for 23 hours. Water was added to the reaction, and the resulting mixture was extracted with EtOAc. The organic layer was dried over $MgSO_4$, filtered, and concentrated. The crude product was purified by silica gel flash chromatography (0-20% EtOAc/hexane) to afford compound 37.2 (0.077 g, 100% yield). MS ESI (pos.) m/e: 524.2 $(M+H_2O)$.

(3R)-3-(4-(((6-(1,1-Dimethylethyl)-2'-fluoro-5'-(methyloxy)-1,1'-biphenyl-3-yl)methyl)oxy)phenyl)heptanoic acid (37). To a stirred solution of 37.2 (0.077 g, 0.15 mmol) in THF (2 mL, 0.2 mmol) and EtOH (2 mL, 0.2 mmol) at 23° C. was added a solution of 1 M sodium hydroxide (1.00 mL, 1.0 mmol). The resulting reaction mixture was stirred for 19 hours. The resulting reaction was concentrated in vacuo. 1 N HCl was added to bring the pH to 1, and the resulting mixture was extracted EtOAc, dried over $MgSO_4$, filtered, and concentrated. The product thus obtained was purified by silica gel flash chromatography (0-20% EtOAc/hexane) to afford compound 37 (60 mg, 80% yield) as a colorless oil. MS ESI (neg.) m/e: 983.5 (2M–H)+, 491.3 (M–H)+.

Example 38

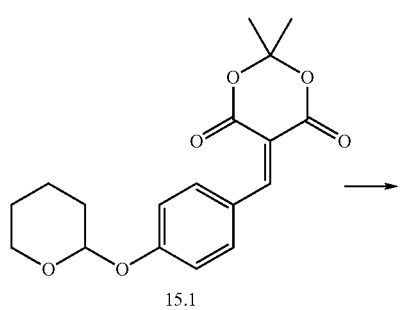

15.1

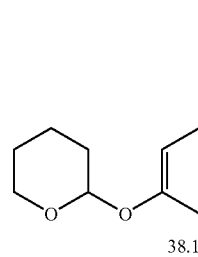

38.1

Ethyl 3-(4-(tetrahydro-2H-pyran-2-yloxy)phenyl)butanoate (38.1). To a stirred solution of 15.1 (11.0 g, 33.1 mmol) (prepared in an analogous manner to the procedure of Example 12 set forth in U.S. Patent Application Publication No. 2006/0004012 which is hereby incorporated by reference) in THF (150 mL) under nitrogen was added methyl magnesium bromide in diethyl ether (3.0 M, 13.2 mL) over a period of 20 minutes. After the addition was complete, the reaction mixture was stirred for 30 minutes, quenched with saturated aqueous NH4Cl (50 mL) and extracted with EtOAc (3×50 mL). The combined extracts were washed with water, dried over MgSO4, filtered, and concentrated to a yellow solid. A solution of this yellow solid in pyridine:EtOH (5:1, v:v, 75 mL) was heated at 90° C. for 77 hours. The reaction mixture was cooled to room temperature and concentrated in vacuo. The residue was then purified by flash chromatography (SiO2 gel 60, eluted with 0%-20% EtOAc in hexanes). Fractions containing the desired product were combined and concentrated to give 38.1 (5 g, 52%) as a colorless oil. MS ESI (pos.) m/e: 315.1 (M+Na)+, 310.3 (M+H2O)+.

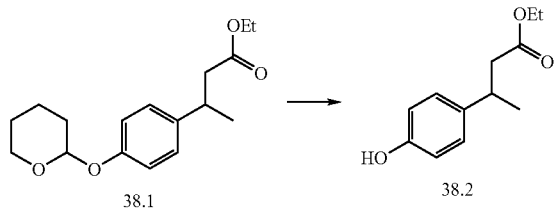

Ethyl 3-(4-hydroxyphenyl)butanoate (38.2). To a stirred solution of 38.1 (5.00 g, 17.1 mmol) in EtOH (100 mL) at room temperature was added PPTS. The resulting solution was stirred for 16 hours and then concentrated in vacuo. The residue was purified by flash chromatography (SiO2 gel 60, eluted with 0%-20% EtOAc in hexanes). Fractions containing the desired product were combined and concentrated to give 38.2 (3.00 g, 84%) as a colorless oil. MS ESI (pos.) m/e: 226.1 (M+H2O)+.

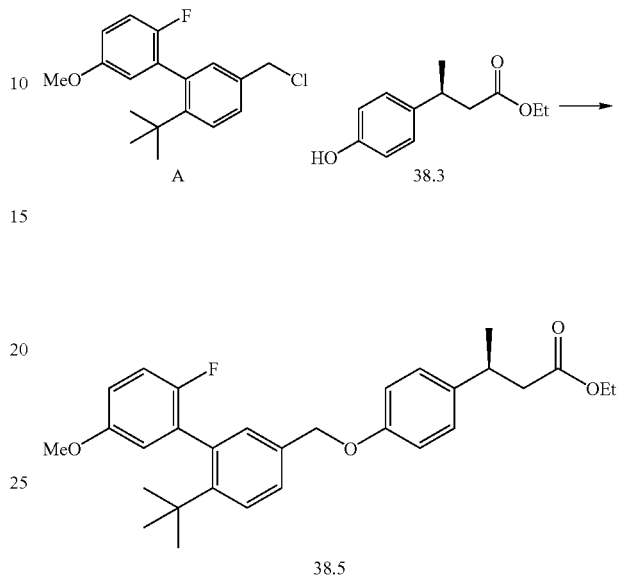

Ethyl (3S)-3-(4-(((6-(1,1-dimethylethyl)-2'-fluoro-5'-(methyloxy)-1,1'-biphenyl-3-yl)methyl)oxy)phenyl)butanoate (26.5). Compound 38.2 was separated by chiral HPLC (Daicel ChiralPAK OD-H column, eluant: 96:4 hexanes:2-propanol) using methods known to those skilled in the art to provide compound (R)-ethyl 3-(4-hydroxyphenyl)butanoate 38.3 and (S)-ethyl 3-(4-hydroxyphenyl)butanoate 38.4. It is believed that 38.3 and 38.4 have the stereochemistry shown, but this could be incorrect. Therefore, the stereochemistry of the products and intermediates shown in Examples 38 and 39 could be the opposite of that shown. However, both 38.3 and 38.4 were used to generate these Example compounds so both enantiomers were synthesized. To a stirred solution of 38.3 (0.025 g, 0.12 mmol) in DMF (2.00 mL, 0.11 mmol) at 23° C. was added A (0.041 g, 0.13 mmol) followed by cesium carbonate (0.047 g, 0.14 mmol). The resulting reaction mixture was stirred for 23 hours. Water was added to the reaction, and the resulting mixture was extracted with EtOAc. The organic layer was dried over MgSO4, filtered, and concentrated. The product thus obtained was purified by silica gel flash chromatography (0-20% EtOAc/hexane) to afford compound 38.5 (0.057 g, 99% yield). MS ESI (pos.) m/e: 496.3 (M+H2O).

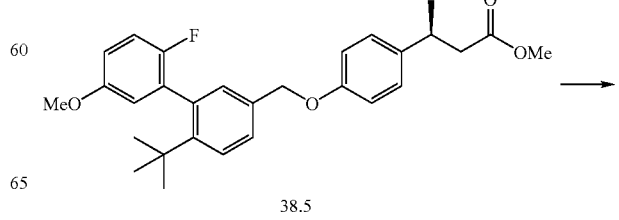

38.5

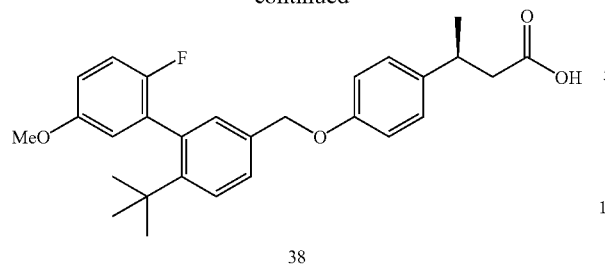

38

(3S)-3-(4-(((6-(1,1-Dimethylethyl)-2'-fluoro-5'-(methyloxy)-1,1'-biphenyl-3-yl)methyl)oxy)phenyl)butanoic acid (38). To a stirred solution of 38.5 (0.057 g, 0.12 mmol) in THF (2 mL, 0.2 mmol) and EtOH (2 mL, 0.2 mmol) at 23° C. was added a solution of 1 M sodium hydroxide (1.00 mL, 1.0 mmol). The resulting reaction mixture was stirred for 21 hours and then concentrated in vacuo. 1 N HCl was added to bring the pH to 1, and the resulting mixture was extracted with EtOAc, dried over MgSO$_4$, filtered, and concentrated. The product was purified by silica gel flash chromatography (0-20% EtOAc/hexane) to afford compound 38 (42 mg, 78% yield) as a colorless oil. MS ESI (neg.) m/e: 899.5 (2M−H)$^+$, 449.2 (M−H)$^+$.

Example 39

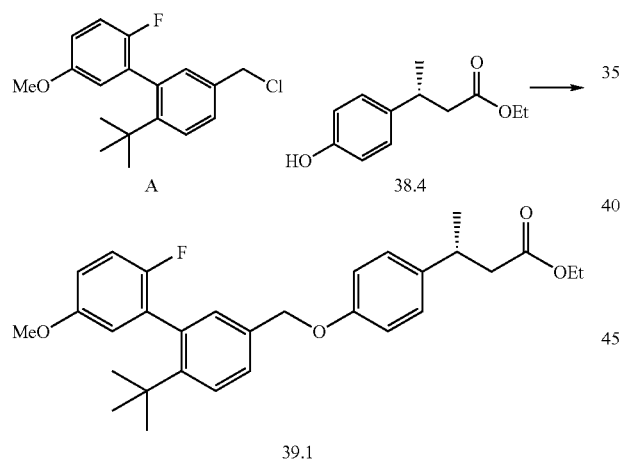

39.1

Ethyl (3R)-3-(4-(((6-(1,1-dimethylethyl)-2'-fluoro-5'-(methyloxy)-1,1'-biphenyl-3-yl)methyl)oxy)phenyl)butanoate (27.1). Compound 38.2 is separated by chiral HPLC (Daicel ChiralPAK OD-H column, eluant: 96:4 hexanes:2-propanol) using methods known to those skilled in the art to provide compound 38.4. See Example 38—it is possible that 38.4 is the enantiomer of the compound shown and that 38.3 is the enantiomer shown although it is believed that 38.4 is the enantiomer shown. To a stirred solution of 38.4 (0.025 g, 0.12 mmol) in DMF (2.00 mL, 0.11 mmol) at 23° C. was added A (0.041 g, 0.13 mmol) followed by cesium carbonate (0.047 g, 0.14 mmol). The resulting reaction mixture was stirred for 23 hours. Water was added to the reaction, and the resulting mixture was extracted with EtOAc. The organic layer was dried over MgSO$_4$, filtered, and concentrated. The product was purified by silica gel flash chromatography (0-20% EtOAc/hexane) to afford compound 39.1 (0.057 g, 99% yield). MS ESI (pos.) m/e: 496.3 (M+H$_2$O).

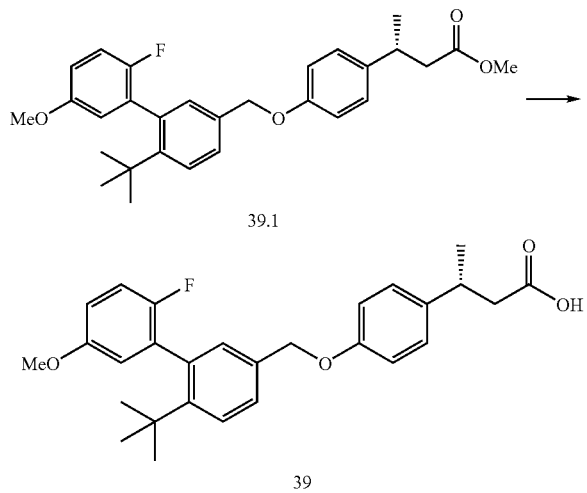

(3R)-3-(4-(((6-(1,1-Dimethylethyl)-2'-fluoro-5'-(methyloxy)-1,1'-biphenyl-3-yl)methyl)oxy)phenyl)butanoic acid (39). To a stirred solution of 39.1 (0.057 g, 0.12 mmol) in THF (2 mL, 0.2 mmol) and EtOH (2 mL, 0.2 mmol) at 23° C. was added a solution of 1 M sodium hydroxide (1.00 mL, 1.0 mmol). The resulting reaction mixture was stirred for 21 hours and then concentrated in vacuo. 1 N HCl was added to bring the pH to 1, and the resulting mixture was extracted with EtOAc, dried over MgSO$_4$, filtered, and concentrated. The product was purified by silica gel flash chromatography (0-20% EtOAc/hexane) to afford compound 39 (40 mg, 74% yield) as a colorless oil. MS ESI (neg.) m/e: 899.5 (2M−H)$^+$, 449.2 (M−H)$^+$.

Example 40

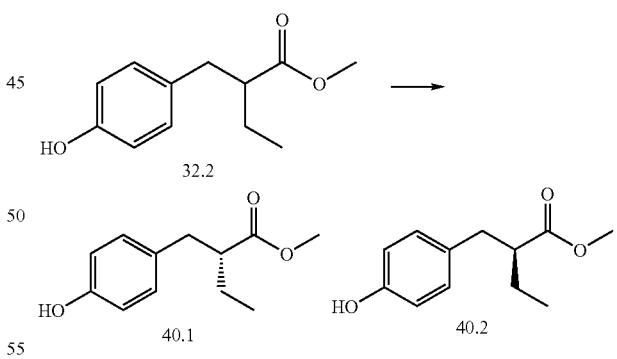

Methyl (2R)-2-((4-hydroxyphenyl)methyl)butanoate (40.1) and Methyl (2S)-2-((4-hydroxyphenyl)methyl)butanoate (40.2) Racemic 32.2 (0.60 g) was separated by ChiralPak OJ-H column, eluted with 10% isopropanol in hexane to give two enantiomer, methyl (2R)-2-((4-hydroxyphenyl)methyl)butanoate (40.1) and methyl (2S)-2-((4-hydroxyphenyl)methyl)butanoate (40.2), MS ESI (pos.) m/e: 209.1 (M+H)$^+$. It is believed that 40.1 and 40.2 have the stereochemistry shown, but this could be incorrect. Therefore, the stereochemistry of the products and intermediates shown in this Example could be the opposite of that shown.

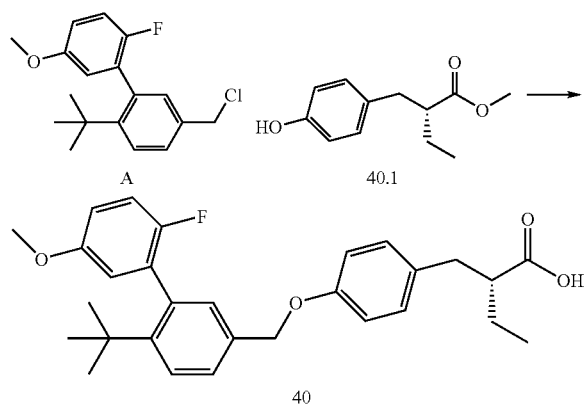

(2R)-2-((4-(((6-(1,1-Dimethylethyl)-2'-fluoro-5'-(methyloxy)-1,1'-biphenyl-3-yl)methyl)oxy)phenyl)methyl)butanoic acid (40) A reaction mixture of (R)-methyl 2-(4-hydroxybenzyl)butanoate 40.1 (25.0 mg, 120 μmol), 5-(chloromethyl)-2-(1,1-dimethylethyl)-2'-fluoro-5'-(methyloxy)-1,1'-biphenyl A (40.5 mg, 132 μmol) and cesium carbonate (78.2 mg, 240 μmol) in DMSO (1.0 mL) was stirred at room temperature for 16 hours. Lithium hydroxide (0.3 mL, 3.33 M in water) and DMSO (1.5 mL) were added, and the reaction was stirred at ambient temperature for 16 hours. The reaction mixture was purified by HPLC (reverse phase) to give the title compound, 40. $^1$H NMR (500 MHz, CD$_3$CN) δ ppm. 0.94 (t, J=7.46 Hz, 3H) 1.23 (s, 9H) 1.52-1.63 (m, 2H) 2.54 (m, 1H) 2.73 (m, 1H) 2.81 (m, 1H) 3.80 (s, 3H) 5.04 (s, 2H) 6.85 (dd, J=5.87, 3.18 Hz, 1H) 6.90-6.98 (m, 3H) 7.08-7.15 (m, 4H) 7.44 (dd, J=8.31, 1.96 Hz, 1H) 7.64 (d, J=8.31 Hz, 1H). MS ESI (neg.) m/e: 463.1 (M−H)$^+$.

Example 41

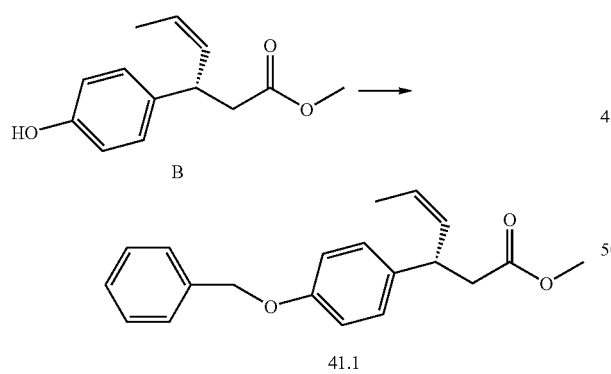

Methyl (3S,4Z)-3-(4-((phenylmethyl)oxy)phenyl)-4-hexenoate (41.1) A reaction mixture of (S,Z)-methyl 3-(4-hydroxyphenyl)hex-4-enoate (385 mg, 1748 μmol), 1-(bromomethyl)benzene (313.9 mg, 1835 μmol, prepared by a method based on that reported in U.S. Patent Application Publication No. 2006/0004012 which is hereby incorporated by reference) and cesium carbonate (1.14 g, 3496 μmol) in DMSO (3.0 mL) was stirred at room temperature overnight. Water was added to quench the reaction, and the mixture was extracted with EtOAc. The product thus obtained was carried on to the next step without further purification $^1$H NMR (500 MHz, CDCl$_3$) δ ppm 1.54-1.62 (m, 3H) 2.47-2.54 (m, 1H) 2.56-2.63 (m, 1H) 3.50 (m, 3H) 4.00-4.07 (m, 1H) 4.93 (s, 2H) 5.38-5.45 (m, 2H) 6.79-6.83 (m, 2H) 7.01-7.08 (m, 2H) 7.20-7.33 (m, 5H). MS ESI (pos.) m/e: 311.1 (M+H)$^+$.

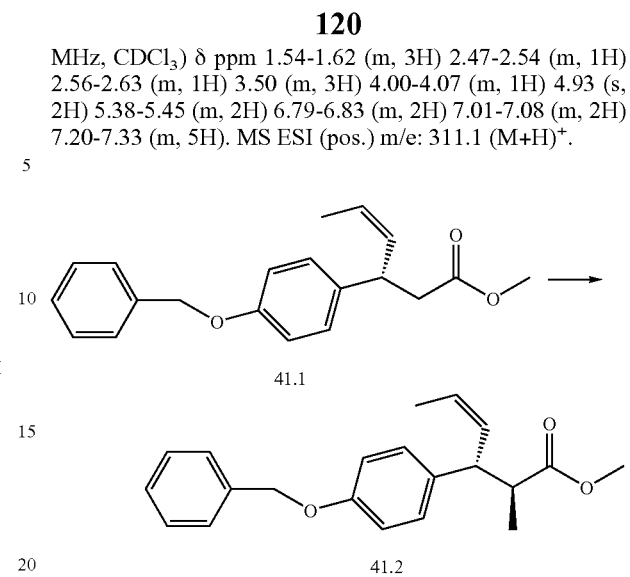

Methyl (2S,3R,4Z)-2-methyl-3-(4-((phenylmethyl)oxy)phenyl)-4-hexenoate (41.2). To a solution of lithium diisopropylamide (0.2 mL, 2 mmol in heptane/THF/ethylbenzene) in THF (1.0 mL) was slowly added (S,Z)-methyl 3-(4-(benzyloxy)phenyl)hex-4-enoate 41.1 (0.50 g, 2 mmol) in THF (5.0 mL) at −78° C. The resulting mixture was stirred at −78° C. for 1 hour and then iodomethane (0.1 mL, 2 mmol) was added. The reaction mixture was stirred at the same temperature for 20 minutes, and then stirred at room temperature for 16 hours. The solvent was removed in vacuo. The residue was purified by silica gel, eluent with hexane/EtOAc 95/5 to 10/90 to give the title compound as a major product 41.2 in a ratio of 95:5. $^1$H NMR (400 MHz, CDCl$_3$) δ ppm 1.08 (d, J=7.04 Hz, 3H) 1.46-1.61 (m, 1H) 2.64 (m, 1H) 3.34 (s, 3H) 4.90 (s, 2H) 5.35-5.53 (m, 2H) 6.76-6.84 (m, 2H) 6.97-7.07 (m, 2H) 7.15-7.34 (m, 5H). MS ESI (pos.) m/e: 325.1 (M+H)$^+$. It is possible that the stereochemistry at the carbon atom adjacent to the carbonyl is opposite that shown which would carry through to the final product of this Example. However, it is believed that the structure of 41.2 is as shown above.

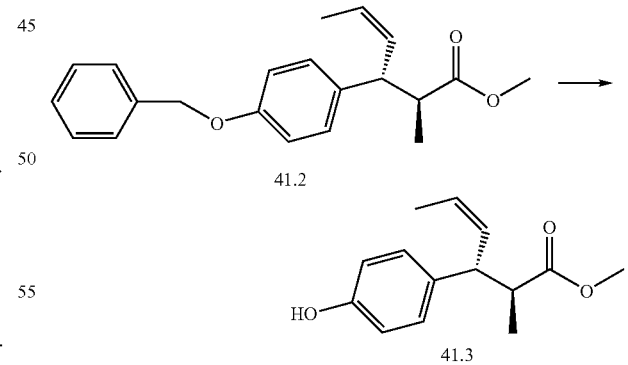

Methyl (2S,3R,4Z)-3-(4-hydroxyphenyl)-2-methyl-4-hexenoate (41.3). A reaction mixture of (2S,3R,Z)-methyl 3-(4-(benzyloxy)phenyl)-2-methylhex-4-enoate 41.2 (0.45 g, 1.4 mmol), trichloroborane (0.99 g, 8.5 mmol) and dimethylsulfane (0.53 g, 8.5 mmol) in DCM (10.0 mL) was stirred at 0° C. for 5 minutes and then at room temperature for 7 hours. A saturated solution of sodium bicarbonate was added slowly at 0° C. to reach a pH of 6.5. EtOAc was added, and the organic layer was washed with brine (2×25 mL) and dried with Na₂SO₄. The product was purified by reverse phase HPLC to give the title compound (41.3) as the major product in a ratio of 95:5. ¹H NMR (500 MHz, CDCl₃) δ ppm 1.21 (d, J=6.85 Hz, 3H) 2.77 (td, J=6.97, 2.93 Hz, 1H) 3.47-3.50 (m, 3H) 3.82 (m, 1H) 5.50-5.65 (m, 2H) 6.71-6.80 (m, 2H) 7.08 (d, J=8.56 Hz, 2H). MS ESI (pos.) m/e: 235.1 (M+H)⁺.

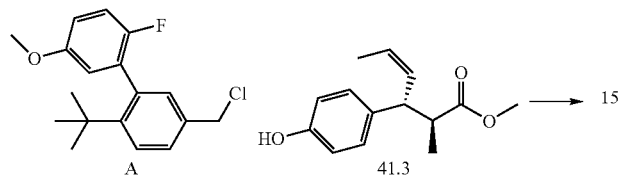

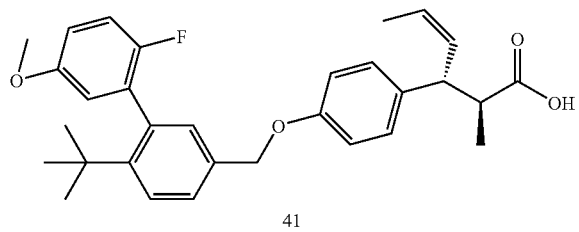

(2S,3R,4Z)-3-(4-(((6-(1,1-Dimethylethyl)-2'-fluoro-5'-(methyloxy)-1,1'-biphenyl-3-yl)methyl)oxy)phenyl)-2-methyl-4-hexenoic acid (41). A reaction mixture of (2S,3R,Z)-methyl 3-(4-hydroxyphenyl)-2-methylhex-4-enoate 41.3 (34.0 mg, 145 µmol), 5-(chloromethyl)-2-(1,1-dimethylethyl)-2'-fluoro-5'-(methyloxy)-1,1'-biphenyl A (44.5 mg, 145 µmol) and cesium carbonate (94.5 mg, 290 µmol) in DMSO (1.0 mL) was stirred at room temperature for 16 hours. Lithium hydroxide (0.4 mL, 3.33M in water) and DMSO (1.5 mL) were added, and the resulting mixture was stirred at ambient temperature for 16 hours. The reaction mixture was purified by HPLC (reverse phase) to give the title compound 41. ¹H NMR (500 MHz, CD₃CN) δ ppm 1.17 (d, J=7.09 Hz, 3H) 1.23 (s, 9H) 2.76 (m, 1H) 3.78-3.82 (m, 4H) 5.04 (s, 2H) 5.53-5.57 (m, 1H) 6.85 (dd, J=5.87, 3.18 Hz, 1H) 6.90-6.98 (m, 3H) 7.07-7.12 (m, 2H) 7.18 (d, J=8.56 Hz, 2H) 7.44 (dd, J=8.31, 1.96 Hz, 1H) 7.64 (d, J=8.31 Hz, 1H). MS ESI (neg.) m/e: 489.2 (M–H)⁺.

Example 42

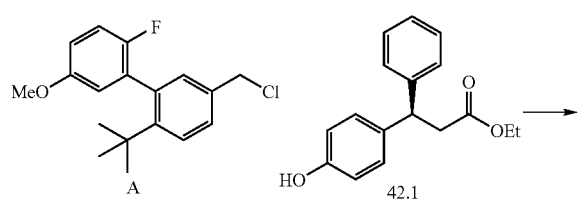

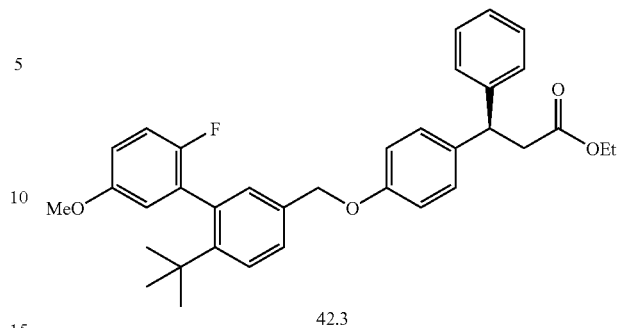

Ethyl (3R)-3-(4-(((6-(1,1-dimethylethyl)-2'-fluoro-5'-(methyloxy)-1,1'-biphenyl-3-yl)methyl)oxy)phenyl)-3-phenylpropanoate (42.3). The racemate of compound 42.1 (prepared in an analogous manner to the procedure of Example 53 set forth in U.S. Patent Application Publication No. 2006/0004012 which is hereby incorporated by reference) is separated by chiral HPLC (Daicel ChiralPAK AD-H column, eluant: 96:4 hexanes:2-propanol) using methods known to those skilled in the art to provide compound (R)-ethyl 3-(4-hydroxyphenyl)-3-phenylpropanoate 42.1 and (S)-ethyl 3-(4-hydroxyphenyl)-3-phenylpropanoate 42.2. It is believed that 42.1 and 42.2 have the stereochemistry shown above and described, but this could be incorrect. Therefore, the stereochemistry of the products and intermediates shown in Examples 42 and 44 could be the opposite of that shown. However, both 42.1 and 42.2 were used to generate these Example compounds so both enantiomers were synthesized. To a mixture of compound 42.1 (0.025 g, 0.09 mmol) in DMF (2.00 mL, 0.11 mmol) at 23° C. was added A (0.031 g, 0.10 mmol) followed by cesium carbonate (0.036 g, 0.11 mmol). The resulting mixture was then stirred for 14 hours. Water was added to the reaction, and the resulting mixture was extracted with EtOAc. The organic layer was dried over MgSO₄, filtered, and concentrated. The crude product was purified by silica gel flash chromatography (0-20% EtOAc/hexane) to afford compound 42.3 (0.048 g, 96% yield). MS ESI (pos.) m/e: 558.3 (M+H₂O).

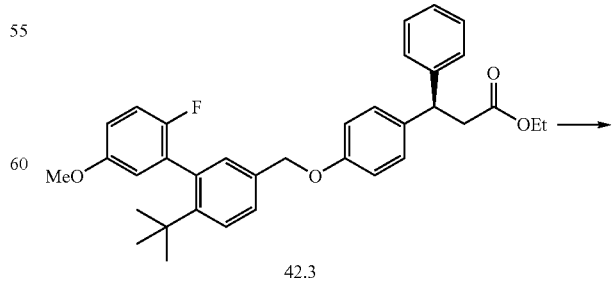

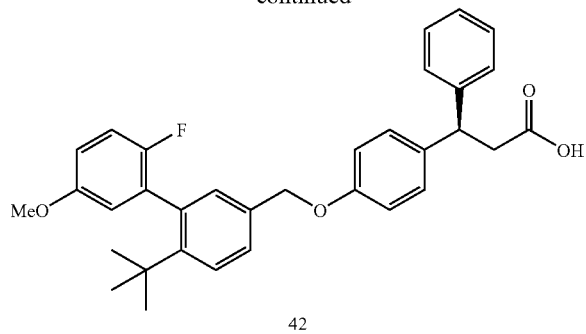

42

(3R)-3-(4-(((6-(1,1-Dimethylethyl)-2'-fluoro-5'-(methyloxy)-1,1'-biphenyl-3-yl)methyl)oxy)phenyl)-3-phenylpropanoic acid (42). To a stirred solution of 42.3 (0.048 g, 0.09 mmol) in THF (2 mL, 0.2 mmol) and EtOH (2 mL, 0.2 mmol) at 23° C. was added a solution of 1 M sodium hydroxide (1.00 mL, 1.0 mmol). The resulting mixture was stirred for 21 hours and then concentrated in vacuo. 1 N HCl was added to bring the pH to 1, and the resulting mixture was extracted with EtOAc, dried over MgSO₄, filtered, and concentrated. The product was purified by silica gel flash chromatography (0-20% EtOAc/hexane) to afford compound 42 (33 mg, 73% yield) as a colorless oil. MS ESI (neg.) m/e: 511.3 (M−H)⁺.

Example 43

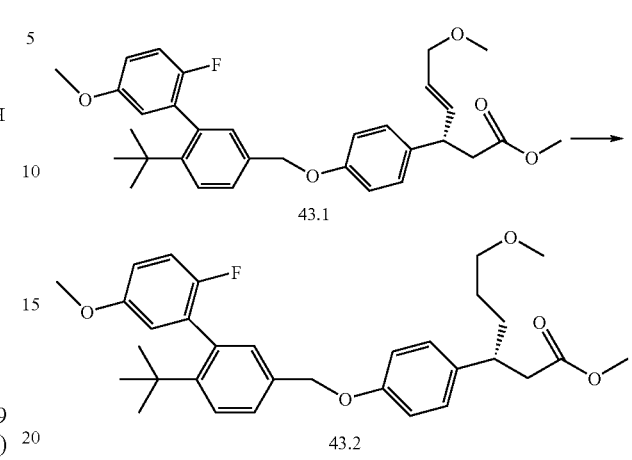

Methyl (3S,4E)-3-(4-(((6-(1,1-dimethylethyl)-2'-fluoro-5'-(methyloxy)-1,1'-biphenyl-3-yl)methyl)oxy)phenyl)-6-(methyloxy)-4-hexenoate (42.1). Reference, *Org. Lett.* 2002, 4, (11), 1939. A reaction mixture of methyl (3S,4Z)-3-(4-(((6-(1,1-dimethylethyl)-2'-fluoro-5'-(methyloxy)-1,1'-biphenyl-3-yl)methyl)oxy)phenyl)-4-hexenoate 9.2 (220.0 mg, 448.4 μmol) and (1,3-bis(2,4,6-trimethylphenyl)-2-imidazolidinyl)(dichloro)((2-((1-methylethyl)oxy)phenyl)methyl)ruthenium (14.05 mg, 22.42 μmol) and 3-methoxyprop-1-ene (2102 mg, 29148 μmol) in DCM (3.0 mL) was heated at 50° C. for 16 hours to provide a reaction product. The product was purified by silica gel column with hexane/EtOAc 100/0 to 95/5 as eluent to give the title compound 43.1, 31.5 mg. ¹H NMR (400 MHz, CDCl₃) δ ppm 1.15 (s, 9H) 2.63 (m, 2H) 3.21 (s, 3H) 3.23 (m, 1H) 3.53 (s, 3H) 3.71 (s, 3H) 3.80 (m, 2H) 4.90 (s, 2H) 5.50 (m, 1H) 5.76 (m, 1H) 6.71-6.84 (m, 4H) 6.92-7.05 (m, 4H) 7.32 (m, 1H) 7.50 (d, J=8.2 Hz, 1H). MS ESI (pos.) m/e: 543.2 (M+Na)⁺.

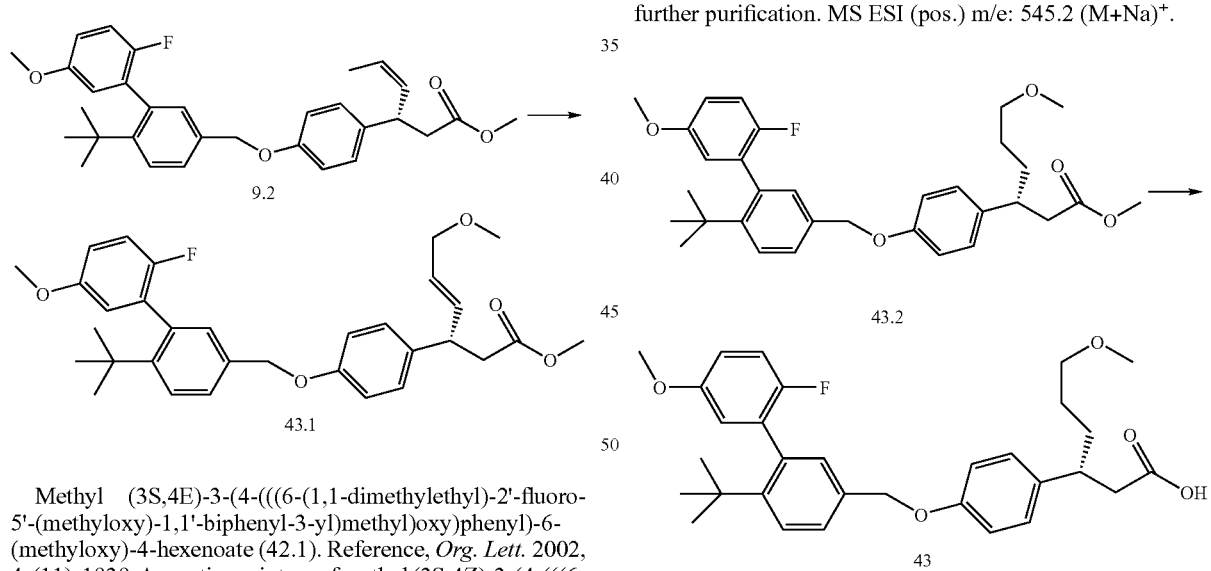

Methyl (3R)-3-(4-(((6-(1,1-dimethylethyl)-2'-fluoro-5'-(methyloxy)-1,1'-biphenyl-3-yl)methyl)oxy)phenyl)-6-(methyloxy)hexanoate (43.2) A mixture of methyl (3S,4E)-3-(4-(((6-(1,1-dimethylethyl)-2'-fluoro-5'-(methyloxy)-1,1'-biphenyl-3-yl)methyl)oxy)phenyl)-6-(methyloxy)-4-hexenoate 43.1 (31.5 mg, 6 μmol) and palladium, 10 wt. % (dry basis) on activated carbon (7.0 mg, 6 μmol) in MeOH (2.0 mL, 1.0% umol of Ph₂S) was flushed with hydrogen. The mixture was then stirred at room temperature for 2 hours. The catalyst was removed by filtration. The solvent was removed to provide the product which was used in the next step without further purification. MS ESI (pos.) m/e: 545.2 (M+Na)⁺.

(3R)-3-(4-(((6-(1,1-Dimethylethyl)-2'-fluoro-5'-(methyloxy)-1,1'-biphenyl-3-yl)methyl)oxy)phenyl)-6-(methyloxy)hexanoic acid (43). A reaction mixture of 43.2 (32.0 mg, 61 μmol) and lithium hydroxide (0.2 mL, 3.33M in water) in MeOH (1.0 mL) was stirred at ambient temperature for 16 hours. The reaction mixture was purified by HPLC (reverse phase) to give the title compound 43. ¹H NMR (400 MHz, CD₃CN) δ ppm 1.16 (s, 9H) 1.19-1.36 (m, 1H) 1.45-1.67 (m, 1H) 2.45 (d, J=8.61 Hz, 1H) 2.53 (d, J=6.65 Hz, 1H) 3.14 (s, 3H) 3.20 (t, J=6.46 Hz, 2H) 3.72 (s, 3H) 4.97 (s, 2H) 6.77 (dd, J=6.26, 3.13 Hz, 1H) 6.83-6.91 (m, 3H) 6.99-7.10 (m, 4H)

7.37 (dd, J=8.22, 1.96 Hz, 1H) 7.57 (d, J=8.22 Hz, 1H). MS ESI (neg.) m/e: 507.2 (M−H)+.

Example 44

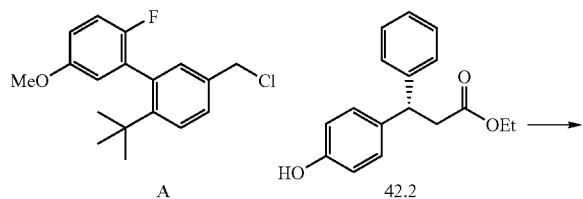

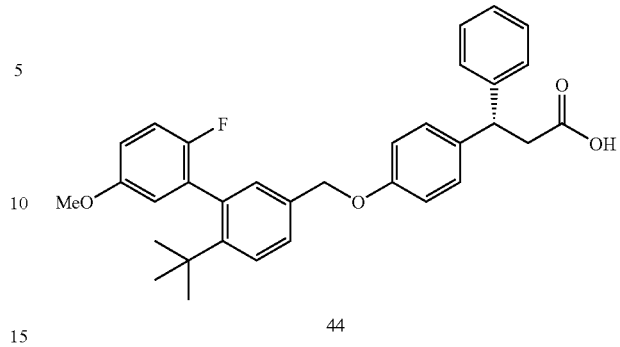

Ethyl (3S)-3-(4-(((6-(1,1-dimethylethyl)-2'-fluoro-5'-(methyloxy)-1,1'-biphenyl-3-yl)methyl)oxy)phenyl)-3-phenylpropanoate (28.3). The racemate of compound 42.2 (prepared in an analogous manner to the procedure of Example 53 set forth in U.S. Patent Application Publication No. 2006/0004012 which is hereby incorporated by reference) is separated by chiral HPLC (Daicel ChiralPAK AD-H column, eluant: 96:4 hexanes:2-propanol) using methods known to those skilled in the art to provide (S)-ethyl 3-(4-hydroxyphenyl)-3-phenylpropanoate 42.2. See Example 42—it is possible that 42.2 is the enantiomer of the compound shown and that 42.1 is the enantiomer shown although it is believed that 42.2 is the enantiomer shown To a stirred solution of (S)-ethyl 3-(4-hydroxyphenyl)-3-phenylpropanoate 42.2 (0.025 g, 0.09 mmol) in DMF (2.00 mL, 0.11 mmol) at 23° C. was added A (0.031 g, 0.10 mmol) followed by cesium carbonate (0.036 g, 0.11 mmol). The resulting reaction mixture was stirred for 14 hours. Water was added to the reaction, and the resulting mixture was extracted with EtOAc. The organic layer was dried over MgSO4, filtered, and concentrated. The product thus obtained was purified by silica gel flash chromatography (0-20% EtOAc/hexane) to afford compound 44.1 (0.047 g, 94% yield). MS ESI (pos.) m/e: 563.2 (M+Na).

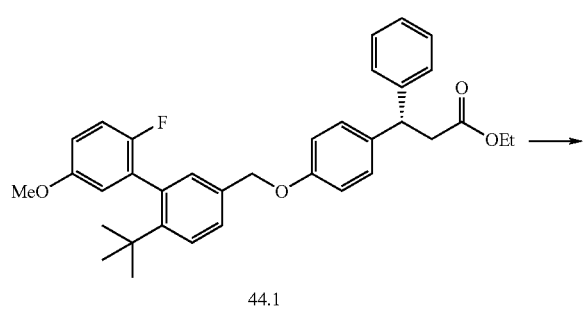

(3S)-3-(4-(((6-(1,1-Dimethylethyl)-2'-fluoro-5'-(methyloxy)-1,1'-biphenyl-3-yl)methyl)oxy)phenyl)-3-phenylpropanoic acid (44). To a stirred solution of 44.1 (0.047 g, 0.09 mmol) in THF (2 mL, 0.2 mmol) and EtOH (2 mL, 0.2 mmol) at 23° C. was added a solution of 1 M sodium hydroxide (1.00 mL, 1.0 mmol). The resulting reaction mixture was stirred for 21 hours and then concentrated in vacuo. 1 N HCl was added to bring the pH to 1, and the resulting mixture was extracted with EtOAc, dried over MgSO4, filtered, and concentrated. The resulting product was purified by silica gel flash chromatography (0-20% EtOAc/hexane) to afford compound 44 (33 mg, 74% yield) as a colorless oil. MS ESI (neg.) m/e: 511.3 (M−H)+.

Example 45

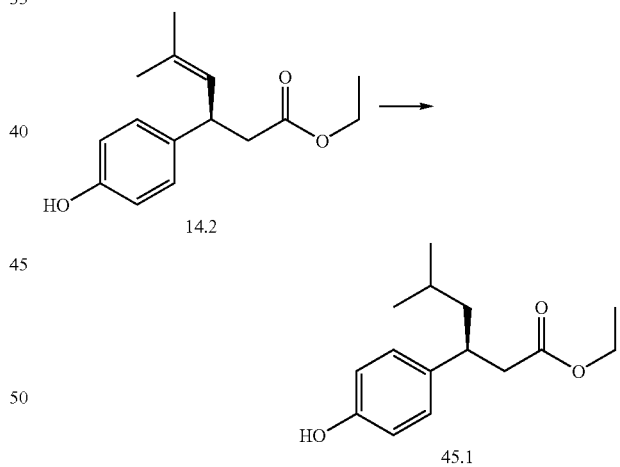

(S)-Ethyl 3-(4-hydroxyphenyl)-5-methylhexanoate (45.1). To a stirred solution of (R)-ethyl 3-(4-hydroxyphenyl)-5-methylhex-4-enoate 14.2 (0.200 g, 0.8 mmol) in EtOAc (5 mL, 51 mmol) at 0° C. was added Pd/C (0.09 g, 0.8 mmol). See Example 14—it is possible that 14.3 is the R enantiomer and that 14.2 is the S enantiomer although it is believed that 14.2 is the enantiomer shown. The reaction mixture was placed under an atmosphere of hydrogen and stirred at 23° C. for 2 hours. The reaction mixture was filtered and concentrated in vacuo. The resulting product was purified by silica gel flash chromatography (0-20% EtOAc/hexane) to afford (S)-ethyl 3-(4-hydroxyphenyl)-5-methylhexanoate 45.1 (0.200 g, 99% yield) as a colorless oil.

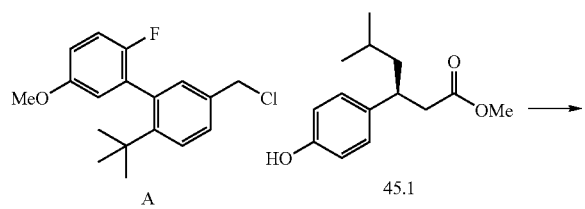

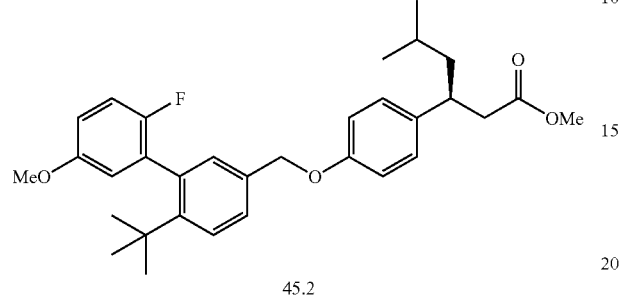

Methyl (3S)-3-(4-(((6-(1,1-dimethylethyl)-2'-fluoro-5'-(methyloxy)-1,1'-biphenyl-3-yl)methyl)oxy)phenyl)-5-methylhexanoate (45.2). To a stirred solution of 45.1 (0.025 g, 0.10 mmol) in DMF (1.0 mL, 0.10 mmol) at 0° C. was added A (0.034 g, 0.11 mmol), followed by cesium carbonate (0.039 g, 0.12 mmol). The resulting mixture was stirred at 23° C. for 22 hours. Water was added to the reaction, and the resulting mixture was extracted with EtOAc. The organic layer was dried over MgSO$_4$, filtered, and concentrated. The crude product was purified by silica gel flash chromatography (0-20% EtOAc/hexane) to afford compound 14.4 (0.048 g, 92% yield). MS ESI (pos.) m/e: 543.2 (M+Na), 538.3 (M+H$_2$O).

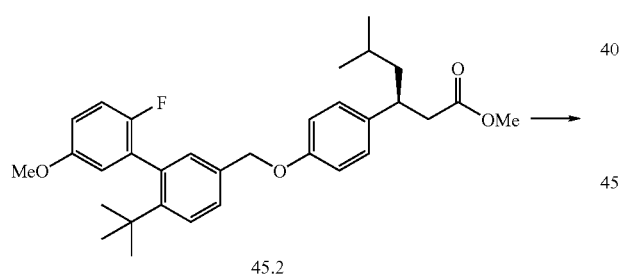

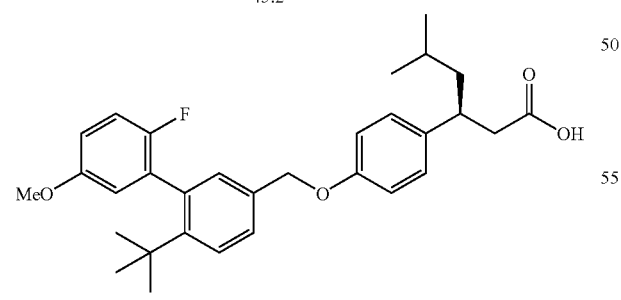

(3S)-3-(4-(((6-(1,1-Dimethylethyl)-2'-fluoro-5'-(methyloxy)-1,1'-biphenyl-3-yl)methyl)oxy)phenyl)-5-methylhexanoic acid (45). To a stirred solution of 45.2 (0.048 g, 0.09 mmol) in THF (2.00 mL, 0.10 mmol) and EtOH (2.00 mL, 0.10 mmol) at 23° C. was added a 1 M solution of sodium hydroxide (1 mL, 1 mmol). The reaction was then stirred for 19 hours. The resulting reaction was concentrated in vacuo. 1 N HCl was added to bring the pH to 1, and the resulting mixture was extracted with EtOAc, dried over MgSO$_4$, filtered, and concentrated. The crude product was purified by silica gel flash chromatography (0-20% EtOAc/hexane) to afford compound 45 (32 mg, 71% yield) as a colorless oil. MS ESI (neg.) m/e: 983.5 (M−H)$^+$, 491.2 (M−H)$^+$.

Example 46

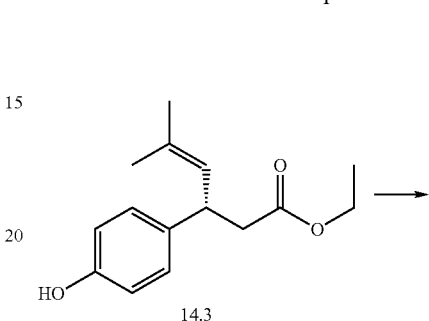

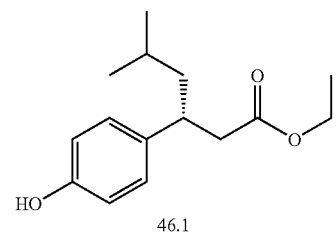

(R)-Ethyl 3-(4-hydroxyphenyl)-5-methylhexanoate (45.1). To a stirred solution of (S)-ethyl 3-(4-hydroxyphenyl)-5-methylhex-4-enoate 14.3 (0.223 g, 0.9 mmol) in EtOAc (5 mL, 51 mmol) at 0° C. was added Pd/C (0.10 g, 0.9 mmol). See Example 14—it is possible that 14.3 is the R enantiomer and that 14.2 is the S enantiomer although it is believed that 14.3 is the enantiomer shown. The reaction mixture was placed under an atmosphere of hydrogen and stirred at 23° C. for 2 hours. The reaction mixture was filtered and concentrated in vacuo. The crude product was purified by silica gel flash chromatography (0-20% EtOAc/hexane) to afford (R)-ethyl 3-(4-hydroxyphenyl)-5-methylhexanoate 46.1 (0.223 g, 99% yield) as a colorless oil.

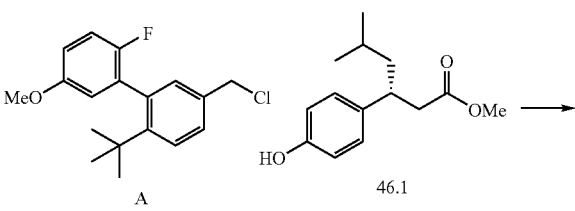

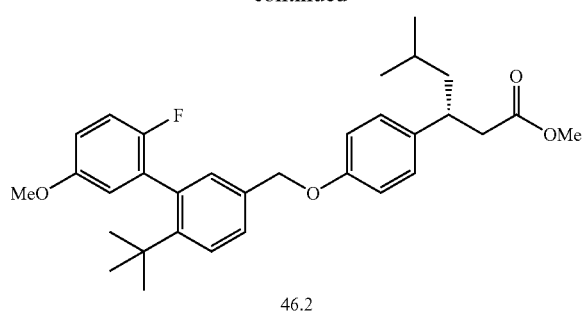

46.2

Methyl (3R)-3-(4-(((6-(1,1-dimethylethyl)-2'-fluoro-5'-(methyloxy)-1,1'-biphenyl-3-yl)methyl)oxy)phenyl)-5-methylhexanoate (46.2). To a stirred solution of 46.1 (0.025 g, 0.10 mmol) in DMF (1.0 mL, 0.10 mmol) at 0° C. was added A (0.034 g, 0.11 mmol), followed by cesium carbonate (0.039 g, 0.12 mmol). The resulting mixture was stirred at 23° C. for 22 hours. Water was added to the reaction, and the resulting mixture was extracted with EtOAc. The organic layer was dried over MgSO$_4$, filtered, and concentrated. The crude product was purified by silica gel flash chromatography (0-20% EtOAc/hexane) to afford compound 46.2 (0.047 g, 90% yield). MS ESI (pos.) m/e: 538.3 (M+H$_2$O).

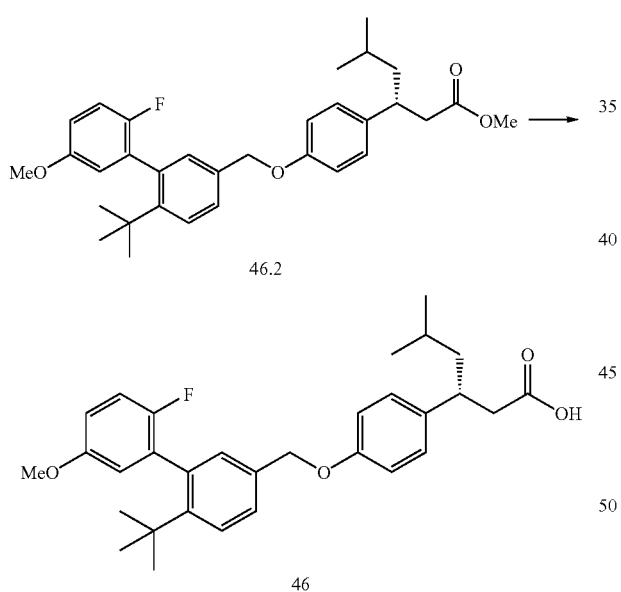

46.2

46

(3R)-3-(4-(((6-(1,1-Dimethylethyl)-2'-fluoro-5'-(methyloxy)-1,1'-biphenyl-3-yl)methyl)oxy)phenyl)-5-methylhexanoic acid (46). To a stirred solution of 46.2 (0.047 g, 0.09 mmol) in THF (2.00 mL, 0.10 mmol) and EtOH (2.00 mL, 0.10 mmol) at 23° C. was added a 1 M solution of sodium hydroxide (1 mL, 1 mmol). The resulting reaction mixture was stirred for 19 hours. The resulting reaction was concentrated in vacuo. 1 N HCl was added to bring the pH to 1, and the resulting mixture was extracted EtOAc, dried over MgSO$_4$, filtered, and concentrated. The crude product was purified by silica gel flash chromatography (0-20% EtOAc/hexane) to afford compound 46 (36 mg, 80% yield) as a colorless oil. MS ESI (neg.) m/e: 983.5 (M–H)$^+$, 491.2 (M–H)$^+$.

Example 47

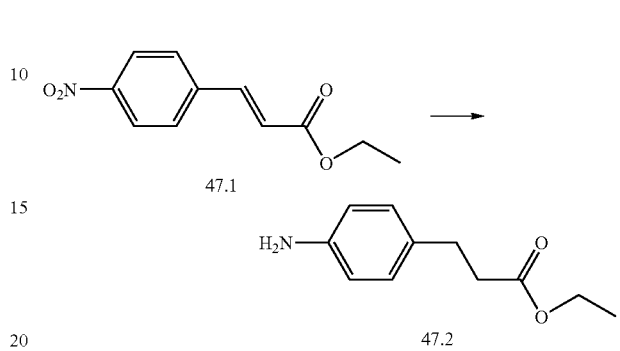

47.1

47.2

Ethyl 3-(4-aminophenyl)propanoate (47.2). A mixture of (E)-ethyl 3-(4-nitrophenyl)acrylate (commercially available from Aldrich, 5.00 g, 26.0 mmol) and 2.8 g of 10% Pd/C (wet, 50% water) in MeOH (26 mL) was shaken under 20 psi of hydrogen at room temperature for 20 hours. The mixture was then filtered through a pad of celite, the filtrate was concentrated, and the residue was purified through a short column of silica gel using 20% EtOAc/hexane as the eluent to give 3.48 g (69%) of the desired product ethyl 3-(4-aminophenyl)propanoate 47.2. MS ESI (pos.) m/e: 194 (M+H)$^+$.

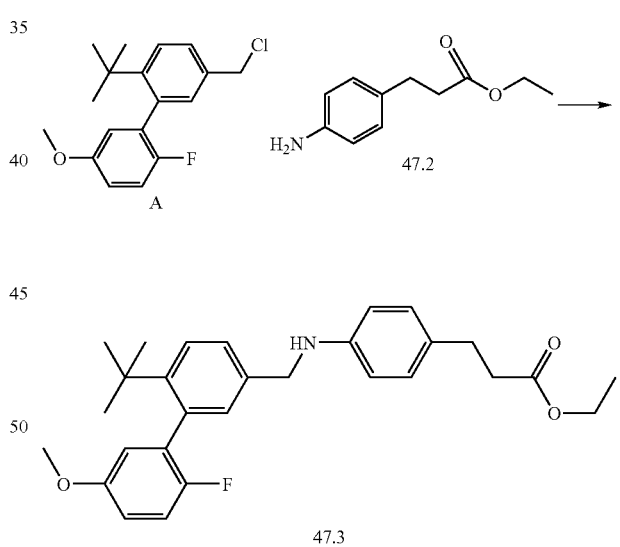

A 47.2

47.3

Ethyl-3-(4-(((6-(1,1-dimethylethyl)-2'-fluoro-5'-(methyloxy)-1,1'-biphenyl-3-yl)methyl)amino)phenyl)-4-propanoate (47.3). A mixture of A (15 mg, 0.049 mmol) and ethyl 3-(4-aminophenyl)propanoate 47.2 (19 mg, 0.098 mmol) in toluene (1.0 mL) was stirred at 110° C. for 24 hours. The mixture was directly subjected to HPLC purification to give ethyl-3-(4-(((6-(1,1-dimethylethyl)-2'-fluoro-5'-(methyloxy)-1,1'-biphenyl-3-yl)methyl)amino)phenyl)-4-propanoate 47.3 (7.0 mg). MS ESI (pos.) m/e: 464 (M+H)$^+$.

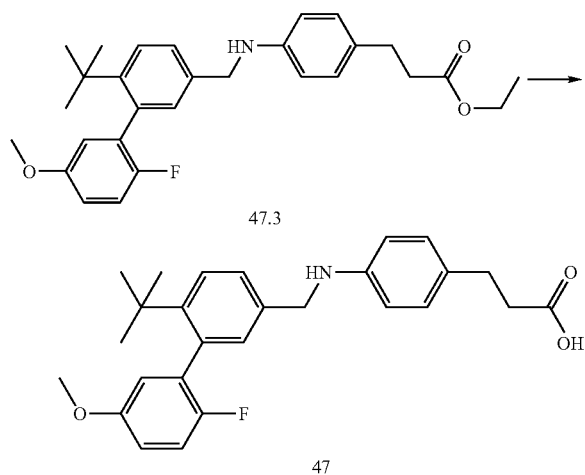

(3-(4-((((6-(1,1-dimethylethyl)-2'-fluoro-5'-(methyloxy)-1,1'-biphenyl-3-yl)methyl)amino)phenyl)-4-propanoic acid (47). To a stirred solution of 47.3 (7.0 mg, 0.02 mmol) in 1.0 mL of MeOH at 23° C. was added a solution of lithium hydroxide (5.0 mg, 0.20 mmol) in 1 mL of water. The resulting mixture was stirred at room temperature for 24 hours. The reaction was concentrated in vacuo. 1 N HCl was added to bring the pH to 1, and the resulting mixture was extracted with EtOAc (3×10 mL), dried over $Na_2SO_4$ and concentrated in vacuo. The residue was then purified by HPLC to give the desired product (5.1 mg, 78%) 47. $^1$H NMR (500 MHz, $CDCl_3$) δ ppm 7.45 (dd, J=10.0, 5.0 Hz, 1H), 7.25 (d, J=10.O Hz, 1H), 7.19 (d, J=5.0 Hz, 2H), 7.03 (d, J=5.0 Hz, 1H), 6.95 (d, J=5.0 Hz, 2H), 6.92 (m, 1H), 6.76 (m, 1H), 6.70 (m, 1H), 6.51 (m, 1H), 4.19 (br s, 2H), 3.71 (s, 3H), 2.78 (m, 2H), 2.57 (m, 2H), 1.16 (s, 9H). MS ESI (neg.) m/e: 434 (M–H).

Examples 48-62

Compounds 48-62 are prepared by reacting compound 13.5 with the appropriate phenol using the methods and compounds described herein.

Cell-Based Aequorin Assay

Cell-based aequorin assays were employed to characterize the modulatory activity of compounds on the GPR40 signaling pathway. In an exemplary assay, CHO cells were stably transfected with both GPR40 and Aequorin (Euroscreen). Cells were detached from the tissue culture dish with 2 mL of trypsin (0.25% (w/v)). Trypsinization was halted with 28 mL of Hanks Buffered Salt Solution containing 20 mM Hepes (H/HBSS) and 0.01% fatty acid-free human serum albumin (HSA). Coelantrazine is added to 1 ug/mL, and the cells were incubated for 2 hours at room temperature. Compounds were dissolved in DMSO for preparation of 10 mM stock solutions. Compounds were diluted in H/HBSS containing 0.01% HSA. Serial dilutions of the test compounds were prepared to determine dose response.

Aequorin luminescence measurements were made using an EG&G Berthold 96-well luminometer, and the response was measured over a 20 second interval after cells and compounds were mixed. The maximum relative light units was plotted to determine dose response. The $EC_{50}$ (effective concentration to reach 50% maximal response) was determined from the dose response plot.

Table 1 presents representative data ($EC_{50}$ values) obtained for exemplary compounds of the invention for the activation of human GPR40.

NFAT-Luciferase Assay

CHO cells were plated in 15 cm plates containing 6 million cells/plate in DMEM/F12 containing 10% FBS. The following day, cells were transfected with 1 μg of GPR40 expression plasmid, 4 μg of NFAT-luciferase reporter plasmid and 16 ug of pcDNA3.1 complexed with 60 μL of Lipofectamine 2000. Sixteen to twenty-four hours post-transfection, cells were washed with PBS and detached from the plate with 2 mL of trypsin (0.25% (w/v)). 28 mL of Optimem (Invitrogen) containing 3.5% fatty acid-free human serum albumin (HSA) was added to the detached cells and then split into 96-well plates. Test compounds at various test concentrations were added, and the cells were incubated for 4.5 hours. Luciferase activity was measured using an EG&G Berthold 96-well luminometer and the $EC_{50}$ (effective concentration to reach 50% maximal response) was determined from the dose response plot. Table 1 includes NFAT assay $EC_{50}$ values for the compounds tested with this assay.

Compounds of the invention may be assayed under various conditions (e.g. hGPR40Aequorin and NFAT assays as described above) that may highlight certain advantages the compounds may possess. In particular, the NFAT assay described above is carried out in the presence of the full physiological concentration of human serum albumin (HSA). Fatty acids, the putative physiological ligands for GPR40 (see Itoh, Nature, 2003, 422, 173-176), are highly bound by HSA with only low nanomolar concentrations present in the free state (Kleinfeld, J. Lipid Res., 1995, 36, 229-240) despite total plasma fatty acid concentrations up to the millimolar range. Compounds of the invention are characterized by a carboxylic acid and a lipophilic moiety. However, unexpectedly, compounds of the invention that show moderate to good potency in the GPR40 aequorin assay run in the presence of very little HSA display excellent $EC_{50}$s in the NFAT assay run in the presence of the full physiological concentration of HSA. Compounds of the invention are therefore expected to show enhanced activity in modulating GPR40 under physiological conditions.

The stereoisomers in Table 1 are as specified, i.e., S-enantiomers or R-enantiomers, and if not specified, or if shown with wavy bonds, are mixtures of S-enantiomers and R-enantiomers. In addition, the present invention provides the S-enantiomers, the R-enantiomers, and mixtures of both S-enantiomers and R-enantiomers including racemates of each compound prepared according to the synthetic methods described herein or adapted with the necessary minor modifications from these methods.

Insulin Secretion Assay

Human islets are isolated from cadaveric donors. Islets are treated with trypsin (0.25% (w/v) and cells are seeded in 96-well plates containing 3,000 cells per well. Cells are cultured in Roswell Park Memorial Institute (RMPI) media containing 10% fetal bovine serum.

For determination of insulin secretion, media is removed from islet cells and replaced with Krebs-Ringer bicarbonate buffer containing 10 mM HEPES (KRBH) and 2 mM glucose. After one hour incubation, media is replaced with KRBH containing 11.2 mM glucose and test compounds. Insulin released into the medium from the islet cells is measured using scintillation proximity assay (SPA).

For determination of insulin secretion from rodent islets, C57/B16 mice are euthanized with carbon dioxide gas. The pancreatic bile duct is clamped proximal to the duodenum and then cannulated. H/HBSS containing 0.75 mg/mL collagenase XI (Sigma) is then infused into the pancreas through the cannula. The pancreas is excised and then incubated at 37° C. for 13 minutes to complete enzymatic digestion. The collagenase digestion is quenched in H/HBSS containing 1% BSA and washed once in the same buffer. Islets can be purified using density gradient centrifugation using Histopaque (Sigma) and are hand-picked under a stereomicroscope.

Islets are cultured overnight in Roswell Park Memorial Institute (RMPI) media containing 10% fetal bovine serum and 50 uM beta-mercaptoethanol. Following overnight culture, islets are incubated in KRBH containing 2.8 mM glucose for one hour.

For determination of insulin secretion, islets are incubated in DMEM containing 12.5 mM glucose and test compounds for one hour. Insulin released into the culture medium from the islets is measured using an insulin ELISA.

TABLE 1

Assay Data For Human GPR40

| No. | Structure$^a$ | Aequorin EC$_{50}$$^{b,c}$ | NFAT EC$_{50}$$^{c,d}$ |
|---|---|---|---|
| 1 | | ++ | +++ |
| 2 | | ++ | + |
| 3 | | ++ | +++++ |

TABLE 1-continued
Assay Data For Human GPR40
| No. | Structure[a] | Aequorin EC$_{50}$[b,c] | NFAT EC$_{50}$[c,d] |
|-----|-----------|------------------------|---------------------|
| 4   | 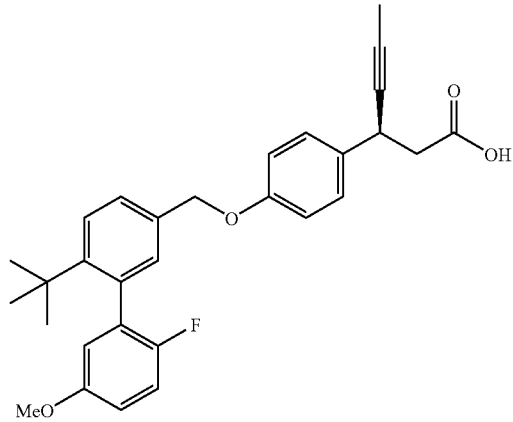 | +++ | +++++ |
| 5   | 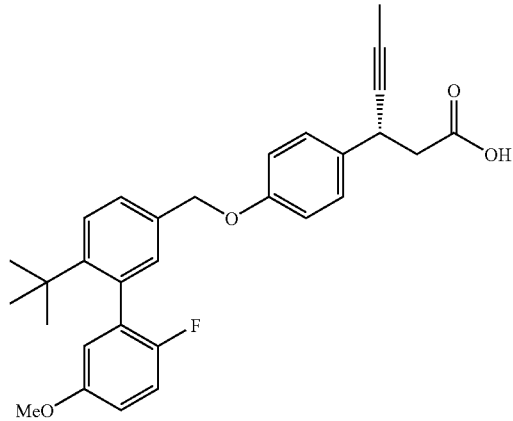 | ++  | +++   |
| 6   | 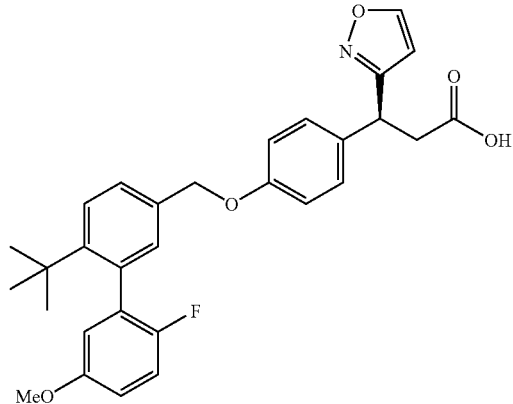 | +++ | +++++ |

TABLE 1-continued

Assay Data For Human GPR40

| No. | Structure[a] | Aequorin EC$_{50}$[b,c] | NFAT EC$_{50}$[c,d] |
|---|---|---|---|
| 7 | | ++ | ++++ |
| 8 | | ++ | ++++ |
| 9 | | +++ | +++ |
| 10 | | ++ | +++ |

TABLE 1-continued
Assay Data For Human GPR40
| No. | Structure[a] | Aequorin EC$_{50}$[b,c] | NFAT EC$_{50}$[c,d] |
|---|---|---|---|
| 11 | 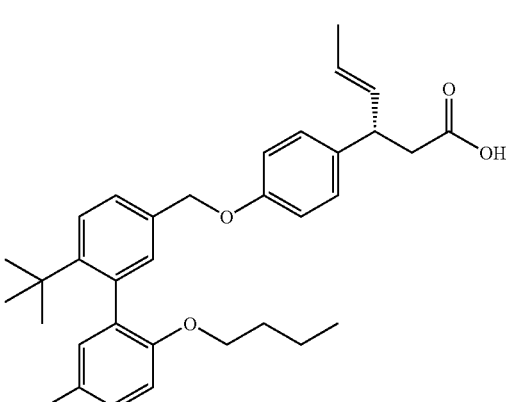 | ++ | ++++ |
| 12 | 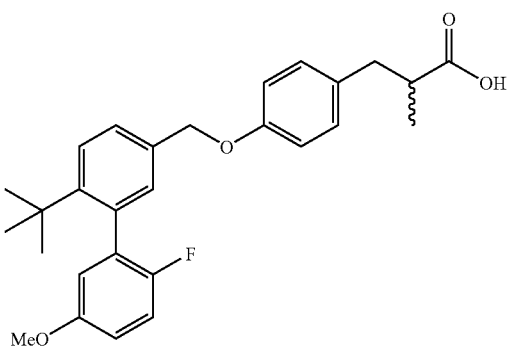 | ++ | +++ |
| 13 | 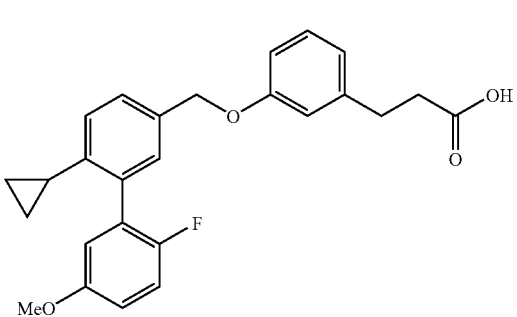 | ++ | [e]ND |

TABLE 1-continued

Assay Data For Human GPR40

| No. | Structure[a] | Aequorin EC$_{50}$[b,c] | NFAT EC$_{50}$[c,d] |
|---|---|---|---|
| 14 | | ++ | ND |
| 15 | | +++ | ND |

TABLE 1-continued

Assay Data For Human GPR40

| No. | Structure[a] | Aequorin EC$_{50}$[b,c] | NFAT EC$_{50}$[c,d] |
|---|---|---|---|
| 16 | Enantiomer of Example 14 | ++ | ND |
| 17 | Enantiomer of Example 15 | +++ | ND |
| 18 | *(structure shown)* | ++ | ND |
| 19 | *(structure shown)* | +++ | ND |
| 20 | *(structure shown)* | ++ | ND |

TABLE 1-continued
Assay Data For Human GPR40
| No. | Structure[a] | Aequorin EC$_{50}$[b,c] | NFAT EC$_{50}$[c,d] |
|---|---|---|---|
| 21 | 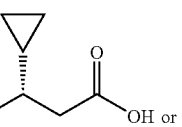 | ++ | ND |
| 22 | Enantiomer of Example 21 | ++ | ND |
| 23 | 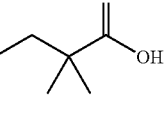 | ++ | ND |

TABLE 1-continued
Assay Data For Human GPR40
| No. | Structure[a] | Aequorin EC$_{50}$[b,c] | NFAT EC$_{50}$[c,d] |
|---|---|---|---|
| 24 | 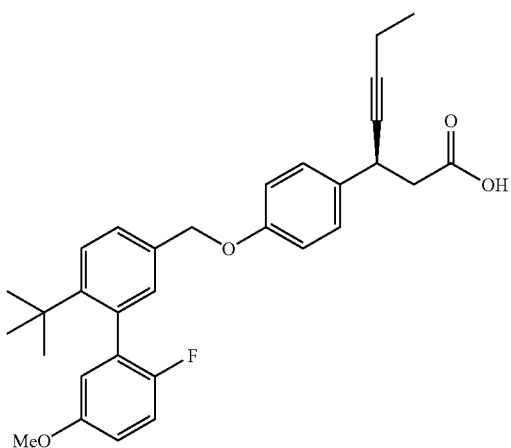 | ++ | ND |
| 25 | 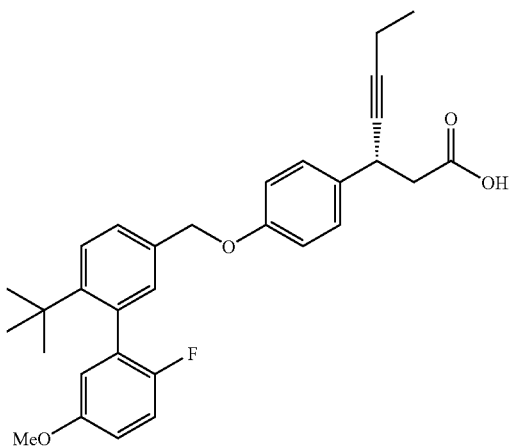 | ++ | ND |

TABLE 1-continued
Assay Data For Human GPR40
| No. | Structure[a] | Aequorin EC$_{50}$[b,c] | NFAT EC$_{50}$[c,d] |
|---|---|---|---|
| 26 | 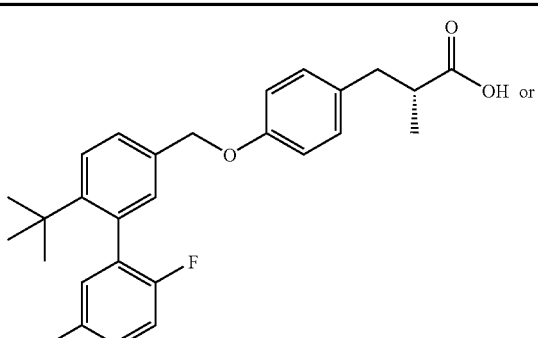 | ++ | ND |
| 27 | 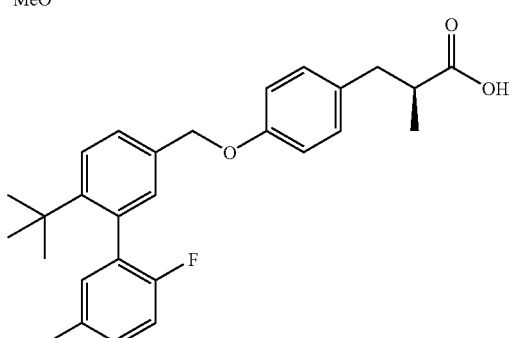 | ++ | ND |
| 28 | 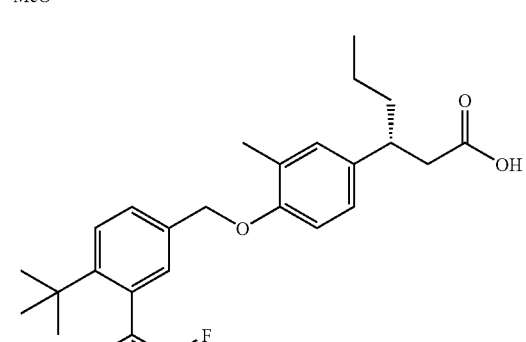 | ++ | ND |

TABLE 1-continued

Assay Data For Human GPR40

| No. | Structure[a] | Aequorin EC$_{50}$[b,c] | NFAT EC$_{50}$[c,d] |
|---|---|---|---|
| 29 | | ++ | ND |
| 30 | | ++ | ND |
| 31 | Enantiomer of Example 26 | ++ | ND |
| 32 | | ++ | ND |
| 33 | | ++ | ND |

TABLE 1-continued

Assay Data For Human GPR40

| No. | Structure[a] | Aequorin EC$_{50}$[b,c] | NFAT EC$_{50}$[c,d] |
|---|---|---|---|
| 34 | | ++ | ND |
| 35 | | +++ | ND |
| 36 | | ++ | ND |
| 37 | | ++ | ND |

TABLE 1-continued
Assay Data For Human GPR40
| No. | Structure[a] | Aequorin EC$_{50}$[b,c] | NFAT EC$_{50}$[c,d] |
|---|---|---|---|
| 38 | 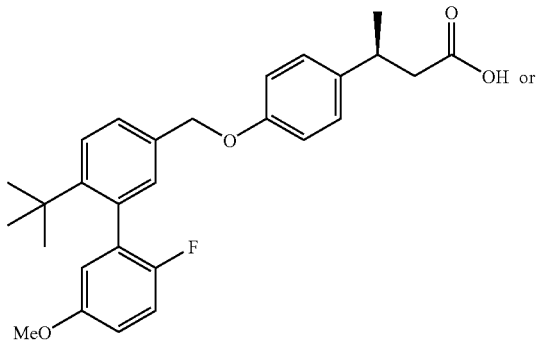 or 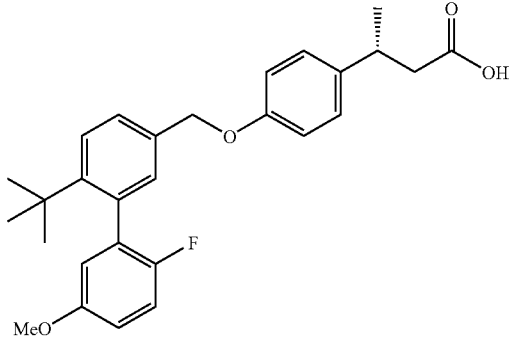 | +++ | ND |
| 39 | Enantiomer of Example 38 | ++ | ND |
| 40 | 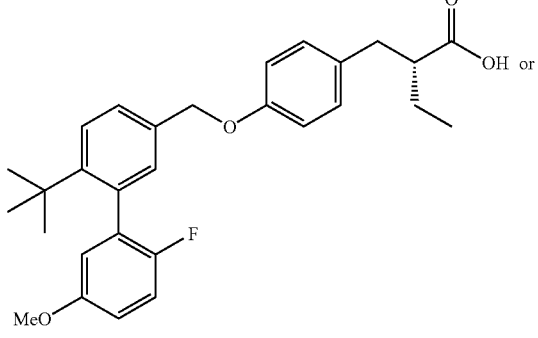 or 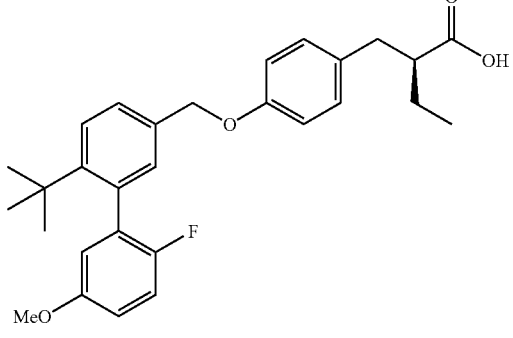 | ++ | ND |

TABLE 1-continued
Assay Data For Human GPR40
| No. | Structure[a] | Aequorin EC$_{50}$[b,c] | NFAT EC$_{50}$[c,d] |
|---|---|---|---|
| 41 | 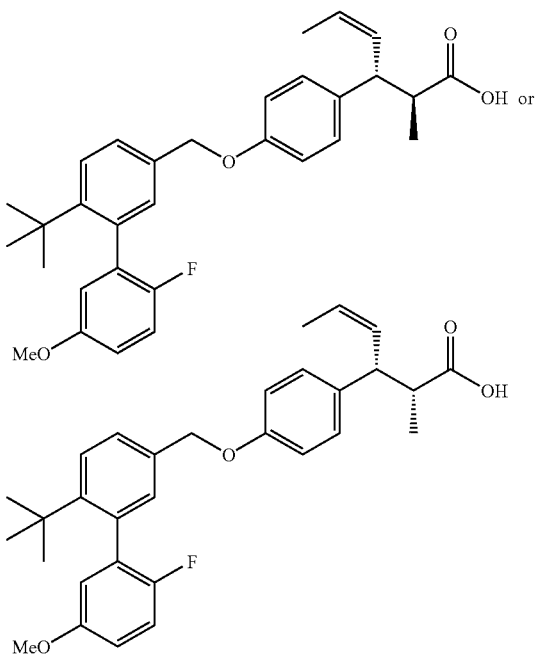 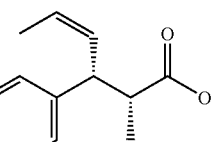 | +++ | ND |
| 42 | 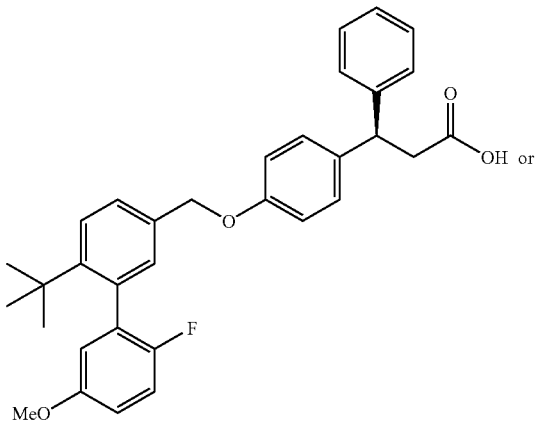 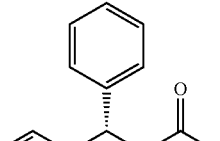 | +++ | ND |

TABLE 1-continued
Assay Data For Human GPR40
| No. | Structure[a] | Aequorin EC$_{50}$[b,c] | NFAT EC$_{50}$[c,d] |
|---|---|---|---|
| 43 | 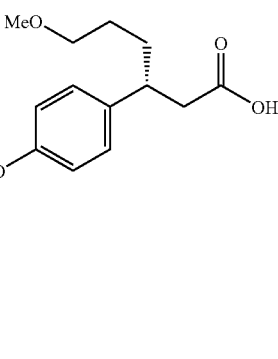 | ++ | ND |
| 44 | Enantiomer of Example 42 | ++ | ND |
| 45 | 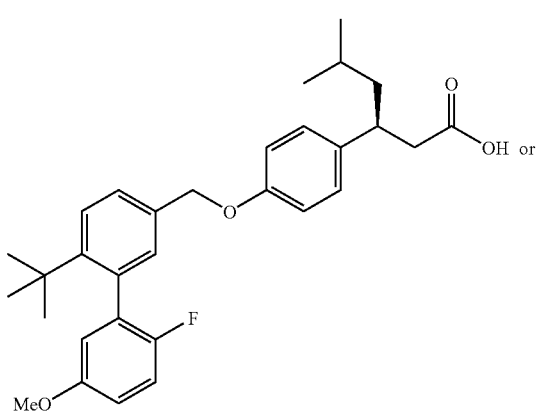 | ++ | ND |
| 46 | Enantiomer of Example 45 | ++ | ND |

TABLE 1-continued
Assay Data For Human GPR40
| No. | Structure[a] | Aequorin EC$_{50}$[b,c] | NFAT EC$_{50}$[c,d] |
|---|---|---|---|
| 47 | 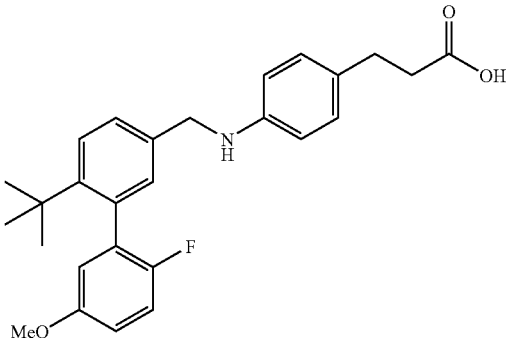 | ++ | ND |
| 48 | 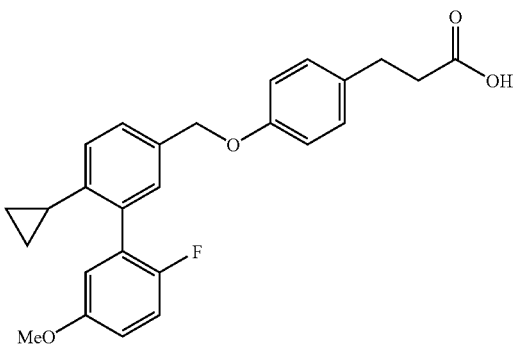 | | |
| 49 | 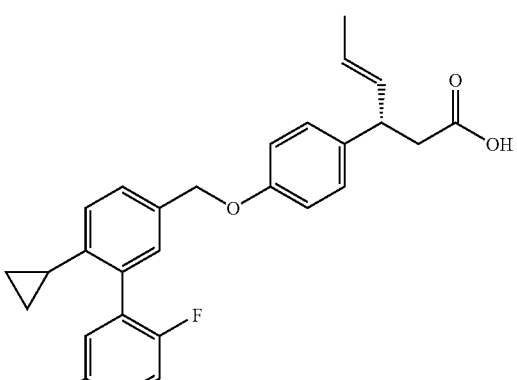 | ND | ND |
| 50 | 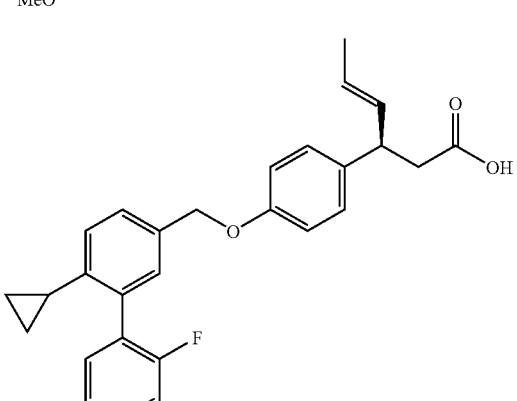 | ND | ND |

TABLE 1-continued
Assay Data For Human GPR40
| No. | Structure[a] | Aequorin EC$_{50}$[b,c] | NFAT EC$_{50}$[c,d] |
|---|---|---|---|
| 51 | 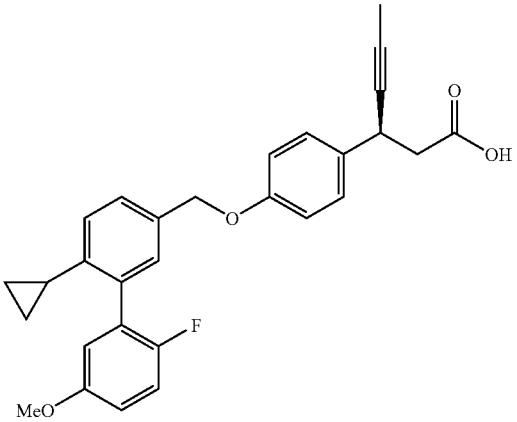 | ND | ND |
| 52 | 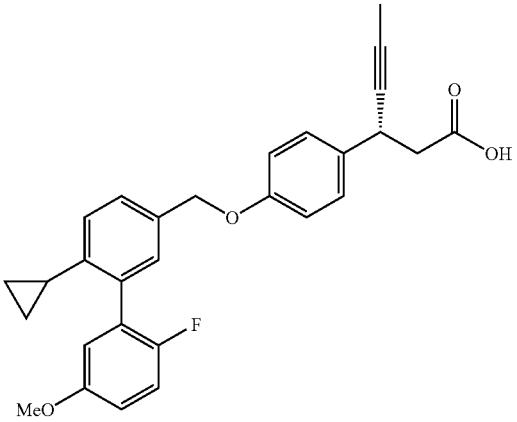 | ND | ND |
| 53 | 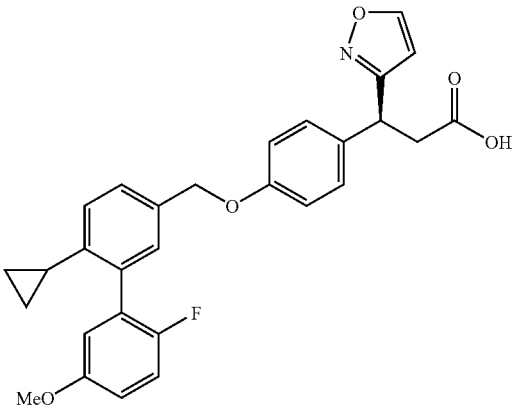 | ND | ND |

TABLE 1-continued

Assay Data For Human GPR40

| No. | Structure | Aequorin EC$_{50}$[b,c] | NFAT EC$_{50}$[c,d] |
|---|---|---|---|
| 54 | | ND | ND |
| 55 | | ND | ND |
| 56 | | ND | ND |
| 57 | | ND | ND |

TABLE 1-continued

Assay Data For Human GPR40

| No. | Structure[a] | Aequorin EC$_{50}$[b,c] | NFAT EC$_{50}$[c,d] |
|---|---|---|---|
| 58 | | ND | ND |
| 59 | | ND | ND |
| 60 | | ND | ND |

TABLE 1-continued

Assay Data For Human GPR40

| No. | Structure[a] | Aequorin EC$_{50}$[b,c] | NFAT EC$_{50}$[c,d] |
|---|---|---|---|
| 61 | | ND | ND |
| 62 | | ND | ND |

[a]When present, the "〰" bond indicates a mixture of steroisomers are present in the exemplary compound.
[b]Aequorin assay data
[c]EC$_{50}$ Ranges
  + EC$_{50}$ > 10 μM
  ++ 1 μM ≤ EC$_{50}$ ≤ 10 μM
  +++ 0.1 μM ≤ EC$_{50}$ ≤ 1 μM
  ++++ 0.01 μM ≤ EC$_{50}$ ≤ 0.1 μM
  +++++ EC$_{50}$ < 0.01 μM
[d]NFAT assay data
[e]ND means not determined All publications and patent applications cited in this specification are hereby incorporated by reference as if each individual publication or patent application were specifically and individually indicated to be incorporated by reference. Each publication and patent application cited herein is incorporated in its entirety as if fully set forth herein. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A compound having the formula I:

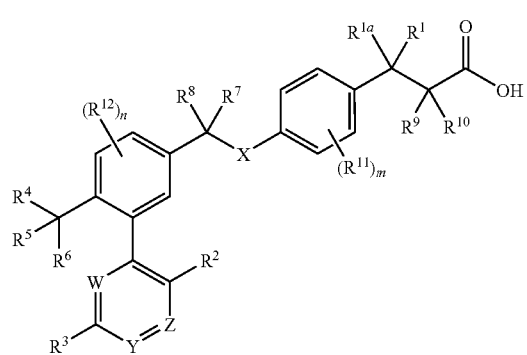

or a pharmaceutically acceptable salt, solvate, stereoisomer, or $C_1$-$C_6$ alkyl ester thereof; or a tautomer or a pharmaceutically acceptable salt, solvate, stereoisomer, or $C_1$-$C_6$ alkyl ester thereof; or a mixture thereof, wherein X is O or S;

W, Y, and Z are selected from N or C—H; wherein no more than one of W, Y, and Z is N; and further wherein Z is not N if $R^2$ is F;

$R^1$ is selected from H, ($C_1$-$C_6$)alkyl, ($C_2$-$C_6$)alkenyl, ($C_2$-$C_6$)alkynyl, heterocyclyl, or heteroaryl;

$R^{1a}$ is selected from H and ($C_1$-$C_4$)alkyl;

$R^2$ is selected from F or ($C_3$-$C_6$)alkoxy;

$R^3$ is ($C_1$-$C_2$)alkoxy;

$R^4$, $R^5$, and $R^6$ are independently slected from H, ($C_1$-$C_4$) alkyl, or substituted ($C_1$-$C_4$)alkyl, and two of $R^4$, $R^5$, and $R^6$ may join together to form a 3-7 membered ring; wherein at least two of $R^4$, $R^5$, and $R^6$ are other than H;

$R^7$ and $R^8$ are independently selected from H and ($C_1$-$C_4$) alkyl;

$R^9$ and $R^{10}$ are independently selected from H and ($C_1$-$C_4$) alkyl;

Each $R^{11}$ is independently selected from F, Cl, ($C_1$-$C_4$) alkyl, or ($C_1$-$C_4$)alkoxy and m is 0, 1, or 2; and Each $R^{12}$ is independently selected from F, Cl, ($C_1$-$C_4$) alkyl, or ($C_1$-$C_4$)alkoxy and n is 0, 1, or 2.

2. The compound of claim 1, wherein m and n are both 0.
3. The compound of claim 1, wherein $R^{1a}$ is H.
4. The compound of claim 1, wherein W, Y, and Z are all C—H.
5. The compound of claim 1, wherein $R^4$, $R_5$ and $R^6$ are independently selected from H and ($C_1$-$C_4$)alkyl groups and at least two of $R^4$, $R^5$, and $R^6$ are($C_1$-$C_4$)alkyl groups.
6. The compound of claim 5, wherein $R^4$, $R^5$, and $R^6$ are all methyl groups.
7. The compound of claim 1, wherein $R^2$ is F or butoxy.
8. The compound of claim 7, wherein $R^2$ is F.
9. The compound of claim 1, wherein $R^2$ is batoxy.
10. The compound of claim 1, wherein $R^3$ is methoxy.
11. The compound of claim 1, wherein X is O.
12. The compound of claim 1, wherein $R^7$ and $R^8$ are both H.
13. The compound of claim 1, wherein $R^9$ and $R^{10}$ are both H.
14. The compound of claim 1, wherein $R^1$ is ($C_1$-$C_4$)alkyl.
15. The compound of claim 14, wherein $R^1$ is propyl.
16. The compound of claim 1, wherein $R^1$ is ($C_2$-$C_4$)alkenyl.
17. The compound of claim 16, wherein $R^1$ is —CH=CH—$CH_3$.
18. The compound of claim 17, wherein $R^1$ has the formula

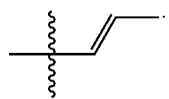

19. The compound of claim 17, wherein $R^1$ has the formula

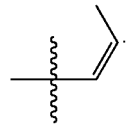

20. The compound of claim 13, wherein $R^1$ is ($C_2$-$C_4$) alkynyl.
21. The compound of claim 1, wherein m is 0; n is 0; $R^{1a}$ is H; W is C—H; Y, is C—H; Z is C—H; $R^1$ is a ($C_2$-C4)alkenyl; $R^2$ is F; $R^3$ is methoxy; $R^4$ is methyl; $R^5$ is methyl; $R^6$ is methyl; $R^7$ is H; $R^8$ is H; $R^9$ is H; $R^{10}$ is H; and X is O.
22. The compound of claim 1, wherein the compound has the formula II

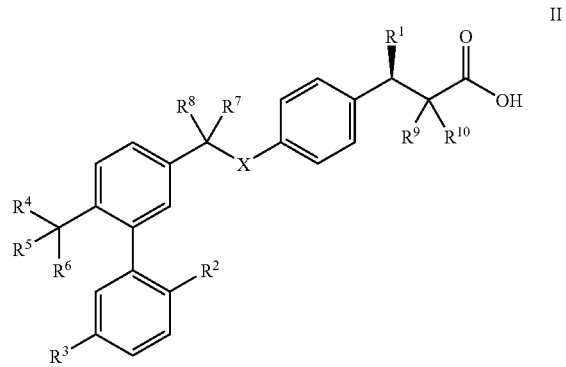

or a pharmaceutically acceptable salt, solvate, or $1C_1$-$C_6$ alkyl ester thereof; or a tautomer or a pharmaceutically acceptable salt, solvate, or $C_1$-$C_6$ alkyl ester thereof; or a mixture thereof.

23. The compound of claim 1, wherein the compound is selected from

173
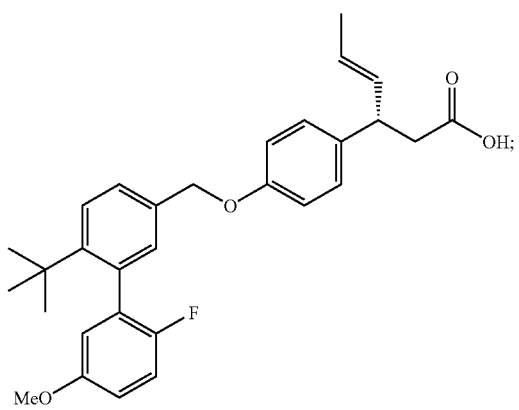
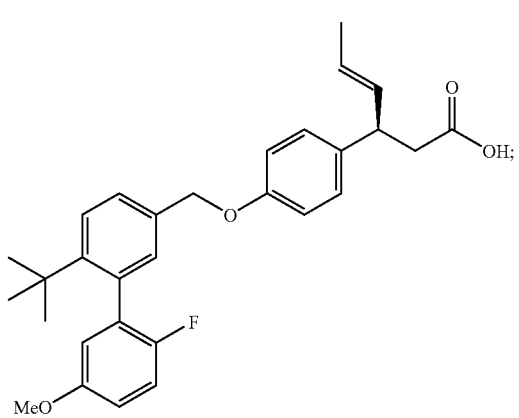
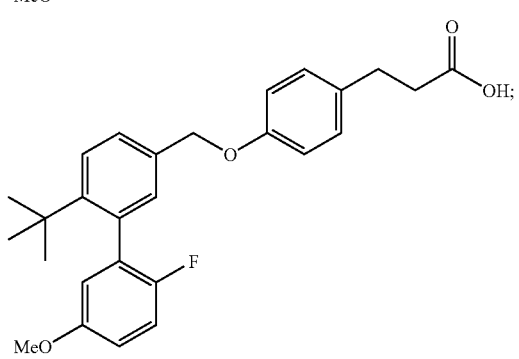
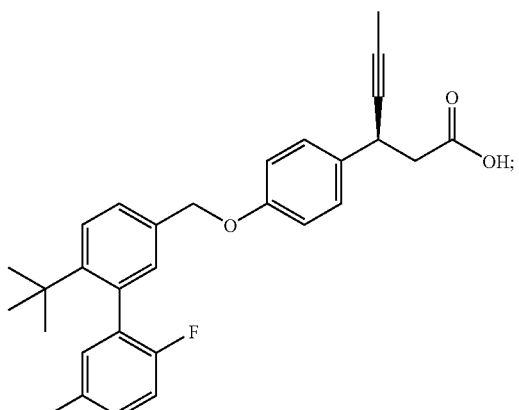
174
-continued
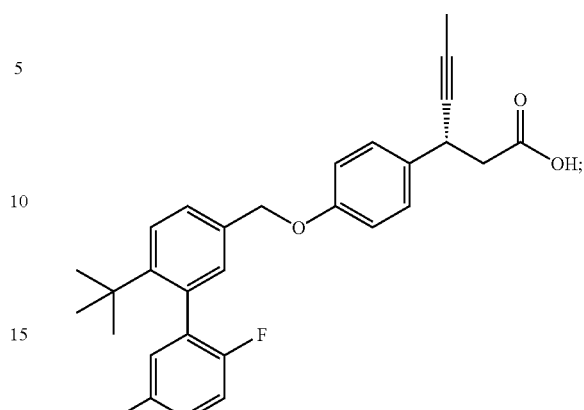
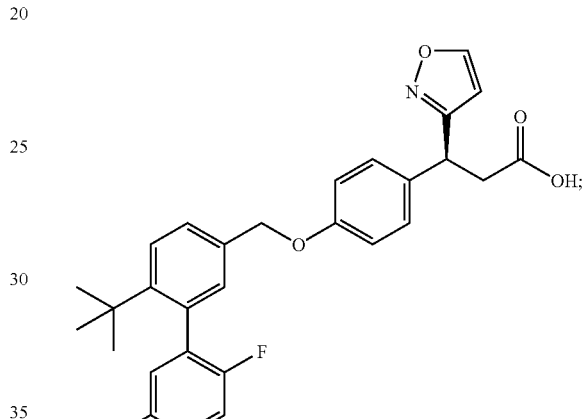
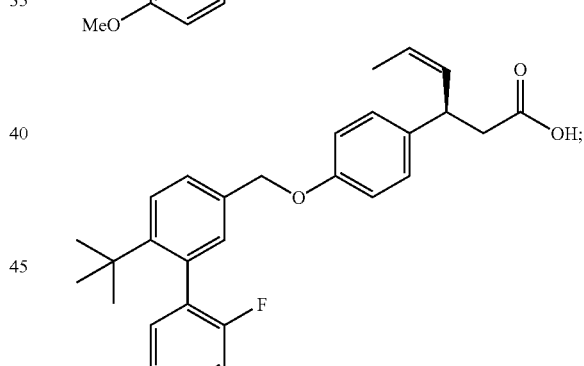
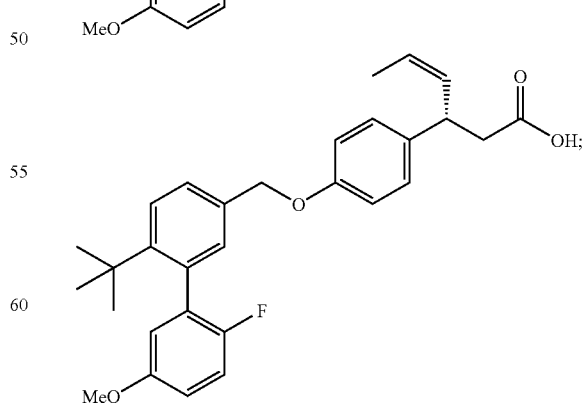

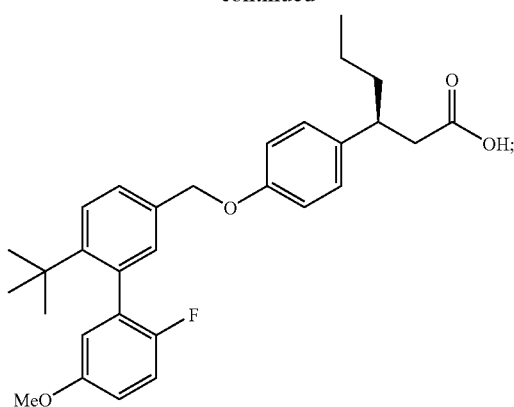

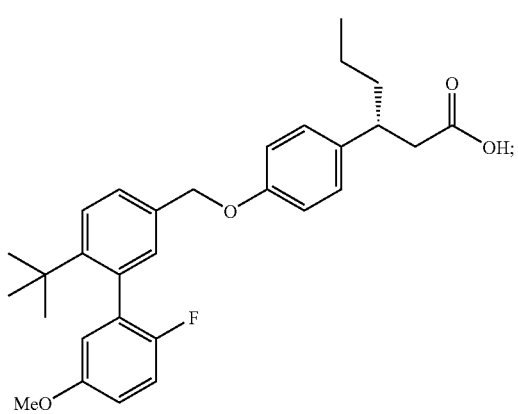

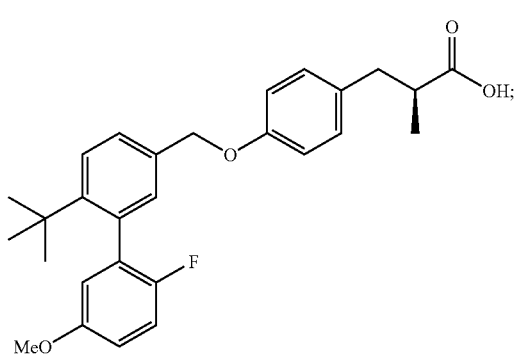

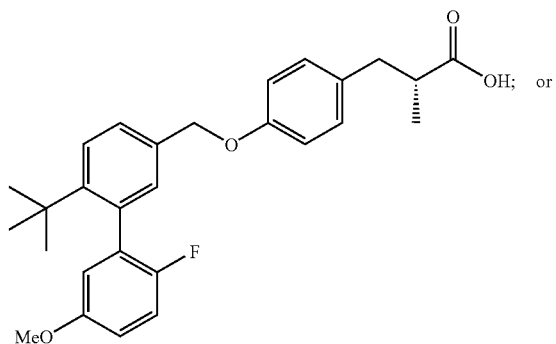

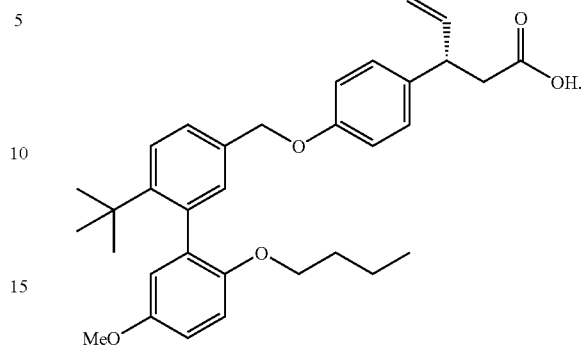

24. The compound of claim 1, wherein the compound is a salt.

25. The compound of claim 1, wherein the ester is a methyl or ethyl ester.

26. A pharmaceutical composition, comprising: a pharmaceutically acceptable carrier, diluent, or excipient, and the compound of claim 1.

27. A method for treating a disease or condition by activating GPR40, comprising: administering to a subject in need thereof, a therapeutically effective amount of the compound of claim 1, wherein the disease or condition is selected from the group consisting of type II diabetes, hyperglycemia, glucose intolerance, insulin resistance, hyperinsulinemia, and hypoglycemia.

28. The method of claim 27, wherein the disease or condition is type II diabetes.

29. The method of claim 27, wherein the compound is administered in combination with a second therapeutic agent.

30. The method of claim 29, wherein the second therapeutic agent is metformin or is a thiazolidinedione.

31. A method for activating GPR40 in a cell, comprising: contacting the cell with the compound of claim 1.

32. A method for activating GPR40, comprising: contacting GPR40 with the compound of claim 1.

33. A method for increasing circulating insulin concentration in a subject, comprising: administering the compound of claim 1 to the subject.

34. A compound having the formula I:

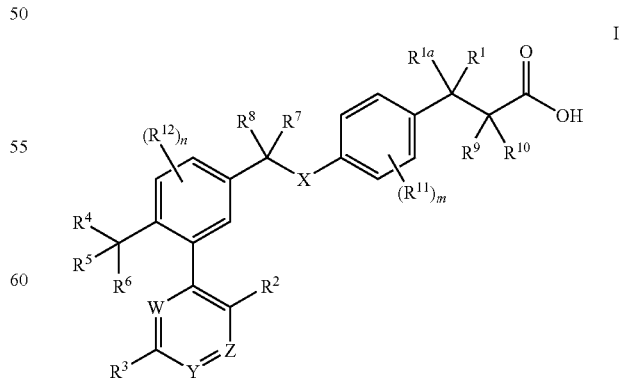

or a pharmaceutically acceptable salt, solvate, stereoisomer, or $C_1$-$C_6$ alkyl ester thereof; or a tautomer or a pharmaceutically acceptable salt, solvate, stereoisomer, or $C_1$-$C_6$ alkyl ester thereof; or a mixture thereof, wherein X is O, S, or $NR_a$, wherein $R_a$ is selected from H and ($C_1$-$C_4$)alkyl;

W, Y, and Z are selected from N or C—H; wherein no more than one of W, Y, and Z is N; and further wherein Z is not N if $R^2$ is F;

$R^1$ is selected from H, ($C_1$-$C_6$)alkyl, ($C_2$-$C_6$)alkenyl, ($C_2$-$C_6$)alkynyl, heterocyclyl, heteroaryl, or aryl;

$R^{1a}$ is selected from H and ($C_1$-$C_4$)alkyl;

$R^2$ is selected from F or ($C_3$-$C_6$)alkoxy;

$R^3$ is ($C_1$-$C_2$)alkoxy;

$R^4$, $R^5$, and $R^6$ are independently selected from H, ($C_1$-$C_4$)alkyl, or substituted ($C_1$-$C_4$)alkyl, and two of $R^4$, $R^5$, and $R^6$ may join together to form a 3-7 membered ring; wherein at least two of $R^4$, $R^5$, and $R^6$ are other than H; and wherein at least one of $R^4$, $R^5$, and $R^6$ may be OH;

$R^7$ and $R^8$ are independently selected from H and ($C_1$-$C_4$)alkyl;

$R^9$ and $R^{10}$ are independently selected from H, ($C_1$-$C_4$)alkyl, and ($C_2$-$C_6$)alkenyl;

Each $R^{11}$ is independently selected from F, Cl, ($C_1$-$C_4$)alkyl, or ($C_1$-$C_4$)alkoxy and m is 0, 1, or 2; and Each $R^{12}$ is independently selected from F, Cl, ($C_1$-$C_4$)alkyl, or ($C_1$-$C_4$)alkoxy and n is 0, 1, or 2.

35. The compound of claim 34, wherein m and n are both 0.

36. The compound of claim 34, wherein $R^{1a}$ is H.

37. The compound of claim 34, wherein W, Y, and Z are all C—H.

38. The compound of claim 34, wherein $R_4$, $R^5$, and $R^6$ are independently selected from H and ($C_1$-$C_4$)alkyl groups and at least two of $R^4$, $R^5$, and $R^6$ are ($C_1$-$C_4$)alkyl groups.

39. The compound of claim 34, wherein $R^4$, $R^5$, and $R^6$ are all methyl groups.

40. The compound of claim 34, wherein $R^2$ is F or butoxy.

41. The compound of claim 40, wherein $R^2$ is F.

42. The compound of claim 40, wherein $R^2$ is butoxy.

43. The compound of claim 34, wherein $R^3$ is methoxy.

44. The compound of claim 34, wherein X is $NR_a$.

45. The compound of claim 44, wherein $R_a$ is H.

46. The compound of claim 34, wherein X is O.

47. The compound of claim 34, wherein $R^7$ and $R^8$ are both H.

48. The compound of claim 34, wherein $R^9$ and $R^{10}$ are both H.

49. The compound of claim 34, wherein $R^1$ is ($C_1$-$C_4$)alkyl).

50. The compound of claim 49, wherein $R^1$ is propyl.

51. The compound of claim 34, wherein $R^1$ is ($C_2$-$C_4$)alkenyl.

52. The compound of claim 51, wherein $R^1$ is —CH=CH—CH$_3$.

53. The compound of claim 52, wherein $R^1$ has the formula

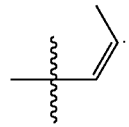

54. The compound of claim 52, wherein $R^1$ has the formula

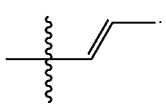

55. The compound of claim 34, wherein $R^1$ is ($C_2$-$C_4$) alkynyl.

56. The compound of claim 34, wherein $R^1$ is aryl.

57. The compound of claim 56, wherein $R^1$ is phenyl.

58. The compound of claim 34, wherein $R^9$ is selected from ($C_1$-$C_4$)alkyl and ($C_2$-$C_6$)alkenyl.

59. The compound of claim 34, wherein the compound has the formula II

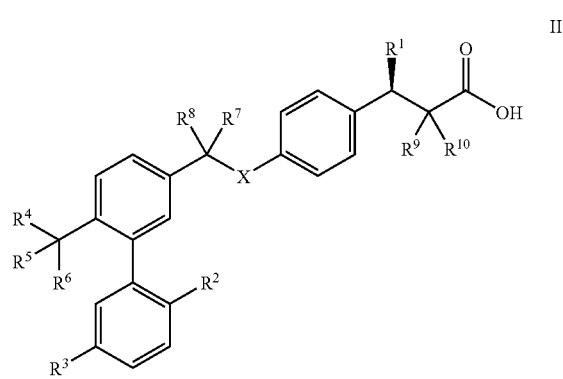

or a pharmaceutically acceptable salt, solvate, or $C_1$-$C_6$ alkyl ester thereof; or a tautomer or a pharmaceutically acceptable salt, solvate, or $C_1$-$C_6$ alkyl ester thereof; or a mixture thereof.

60. The compound of claim 34, wherein the compound is selected from

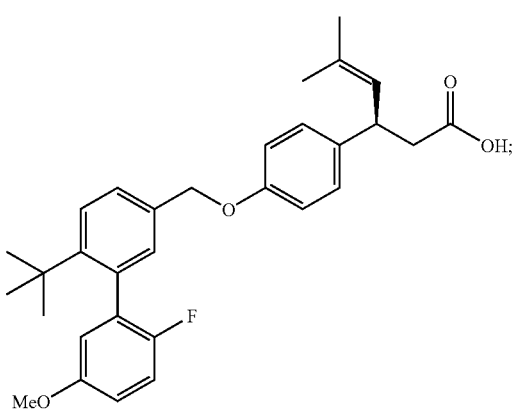

-continued
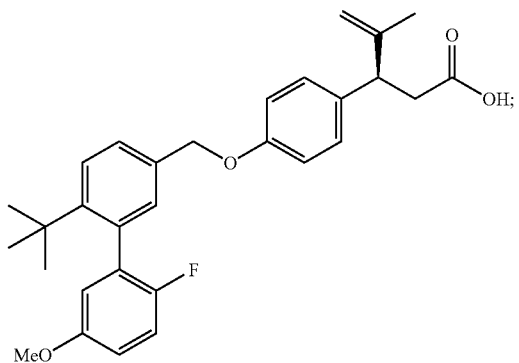
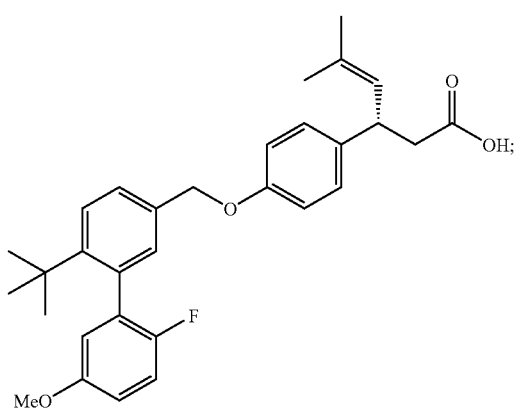
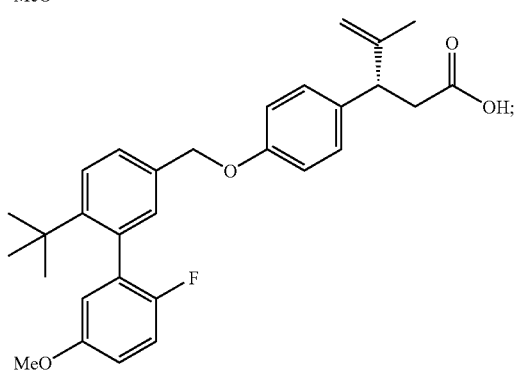
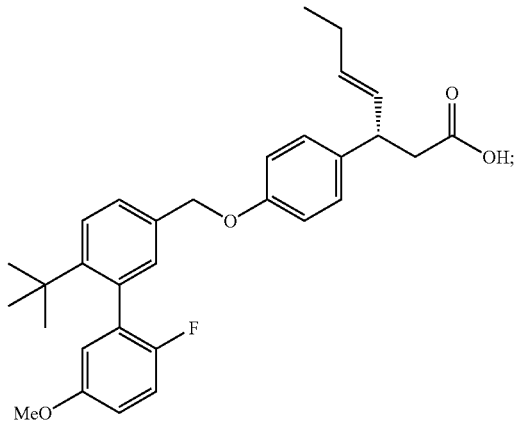
-continued
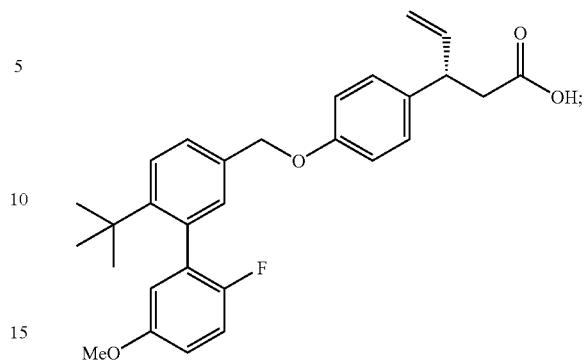
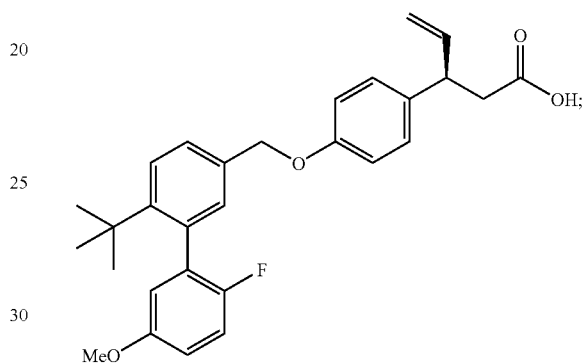
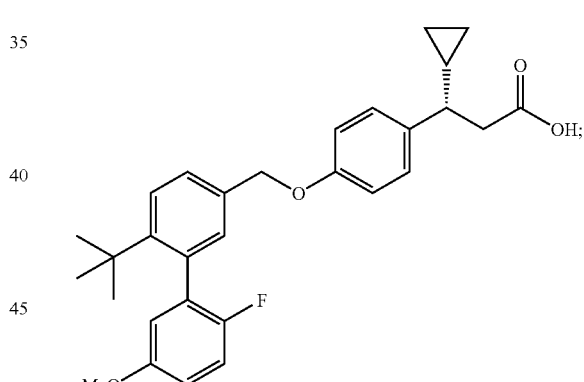
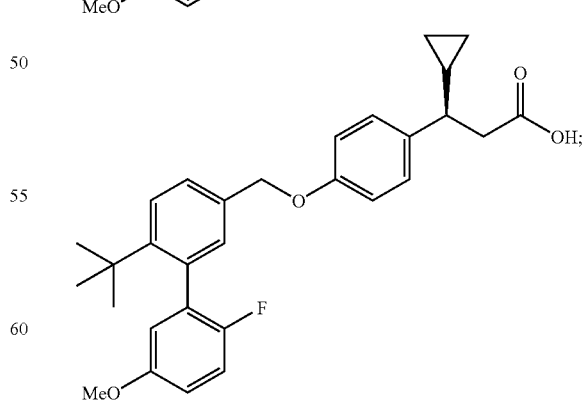

-continued
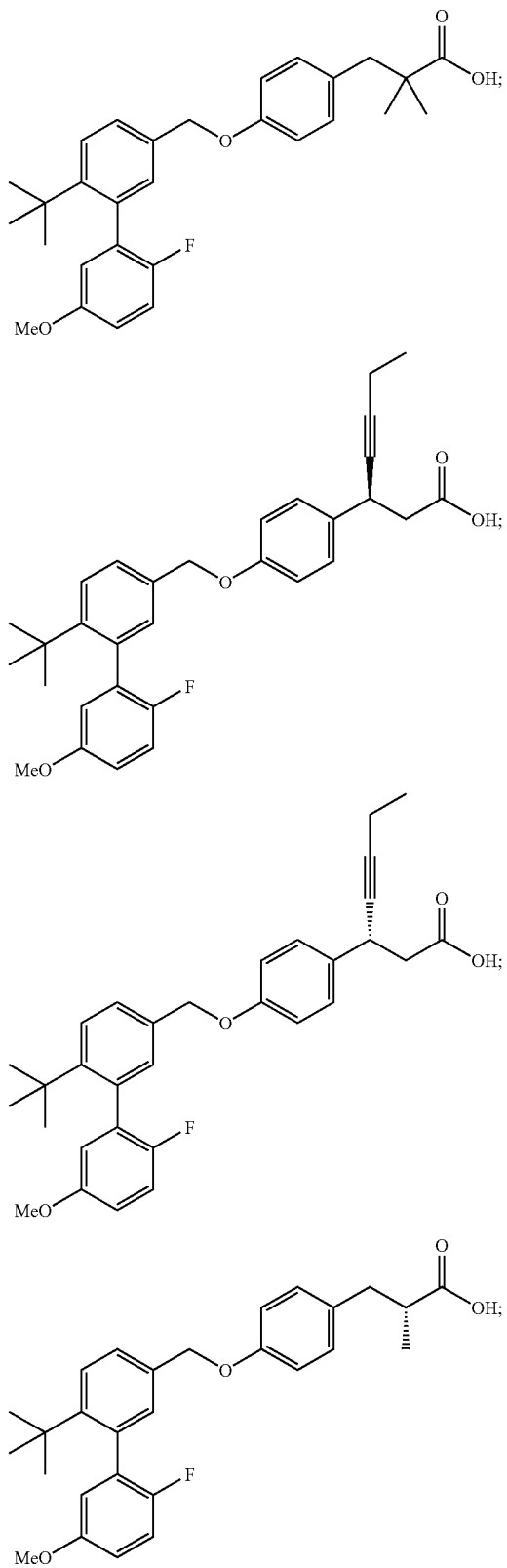
-continued
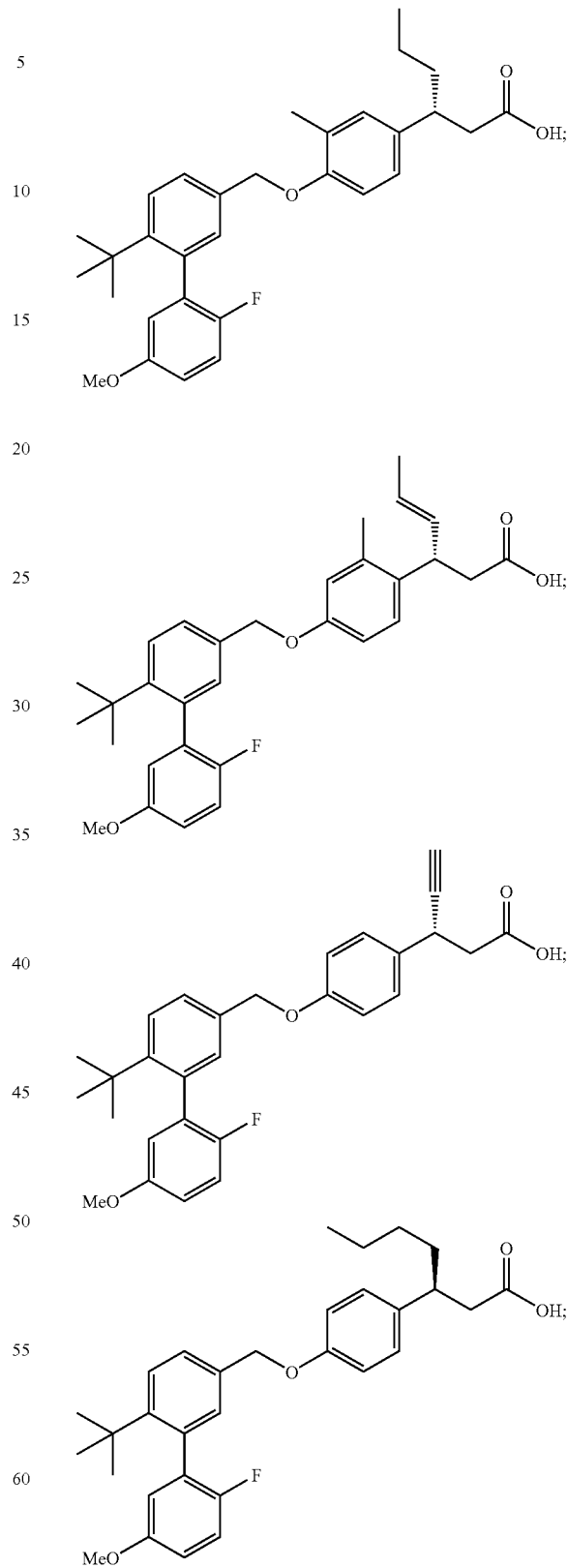

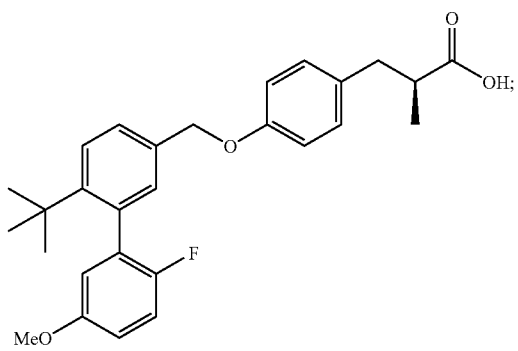
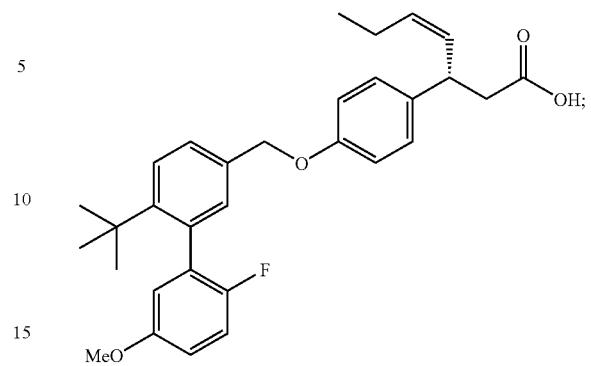
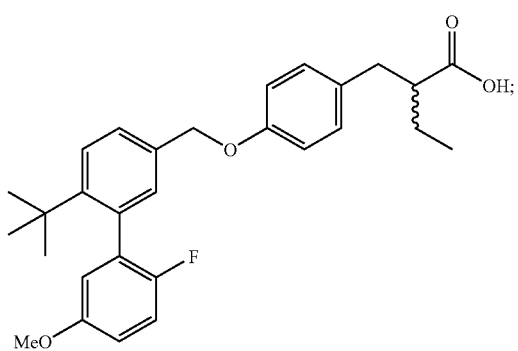
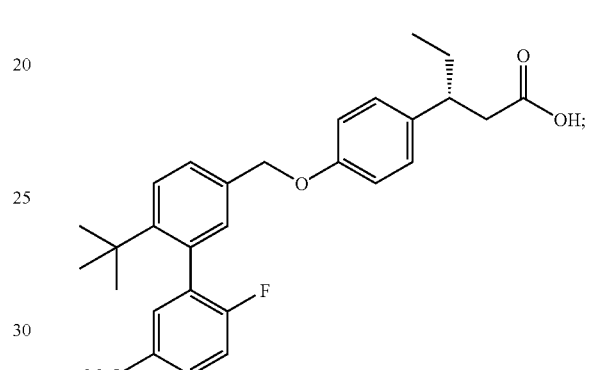
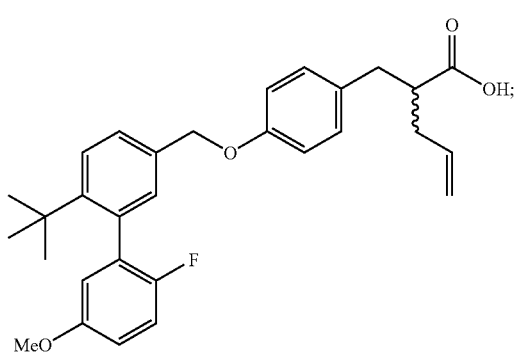
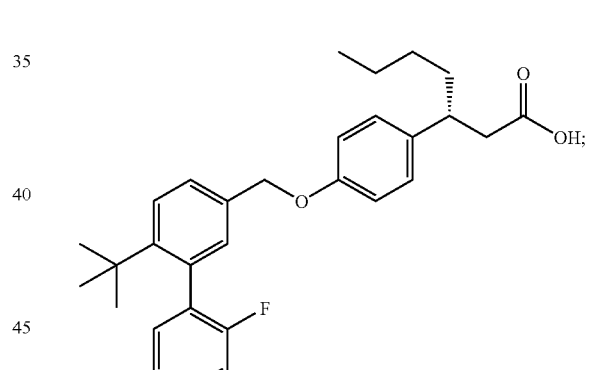
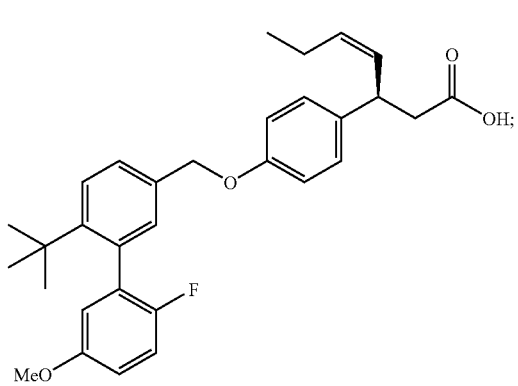
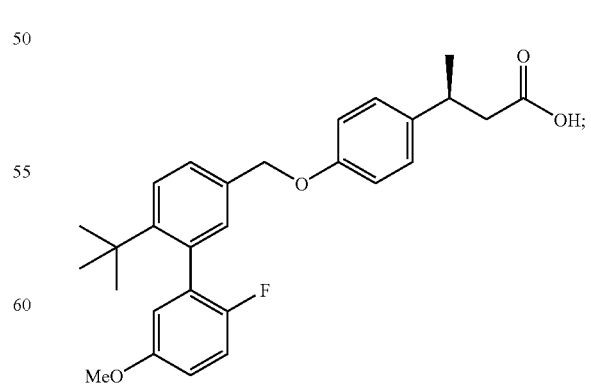

-continued
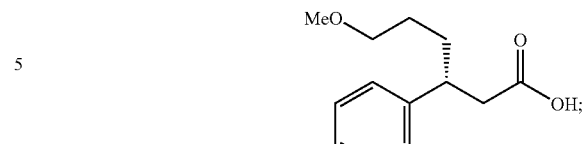
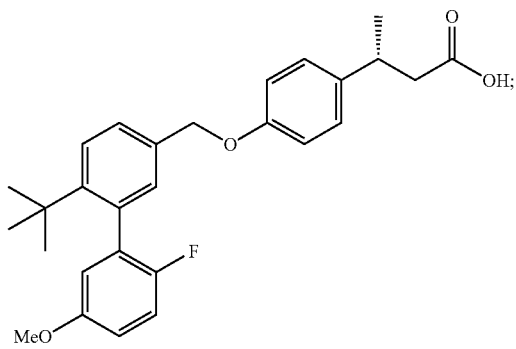
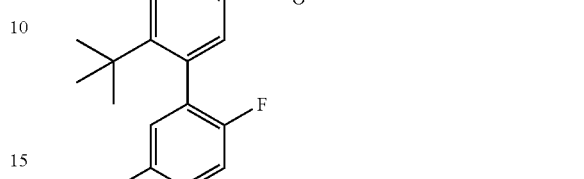
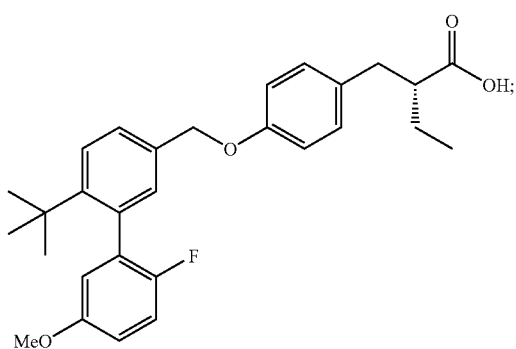
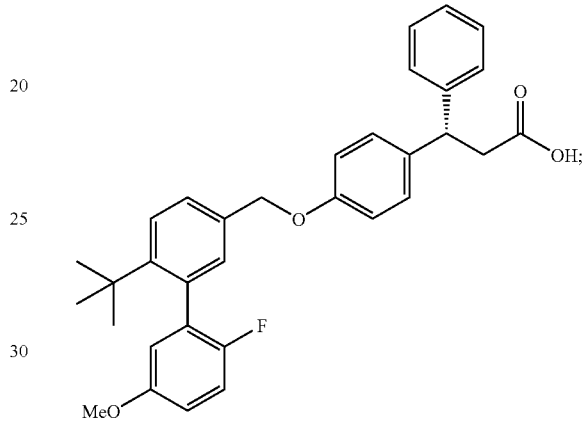
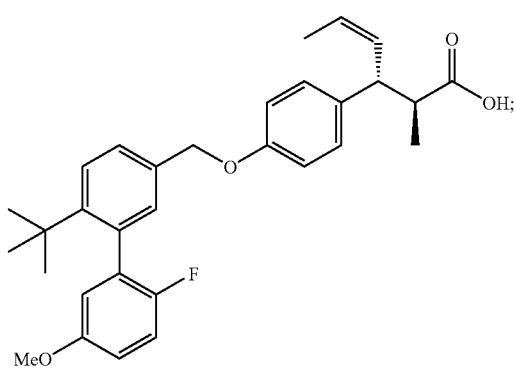
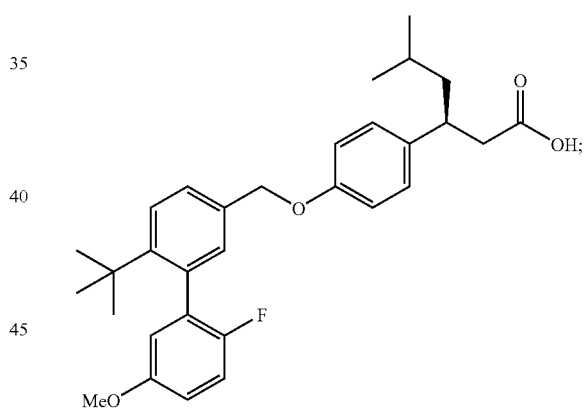
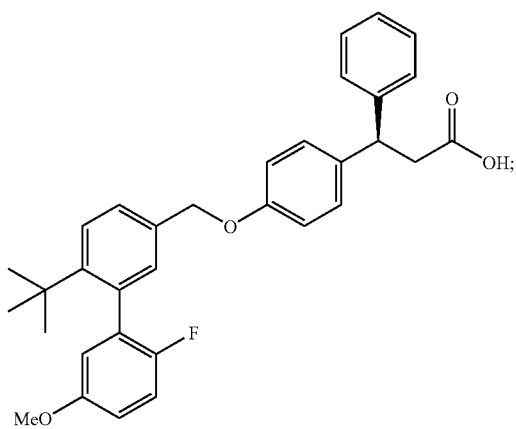
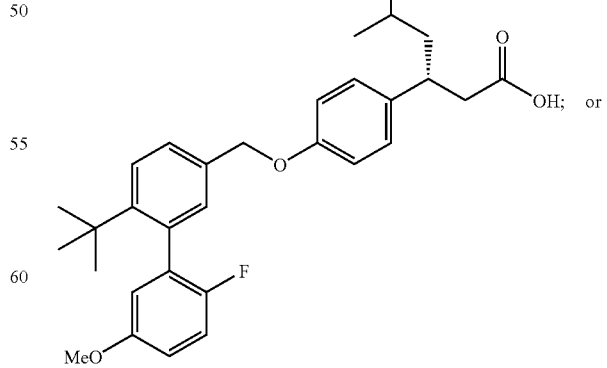

-continued

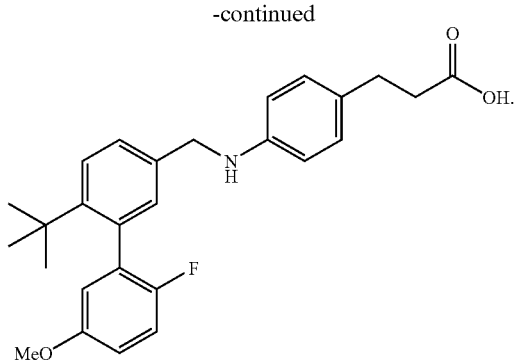

61. The compound of claim 34, wherein the compound is a salt.

62. The compound of claim 34, wherein the ester is a methyl or ethyl ester.

63. A pharmaceutical composition, comprising: a pharmaceutically acceptable carrier, diluent or excipient, and the compound of claim 34.

64. A method for treating a disease or condition by activating GPR40, comprising: administering to a subject in need thereof, a therapeutically effective amount of the compound of claim 34, wherein the disease or condition is selected from the group consisting of type II diabetes, hyperglycemia, glucose intolerance, insulin resistance, hyperinsulinemia, and hypoglycemia.

65. The method of claim 64, wherein the disease or condition is type II diabetes.

66. The method of claim 64, wherein the compound is administered in combination with a second therapeutic agent.

67. The method of claim 66, wherein the second therapeutic agent is metformin or is a thiazolidinedione.

68. A method for activating GPR40 in a cell, comprising: contacting the cell with the compound of claim 34.

69. A method for activating GPR40, comprising: contacting GPR40 with the compound of claim 34.

70. A method for increasing circulating insulin concentration in a subject, comprising: administering the compound of claim 34 to the subject.

* * * * *

UNITED STATES PATENT AND TRADEMARK OFFICE
CERTIFICATE OF CORRECTION

PATENT NO.       : 7,572,934 B2
APPLICATION NO.  : 12/082645
DATED            : August 11, 2009
INVENTOR(S)      : Brown et al.

Page 1 of 1

It is certified that error appears in the above-identified patent and that said Letters Patent is hereby corrected as shown below:

In claim 5, column 171, line 61, the phrase "wherein $R^4$, $R_5$ and $R^6$" should read as --wherein $R^4$, $R^5$, and $R^6$--.

In claim 21, column 172, line 38, the phrase, "$R^1$ is a $(C_2-C4)$alkenyl;" should read as --$R^1$ is a $(C_2-C_4)$alkenyl;--.

In claim 22, column 172, lines 61 through 62, the phrase "or $1C_1-C_6$ alkyl ester thereof;" should read as --or $C_1-C_6$ alkyl ester thereof;--.

In claim 38, column 177, line 33, the phrase "wherein $R_4$, $R^5$, and $R^6$" should read as --wherein $R^4$, $R^5$, and $R^6$--.

Signed and Sealed this

Twenty-second Day of September, 2009

David J. Kappos
*Director of the United States Patent and Trademark Office*